United States Patent
Edwards et al.

(10) Patent No.: US 11,667,705 B2
(45) Date of Patent: *Jun. 6, 2023

(54) IL-17A BINDING PROTEINS

(71) Applicant: Crescendo Biologics Limited, Cambridge (GB)

(72) Inventors: Bryan Edwards, Cambridge (GB); Ulla Lashmar, Cambridge (GB); Brian McGuinness, Cambridge (GB); Mike Romanos, Cambridge (GB); Thomas Sandal, Cambridge (GB); Yumin Teng, Cambridge (GB)

(73) Assignee: Crescendo Biologics Limited, Cambridge (GB)

( * ) Notice: Subject to any disclaimer, the term of this patent is extended or adjusted under 35 U.S.C. 154(b) by 383 days.

This patent is subject to a terminal disclaimer.

(21) Appl. No.: 16/843,474

(22) Filed: Apr. 8, 2020

(65) Prior Publication Data
US 2020/0347127 A1 Nov. 5, 2020

Related U.S. Application Data

(63) Continuation of application No. 15/541,889, filed as application No. PCT/GB2016/005007 on Jan. 12, 2016, now Pat. No. 10,654,924.

(30) Foreign Application Priority Data

Jan. 12, 2015 (GB) ...................................... 1500463

(51) Int. Cl.
| C07K 16/24 | (2006.01) |
| A61K 39/395 | (2006.01) |
| A01K 67/027 | (2006.01) |
| C12N 15/63 | (2006.01) |
| A61P 37/02 | (2006.01) |
| A61P 31/00 | (2006.01) |
| A61P 37/06 | (2006.01) |
| A61P 37/08 | (2006.01) |
| G01N 33/68 | (2006.01) |
| A61K 39/00 | (2006.01) |

(52) U.S. Cl.
CPC ........ *C07K 16/244* (2013.01); *A01K 67/0278* (2013.01); *A61K 39/3955* (2013.01); *A61P 31/00* (2018.01); *A61P 37/02* (2018.01); *A61P 37/06* (2018.01); *A61P 37/08* (2018.01); *C12N 15/63* (2013.01); *G01N 33/6869* (2013.01); *A01K 2217/072* (2013.01); *A01K 2217/075* (2013.01); *A01K 2217/15* (2013.01); *A01K 2227/105* (2013.01); *A01K 2267/01* (2013.01); *A61K 2039/505* (2013.01); *C07K 2317/565* (2013.01); *C07K 2317/569* (2013.01); *C07K 2317/92* (2013.01); *G01N 2333/54* (2013.01)

(58) Field of Classification Search
None
See application file for complete search history.

(56) References Cited

U.S. PATENT DOCUMENTS

| 2006/0034833 A1 | 2/2006 | Beirnaert |
| 2006/0034845 A1 | 2/2006 | Silence et al. |
| 2010/0122358 A1 | 5/2010 | Bruggemann et al. |
| 2012/0014975 A1 | 1/2012 | Hegen et al. |
| 2018/0362666 A1 | 12/2018 | Teng et al. |

FOREIGN PATENT DOCUMENTS

| CN | 103119062 A2 | 5/2013 |
| EP | 1867323 | 12/2007 |
| JP | 2009-540824 A | 11/2009 |
| JP | 2010-500028 | 1/2010 |
| JP | 2012-519708 | 8/2012 |
| JP | 2014-516945 A | 7/2014 |
| WO | 2005/035572 | 4/2005 |
| WO | 2007/104529 | 9/2007 |
| WO | 2007/149032 | 12/2007 |
| WO | 2008/021156 | 2/2008 |
| WO | 2008/071751 | 6/2008 |
| WO | 2010/102251 | 9/2010 |
| WO | 2011/161263 | 12/2011 |
| WO | 2012007880 A2 | 1/2012 |
| WO | 2012/156219 | 11/2012 |
| WO | 2013/063110 | 5/2013 |
| WO | 2014/141192 | 9/2014 |

OTHER PUBLICATIONS

Lloyd et al, Protein Engineering, Design & Selection, 2009, vol. 22, No. 3, pp. 159-168.*
Goel et al. The Journal of Immunology, 2004, 173(12):7358-7367.*
Edwards et al, Journal of Molecular Biology, 2003, vol. 334, pp. 103-118.*
Mills et al, Nature Reviews Immunology,vol. 23, No. 1, pp. 38-54, 2023; published online Jul. 5, 2022.*
Brummell et al, Biochemistry; 1993; vol. 32, pp. 1180-1187.
Kobayashi et al. Protein Engineering; 1999; vol. 12, pp. 879-844.
Brorson et al. J. Immunol; 1999; vol. 163, pp. 6694-6701.
Coleman Research in Immunol; 1994; vol. 145; pp. 33-36.
Rouet et al, the Journal of Biological Chemistry; 2015; vol. 290, No. 19, pp. 11905-11917.
Muyldermans, Annual Review of Biochemistry; 2013; vol. 82, pp. 775-797.
Kai-Jye Lou, Science-Business exchange, 2010.
Hueber et al, Science Translational Medicine; 201 O; vol. 2, No. 52, pp. 1-11.

(Continued)

Primary Examiner — Bridget E Bunner
Assistant Examiner — Fozia M Hamud
(74) Attorney, Agent, or Firm — McDermott Will & Emery LLP; Judy M. Mohr; Alexandra Cavazos

(57) ABSTRACT

Binding molecules to IL-17A. The binding molecules are useful in the treatment of disorders, for example psoriasis.

Figure 9A:
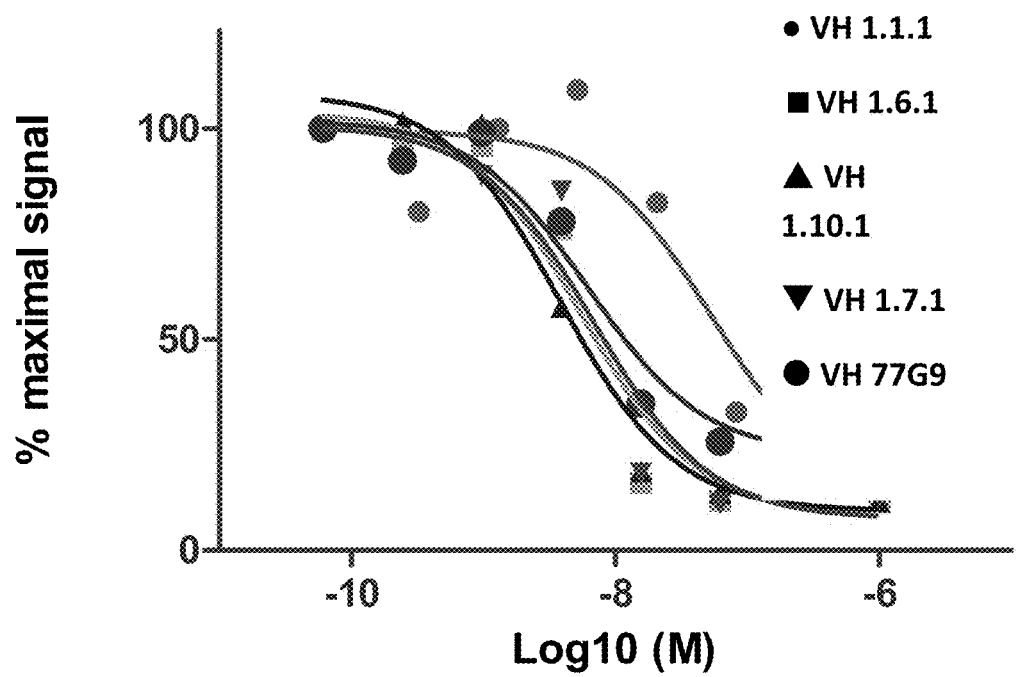

7 Claims, 26 Drawing Sheets
(22 of 26 Drawing Sheet(s) Filed in Color)
Specification includes a Sequence Listing.

(56) References Cited

OTHER PUBLICATIONS

Sullens et al, Clinical and Developmental Immunology, 2013, vol. 2013, pp. 1-8Sullens et al, Clinical and Developmental Immunology, 2013, vol. 2013, pp. 1-8.
Summers et al; Clinical and Experimental Immunology, 2014; vol. 176, pp. 341-350.
Bullens, et al., IL-17 A in Human Respiratory Diseases: Innate or Adaptive Immunity Clinical Implications? Clinical and Developmental Immunology (2013) pp. 1-8.
Park, et al., Interleukin-17 Regulation: An Attractive Therapeutic Approach for Asthma, Respiratory Research (2010) 11:78, Bio Med Central, pp. 1-11.
Chyuan, et al., Role of Interleukin-(IL-) 17 in the Pathogenisis and Targeted Therapies in Spondyloar-thropathies, Hindawi. Mediators of Inflammation (2018) Article ID 2403935, 8 pages. https:i/doi.org/10 115.5/2018/2403935.
Holt J et al., Domain antibodies: proteins for therapy, Trends in Biotechnology, Elsevier Publications, Cambridge, GB, (Nov. 1, 2003) vol. 21, No. 11, pp. 484-490.
Wong et al., Structural Requirements for a Specificity Switch and for Maintenance of Affinity Using Mutational Analysis of a Phase-Displayed Anti-Arsonate Antibody of Fab Heavy Chain First Complementarily-Determining Region, The Journal of Immunology (1998) 160, pp. 5990-5997.
Rudikoff et al., Single Amino Acid Substitution Altering Antigen-Binding Specificity, Proceedings of the National Academy of Sciences (1982) vol. 79, pp. 1979-1983.
Roe, Superior Human Single Domain Vh Antibody Fragments from a Transgenic Mouse, Crescendo Biologics (Apr. 12, 2013).
Vanheusden K, et al. Pre-clinical proof-of-concept of ALX-0761, a nanobody (R) neutralizing both IL-17 A and F in a cynomolgus monkey collage induced arthritis model, Annual Meeting of the American College of Rheumatology (Oct. 30, 2013) vol. 66, S543, Abstract No. 1287, San Diego, CA.
Crescendo Biologics Limited, Search Report under Section 17(5) for GB 1500463.3, dated Oct. 15, 2015, 6 pages.
VH Fragments, Crescendo Biologics (Mar. 24, 2014).
Anonymous; Crescendo Biologics Announces the Crescendo Mouse, Crescendo Biologics. Jan. 16, 2013.
One Nucleus Life Science Leadership Series: Antibody Based Therapeutics, Crescendo Biologics. Jan. 23, 2013.
El Maghrary GM, Microemulsions as transdermal drug delivery systems, Current Nanoscience, vol. 8, No. 4 (Jan. 1, 2012) pp. 504-511, Bentham Science Publishers Ltd., Bussum, NL.

* cited by examiner

Figure 1A

| Clone | FR1 | CDR1 | FR2 | CDR2 | FR3 | CDR3 | FR4 |
|---|---|---|---|---|---|---|---|
| 1.1 | EVQLVESGGGLVQPGGSLRLSCAASGFTFS | SYSMY | WVRQAPGKGLEWVA | NIKQDGSEKYYVDSVKG | RFTISRDNAKNSLFLQMNSLRAEDTAVYYCAK | GEILPLHFDY | WGQGTLVTVSS |
| 1.2 | EVQLVESGGGLVQPGGSLRLSCAASGFTFS | SYSMY | WVRQAPGKGLEWVA | EIKQDGSVQYYVSDVKG | RFTISRDNAKNSLYLQMNSLRAEDTAVYYCAK | GEILPLYFDY | WGQGTLVTVSS |
| 1.3 | EVQLVESGGGLVQPGGSLRLSCAASGFTFS | SYSMY | WVRQAPGKGLEWVA | EIKQDGSVQYYVSDVKG | RFTISRDNAKNSLYLQMNSLRAEDTAVYYCAK | GEILPLYFDY | WGQGTLVTVSS |
| 1.4 | EVQLVESGGGLVQPGGSLRLSCAASGFTFS | SYSMY | WVRQAPGKGLEWVA | EIKQTGSVQYYVDSVKG | RFTISRDNAKNSLYLQMNSLRAEDTAVYYCAK | GEILPLYFDY | WGQGTLVTVSS |
| 1.5 | EVQLVESGGGLVQPGGSLRLSCAASGFTFS | SYSMY | WVRQAPGKGLEWVA | EIKPTGSVQYYVDSVKG | RFTISRDNAKNSLYLQMNSLRAEDTAVYYCAK | GEILPLYFDY | WGQGTLVTVSS |
| 1.6 | EVQLVESGGGLVQPGGSLRLSCAASGFTFS | SYSMY | WVRQAPGKGLEWVA | EIKQDGSEEKYYVDSVKG | RFTISRDNAKNSLYLQMNSLRAEDTAVYYCAK | GEILPLYFDY | WGQGTLVTVSS |
| 1.7 | QVQLVESGGGLVQPGGSLRLSCAASGFTFS | SYSMY | WVRQAPGKGLEWVA | EIKQDGSEQYYVDSVKG | RFTISRDNAKNSLYLQMNSLRAEDTAVYYCAK | GEILPLYFDY | WGQGTLVTVSS |
| 1.8 | QVQLVESGGGLVQPGGSLRLSCAASGFTFS | SYSMY | WVRQAPGKGLEWVA | KIEQDGSEKYYVDSVKG | RFTISRDNAKKNSLYLQMNSLRAEDTAVYYCAK | GEILPLYFDY | WGQGTLVTVSS |
| 1.9 | QVQLVESGGGLVQPGGSLRLSCAASGFTFS | SYGMY | WVRQAPGKGLEWVA | EIKQDGSEEYYVDSVKG | RFTISRDNAKNSLYLQMNSLRAEDTAVYYCAK | GEILPLYFDY | WGQGTLVTVSS |
| 1.10 | EVQLVESGGGLVQPGGSLRLSCAASGFTFS | SYRMY | WVRQAPGKGLEWVA | SIEQDGSEEYYVDSVKG | RFTISRDNAKNSLFLQMNSLRAEDTAVYYCAK | GEILPLYFDY | WGQGTLVTVSS |
| 1.11 | EVQLVESGGGLVQPGGSLRLSCAASGFTFS | SYQMY | WVRQAPGKGLEWVA | SIKQDGSEEYYVDSVKG | RFTISRDNAKNSLYLQMNSLRAEDTAVYYCAK | GEILPLYFDY | WGQGTLVTVSS |
| 1.12 | EVQLVESGGGLVQPGGSLRLSCAASGFTFS | SYGMY | WVRQAPGKGLEWVA | KIEQDGSEKYYVDSVKG | RFTISRDNAKNSLYLQMNSLRAEDTAVYYCAK | GEILPLYFDY | WGQGTLVTVSS |
| 1.13 | QVQLVESGGGLVQPGGSLRLSCAASGFTFS | SYGMY | WVRQAPGKGLEWVA | SIEQDGSEEYYVDSVKG | RFTISRDNAKNSLYLQMNSLRAEDTAVYYCAK | GEILPLYFDY | WGQGTLVTVSS |
| 1.14 | EVQLVESGGGLVQRGGSLRLSCAASGFTFS | SYSMY | WVRQAPGKGLEWVA | EIRQDGSEQYYVDSVKG | RFTISRDNAKNSLYLQMNGLRAEDTAVYYCAK | GEILPLYFDY | WGQGTLVTVSS |
| 1.15 | QVQLVESGGGLVQPGGSLRLSCAASGFTFS | SYSMY | WVRQAPGKGLEWVA | EIKQDGSEKYYVDSVKG | RFTISRDNAKNSLYLQMNSLRAEDTAVYYCAK | GEILPLYFDY | WGQGTLVTVSS |
| 1.16 | EVQLVESGGGLVQPGGSLRLSCAASGFTFS | SYGMY | WVRQAPGKGLEWVA | EIKPTGSVQYYVGGVKG | RFTISRDNAKNSLYLQMNSLRAEDTAVYYCAK | GEILPLYFDY | WGQGTLVTVSS |
| 1.17 | QVQLVESGGGLVQPGGSLRLSCAASGFTFS | SYSMY | WVRQAPGKGLEWVA | EIKPTGSVQYYVDSVKG | RFTISRDNAKNSLYLQMNSLRAEDTAVYYCAK | GEILPLYFDY | WGQGTLVTVSS |
| 1.18 | EVQLVESGGGLVQPGGSLRLSCAASGFTFS | SYSMY | WVRQAPGKGLEWVA | EIKQDGSEKYYVDSVKG | RFTISRDNAKNSLFLQMNSLRAEDTAVYYCAK | GEILPLYFDY | WGQGTLVTVSS |
| 1.19 | EVQLVESGGGLVQPGGSLRLSCATSGFTFS | SYGMY | WVRQAPGKGLEWVA | KIEQDGSEKYYADSVKG | RFTISRDNAKNSLYLQMNSLRAEDTAVYYCAK | GEILPLYFDY | WGQGTLVTVSS |
| 1.20 | EVQLVESGGGLVQPGGSLRLSCAASGFTFS | SYSMY | WVRQAPGKGLEWVA | KIEQDGSEQYYVDSVKG | RFTISRDNAKNSLYLQMNSLRAEDTAVYYCAK | GEILPLYFDY | WGQGTLVTVSS |
| 1.21 | EVQLVESGGGLVLPGGSLRLSCAASGFTFS | SYSMY | WVRQAPGKGLEWVA | EIKQDGSEQYYVDSVKG | RFTISRDNAKNSLYLQMNSLRAEDTAVYYCAK | GEILPLYFDY | WGQGTLVTVSS |
| 1.22 | EVQLVESGGGLVRPGGSLRLSCAASGFTFS | SYSMY | WVRQAPGKGLEWVA | SIKQDGSEEYYVDSVKG | RFTISRDNAKNSLYLQMNSLRAEDTAVYYCAK | GEILPLYFDY | WGQGTLVTVSS |
| 1.23 | QVQLVESGGGLVQPGGSLRLSCAASGFTFS | SYGMY | WVRQAPGKGLEWVA | EIKQDGSEKYYVDSVKG | RFTISRDNAKKNSLYLQMNSLRAEDTAVYYCAK | GEILPLYFDY | WGQGTLVTVSS |
| 1.24 | QVQLVESGGGLVQPGGSLRLSCAASGFTFS | SYEMY | WVRQAPGKGLEWVA | EIKQDGSEQYYVDSVKG | RFTISRDNAKNSLYLQMNSLRAEDTAVYYCAK | GEILPLYFDY | WGQGTLVTVSS |
| 1.25 | EVQLVESGGGLVQPGGSLRLSCAASGFTFS | SYSMY | WVRQAPGKGLEWVA | SIKQDGSEQYYVDSVKG | RFTISRDNAKKNSLYLQMNSLRAEDTAVYYCAK | GEILPLYFDY | WGQGTLVTVSS |
| 1.26 | EVQLVESGGGLVQPGGSLRLSCAASGFTFS | SYSMY | WVRQAPGKGLEWVA | RIGQDGSEEYYVDSVKG | RFTISRDNAKNSLYLQMNSLRAGDTAVYYCAK | GEILPLYFDY | WGQGTLVTVSS |
| 1.27 | QVQLVESGGGLVQPGGSLRLSCAASGFTFS | SYRMY | WVRQAPGKGLEWVA | SIEQDGSEEYYVDSVKG | RFTISRDNAKKNSLYLQMNSLRAEDTAVYYCAK | GEILPLYFDY | WGQGTLVTVSS |
| 1.28 | EVQLVESGGGLVQPGGSLRLSCAASGFTFS | SYSMY | WVRQAPGKGLEWVA | SIDQDGSEEYYVDSVKG | RFTISRDNAKNSLYLQMNSLRAEDTAVYYCAK | GEILPLYFDY | WGQGTLVTVSS |
| 1.29 | EVQLVESGGGLVQPGGSLRLSCAASGFTFS | SYRMY | WVRQAPGKGLEWVA | SIEQDGSEEYYVDSVKG | RFTISRDNAKNSLYLQMNSLRAEDTAVYYCAK | GEILPLYFDY | WGQGTLVTVSS |
| 1.30 | EVQLVESGGGLVQPGGSLRLSCAASGFTFS | SYNMY | WVRQAPGKGLEWVA | NIEQDGSEEYYVDSVKG | RFTISRDNAKNSLYLQMNSLRAEDTAVYYCAK | GEILPLYFDY | WGQGTLVTVSS |
| 1.31 | QVQLVESGGGLVQPGGSLRLSCAASGFTFS | SYRMY | WVRQAPGKGLEWVA | GIEQDGSEEYYVDSVKG | RFTISRDNAKNSLYLQMNSLRAEDTAVYYCAK | GEILPLYFDY | WGQGTLVTVSS |
| 1.32 | QVQLVESGGGLVQPGGSLRLSCAASGFTFS | SYGMY | WVRQAPGKGLEWVA | GIEQDGSEEYYVDSVKG | RFTISRDNAKNSLYLQMNSLRAEDTAVYYCAK | GEILPLYFDY | WGQGTLVTVSS |
| 1.33 | QVQLVESGGGLVQPGGSLRLSCAASGFTFS | SYGMY | WVRQAPGKGLEWVA | GIEQDGSEEYYVDSVKG | RFTISRDNAKKNSLYLQMNSLRAEDTAVYYCAK | GEILPLYFDY | WGQGTLVTVSS |
| 1.34 | EVQLVESGGGLVQPGGSLRLSCAASGFTFS | SYGMY | WVRQAPGKGLEWVA | GIEQDGSEEYYVDSVKG | RFTISRDNAKNSLYLQMNSLRAEDTAVYYCAK | GEILPLYFDY | WGQGTLVTVSS |
| 1.35 | QVQLVESGGGLVQPGGSLRLSCAASGFTFS | SYRMY | WVRQAPGKGLEWVA | RIEQDGSEQYYVDSVKG | RFTISRDNAKNSLYLQMNSLRAEDTAVYYCAK | GEILPLYFDY | WGQGTLVTVSS |
| 1.36 | EVQLVESGGGLVQPGGSLRLSCAASGFTFS | SYGMY | WVRQAPGKGLEWVA | NIKQDGSEEYYVDSVKG | RFTISRDNAKNSLYLQMNSLRAEDTAVYYCAK | GEILPLYFDY | WGQGTLVTVSS |
| 1.37 | EVQLVESGGGLVQPGGSLRLSCAASGFTFS | SYGMY | WVRQAPGKGLEWVA | NIKQDGSEEYYVDSVKG | RFTISRDNAKNSLYLQMNSLRAEDTAVYYCAK | GEILPLYFDY | WGQGTLVAVSS |
| 1.38 | EVQLVESGGGLVQPGGSLRLSCAASGFTFS | SYGMY | WVRQAPGKGLEWVA | NIKQDGSEEYYVDSVKG | RFTISRDNAKNSLYLQMNSLRAEDTAVYYCAK | GEILPLYFDY | WGQGTLVTVSS |

Figure 1B

| Clone | Sequence |
|---|---|
| 1.39 | EVQLVESGGGLVQPGGSLRLSCAASGFTFS SYGMY WVRQAPGKGLEWVA NIKQDGSEEYYYVDSVKG RFTISRDNAKNSLYLQMNSLRAEDTAVYYCAK GEILPLYFDY WGQGTLVTVSS |
| 1.40 | EVQLVESGGGLVQPGGSLRLSCAASGFMFS SYGMY WVRQAPGKGLEWVA NIEQDGSEKYYYVDSVKG RFTISRDNAKKSLYLQMNSLRAEDTAVYYCAK GEILPLHFDY WGQGTLVTVSS |
| 1.41 | EVQLVESGGGLVKPGGSLRLSCAASGFMFS SYGMY WVRQAPGKGLEWVA NIEQDGSEKYYYVDSVKG RFTISRDNAKKSLYLQMNSLRAEDTAVYYCAK GEILPLHFDY WGQGTLVTVSS |
| 1.42 | EVQLVESGGGLVQPGGSLRLSCAASGFTFS SYGMY WVRQAPGKGLEWVA NIKQDGSEQYYYVDSVKG RFTISRDNAKKSLYLQMNSLRAEDTAVYYCAK GEILPLHFDY WGQGTLVTVSS |
| 1.43 | EVQLVESGGGLVQPGGSLRLSCAVSGFTFS SYSMY WVRQAPGKGLEWVA NIKQDGSEKYYYVDSVKG RFTISRDNAKNSLYLQMNSLRAEDTAVYYCAK GEILPLHFDY WGQGTLVTVSS |
| 1.44 | EVQLVESGGGLVQPGGSLRLSCAASGFTFS SYSMY WVRQAPGKGLEWVA NIKQDGSEKYYYVDSVKG RFTISRDNAKNSLFLQMNSLRAEDTAVYYCAK GEILPLYFDY WGQGTLVTVSS |
| 1.45 | EVQLVESGGGLVQRGGSLRLSCAASGFTFS SYWMY WVRQAPGKGLEWVA KINQDGSEKYYYVDSVKG RFTISRDNAKNSLYLQMNSLRAEDTAVYYCAK GEILPLQFDY WGQGTLVTVSS |
| 1.46 | EVQLVESGGGLVQRGGSLRLSCAASGFTFS SYWMY WVRQAPGKGLEWVA KINQDGSEKYYYVDSVKG RFTISRDNAKNSLYLQMNSLRAEDTAVYYCAK GEILPLQFDY WGQGTLVTVSS |
| 1.47 | QVQLVESGGGLVQRGGSLRLSCAASGFTFS SYWMY WVRQAPGKGLEWVA KINQDGSEKYYYVDSVKG RFTISRDNAKNSLYLQMNSLRAEDTAVYYCAK GEILPLQFDY WGQGTLVTVSS |
| 1.48 | QVQLVESGGGLVQPGGSLRLSCAASGFTFS SYWMY WVRQAPGKGLEWVA EIKQDGSEKYYYVDSVKG RFTISRDNAKNSLFLQMNSLRAEDTAVYYCAK GEILPLYFDH WGQGTLVTVSSP |
| 1.49 | EVQLVESGGGLVQPGGSLRLSCAASGFTFS SYQMY WVRQAPGKGLEWVA EIKQDGSEKYYYVDSVKG RFTISRDNAKNSLFLQMNSLRAEDTAVYYCAK GEILPLYFDH WGQGTLVTVSS |
| 1.50 | EVQLVESGGGLVQPGGSLRLSCAASGFTFS SYSMI WVRQAPGKGLEWVA DIKQDGSEKYYYVDSVKG RFTISRDNAKNSLYLQMNSLRAEDTAVYYCAK GEVLPLYFDY WGQGTLVTVSS |
| 1.51 | EVQLVESGGGLVQPGGSLRLSCAASGFTFS SYNMY WVRQAPGKGLEWVA DIKQDGSEKYYYVDSVKG RFTISRDNAKNSLYLQMNSLRAEDTAVYYCAK GEVLPLYFDY WGQGTLVTVSS |
| 1.52 | EVQLVESGGGLVQPGGSLRLSCAASGFTFS SYNMY WVRQAPGKGLEWVA EIDDDGSEKYYYVDSVKG RFTISRDNAKNSLFLQMNSLRAEDTAVYYCAK GEILPLYFDH WGQGTLVTVSS |
| 1.53 | QVQLVESGGGLVQPGGSLRLSCAASGFTFS SYRMY WVRQAPGKGLEWVA SIEQDGSEKYYYVDSVKG RFTISRDNAKNSLFLQMSSLRAEDSAVYYCAK GEILPLYFDY WGQGTLVTVSS |
| 1.54 | QVQLVESGGGLVQPGGSLRLSCAVSGFTFS SYEMY WVRQAPGKGLEWVA GIEQDGSEKYYYVDSVKG RFTISRDNAKNLLYLQMNSLRAVEDTAMYYCAK GEILPLYFDY RGQGTLVTVSS |
| 1.55 | EVQLVESGGGLVQPGGSLRLSCAVSGFTFS SYRMY WVRQAPGKGLEWVA NIKQDGSEKYYYVDSVKG RFTISRDNAKRSLFLQMNSLRAEDTAMYYCAK GEILPLYFDY RGQGTLVTVSS |
| 1.56 | EVQLVESGGGLVQPGGSLRLSCAVSGFTFS SYEMY WVRQAPGKGLEWVA SINQDGSEKYYYVDSVKG RFTISRDNARNSLYLQMISLRAEDTAMYYCAK GEILPLHFDY RGQGTLVTVSS |
| 1.57 | QVQLVESGGGLVQPGGSLRLSCTASGFTFS SYWMY WVRQAPGKGLEWVA SINQDGSEKYYYVDSVKG RFTISRDNARNSLYLQMISLRAEDTAVYYCAK GEILPLHFDY WGQGTLVTVSS |
| 1.58 | QVQLVESGGGMVQPGGSLRLSCTASGFTFS SYWMY WVRQAPGKGLEWVA KIKQDGTEKYYYVDSVKG RFTISRDNAKNSLYLQMNSLRAEDTAVYYCAK GEILPHYFDY WGQGTLVTVSS |
| 1.59 | QVQLQESGGDWVQPGGSLRLSCGAASGFTFS SYWMY WVRQAPGKGLEWVA NIKQDGSEEYYYVDSVKG RFTISRDNARNSLYLQMNSLRAEDTAVYYCAK GEILPLYFDH WGQGTLVTVSS |
| 1.60 | EVQLVESGGGLVQPGGSLRLCTASGFTFS NYSMY WVRQAPGKGLEWVA KIEQDGSEKYYYVDSVKG RFTISRDNARNSLYLQMI SLRAEDTAVYYCAK GEILPLYFDH WGQGTLVTVSS |
| 1.61 | EVQLVESGGGLVQPGGSLRLSCTASGFTFS NYSMY WVRQAPGKGLEWVA NIKQDGSEEYYYVDSVKG RFTISRDNARNSLYLQMNSLRAEDTAVYYCAK GEILPLYFDY WGQGTLVTVSS |
| 1.62 | QVQLVESGGGMVQPGGSLRLSCAVSGFTFS SYRMY WVRQAPGKGLEWVA EIEQDGSEQYYYVDSVKG RFTISRDNAKNSLYLQMNSLRAEDTAVYYCAK GEILPLYFDY WGQGTLVTVSS |
| 1.63 | EVQLVESGGGLVQPGGSLRLSCAASGFTFS SYGMY WVRQAPGKGLEWVA EINQDGSEKYYYVDSVKG RFTISRDNAKNSLYLQMNSLRAEDTAVYYCAK GEILPLYFDY WGQGTLVTVSS |
| 1.64 | EVQLVESGGGLVQPGGSLRLSCAASGFTFS SYGMG WVRQAPGKGLEWVA KIEQDGSVEYYVDSVKG RFTISRDNAKKSLFLQMNSLRAEDTAVYYCAK GEILPLYFDH WGQGTLVTVSS |
| 1.65 | EVQLVESGGGLVQPGGSLRLSCAASGFTFS SYGMY WVRQAPGKGLEWVA GIKQDGSEQYYYVDSVKG RFTISRDNAKKSLYLQMNSLRAEDTAVYYCAK GEILPLYFDY WGQGTLVTVSS |
| 1.66 | EVQLVESGGGLVQPGGSLRLSCAASGFTFS SYGMY WVRQAPGKGLEWVA EIKQDGSEQYYYVDSVKG RFTISRDNAKNSLFLQMNSLRAEDTAVYYCAK GEILPLYFDY WGQGTLVTVSS |
| 1.67 | EVQLVESGGGLVQPGGSLRLSCAASGFTFS SYSMY WVRQAPGKGLEWVA GIEQDGSEKYYYVDSVKG RFTISRDNAKNSLFLQMNSLRAEDTAVYYCAK GEILPLYFDY WGQGTLVTVSS |
| 1.68 | EVQLVESGGGMVQPGGSLRLSCAASGFTFS SYRMY WVRQAPGKGLEWVA EIEQDGSEQYYYVDSVKG RFTISRDNAKNSLYLQMNSLRAEDTAVYYCAK GEILPLYFDY WGQGTLVTVSS |
| 1.69 | EVQLVESGGGLVQPGGSLRLSCAASGFTFS SYGMY WVRQAPGKGLEWVA EINQDGSEKYYYVDSVKG RFTISRDNAKNSLYLQMNSLRAEDTAVYYCAK GEILPLYFDY WGQGTLVTVSS |

Figure 2A

| Clone | FR1 | CR1 | FR2 | CDR2 | FR3 | CDR3 | FR4 |
|---|---|---|---|---|---|---|---|
| 2.1 | QVQLVESGGGLVQPGGSLRLSCAASGFTFS | SYGMG | WVRQAPGKGLEWVA | KIKQDGSEKDYVDSVKG | RFTISRDNAKKSLFLQMNSLRAEDTAVYYCAR | ESIFGIPED | WGQGTLVTVSS |
| 2.2 | EVQLVESGGGLVQPGGSLRLSCAASGFTFS | AYWMG | WVRQAPGKGLEWVA | KIKQDGSEKDYVDSVKG | RFTISRDNAKNSLFLQMNSLRAEDTAVYYCAR | ESIFGIPED | WGQGTLVTVSS |
| 2.3 | QVQLVESGGGLVQPGGSLRLSCTTSGFTFS | AYWMG | WVRQAPGKGLEWVA | KIKQDGSEKDYVDSVKG | RFTISRDNAKNSLYLQMNSLRAEDTAVYYCAR | ESIFGTPED | WGQGTLVTVSS |

Figure 2B

```
2.4  QVQLVESGGGLVQPGGSLRLSCAASGFTFS SYWMS WVRQAPGKGLEWVA KIKQDGSEKDYVDSVKG RFTISRDNAKNSLFLQMNSLRAEDTAVYYCAR ESIFGIPED WGQGTLVTVSS
2.5  QVQLVESGGGLVQPGGSLRLSCAASGFTFS GYWMG WVRQAPSKGLEWVA KIKQDGSEKDYVDSVKG RFTISRDNAKNSLFLQMNSLRAEDTAVYYCAR ESIFGIPED WGQGTLVTVSS
2.6  EVQLVESGGGLVQPGGSLRLSCAASGFTFS AYWMG WVRQAPGRGLEWVA KIKQDGSEKDYVDSVKG RFTISRDNAKKALFLQMNSLRAEDTAVYYCAR ESIFGTPED WGQGTLVTVSS
2.7  EVQLVESGGGLVQPGGSLRLSCAASGFTFS SYWMS WVRQAPGKGLEWVA NIKQDGSEKDYVDSVKG RFTISRDNAKNSLFLQMNSLRAEDTAVYYCAR ESIFGIPED WGQGTLVTVSS
2.8  EVQLVESGGGLVQPGGSLRLSCAASGFTFS GYWMG WVRQAPGRGLEWVA KIKQDGSEKDYVDSVKG RFTISRDNAKNSLFLQMNSLRAEDTAVYYCAR ESIFGTPED WGQGTLVTVSS
2.9  EVQLVESGGGLVQPGGSLRLSCAASGFTFS AYWMG WVRQAFGRGLEWVA KIKQDGSEKDYVDSVKG RFTISRDNAKNSLFLQMNSLRAEDTAVYYCAR ESIFGIPED WGQGTLVTVSS
```

Figure 3

```
Clone  FR1                             CDR1   FR2              CDR2              FR3                                         CDR3                  FR4
3.1   QVQLVQSGAEVKKPGASVKVSCKASGYTFT  GYYMH  WVRQAPGQGLEWMG   WINPNSGGTNYAQKFQG RVTMTRDTSISTAYMELSRLRSDDTAVYYCAS  MDRDYYDTSGYFGWFDS  WGQGTLVTVSS
3.2   QVQLVQSGAEVKKPGASVKVSCKASGYTFT  AYYIN  WVRQAPGQGLEWMG   SIKPNTGATKYAQKFQG RVTMTRDTSISTAYMELSRLRSDDTAVYYCAS  LDRDTWYPHSYAGWFDA  WGQGTLVTVSS
3.3   QVQLVQSGAEVKKPGASVKVSCKASGYTFT  DYYLH  WVRQAPGQGLEWMG   WINPNTGTTKYAREFEG RVTMTRDTSISTAYMELSRLRSDDTAVYYCAS  MDRDYYDTSGYFGWFDS  WGQGTLVTVSS
3.4   QVQLVQSGAEVKKPGASVKVSCKASGYTFT  DYYLH  WVRQAPGQGLEWMG   WINPNTGTTKYAREFEG RVTMTRDTSISTAYMELSRLRSDDTAVYYCAS  MDRDYYDTSGYFGWFDS  WGQGTLVTVSS
3.5   QVQLVQSGAEVKKPGASVKVSCKASGYTFT  DYYLH  WVRQAPGQGLEWMG   WINPNTGTTKYAREFEG RVTMTRDTSISTAYMELSRLRSDDTAVYYCAS  MDRDWRSPNDYFGWFDS  WGQGTLVTVSS
3.6   QVQLVQSGAEVKKPGASVKVSCKASGYTFT  DYYLH  WVRQAPGQGLEWMG   WINPNTGTTKYAREFEG RVTITRDTSISTAIMELSRLRSDDTAVYYCAS  LDRDWRSPNDYGWFDS   WGQGTLVTVSS
3.7   QVQLVQSGAEVKKPGASVKVSCRASGYTFT  DYYLH  WVRQAPGQGLEWMG   WINPNTGTTKYAREFEG RVTITRDTSISTAIMELSRLRSDDTAVYYCAS  LDRDWRSPNDYFGWFDS  WGQGTLVTVSS
3.8   QVQLVQSGAEVKKPGASVKVSCAASGYTLF  DYYLH  WVRQAPGQGLEWMG   WINPNTGTTKYAREFEG RVTMTRDTSISTAIMELSGLRSDDTAVYYCAS  LDRDWRSPNDYFGWFDS  WGQGTLVTVSS
3.9   QVQLVQSGAEVKKPGASVKVSCRASGYNFD  AYHIN  WVRQAPGQGLEWMG   SIKPNSGATKYAQKFQG RVTMTRDTSISTAIMELSRLRSDDTAVYYCAS  MDRDYYDTSGYFGWFDS  WGQGTLVTVSS
3.10  QVQLVQSGAEVKKPGASVKVSCRASGYNFD  AYHIN  WVRQAPGQGLEWMG   SIKPNSGATKYAQKFQG RVTITRDTSISTAIMELSRLRSDDTAVYYCAS  MDRDQFYFGDYFGWFDS  WGQGTLVTVSS
3.11  QVQLVQSGAEVKKPGASVKVSCRASGYNFD  AYHIN  WVRQAPGQGLEWMG   SIKPNSGATKYAQKFQG RVTITRDTSISTAIMELSRLRSDDTAVYYCAS  LDRDTWYPHSYFGWFDS  WGQGTLVTVSS
3.12  QVQLVQSGAEVKKPGASVKVSCRASGYNFD  AYHIN  WVRQAPGQGLEWMG   SIKPNSGATKYAQKFQG RVTITRDTSISTAIMELSRLRSDDTAVYYCAS  MDRDTWYPHSYFGWFDS  WGQGTLVTVSS
3.13  QVQLVQSGAEVKKPGASVKVSCRASGYNFD  AYHIN  WVRQAPGQGLEWMG   SIKPNSGATKYAQKFQG RVTITRDTSISTAIMELSRLRSDDTAVYYCAS  LDRDTWYPHSAGWFDS   WGQGTLVTVSS
3.14  QVQLVQSGAEVKKPGASVKVSCRASGYNSD  AYYIN  WVRQAFGQGLEWMG   SIKPNSGATKYAQKFQG RVTITRDTSISTAIMELSRLRSDDTAVYYCAS  LDRDTWYPHSYFGWFDS  WGQGTLVTVSS
```

Figure 4

```
Clone  FR1                                                CDR1  FR2              CDR2              FR3                                                      CDR3           FR4
4.1   QVQLVESGGGLVQPGGSLRLSCAASGFTFS SYWMN WVRQAPGKGLEWVA  TIKQDGSEKYYVDSVKG RFTISRDNATNSLFLQMNSLRAEDTAVYYCAR GDTIFDGAFDI WGQGTMVTVSS
```

Figure 5

```
Clone  FR1                                                 CDR1  FR2             CDR2               FR3                                                   CDR3     FR4
5.1  EVQLVESGGGLVQPGGSLRLSCAASGFTFS SYWMS WVRQAPGKGLEWVA  NIKQDGSEKYYVDSVKG RFTISRDNAKNSLYLQMNSLRAEDTAVYYCAH GQWPFFDY WGQGTMVTVSS
```

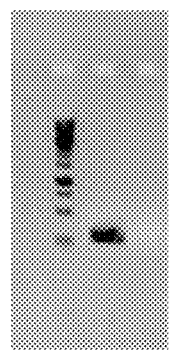
Figure 6A
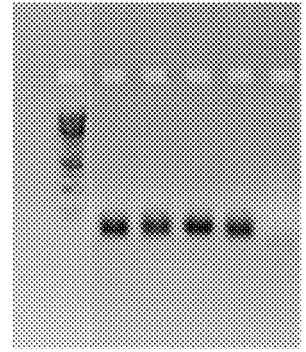
Figure 6B
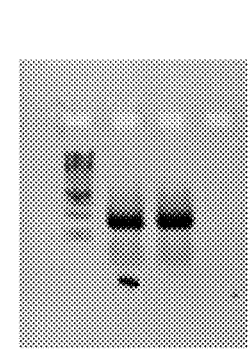
Figure 6C
Figure 7
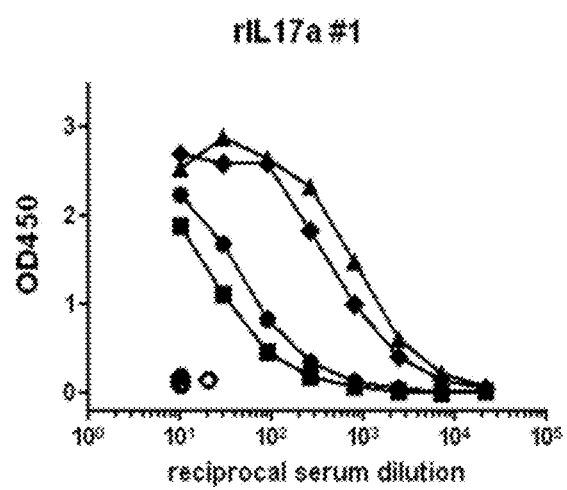
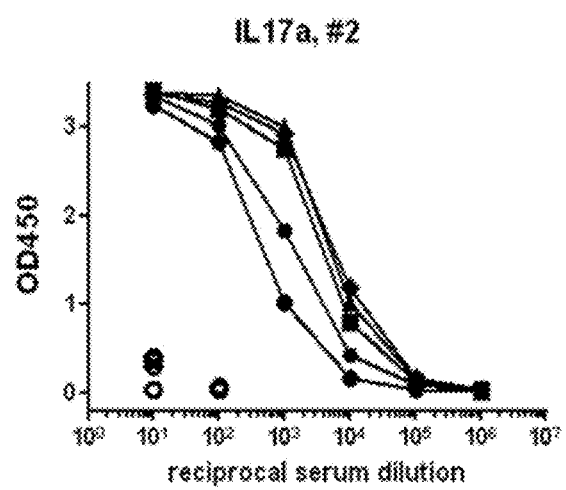

Figure 8A

|   | 1 | 2 | 3 | 4 | 5 | 6 | 7 | 8 | 9 | 10 | 11 | 12 |
|---|---|---|---|---|---|---|---|---|---|---|---|---|
| A | 0.65 | 0.085 | 0.641 | 0.562 | 0.224 | 0.093 | 1.286 | 0.187 | 0.108 | 2.649 | 0.507 | 0.282 |
| B | 0.127 | 0.057 | 0.045 | 0.395 | 0.428 | 0.097 | 0.513 | 0.214 | 1.527 | 0.486 | 0.943 | 2.302 |
| C | 0.056 | 0.043 | 0.292 | 0.108 | 0.073 | 0.312 | 0.06 | 0.355 | 0.463 | 0.501 | 0.234 | 0.422 |
| D | 0.86 | 0.106 | 0.397 | 0.984 | 0.341 | 0.621 | 0.07 | 0.276 | 0.376 | 0.061 | 0.617 | 0.504 |
| E | 0.132 | 0.138 | 0.331 | 0.376 | 0.697 | 0.37 | 2.058 | 0.055 | 1.684 | 1.394 | 0.365 | 0.29 |
| F | 0.526 | 0.039 | 0.049 | 0.585 | 0.485 | 0.289 | 0.273 | 0.644 | 0.047 | 1.617 | 0.073 |  |
| G | 0.676 | 0.584 | 0.301 | 0.486 | 0.232 | 0.058 | 0.453 | 0.569 | 0.071 | 0.524 | 0.333 |  |
| H | 1.138 | 0.114 | 0.537 | 1.196 | 0.455 | 0.522 | 0.47 | 0.467 | 0.129 | 0.641 | 0.11 | 0.043 |

Figure 8B

|   | 1 | 2 | 3 | 4 | 5 | 6 | 7 | 8 | 9 | 10 | 11 | 12 |
|---|---|---|---|---|---|---|---|---|---|---|---|---|
| A | 0.037 | 0.036 | 0.039 | 0.571 | 0.04 | 0.037 | 0.041 | 0.039 | 0.043 | 0.041 | 0.039 | 0.047 |
| B | 0.042 | 0.042 | 0.043 | 0.043 | 0.043 | 0.043 | 0.045 | 0.045 | 0.067 | 0.045 | 0.049 | 0.049 |
| C | 0.046 | 0.038 | 0.093 | 0.038 | 0.037 | 0.037 | 0.039 | 0.038 | 0.038 | 0.038 | 0.038 | 0.037 |
| D | 0.039 | 0.039 | 0.039 | 0.042 | 0.04 | 0.04 | 0.045 | 0.039 | 0.04 | 0.039 | 0.039 | 0.04 |
| E | 0.04 | 0.04 | 0.04 | 0.041 | 0.044 | 0.041 | 0.041 | 0.041 | 0.043 | 0.041 | 0.042 | 0.042 |
| F | 0.048 | 0.049 | 0.046 | 0.04 | 0.038 | 0.054 | 0.038 | 0.035 | 0.037 | 0.041 | 0.042 | 0.051 |
| G | 0.059 | 0.037 | 0.029 | 0.039 | 0.034 | 0.033 | 0.032 | 0.034 | 0.027 | 0.028 | 0.03 | 0.027 |
| H | 0.955 | 0.043 | 0.04 | 0.043 | 0.041 | 0.039 | 0.039 | 0.039 | 0.044 | 0.04 | 0.04 | 0.045 |

Figure 15A. VH 1.10.1
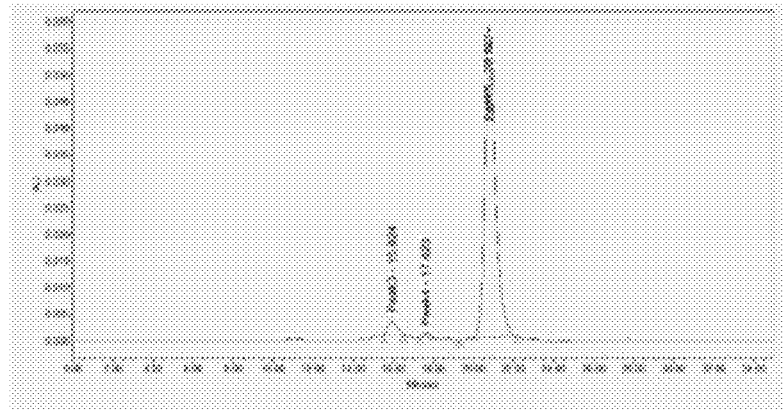
Figure 15B. VH 1.17.1
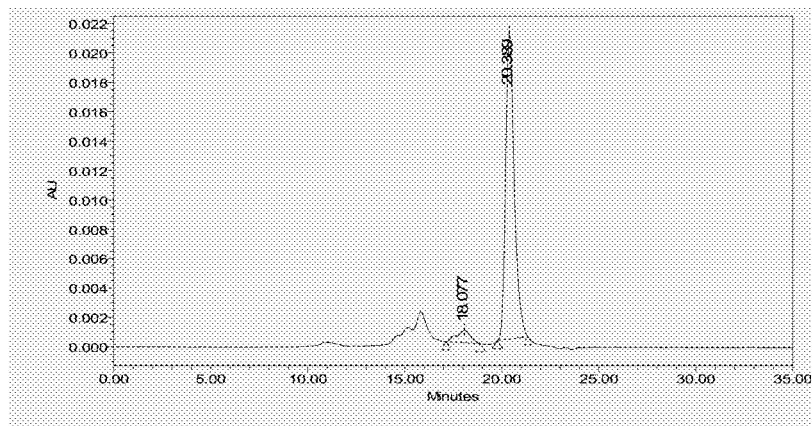
Figure 15C. VH 1.3.1
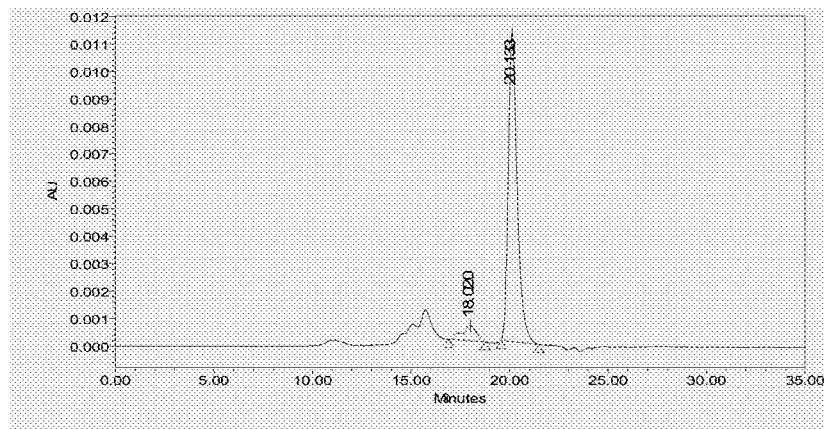

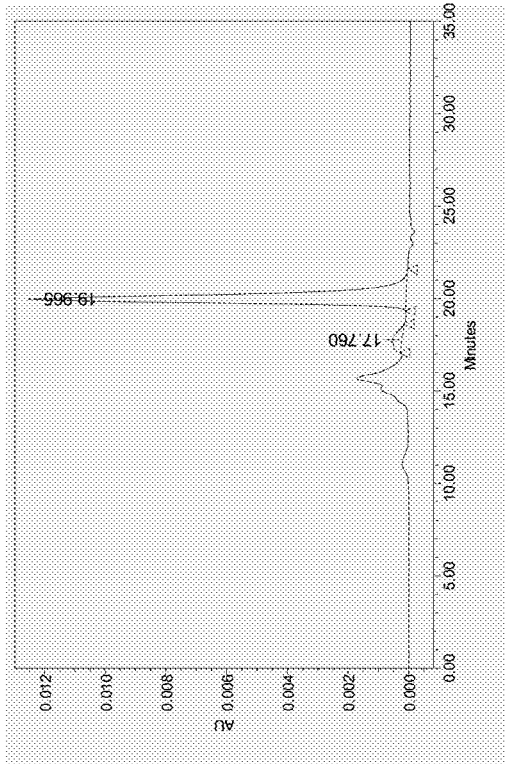
Figure 15E. VH 186D2
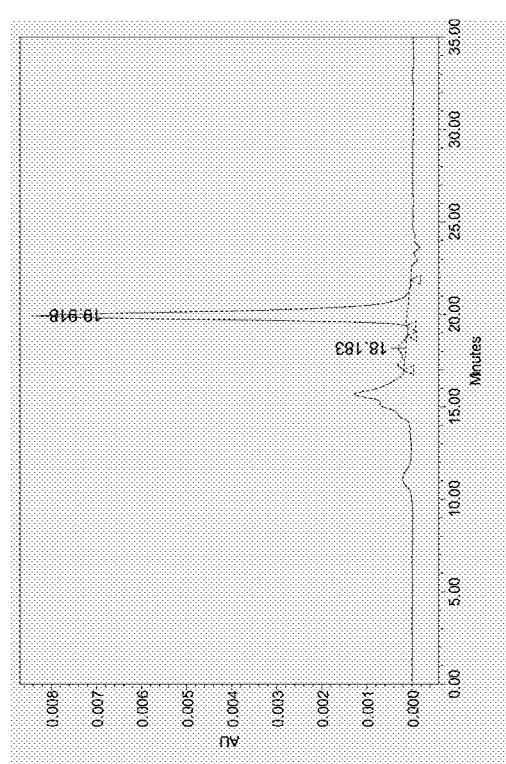
Figure 15G. VH 1.22.1
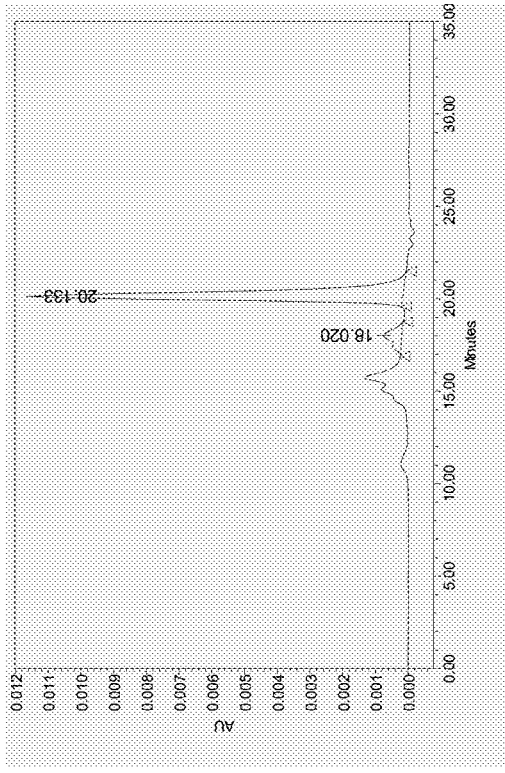
Figure 15D. VH 1.3.1
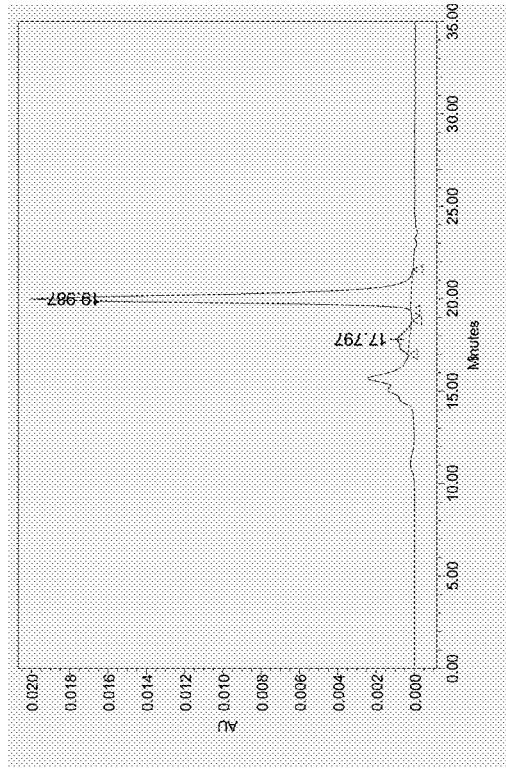
Figure 15F. VH 1.16.1

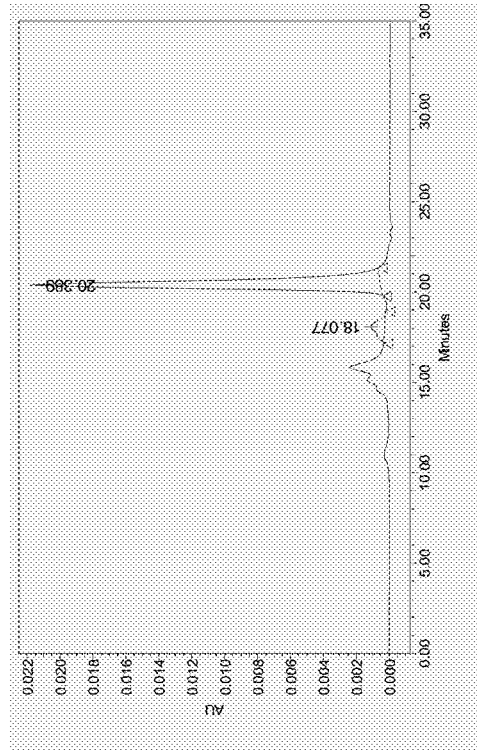
Figure 15I. VH 1.17.1
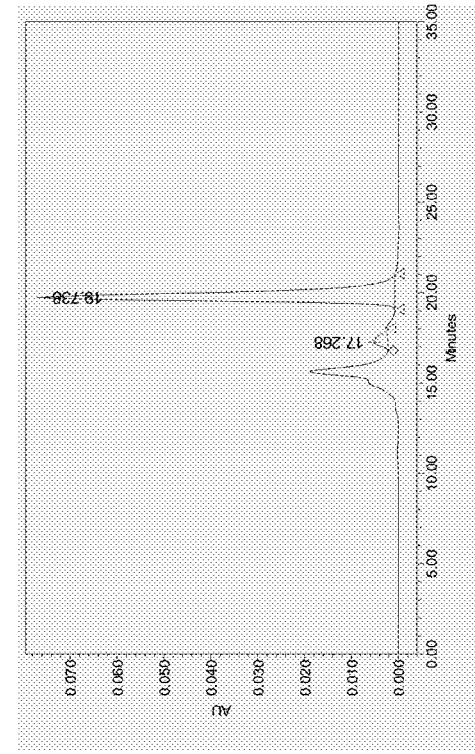
Figure 15K. VH 1.20.1
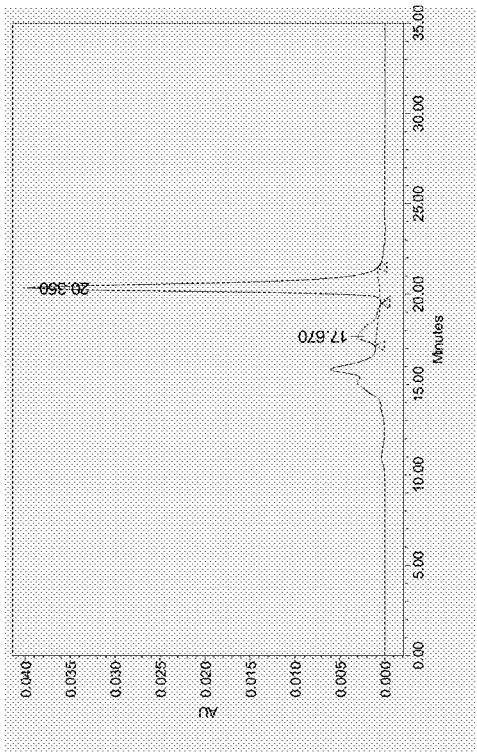
Figure 15H. VH 1.18.1
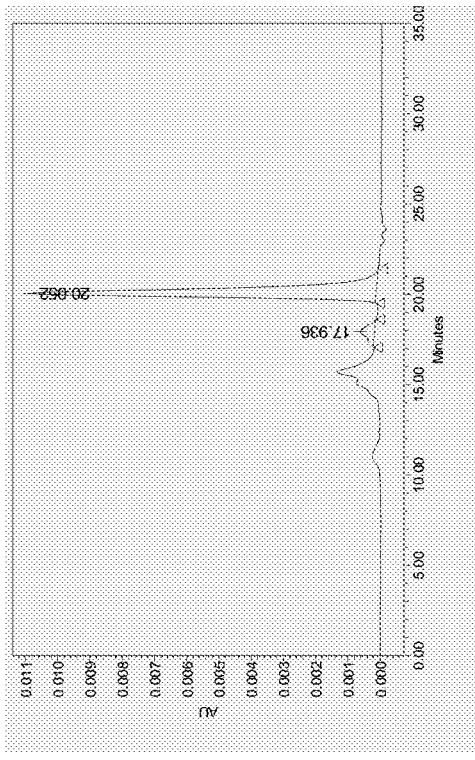
Figure 15J. VH 1.21.1

Figure 16A. VH 1.3.2 (HIS) (630pM)   VH 1.3.3 No HIS (680pM)
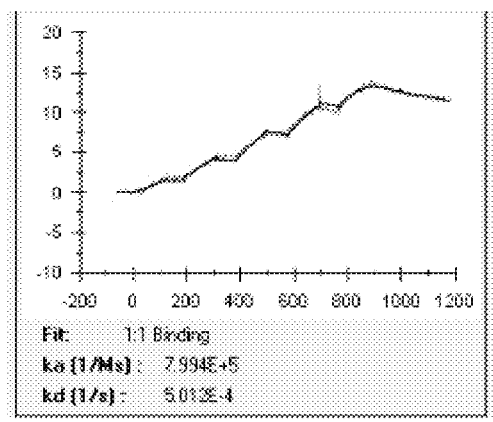 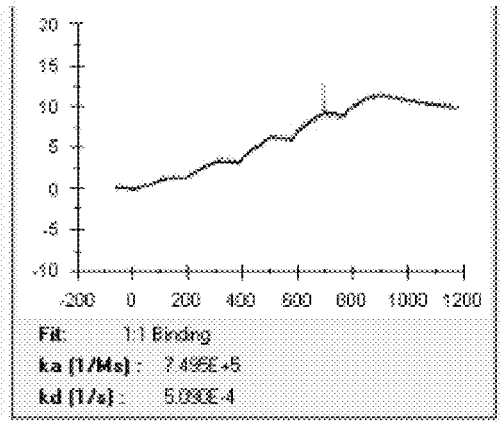
Figure 16B. VH 1.2.2 (+HIS) (550pM)   VH 1.2.3 No HIS (620pM)
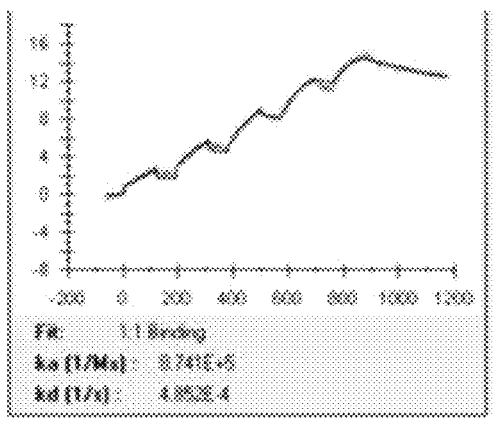 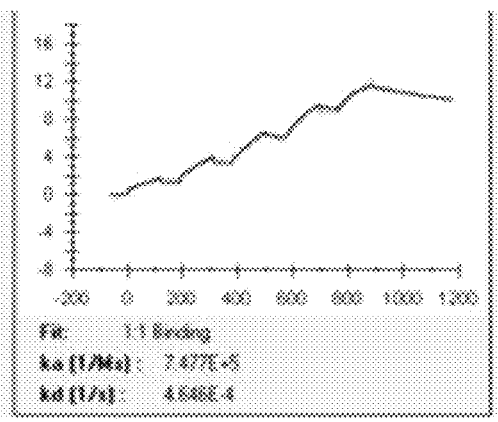
Figure 16C
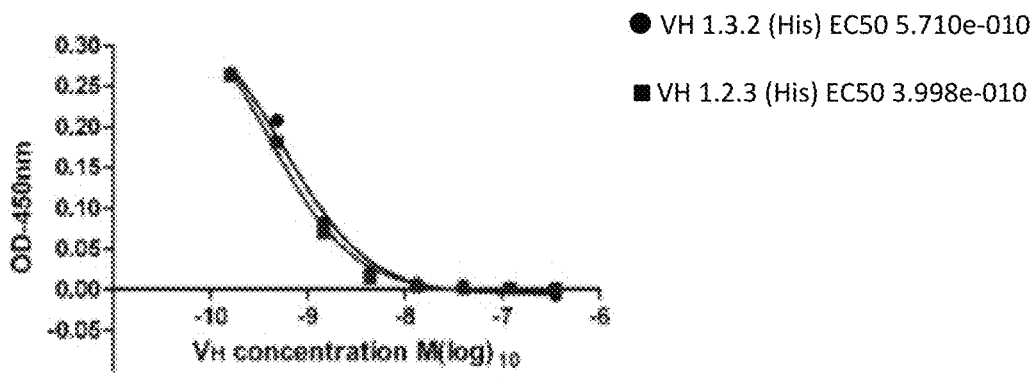
● VH 1.3.2 (His) EC50 5.710e-010
■ VH 1.2.3 (His) EC50 3.998e-010

KD- 2.12E-10

KD- 5.7E-10

KD- 4.5E-11

KD- 2.0E-11

|  | 1 | 2 | 3 | 4 |
|---|---|---|---|---|
| EC50 | 7.870e-010 | 1.032e-008 | 1.071e-009 | 9.234e-010 |

IL-17A BINDING PROTEINS

RELATED APPLICATIONS AND INCORPORATION BY REFERENCE

This application is a continuation of U.S. application Ser. No. 15/541,889 filed Jul. 6, 2017, now U.S. Pat. No. 10,654,924, which is a § 371 National Phase of PCT/GB2016/050070 filed Jan. 12, 2016 and which claims the benefit of priority to GB 1500463.3 filed Jan. 12, 2015.

The foregoing applications, and all documents cited therein or during the prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Oct. 17, 2017, is named 25966_105003_SL.txt and is 216,991 bytes in size.

FIELD OF THE INVENTION

The invention relates to IL-17A binding molecules, and the use of such binding molecule in the treatment of disease.

INTRODUCTION

Psoriasis is a chronic relapsing and remitting inflammatory skin disease affecting 2-3% of the world's population (~125 m sufferers) that causes significant morbidity and decreased quality of life, largely due to clinical flare-ups and disfiguring lesions in visible areas of the skin, systemic manifestations and drug-related side effects. The common form of the disease, termed 'plaque psoriasis vulgaris', is observed in more than 80% of patients and is characterized by erythematous scaly plaques (typically on elbows, knees, scalp and buttocks) which can vary in size from minimal to the involvement of the entire skin surface.

Depending on the degree of body surface area (BSA) involvement, psoriasis can be categorised into mild (<3% BSA involvement), moderate (3-10% BSA) and severe (>10% BSA) disease. Topical agents such as corticosteroids, vitamin D derivatives, coal tar and topical retinoids are the cornerstone of the initial management of psoriasis and are an important part of the treatment ladder applied to patients across the spectrum of disease severity. Patients diagnosed with mild-to-moderate disease are typically prescribed topical agents as monotherapy. Patients with severe disease are typically prescribed topical agents as an adjunct to phototherapy or systemic (small molecule) therapies such as methotrexate, cyclosporine or oral retinoids. The treatment regime for moderate-to-severe psoriasis also includes antibody-based therapies.

The therapeutic products currently on the market for the treatment of psoriasis offer varying degrees of symptomatic relief and reduced relapse rates but none are currently considered curative and they therefore require chronic administration. While many pre-existing topical agents can be effective for short periods of time, due to treatment-limiting toxicity most are restricted to short term use. This means that patients need routine monitoring for side effects and regular cycling onto new treatment protocols.

Patients with severe disease are typically prescribed topical agents as an adjunct to phototherapy or systemic (small molecule) therapies such as methotrexate, cyclosporine or oral retinoids (Nast et al., Arch Dermatol Res (2007) 299: 111-138). Phototherapy can be effective, but is inconvenient and associated with a significant risk of skin cancer. Small molecule systemic therapies are associated with increased cardiovascular risk; renal dysfunction, leucopenia and thrombocytopenia. For example, methotrexate may cause a neutropenia and liver damage and is contraindicated for males and females of reproductive age without due precaution. Cyclosporine is a potent immunosuppressant, which has potential adverse effects on the kidneys and blood pressure. Acitretin is an oral retinoid that has a range of side effects, and is also contraindicated for females of reproductive age without due precaution (Nast et al., Arch Dermatol Res (2007) 299:111-138).

The treatment regimen for moderate-to-severe psoriasis also includes antibody-based therapies. Approved treatments include adalimumab (Humira®), a humanized monoclonal antibody with activity against TNF-alpha($\alpha$), the TNF-$\alpha$ inhibitor etanercept (Enbrel®), the TNF-$\alpha$ inhibitor infliximab (Remicade®) and most recently ustekinumab (Stelara®), a human mAb that targets the common p40 subunit of IL12 and IL23, thereby blocking the signalling of both cytokines.

In recent years the importance of the Th17 pathway has become well validated in psoriasis and several monoclonal antibodies (mAbs) targeting IL17 have shown the significant importance of modulating these cytokines and influencing psoriasis. IL-17, a T-cell derived cytokine, is a target for topical therapy in skin. While psoriasis may have a systemic component in some patients, the disease is primarily one of the skin. IL-17 secreted by Th17 cells acts on epidermal keratinocytes, via IL-17R complexes present on these cells, to initiate a feedback loop of keratinocyte hyper-proliferation and on-going inflammation, thereby generating the psoriatic plaque. It is believed that the primary element of pathological activity is locally in the skin, and therefore inhibition of the IL-17/IL-17R interaction is the best validated target for topical therapy. This is in contrast to other validated Th17 targets, such as IL-23, where a significant phase of activity is in regional lymph nodes.

Several other monoclonal antibodies agents in development have been shown to markedly reduce disease severity in patients with moderate-to-severe plaque psoriasis. These agents include ixekizumab (Eli Lilly) and secukinumab (Novartis), both of which target IL-17A, and brodalumab (Amgen) that binds to and inhibits signalling of IL-17RA and therefore would be expected to block IL1-7 family members that utilize this receptor, including IL-17A, IL-17F, IL-17A/F and possibly IL-17E. The preliminary clinical results for IL-17 inhibitors indicate the importance of IL-17A in psoriasis pathophysiology. In independent clinical trials programmes up to and including substantial confirmatory Phase III trials, all three agents have been reported to reduce disease severity markedly in patients with moderate-to-severe plaque psoriasis. Secukinumab has been shown to down-regulate cytokines, chemokines and proteins associated with inflammatory responses in lesional skin. In summary, inhibition of IL-17A allows selective intervention to address the dysregulated immune system in plaque (Girolomoni et al., The British Journal of Dermatology. 2012a; 167(4):717-724, Huebner et al., Gut 2012; 61: 1693-700, Papp et al., New Engl J Med 2012; 366: 1181-9, Mease et al., N Engl J Med. 2014 12; 370(24):2295-306 and Langley et al., New Engl J Med 2014; 371: 326-38).

The therapeutic products currently on the market for the treatment of psoriasis offer varying degrees of symptomatic relief and reduced relapse rates but none are currently considered curative and chronic administration is therefore required. While many pre-existing topical agents can be effective for short periods of time, due to treatment-limiting toxicity most are restricted to short term use. This means that patients need routine monitoring for side effects and regular cycling onto new treatment protocols. Phototherapy can be effective but is inconvenient and associated with a significant risk of skin cancer and many conventional (small molecule) systemic therapies are associated with increased cardiovascular risk; renal dysfunction, leucopenia and thrombocytopenia. Systemic biologics have transformed treatment of moderate-to-severe psoriasis but, as with any immunosuppressive regime, chronic use can have significant side-effects such as increased risk of infections or malignancies.

None of the current therapeutic interventions are curative, and therefore all require chronic use. Therapeutic regimens have to take account of this by adopting strategies to reduce toxicity, including rotational or sequential therapies, drug holidays, and combination therapy. Importantly, for some drugs there is an absolute lifetime limit on the exposure that any one patient can safely receive.

Thus, there is a need for new highly effective and safe therapy options for both topical and systemic use. In particular, there is therefore a clear unmet need for new topical drugs with the efficacy of a biological in patients with severe disease, where a long-term maintenance therapy could keep symptoms under control following systemic mAb use and therefore improve the safety profile for chronic use. Similarly, those patients who are not treated systemically because their disease is not severe enough, would greatly benefit from the topical application of a drug with biological efficacy.

Antibodies have proven themselves to be extremely effective therapeutic agents for treating a large number of different disease indications. In particular, there has been a clear trend towards development of fully human antibodies for therapeutic use over the various alternatives. Due to their size and other physical properties, however, it is currently the case that monoclonal antibodies have to be administered either intravenously (iv) or subcutaneously (sc) and therefore have a high systemic exposure. Thus, although the antibodies can be highly effective, their route of delivery can often be suboptimal, resulting either in antibody binding to target antigen at non-disease locations (potentially compromising the healthy function of normal, non-disease tissue) or resulting in suboptimal PK/PD characteristics. Either outcome may result in a loss of efficacy and/or a compromised safety profile by virtue of the suboptimal route of administration.

Due to their size and other favourable biophysical characteristics, antibody fragments are potentially attractive candidates for alternative routes of administration. In particular, $V_H$ fragments are the smallest, most robust portion of an immunoglobulin molecule that retain target specificity and potency. It would therefore be advantageous to deliver $V_H$ domains topically on the skin so that they penetrate to therapeutically beneficial locations within the skin to treat disease locally. Any $V_H$ that might enter the bloodstream will be cleared rapidly and therefore have little or no systemic exposure thereby minimising potential mechanism-related systemic toxicity.

The invention is aimed at providing a safe and effective therapy of conditions associated with the IL-17 pathway, in particular for topical treatment of psoriasis.

SUMMARY OF THE INVENTION

In a first aspect, the invention relates to a binding molecule capable of binding human IL-17A comprising a human heavy chain variable immunoglobulin domain ($V_H$) comprising a CDR3 sequence comprising SEQ ID NO. 3 or a sequence with at least 70%, at least 80%, at least 90% or at least 95% homology to SEQ ID NO. 3.

In a second aspect, the invention relates to a binding molecule comprising at least one immunoglobulin single domain antibody directed against IL-17A wherein said domain is a human heavy chain variable immunoglobulin domain ($V_H$) and wherein said IL-17A binding molecule comprises at least one antigen binding site comprising a CDR3 sequence having SEQ ID NO. 3 or a sequence with at least 70%, at least 80%, at least 90% or at least 95% homology to SEQ ID NO. 3.

In a third aspect, the invention relates to a binding molecule capable of binding human IL-17A comprising a human heavy chain variable immunoglobulin domain ($V_H$) comprising a CDR3 sequence comprising SEQ ID NO. 251 or a sequence with at least 70%, at least 80%, at least 90% or at least 95% homology thereto.

In another aspect, the invention relates to a binding molecule comprising at least one immunoglobulin single domain antibody directed against IL-17 wherein said domain is a human heavy chain variable immunoglobulin domain ($V_H$) and wherein said IL-17 binding molecule comprises at least one antigen binding site comprising a CDR3 sequence having SEQ ID NO. 251 or a sequence with at least 70%, at least 80%, at least 90%, at least 95% homology to SEQ ID NO. 251.

In another aspect, the invention relates to a binding molecule capable of binding human IL-17A comprising a $V_H$ domain comprising a CDR3 sequence comprising SEQ ID NO. 285 or a sequence with at least 70%, at least 80%, at least 90% or at least 95% homology to SEQ ID NO. 285.

In another aspect, the invention relates to a binding molecule comprising at least one immunoglobulin single domain antibody directed against IL-17 wherein said domain is a human $V_H$ domain and wherein said IL-17A binding molecule comprises at least one antigen binding site comprising a CDR3 sequence having SEQ ID NO. 287 or a sequence with at least 60%, at least 70%, at least 80%, at least 90%, at least 95% homology to SEQ ID NO.287.

In another aspect, the invention relates to a binding molecule capable of binding human IL-17A comprising a human $V_H$ domain comprising a CDR3 sequence comprising SEQ ID NO. 343 or a sequence with at least 70%, at least 80%, at least 90% or at least 95% homology to SEQ ID NO. 343.

In another aspect, the invention relates to a binding molecule comprising at least one immunoglobulin single domain antibody directed against IL-17A wherein said domain is a human $V_H$ domain and wherein said IL-17A binding molecule comprises at least one antigen binding site comprising a CDR3 sequence having SEQ ID NO. 343 or a sequence with at least 70%, at least 80%, at least 90%, at least 95% to SEQ ID NO. 343.

In another aspect, the invention relates to a binding molecule capable of binding human IL-17A comprising a human $V_H$ domain comprising a CDR3 sequence comprising SEQ ID NO. 347 or a sequence with at least 70%, at least 80%, at least 90% or at least 95% homology to SEQ ID NO. 347.

In another aspect, the invention relates to a binding molecule comprising at least one immunoglobulin single domain antibody directed against IL-17 wherein said domain is a human $V_H$ domain and wherein said IL-17 binding molecule comprises at least one antigen binding site comprising a CDR3 sequence having SEQ ID NO. 347 or a sequence with at least 70%, at least 80%, at least 90%, at least 95% homology to SEQ ID NO. 347.

In another aspect, the invention relates to a binding molecule according to a preceding claim wherein has an $IC_{50}$ for inhibition of IL-6 production of about 0.2 to about 1000 nM when tested as described in the examples, i.e., by measuring the ability of IL-17 binding $V_H$ to inhibit IL-17 induced IL-6 release from the cell line HT1080.

In another aspect, the invention relates to a binding molecule according to a preceding claim wherein said binding molecule has a KD (M) value of 5×10−9 to 1×10−11, for example 5×10−9 to 2×10−10. In another aspect, the invention relates to a binding molecule according to a preceding claim wherein said binding molecule has a KD (M) value as set out in the examples.

In another aspect, the invention relates to a binding molecule according to a preceding claim wherein said binding molecule comprises two or more immunoglobulin single domain antibody directed against IL-17A wherein said domain is a $V_H$ domain.

In another aspect, the invention relates to a pharmaceutical composition comprising a binding molecule as defined above and optionally a pharmaceutical carrier.

In another aspect, the invention relates to a method for treating an autoimmune disease, inflammatory conditions, allergies and allergic conditions, hypersensitivity reactions, severe infections, and organ or tissue transplant rejection comprising administering an effective amount of a binding molecule or a pharmaceutical composition as defined above.

In another aspect, the invention relates to a binding molecule or a pharmaceutical composition as defined above for use in the treatment of an autoimmune disease, inflammatory conditions, allergies and allergic conditions, hypersensitivity reactions, severe infections, and organ or tissue transplant rejection.

In another aspect, the invention relates a binding molecule or a pharmaceutical composition as defined above in the manufacture of a medicament for the treatment of an autoimmune disease, inflammatory conditions, allergies and allergic conditions, hypersensitivity reactions, severe infections, and organ or tissue transplant rejection.

In another aspect, the invention relates to an in vivo or in vitro method for reducing human IL-17A activity comprising contacting human IL-17A with a binding molecule as defined above.

In another aspect, the invention relates to a method for determining the presence of IL-17A in a test sample by an immunoassay comprising contacting said sample with a binding molecule as defined above and at least one detectable label.

In another aspect, the invention relates to an isolated nucleic acid molecule comprising a nucleotide sequence encoding a binding molecule as defined above.

In another aspect, the invention relates to an isolated nucleic acid construct comprising a nucleic acid as defined above.

In another aspect, the invention relates to an isolated host cell comprising a nucleic acid or a construct as defined above.

In another aspect, the invention relates to a method for producing a binding molecule as defined above comprising expressing a nucleic acid encoding said binding molecule in a host cell and isolating the binding molecule from the host cell culture.

In another aspect, the invention relates to a kit comprising a binding molecule as described above.

In another aspect, the invention relates to a method for producing a binding molecule comprising at least one human immunoglobulin single domain antibody capable of binding human IL-17A wherein said domain is a human $V_H$ domain said method comprising
  a) immunising a transgenic mouse with an IL-17A antigen wherein said mouse expresses a nucleic acid construct comprising human heavy chain V genes and is not capable of making functional endogenous light or heavy chains,
  b) generating a library of sequences comprising $V_H$ domain sequences from said mouse and
  c) isolating sequences comprising $V_H$ domain sequences from said libraries.

In another aspect, the invention relates to a biparatopic, bivalent or multispecific binding molecule comprising a binding molecule as described above.

In another aspect, the invention relates to an isolated binding molecule comprising SEQ ID No. 430, 432, 434 or 436.

DRAWINGS

The patent or application file contains at least one drawing executed in color. Copies of this patent or patent application publication with color drawing(s) will be provided by the Office upon request and payment of the necessary fee.

FIG. 1A-1B. Family 1 amino acid sequences. This figure shows the full length $V_H$ sequence for clones in family 1. Framework (FR) and complementarity-determining regions (CDR) are labelled. CDR1, CDR2 and CDR3 sequences are highlighted in bold, SEQ ID NOs are shown in table 1.

FIG. 2A-2B. Family 2 amino acid sequences. This figure shows the full length $V_H$ sequence for clones in family 2. Framework (FR) and complementarity-determining regions (CDR) are labelled. CDR1, CDR2 and CDR3 sequences are highlighted in bold. SEQ ID NOs are shown in table 2.

FIG. 3. Family 3 amino acid sequences. This figure shows the full length $V_H$ sequence for clones in family 3. Framework (FR) and complementarity-determining regions (CDR) are labelled. CDR1, CDR2 and CDR3 sequences are highlighted in bold. SEQ ID NOs are shown in table 3, FIG. 4. Family 4 amino acid sequences. This figure shows the full length $V_H$ sequence for clones in family 4. Framework (FR) and complementarity-determining regions (CDR) are labelled, CDR1, CDR2 and CDR3 sequences are highlighted in bold. SEQ ID NOs are shown in table 4.

FIG. 5. Family 5 amino acid sequences. This figure shows the full length $V_H$ sequence for clones in family 5. Framework (FR) and complementarity-determining regions (CDR)

are labelled. CDR1, CDR2 and CDR3 sequences are highlighted in bold. SEQ ID NOs are shown in table 5, FIG. 6A-6C. PCR amplification of $V_H$ 1-02 scaffold in which lane M: Generuler 1 kb DNA ladder (Fermentas SM0311), lane 1: $V_H$ 1-02 scaffold, lane 2: no template control for PCR; the arrow shows PCR products approximately 300 bp. M: Generuler 1 kb DNA ladder (Fermentas SM0311). 6B. PCR amplification of human CDR3 domains from cDNA in which M: Generuler 1 kb DNA ladder (Fermentas SM0311), lane 1: CDR3 domains amplified from human lymph node cDNA; lane 2: CDR3 domains amplified from human bone marrow cDNA, lane 3: CDR3 domains amplified from human spleen cDNA; lane 4: CDR3 domains amplified from human peripheral blood leukocyte cDNA, lane 5: no template control for PCR. The arrow shows PCR amplification products in the range 50-100 bp. M: Generuler 1 kb DNA ladder (Fermentas SM0311). 6C. Assembly and pull-through PCR amplification of $V_H$ 1-02 scaffold plus human CDR3 domains, lane M: Generuler 1 kb DNA ladder (Fermentas SM0311), lanes 1 and 2: $V_H$ 1-02 scaffold+ human CDR3 domains, and lane 3: no template control for PCR. Arrow shows PCR products approximately 400 bp. M: Generuler 1 kb DNA ladder (Fermentas SM0311).

FIG. 7. shows serum ELISAs confirming immunogen-induced heavy chain only antibody response.

FIG. 8A-8B. shows A: phage ELISA binding to IL-17A and B: phage ELISA binding to irrelevant antigen.

Figure 9B:
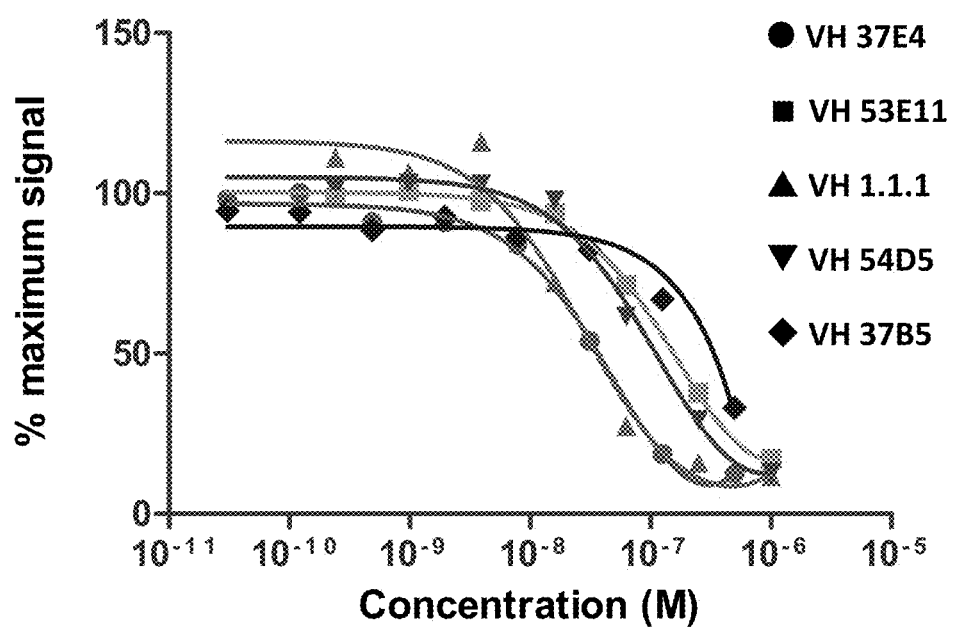

FIG. 9A-9B. shows data from biochemical inhibition assays: A: x-axis $\log_{10}$ M concentration, y-axis % maximal signal; for $V_H$ 1.1.1 (●) the $IC_{50}$ (nM) was 53, for $V_H$ 1.6.1 (■) the $IC_{50}$ (nM) was 5, for $V_H$ 1.10.1 (▲), the $IC_{50}$ (nM) was 4; for $V_H$ 1.7.1 (▼), the $IC_{50}$ (nM) was 7 (●), for $V_H$ 77 G9 the $IC_{50}$ (nM) was 6. B: x-axis concentration (M), y-axis % maximum signal; for $V_H$ 37 E4 (●) the $IC_{50}$ (nM) was 56, for $V_H$ 53 E11 (■) the $IC_{50}$ (nM) was 195, for $V_H$ 1.1.1 (♦), the $IC_{50}$ (nM) was 29; for $V_H$ 54 D5 (▼), the $IC_{50}$ (nM) was 124 (●), for $V_H$ 37 B5 (♦) the $IC_{50}$ (nM) was not determined.

Figure 10A:
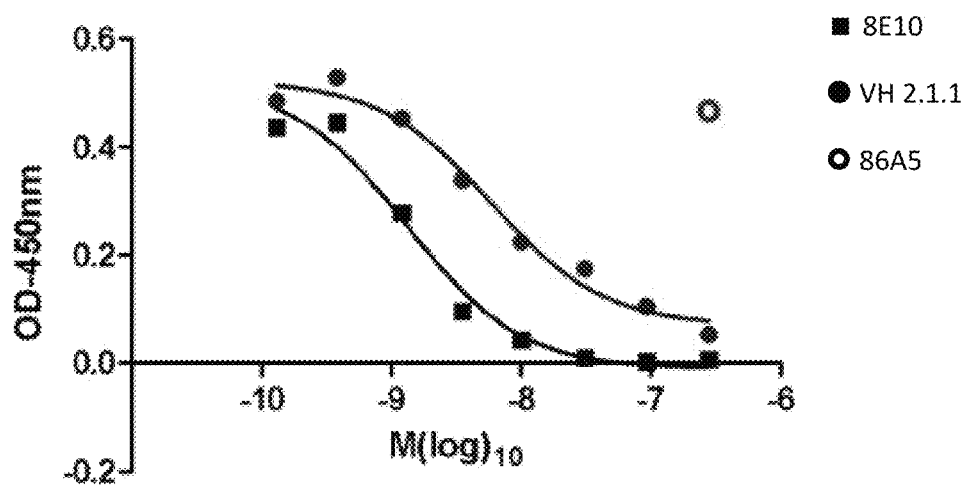
Figure 10B:
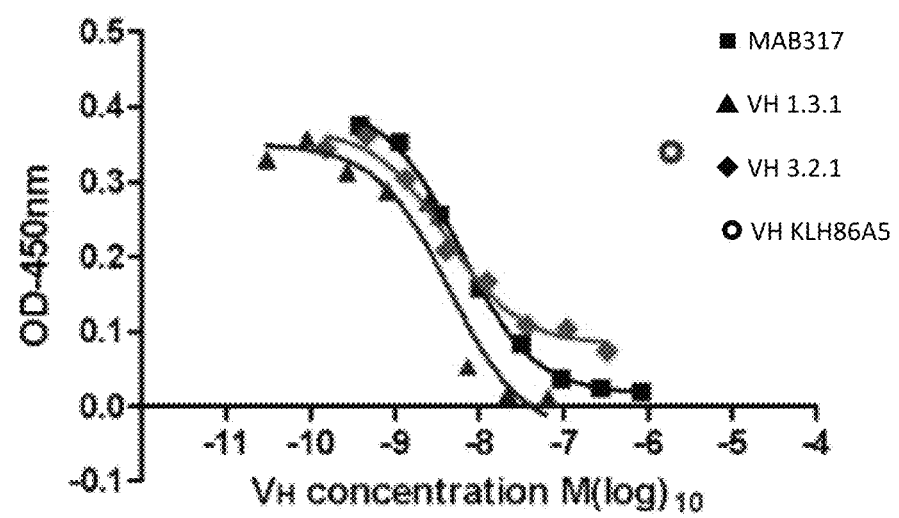
Figure 11B:
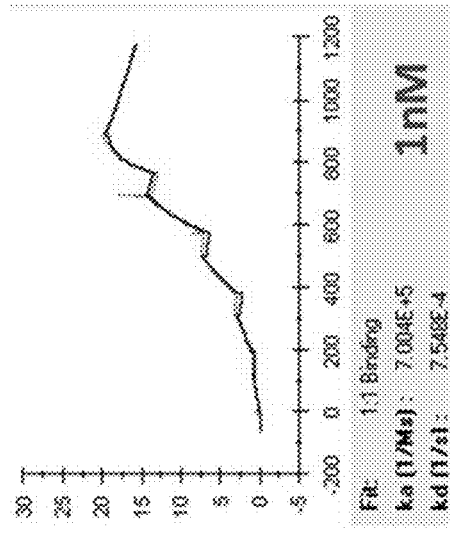
Figure 11D:
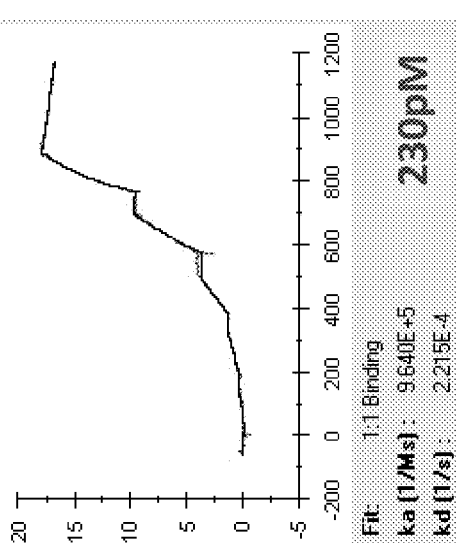
Figure 11A:
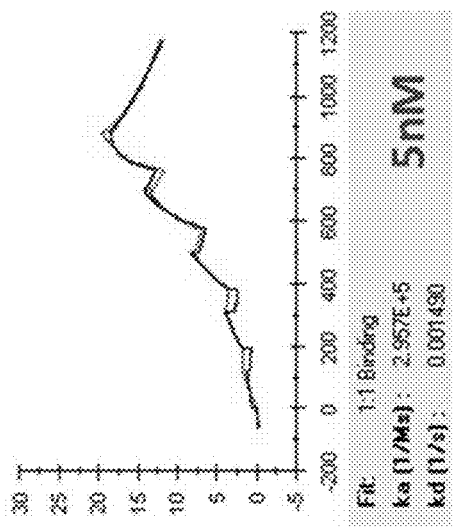
Figure 11C:
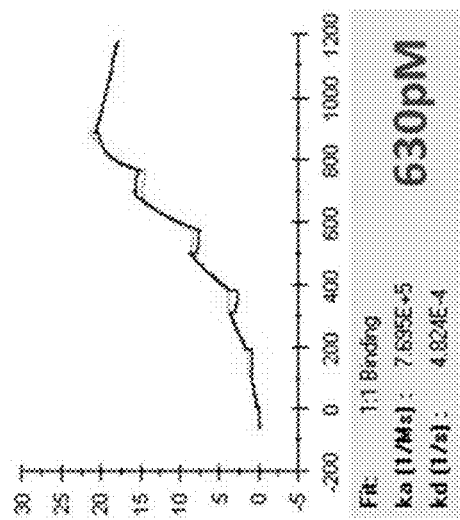

FIG. 10A-10B. shows data from cell-based assays: A: A: x-axis shows concentration M(log)$_{10}$, y-axis shows optical density OD 450 nm, for $V_H$ 8 E10 (■), $V_H$ 2.1.1 (●) and $V_H$ 86A5 (○). B: x-axis shows $V_H$ concentration M(log)$_{10}$, y-axis shows optical density OD 450 nm, for MAB317 (■), $V_H$ 1.3.1 (▲), $V_H$ 3.2.1 (♦) and $V_H$ KLH86A5 (○).

FIG. 11A-11D. shows the results of the BIAcore® binding assays for A: $V_H$ 1.1.1 (5 nM), $V_H$ 1.10.1 (1 nM), $V_H$ 1.6.1 (630 pM), $V_H$ 1.3.1 (230 pM).

Figure 12A:
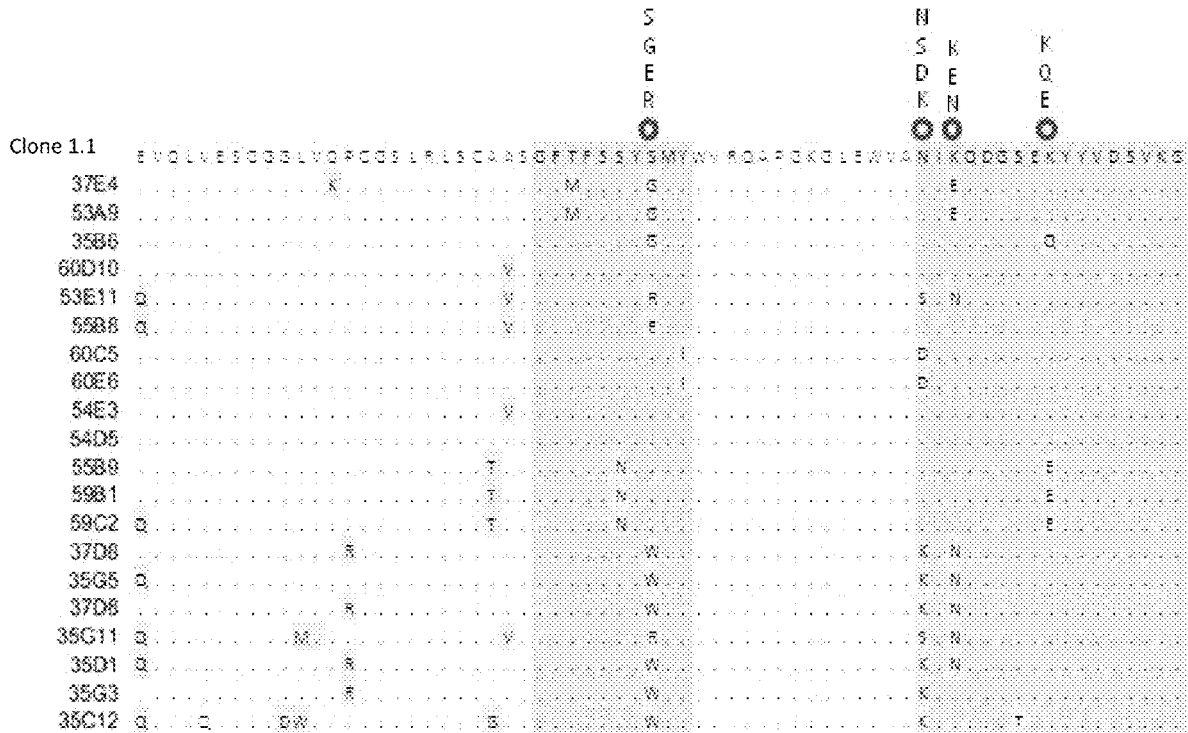
Figure 12B:
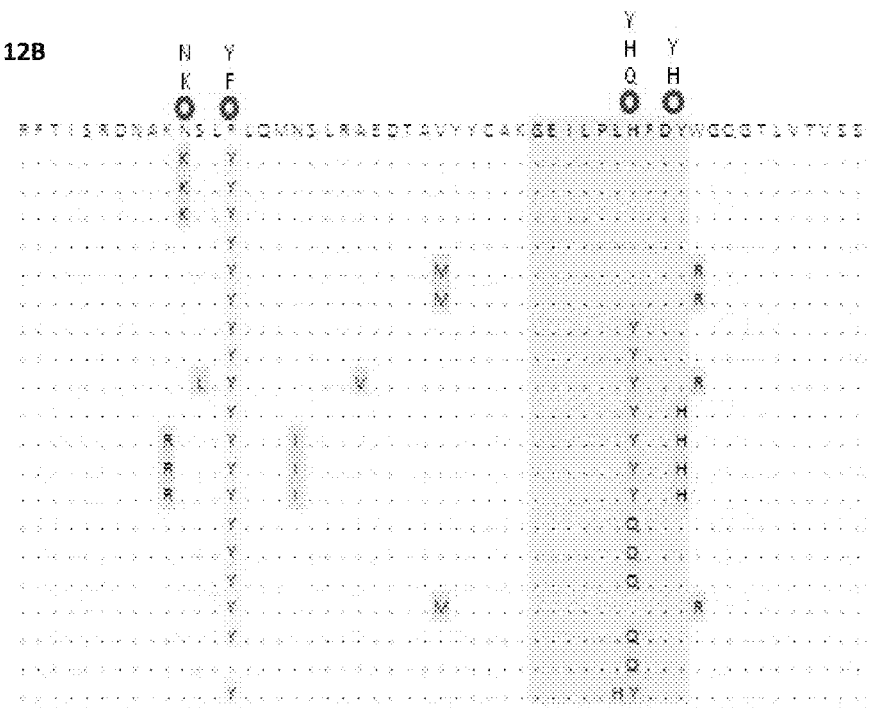

FIG. 12A-12B. Optimisation of $V_H$ clone 1.1. the amino acid sequence of clone 1.1. is shown on the top line.

Figure 13A:
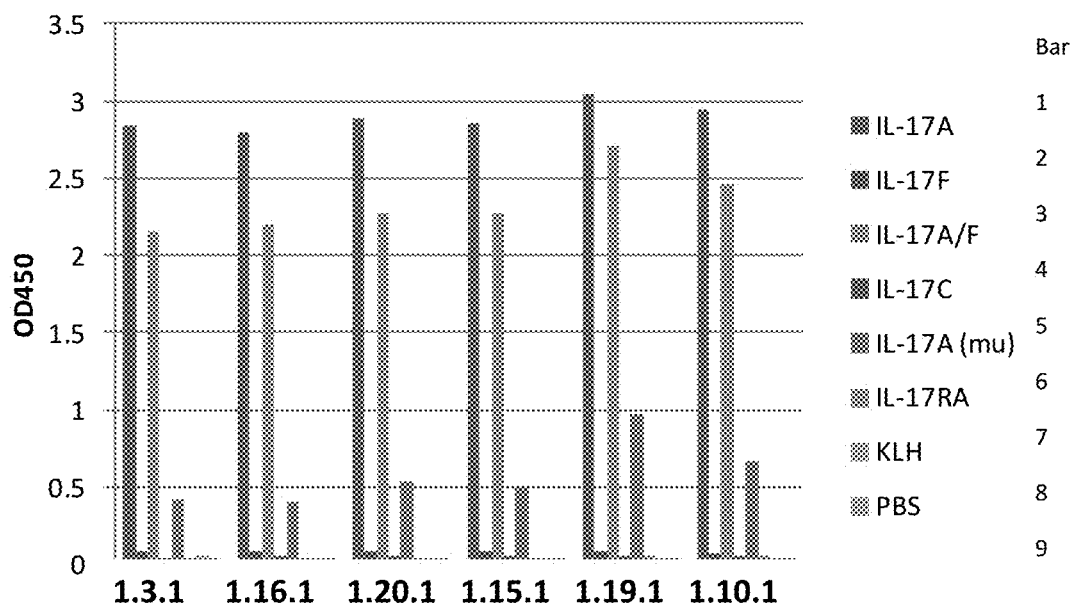
Figure 13B:
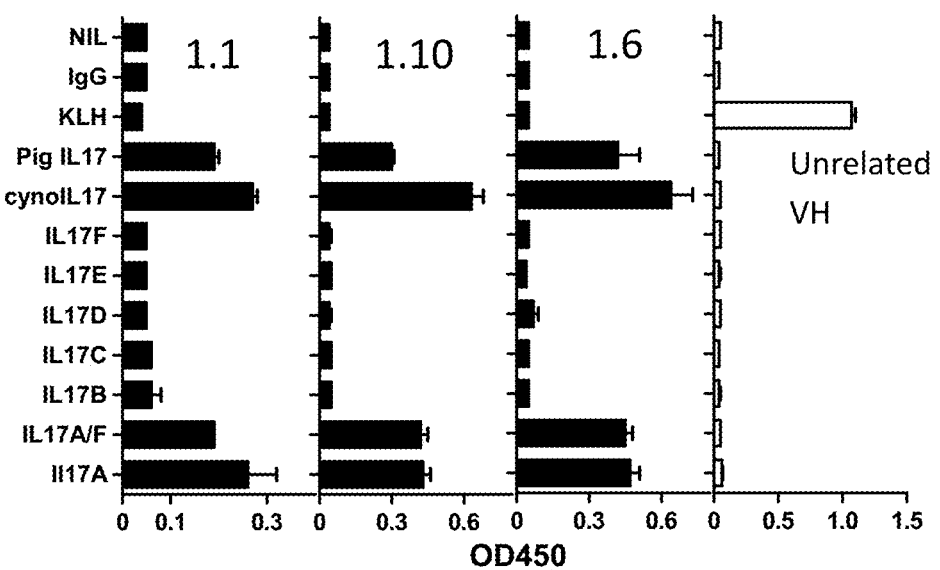

FIGS. 13A and 13B. show the results of specificity ELISAs.

Figure 14:
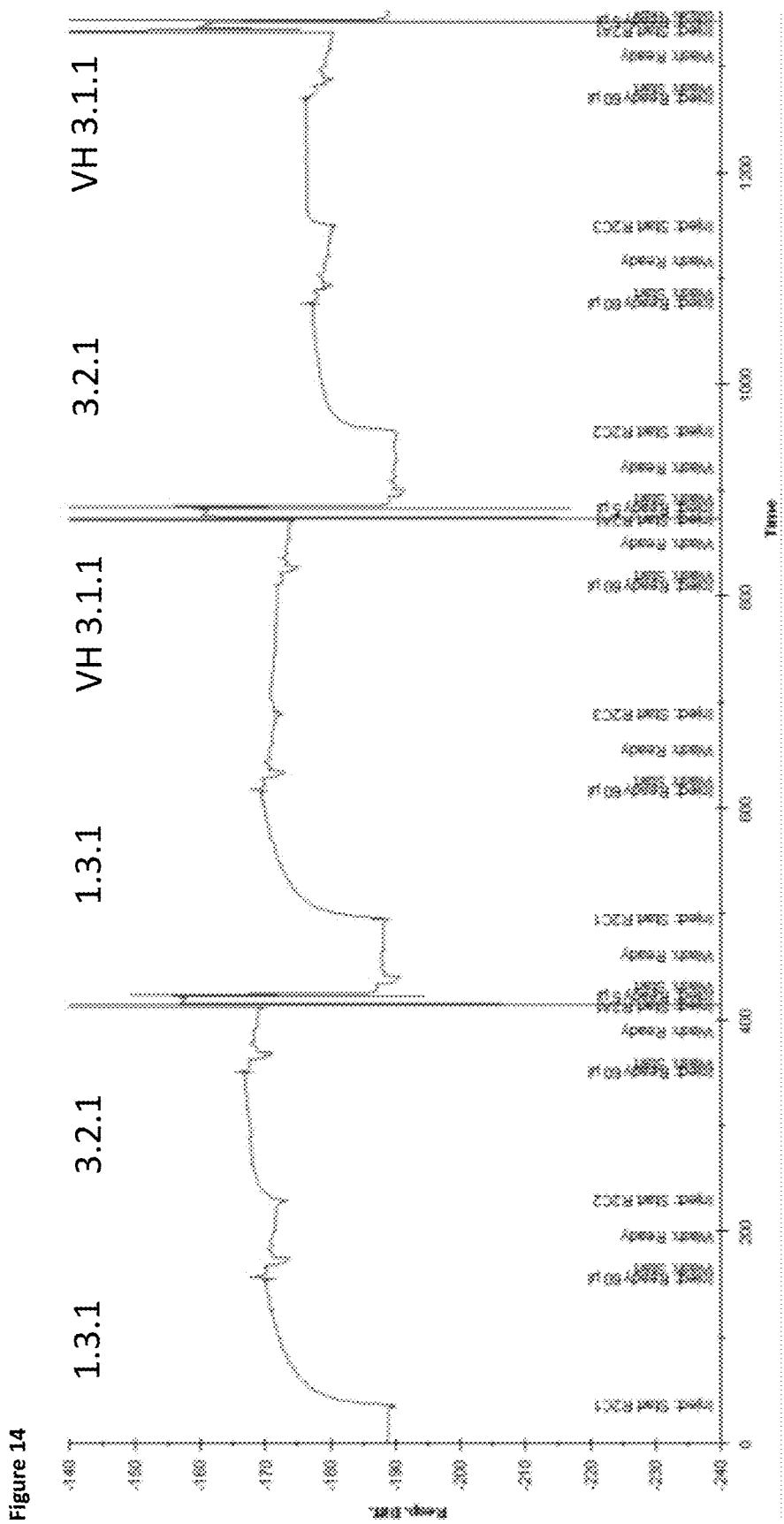

FIG. 14. shows the results of epitope competition, 1.3.1 and $V_H$ 3.1.1 bind to same epitope, 3.2.1 binds to a different epitope.

FIG. 15A-15K. shows the results of HPLC for A. $V_H$ 1.10.1, B. $V_H$ 1.17.1, C. $V_H$ 1.3.1, D. $V_H$ 186 D2, E. $V_H$ 1.16.1, F. $V_H$ 1.22.1, G. $V_H$ 1.18.1, H. $V_H$ 1.17.1, I. $V_H$ 1.21.1, J. $V_H$ 1.20.1.

FIG. 16A-16C. shows A: BIAcore® results for $V_H$ 1.3.2 (KD 630 pM) and $V_H$ 1.3.3, B: BIAcore® results for $V_H$ 1.2.2 and $V_H$ 1.3.3 (KD 550 pM) and C: results of a cell based assay, inhibition of IL-17A-induced IL6 release (18 hours) $V_H$ 1.3.2 (●) EC50 5.710e-010; $V_H$ 1.2.3 (■) EC50 3.998e-010.

Figure 17A:
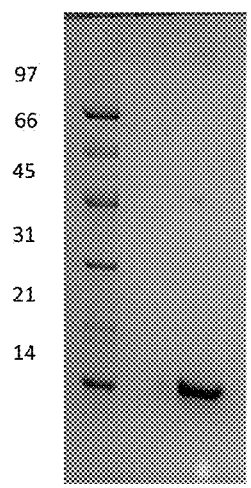
Figure 17B:
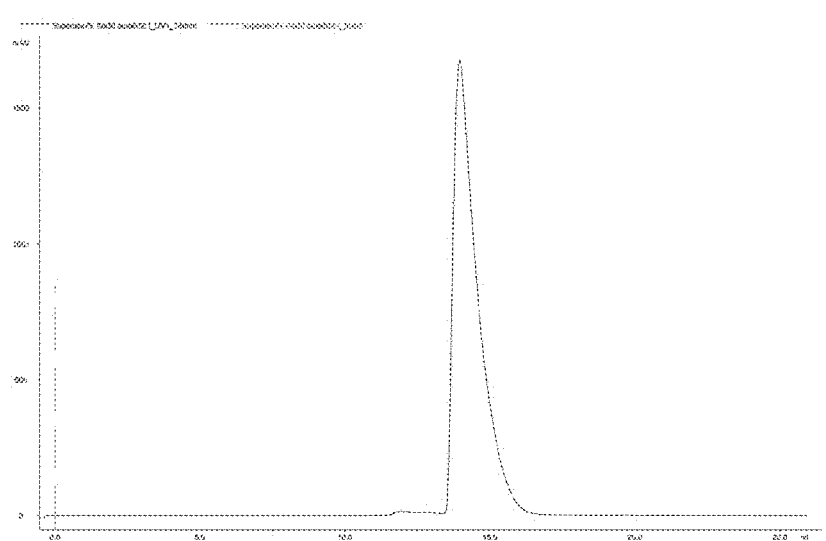

FIG. 17A-17B. A. Analysis of final purified $V_H$ fraction clone 1.10.2 by SDS-PAGE and SEC-HPLC. Fractions were analysed under reducing conditions, through a 4-20% gel. Lane 1, Protein standards (500 ng each); Lane 2, purified clone 1.10.2 (5 pg). B. Purified clone 1.10.2 was further analysed by SEC-HPLC to confirm that the protein was monomeric.

Figure 18:
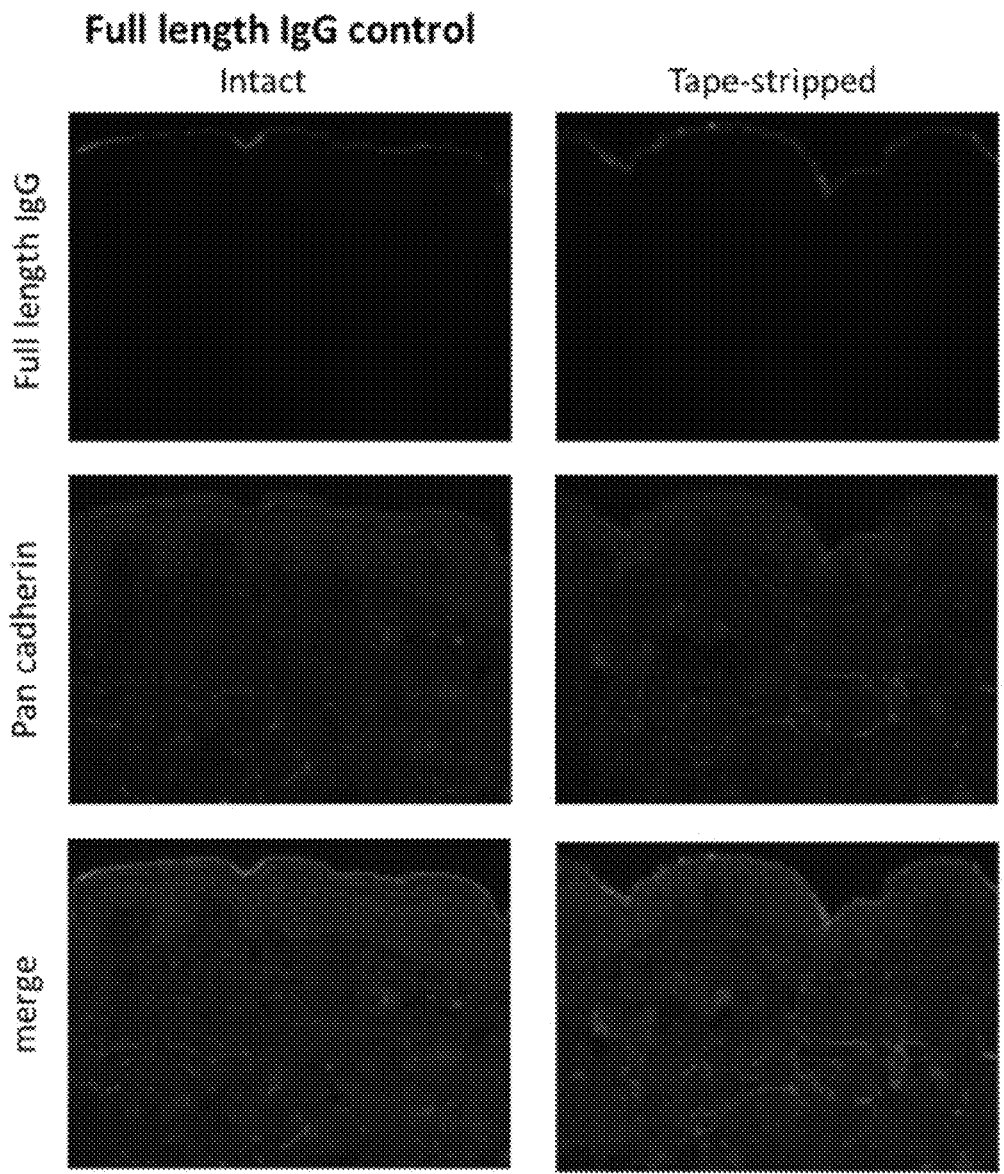

FIG. 18. Immunofluorescence. Intact and tape stripped human skin was placed in Bronaugh cells and incubated 24 hours with PBS with IgG. Staining in these experiments and which can be seen in the original colour image is as follows: Red=IgG, green=cadherin in the cell membranes. Top row shows only IgG detection in brighter areas (red in the IHC image). Middle row shows only cadherin in brighter areas (green in the IHC image). Bottom row shows IgG and cadherin detection merged into one image.

Figure 19:
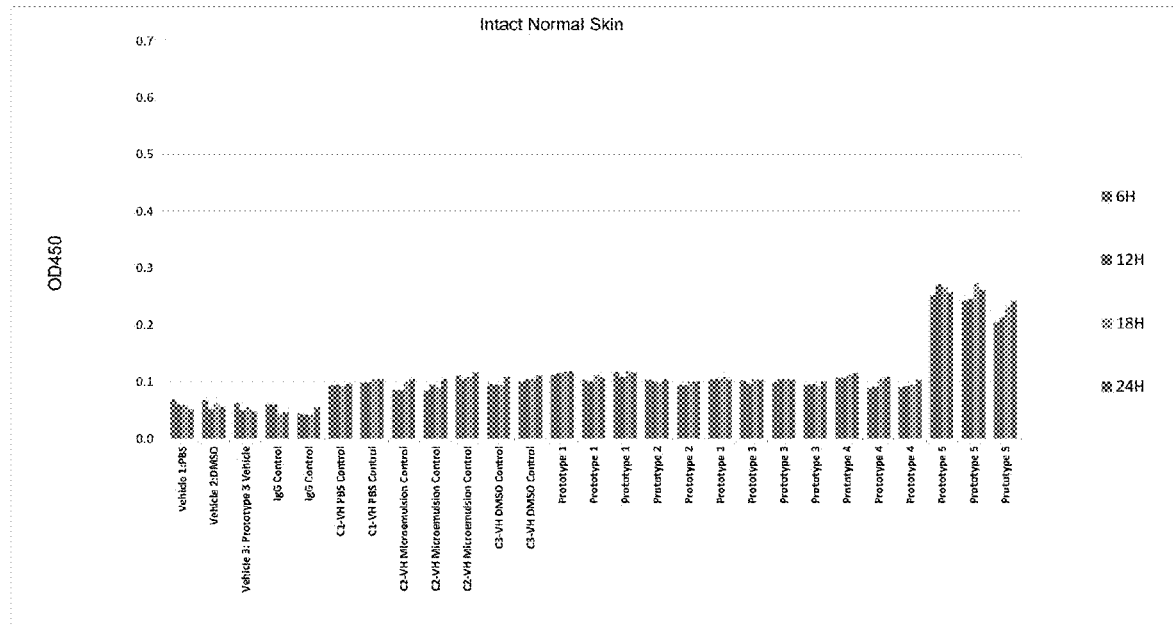

FIG. 19. ELISA results on receiver fluids (neat) from penetration study on intact normal skin with clone 1.10.2. Sampled at 6, 12, 18 and 24 hour interval for each sample from left to right.

Figure 20:
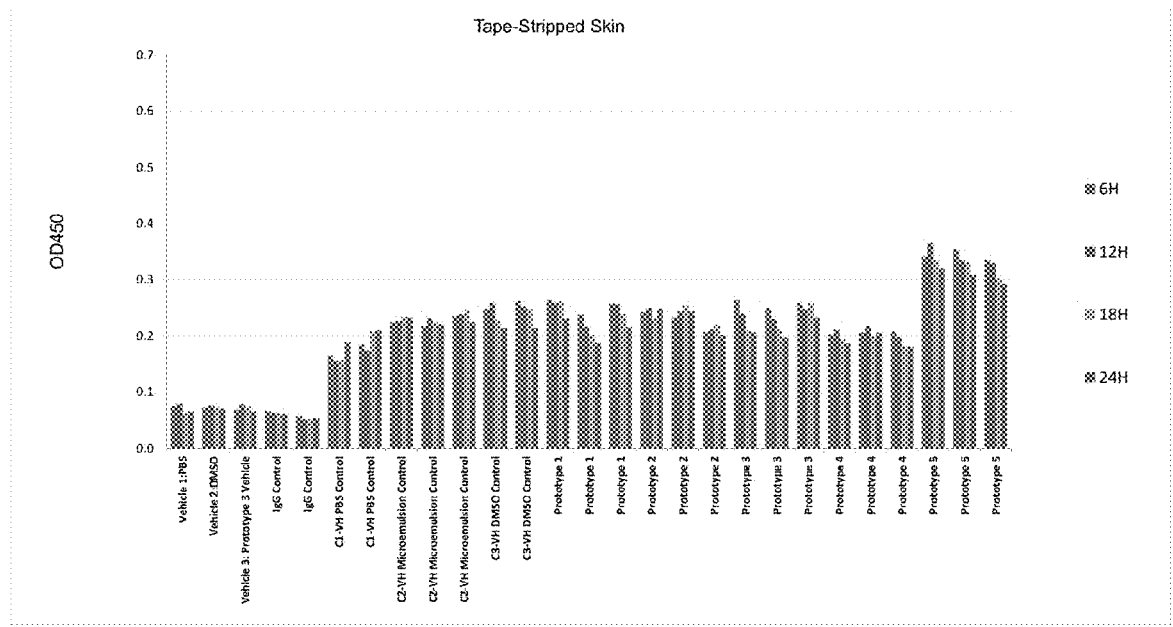

FIG. 20. ELISA results on receiver fluids (neat) from penetration study on tape-stripped skin with clone 1.10.2. Sampled at 6, 12, 18 and 24 hour interval for each sample from left to right.

Figure 21:
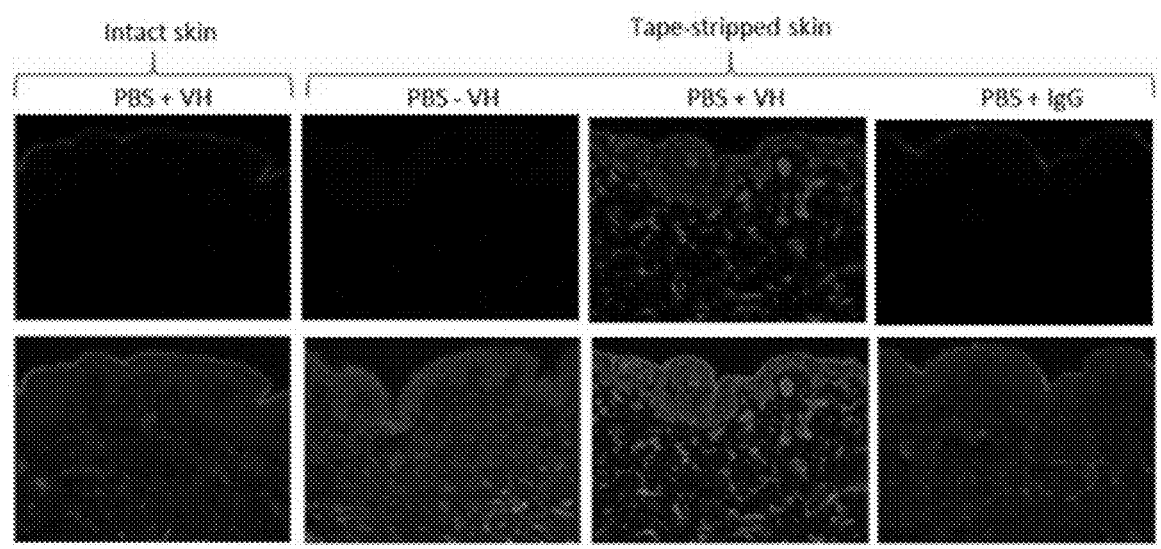

FIG. 21. IHC image of clone 1.10.2 and IgG in skin (in prototype formulation C1; PBS). Staining in these experiments is as follows: Red=$V_H$ (anti-His tag) or IgG (anti-mouse IgG); Green=cadherin (cell membranes); Blue=nuclei (DNA). Top row shows only $V_H$ detection in red except the last column shows IgG detection (brighter areas, red in the IHC image). Bottom row has $V_H$/IgG detection (brighter areas, red in the IHC image) merged with cadherin (brighter areas, green in the IHC image) and nuclei (brighter areas, blue in the IHC image) detection.

Figure 22:
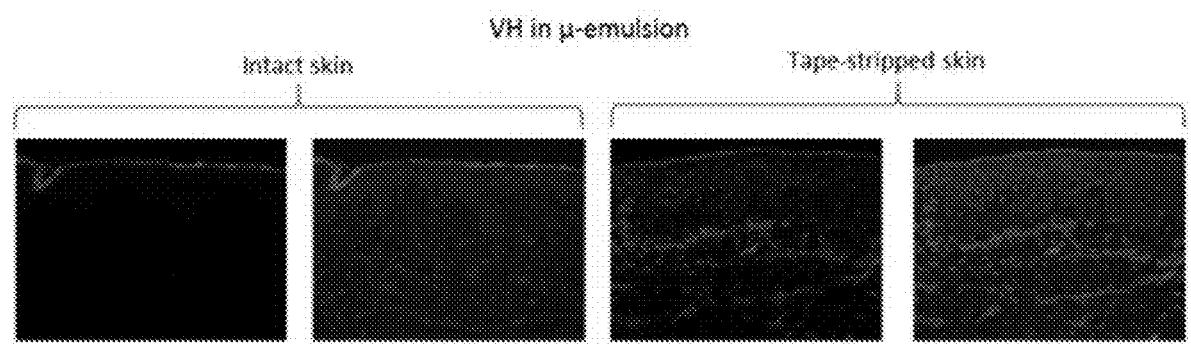

FIG. 22. IHC image of clone 1.10.2 (in prototype formulation C2; μ-emulsion) in skin. Staining in these experiments is as follows: Red=$V_H$ (anti-His tag); Green=cadherin (cell membranes); Blue=nuclei (DNA). From left; $1^{st}$ image $V_H$ detection (brighter areas, red) only, $2^{nd}$ $V_H$ detection (brighter areas, red) merged with cadherin (brighter areas, green in the IHC image) and nuclei (brighter areas, blue in the IHC image) detection, $3^{rd}$ $V_H$ detection (red) only, $4^{th}$ $V_H$ detection (brighter areas, red in the IHC image) merged with cadherin (brighter areas, green in the IHC image) and nuclei (brighter areas, blue in the IHC image).

Figure 23:
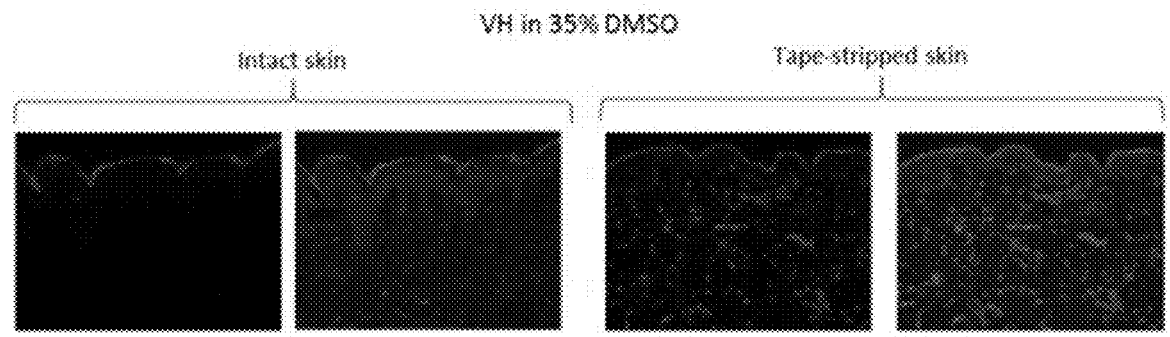

FIG. 23. IHC image of clone 1.10.2 (in prototype formulation C3; 35% DMSO) in skin. Staining in these experiments is as follows: Red=$V_H$ (anti-His tag); Green=cadherin (cell membranes); Blue=nuclei (DNA). From left; $1^{st}$ image $V_H$ detection (brighter areas, red in the IHC image) only, $2^{nd}$ $V_H$ detection (brighter areas, red in the IHC image) merged with cadherin (brighter areas, green in the IHC image) and nuclei (brighter areas, blue in the IHC image) detection, $3^{rd}$ $V_H$ detection (brighter areas, red in the IHC image) only, $4^{th}$ $V_H$ detection (brighter areas, red in the IHC image) merged with cadherin (brighter areas, green in the IHC image) and nuclei (brighter areas, blue in the IHC image).

Figure 24:
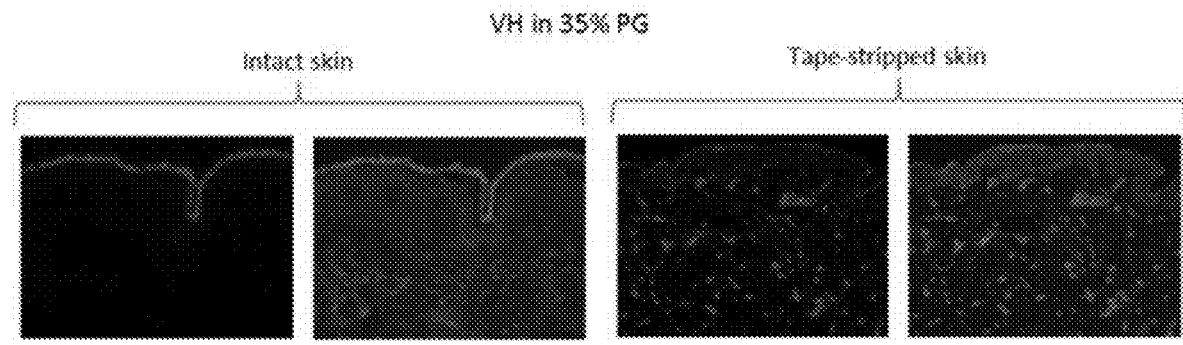

FIG. 24. IHC image of clone 1.10.2 (in prototype formulation 1; 35% Propylene Glycol) in skin. Staining in these experiments is as follows: Red=$V_H$ (anti-His tag); Green=cadherin (cell membranes); Blue=nuclei (DNA). From left; $1^{st}$ image $V_H$ detection (brighter areas, red in the IHC image) only, $2^{nd}$ $V_H$ detection (brighter areas, red in the IHC image) merged with cadherin (brighter areas, green in the IHC image) and nuclei (brighter areas, blue in the IHC image) detection, $3^{rd}$ $V_H$ detection (brighter areas, red in the IHC image) only, $4^{th}$ $V_H$ detection (brighter areas, red in the IHC image) merged with cadherin (brighter areas, green in the IHC image) and nuclei (brighter areas, blue).

Figure 25:
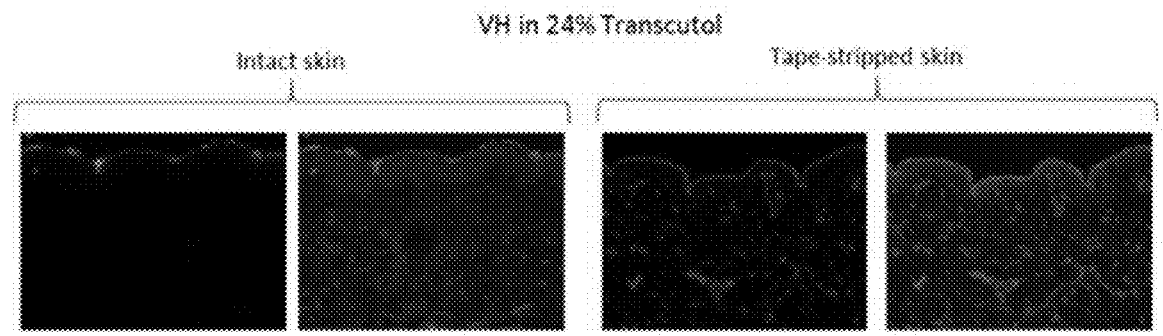

FIG. 25. IHC image of clone 1.10.2 (in prototype formulation 2; 24% Transcutol®) in skin. Staining in these experiments is as follows: Red=$V_H$ (anti-His tag); Green=cadherin (cell membranes); Blue=nuclei (DNA). From left; $1^{st}$ image $V_H$ detection (brighter areas, red green in the IHC image) only, $2^{nd}$ $V_H$ detection (brighter areas, red in the IHC image) merged with cadherin (brighter areas, green in the IHC image) and nuclei brighter areas, (brighter areas, blue in the IHC image) detection, $3^{rd}$ $V_H$ detection (brighter areas, red in the IHC image) only, $4^{th}$ $V_H$ detection (brighter areas, red in the IHC image) merged with cadherin (brighter areas, green in the IHC image) and nuclei (brighter areas, blue in the IHC image).

Figure 26:
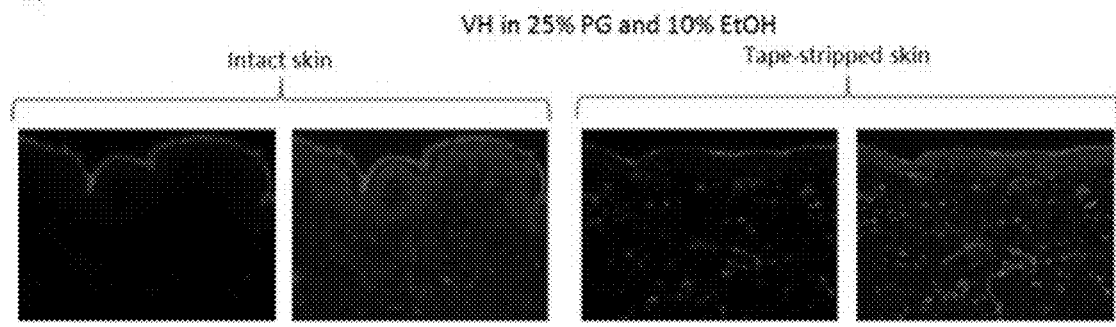

FIG. 26. IHC image of clone 1.10.2 (in prototype formulation 3; 25% Propylene Glycol and 10% EtOH) in skin. Staining in these experiments is as follows: Red=$V_H$ (anti-His tag); Green=cadherin (cell membranes); Blue=nuclei (DNA). From left; $1^{st}$ image $V_H$ detection (brighter areas, red in the IHC image) only, $2^{nd}$ $V_H$ detection (brighter areas, red in the IHC image) merged with cadherin (brighter areas, green in the IHC image) and nuclei (brighter areas, blue in the IHC image) detection, $3^{rd}$ $V_H$ detection (brighter areas, (brighter areas, red in the IHC image) only, $4^{th}$ $V_H$ detection (brighter areas, red in the IHC image) merged with cadherin (brighter areas, green in the IHC image) and nuclei (brighter areas, blue in the IHC image).

Figure 27:
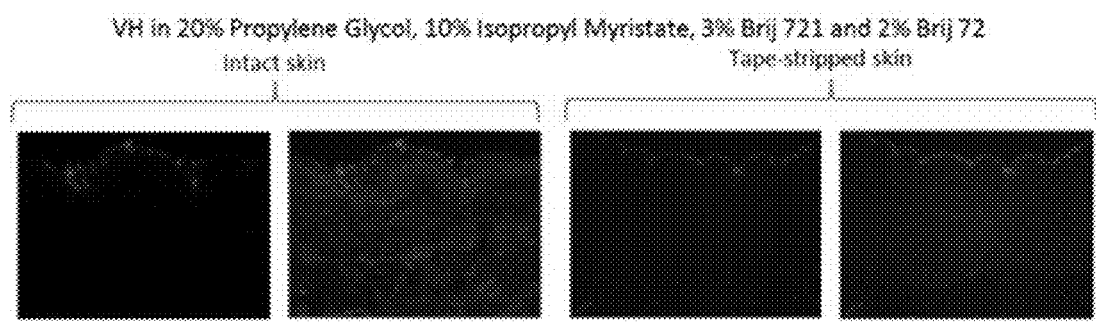

FIG. 27. IHC image of clone 1.10.2 in prototype formulation 4; 20% Propylene Glycol, 10% Isopropyl Myristate, 3% Brij® 721 and 2% Brij® 72) in skin. Staining in these experiments is as follows: Red=$V_H$ (anti-His tag); Green=cadherin (cell membranes); Blue=nuclei (DNA). From left; $1^{st}$ image $V_H$ detection (brighter areas, red in the IHC image) only, $2^{nd}$ $V_H$ detection brighter areas, (brighter areas, red in the IHC image) merged with cadherin (brighter areas, green in the IHC image) and nuclei (brighter areas, blue in the IHC image) detection, $3^{rd}$ $V_H$ detection brighter areas, (brighter areas, red in the IHC image) only, $4^{th}$ $V_H$ detection (brighter areas, red in the IHC image) merged with cadherin (brighter areas, green in the IHC image) and nuclei (brighter areas, blue in the IHC image).

Figure 28:
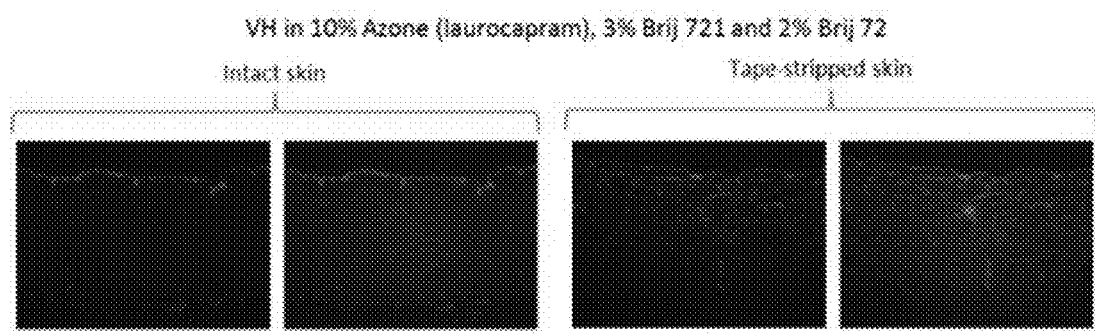

FIG. 28. IHC image of clone 1.10.2: (in prototype formulation 5; 10% Azone (laurocapram), 3% Brij® 721 and 2% Brij® 72) in skin. Staining in these experiments is as follows: Red=$V_H$ (anti-His tag); Green=cadherin (cell membranes); Blue=nuclei (DNA). From left; $1^{st}$ image $V_H$ detection (brighter areas, red in the IHC image) only, $2^{nd}$ $V_H$ detection (brighter areas, red in the IHC image) merged with cadherin (brighter areas, green in the IHC image) and nuclei (brighter areas, blue in the IHC image) detection, $3^{rd}$ $V_H$ detection (brighter areas, red in the IHC image) only, $4^{th}$ $V_H$ detection (brighter areas, red in the IHC image) merged with cadherin (brighter areas, green) and nuclei (brighter areas, blue in the IHC image).

Figure 29A:
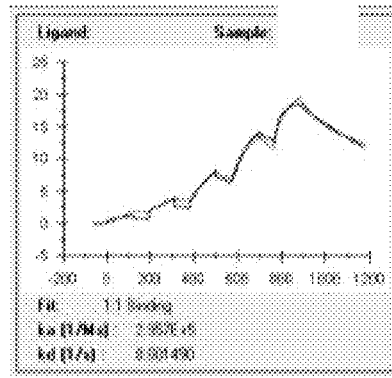
Figure 29B:
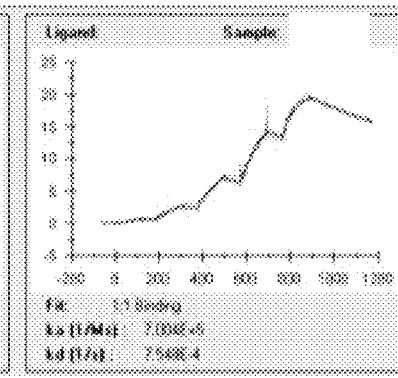
Figure 29C:
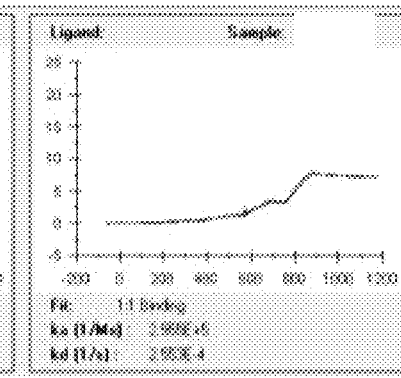

FIG. 29A-29C. shows the results of the BIAcore® binding assays. A:1.1 B. 1.10 C. 1.1-1.10.

Figure 30A:
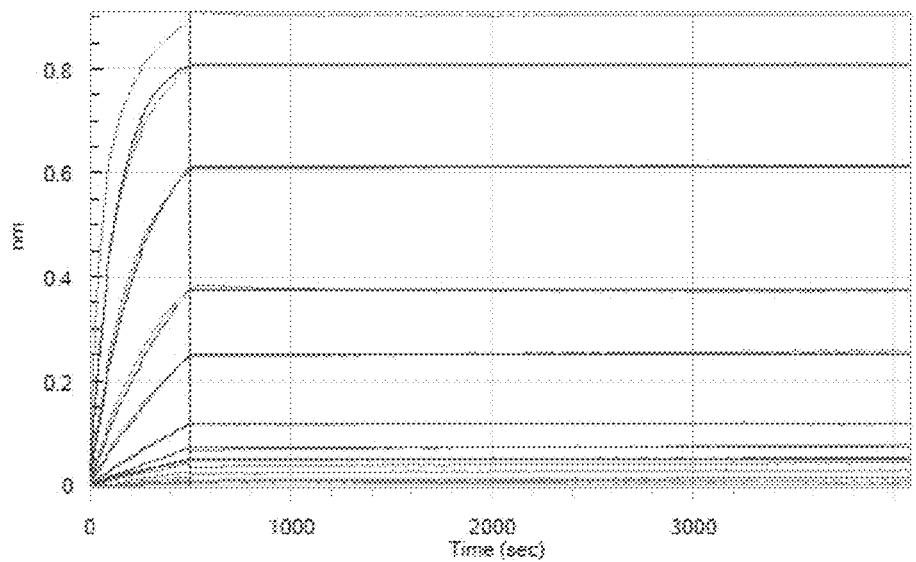
Figure 30B:
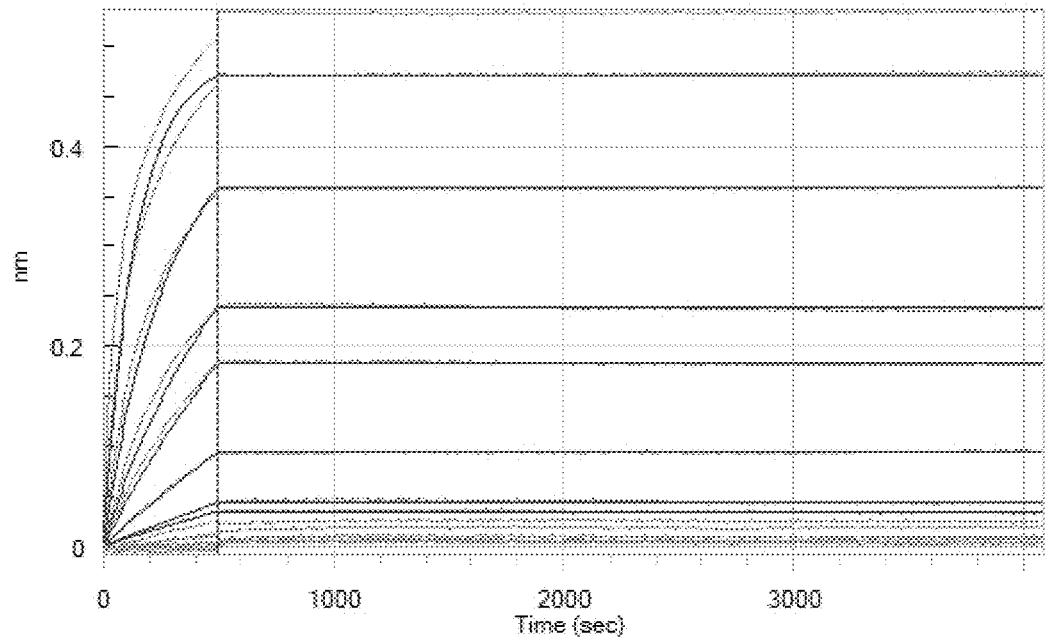
Figure 30C:
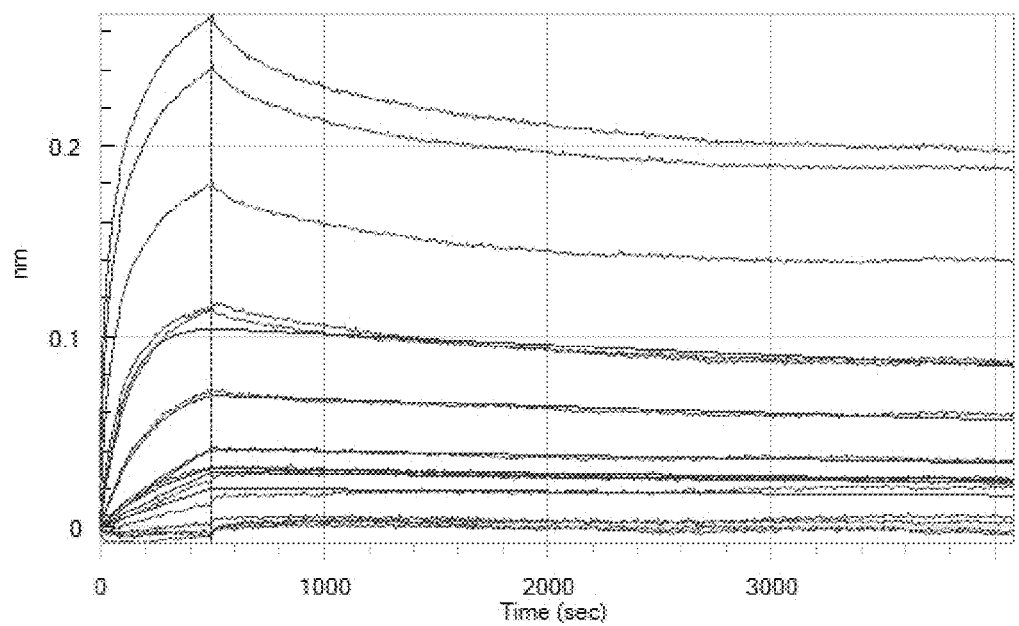
Figure 31A:
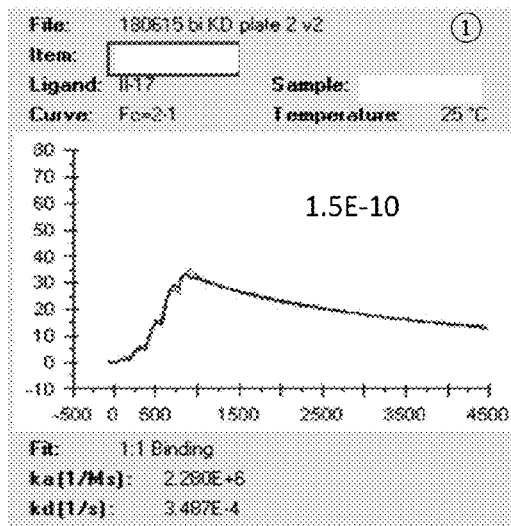
Figure 31B:
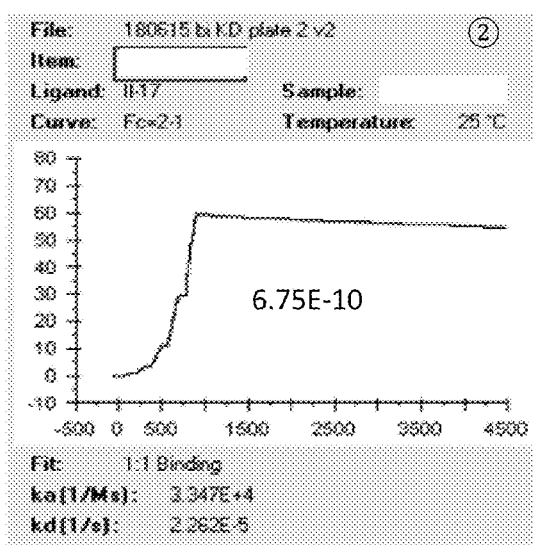
Figure 31C:
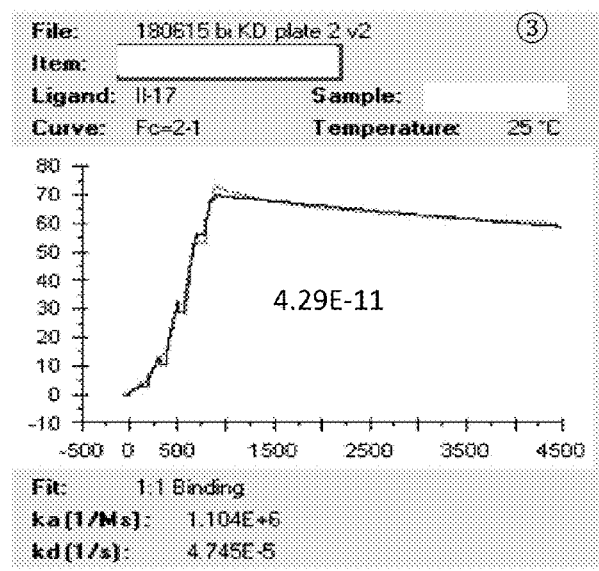
Figure 31D:
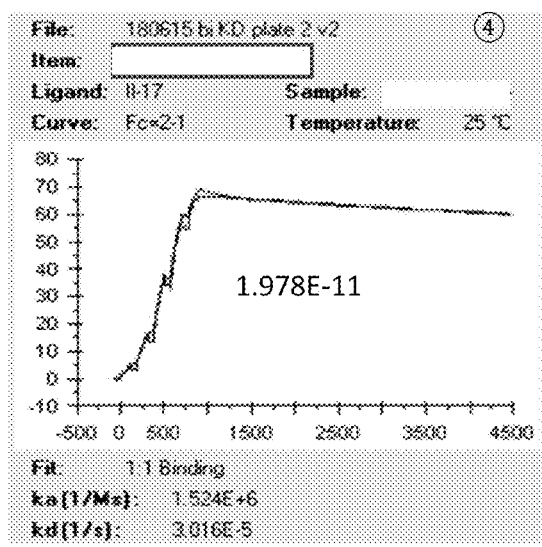
Figure 32A:
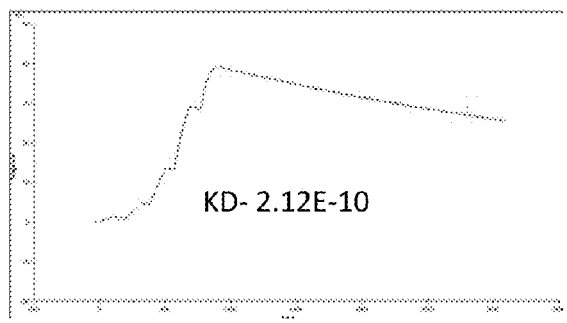
Figure 32B:
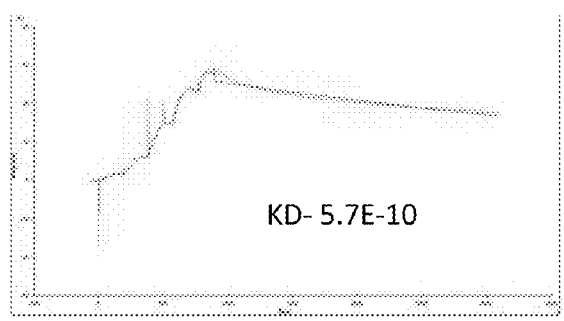
Figure 32C:
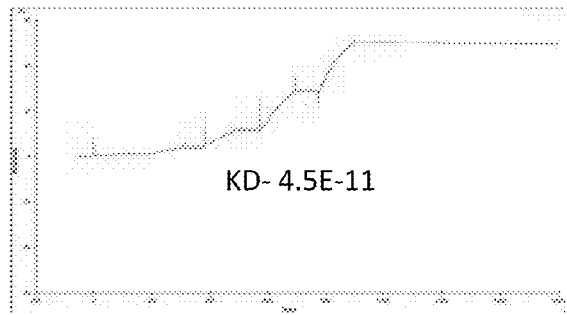
Figure 32D:
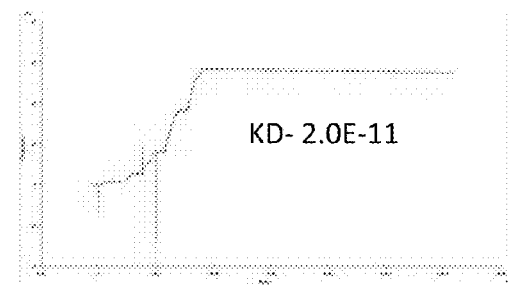

FIG. 30A-30C. shows the results for Octet analysis for A. 3.2-2($G_4S$)-1.2 B. 3.2-6($G_4S$)-1.2 C. 1.2.

FIG. 31A-31D. shows the results of the BIAcore® binding assays. A: 3.2 B: 1.2 C: 3.2-2($G_4S$)-1.2 D: 3.2-6($G_4S$)-1.2; n=1.

FIG. 32A-32D. shows the KD determination on BIAcore® binding assays. A: 3.2 B: 1.2 C: 3.2-2($G_4S$)-1.2 D: 3.2-6($G_4S$)-1.2 n=2.

Figures 33A, 33B:
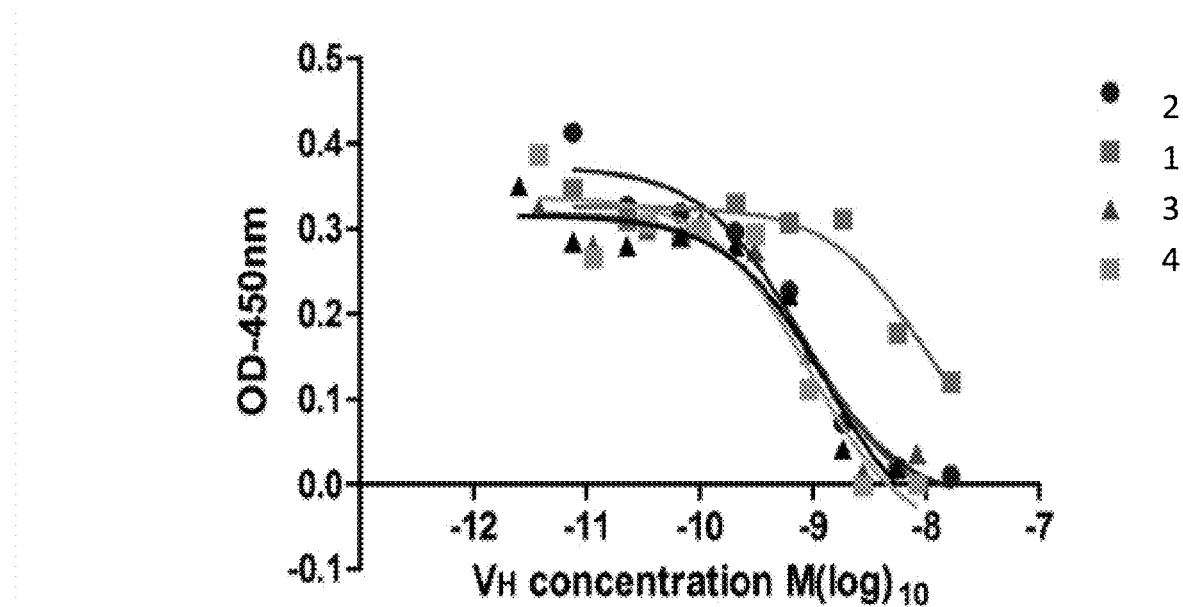

FIG. 33A-33B. shows the results of an IL-6 release assay. EC50 values are shown in B 1■ (upper curve): 3.2 2●: 1.2 3▲: 3.2-2($G_4S$)-1.2 4■: 3.2-6($G_4S$)-1.2.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual (2d ed., Cold Spring Harbor Laboratory Press, Cold Spring Harbor, N.Y. (1989)). Enzymatic reactions and purification techniques are performed according to the manufacturer's specifications, as commonly accomplished in the art or as described herein. The nomenclatures used in connection with, and the laboratory procedures and techniques of, analytical chemistry, synthetic organic chemistry, medicinal and pharmaceutical chemistry described herein are those well-known and commonly used in the art. Standard techniques are used for chemical syntheses, chemical analyses, pharmaceutical preparation, formulation, and delivery, and treatment of patients.

The IL-17 family of cytokines includes six members, IL-17/IL-17A, IL-17B, IL-17C, IL-17D, IL-17E/IL-25, and IL-17F, which are produced by multiple cell types. Members of this family have a highly conserved C-terminus containing a cysteine-knot fold structure. Most IL-17 proteins are secreted as disulfide-linked dimers, with the exception of IL-17B, which is secreted as a non-covalent homodimer.

Signaling by IL-17 family cytokines is mediated by members of the IL-17 receptor family, IL-17 R/IL-17 RA, IL-17 B R/IL-17 RB, IL-17 RC, IL-17 RD, and IL-17 RE. Activation of these receptors triggers intracellular pathways that induce the production of pro-inflammatory cytokines and anti-microbial peptides. IL-17A, IL-17F, and IL-17A/F are produced primarily by activated T cells and signal through an oligomerized receptor complex consisting of IL-17 RA and IL-17 RC. Ligand binding to this complex leads to recruitment of the intracellular adaptor proteins, Act1 and TRAF-6, and downstream activation of the transcription factors, NF kappa B, AP-1, and C/EBP. IL-17E activates similar signaling pathways through a receptor complex formed by IL-17 RA and IL-17 B R/IL-17RB. Signaling by IL-17E induces Th2-type immune responses and may be involved in promoting the pathogenesis of asthma. Less is known about the signaling pathways activated by other IL-17 family cytokines. Recent studies suggest that IL-17C is produced primarily by epithelial cells and binds to a receptor complex consisting of IL-17 RA and IL-17 RE. Autocrine signaling by IL-17C in epithelial cells stimulates the production of anti-microbial peptides and pro-inflammatory cytokines, but like IL-17A, overexpression of IL-17C may contribute to the development of autoimmune diseases. Similar to IL-17E, IL-17B binds to IL-17 B R/IL-17 RB, but the major target cells and effects of IL-17B signaling have not been reported. In addition, the receptor for IL-17D and the ligand for IL-17 RD are currently unknown.

The invention provides isolated IL-17A binding molecules that are all capable of binding human IL-17A, pharmaceutical compositions and formulations, in particular for topical administration, comprising such binding molecules, as well as isolated nucleic acids encoding such binding molecules, recombinant expression vectors and host cells comprising such nucleic acids for making such binding molecules. Also provided by the invention are methods of using the binding molecules disclosed herein to detect human IL-17A, to inhibit human IL-17A either in vitro or in vivo, and in methods of treating disease. One aspect of the invention provides isolated human anti-human IL-17A binding molecules, specifically those comprising, or consisting of, at least one single domain antibody that binds to human IL-17A with high affinity, a slow off rate and high neutralizing capacity.

In preferred embodiments of the invention, the binding molecules are capable of binding specifically to human IL-17A and do not cross react with, or do not show substantial binding to, the members of the human IL-17 family. This limited cross-reactivity with human IL-17A homologues exhibited by the binding molecules of the invention offers advantages for their therapeutic and/or diagnostic use, as side effects by undesirable cross reactivity are reduced. This also offers advantages in dosing for therapeutic application. Thus, the binding molecules of the invention are capable of binding/are directed to human IL-17A.

An IL-17A binding molecule of the invention binds to human IL-17A (Accession number Q16552 (Swiss-Prot) showing the full-length precursor IL-17A including the signal peptide, SEQ ID NO. 465) and/or cynomolgus monkey IL-17 (Uniprot G7P4U9). Human IL-17A is a homodimer consisting of two 155 amino acid chains. Each polypeptide chain includes a 23 amino acid N-terminal peptide which is cleaved to produce a mature polypeptide of 132 residues. IL-17A binds to and exerts its effects via activation of the IL-17 receptors A and C.

SEQ ID No. 465
MTPGKTSLVSLLLLLSLEAIVKAGITIPRNPGCPNSEDKNFPRTVMV

NLNIHNRNTNTNPKRSSDYYNRSTSPWNLHRNEDPERYPSVIWEAKC

RHLGCINADGNVDYHMNSVPIQQEILVLRREPPHCPNSFRLEKILVS

VGCTCVTPIVHHVA

The terms "IL-17 binding molecule", "IL-17 binding protein" "anti-IL-17 single domain antibody" or "anti-IL-17 antibody" all refer to a molecule capable of binding to the human IL-17A antigen. Thus, as used herein, IL-17 usually refers to IL-17A, unless otherwise stated or unless the context directs otherwise. The binding reaction may be shown by standard methods (qualitative assays) including, for example, a binding assay, competition assay or a bioassay for determining the inhibition of IL-17 binding to its receptor or any kind of binding assays, with reference to a negative control test in which an antibody of unrelated specificity. The term "IL-17 binding molecule" includes an IL-17 binding protein or a part thereof that is capable of binding human IL-17A.

The invention relates to isolated binding molecules capable of binding to human IL-17A comprising a heavy chain variable immunoglobulin domain ($V_H$) comprising a CDR3 sequence as shown in any of FIGS. 1(A-B) to 5 with reference to tables 1 to 5 or a sequence with at least 60%, 70%, 80%, 90%, 95% or more sequence identity thereto. In one embodiment, the binding molecule comprises a set of CDR1, 2 and 3 sequences selected from the sets of CDR1, 2 and 3 sequences as shown for the any of the clones of any of FIGS. 1(A-B) to 5 with reference to tables 1 to 5. In one embodiment, the binding molecule comprises a $V_H$ domain with a set of CDR1, 2 and 3 sequences selected from the sets of CDR1, 2 and 3 sequences as shown for the any of the clones of any of FIGS. 1(A-B) to 5 with reference to tables 1 to 5. In one embodiment, the binding molecule is a heavy chain only antibody.

In another aspect, the invention relates to an isolated binding molecule comprising at least one immunoglobulin single domain antibody directed against human IL-17A wherein said domain is a $V_H$ domain and wherein said IL-17A binding molecule comprises at least one antigen binding site.

In one embodiment, the binding molecule may comprise at least one immunoglobulin single domain antibody directed against human IL-17A wherein said domain is a $V_H$ domain comprising a CDR3 sequence as shown in any of FIGS. 1(A-B) to 5 with reference to tables 1 to 5 or comprising a CDR3 sequence with at least 60%, 70%, 80%, 90%, 95% or more sequence identity to said CDR sequence.

In one embodiment, said at least one immunoglobulin single domain antibody comprises a set of CDR1, 2 and 3 or a $V_H$ domain with a set of CDR1, 2 and 3 sequences selected from the sets of CDR1, 2 and 3 sequences as shown for any of the clones of any of figures (A-B) 1 to 5 with reference to tables 1 to 5. In another embodiment, the binding molecule comprises or consists of a $V_H$ domain as shown for a clones selected from clones 1.1 to 1.69, 2.1 to 2.9, 3.1 to 3.14, 4.1 or 5.1.

In one embodiment, said sequence homology or identity is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%

"Homology" generally refers to the percentage of amino acid residues in the candidate sequence that are identical with the residues of the polypeptide with which it is compared, after aligning the sequences and in some embodiments after introducing gaps, if necessary, to achieve the maximum percent homology, and not considering any conservative substitutions as part of the sequence identity. Neither N- or C-terminal extensions, tags or insertions shall be construed as reducing identity or homology. Methods and computer programs for the alignment are well known.

The term "antibody", broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. In a full-length antibody, each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity-determining regions (CDR), interspersed with regions that are more conserved, termed framework regions (FR). Each $V_H$ and $V_L$ is composed of three CDRs and four FRs, arranged from amino-terminus to carboxy terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgAI and IgA2) or subclass.

In certain embodiments, the isolated binding molecules of the invention comprise or consist of at least one single domain antibody wherein said domain is a $V_H$ domain. Thus, in one aspect, the binding molecules of the invention comprise or consist of at least one immunoglobulin single variable heavy chain domain antibody (sVD, sdAb or ISV) that has a $V_H$ domain, but is devoid of $V_L$ domains.

Single domain antibodies have been described in the art; they are antibodies whose complementary-determining regions are part of a single domain polypeptide, for example a $V_H$ domain polypeptide.

As further described herein, the binding molecule may comprise two or more $V_H$ domains. Such binding molecules may be monospecific or multispecific, monovalent or multivalent as explained in further detail.

Binding molecules that comprise a single domain antibody wherein said domain is a $V_H$ domain are also termed Humabody® $V_H$.

Thus, in some embodiments of the invention, the binding molecule does not comprise a light chain. In some embodiments, the binding molecule does not comprise heavy chain domains $C_H2$ and $C_H3$. In some embodiments, the binding molecule does not comprise a hinge region and heavy chain domains $C_H2$ and $C_H3$. In some embodiments, the binding molecule does not comprise heavy chain domains $C_H1$, $C_H2$, and $C_H3$. In some embodiments the binding molecule does not comprise heavy chain domain $C_H1$, a hinge region heavy chain domain $C_H2$ and heavy chain domain $C_H3$. In some embodiments the binding molecule does not comprise a light chain, a heavy chain domain $C_H1$, a hinge region heavy chain domain $C_H2$ and heavy chain domain $C_H3$.

Each $V_H$ domain comprises three CDRs and four FRs, arranged from amino terminus to carboxy terminus in the following order: FR1, CDR1, FR2, CDR2, FR3, CDR3, FR4. Modifications to the $V_H$ framework may be made to improve binding properties. For example, the $V_H$ domain may comprise C or N terminal extensions. In one embodiment of the binding molecules of the invention, the $V_H$ domain comprises C terminal extensions of from 1 to 10, for example 1, 2, 3, 4, 5, 6, 7, 8, 9 or 10 additional amino acids. In one embodiment, the $V_H$ domain comprises C terminal extensions of from 1 to 12 amino acid residues, for example 1, 2, 3, 4, 5, 6, 7, 8, 9 or 10 additional amino acids of the $C_H1$ domain. In one embodiment, said extension comprises at least 1 alanine residue, for example a single alanine residue, a pair of alanine residues or a triplet of alanine residues. Such extended $V_H$ domains are within the scope of the invention. Also within the scope of the invention are $V_H$ domains that comprise additional C or N terminal residues, for example linker residues and/or His tags, e.g., hexa-His.

Preferably, the one or more $V_H$ domain is a human $V_H$ domain. As used herein, a human $V_H$ domain includes a $V_H$ domain that is derived from or based on a human $V_H$ domain amino acid or nucleic acid sequence. Thus, the term includes variable heavy chain regions derived from human germline immunoglobulin sequences. As used herein, the term human $V_H$ domain includes $V_H$ domains that are isolated from transgenic mice expressing human immunoglobulin V genes, in particular in response to an immunisation with an antigen of interest. The human $V_H$ domains of the invention may include amino acid residues not encoded by human germline immunoglobulin sequences (e. g., mutations introduced in vitro, e.g. by random or site-specific mutagenesis, or introduced by somatic mutation in vivo). The term "human $V_H$ domain" therefore also includes modified human $V_H$ sequences.

Thus, the invention provides a binding molecule comprising at least one immunoglobulin single domain antibody capable of binding/directed against IL-17A wherein said domain is a human $V_H$ domain and wherein said IL-17A binding molecule comprises at least one antigen binding site. The single domain antibody is specifically directed against human IL-17A.

As used herein, the term $V_H$ or "variable domain" refers to immunoglobulin variable domains defined by Kabat et al., Sequences of Immunological Interest, 5th ed., U.S. Dept. Health & Human Services, Washington, D.C. (1991). The numbering and positioning of CDR amino acid residues within the variable domains is in accordance with the well-known Kabat numbering convention.

More particularly, the invention provides a $V_H$ immunoglobulin domain that can bind to human IL-17 with an affinity, a Kon-rate, a Koff rate, KD and/or KA as further described herein.

The binding molecules of the invention comprise or consist of an amino acid sequence as shown herein and preferred sequences and/or parts thereof, such as CDRs, are defined herein.

The term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" refers to a group of three CDRs that occur in a single variable region capable of binding the antigen. The exact boundaries of these CDRs have been defined differently according to different systems. The system described by Kabat is used herein. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242).

As described in more detail in the experimental part, five parent binding molecules were isolated (resulting in 5 families of clones: clone 1.1 is the parent clone for family 1 as shown in FIG. 1A, clone 2.1 is the parent clone for family 2 as shown in FIG. 2A, clone 3.1 is the parent clone for family 3 as shown in FIG. 3, clone 4.1 is the parent clone for family 4 as shown in FIG. 4 and clone 5.1 is the parent clone for family 5 as shown in FIG. 5); each parent molecule having a set of CDR sequences (CDR1, 2 and 3) as shown in FIGS. 1A-B, 2A-B, 3, 4 and 5. Through a process of optimization, a panel of clones with CDR3 sequences derived from the parent CDR3 sequence was generated for each of family 1, 2, 3, 4 and 5. Optimised $V_H$ domain sequences show improved affinities to IL-17A and improved potencies in the IL-17 cell-based assay compared to the parent molecule as shown in the examples.

In one aspect, the invention relates to a binding molecule capable of binding human IL-17A comprising a human $V_H$ domain comprising a family-1 or family-1 like sequence.

In one embodiment, the binding molecule comprises or consists of at least one immunoglobulin single domain antibody capable of binding/directed against IL-17A, preferably human IL-17A, wherein said domain is a human $V_H$ domain and wherein said IL-17A binding molecule comprises a family-1 or family 1-like sequence. These include the sequence of the parent clone (clone 1.1, SEQ ID NO. 4) or a part thereof, for example a CDR3 sequence, and sequences of clones that are derived from the parent clone 1.1 through a process of optimization, for example sequences as shown as shown in FIG. 1A-B. CDR sequences, or parts thereof and full length $V_H$ sequences of clones in family 1 are numbered according to table 1 as shown below.

TABLE 1

This shows SEQ ID NOs. of family 1 CDR amino acid sequences and of family 1 full length $V_H$ sequences that are within the scope of the invention. Corresponding sequences are shown in FIG. 1A-B.

| Clone | CDR1 SEQ ID NO. | CDR2 SEQ ID NO. | CDR3 SEQ ID NO. | Full length $V_H$ sequence SEQ ID NO. |
|---|---|---|---|---|
| 1.1 | SEQ ID NO. 1 | SEQ ID NO. 2 | SEQ ID NO. 3 | SEQ ID NO. 4 |
| 1.2 | SEQ ID NO. 5 | SEQ ID NO. 6 | SEQ ID NO. 7 | SEQ ID NO. 8 |
| 1.3 | SEQ ID NO. 9 | SEQ ID NO. 10 | SEQ ID NO. 11 | SEQ ID NO. 12 |
| 1.4 | SEQ ID NO. 13 | SEQ ID NO. 14 | SEQ ID NO. 15 | SEQ ID NO. 16 |
| 1.5 | SEQ ID NO. 17 | SEQ ID NO. 18 | SEQ ID NO. 19 | SEQ ID NO. 20 |
| 1.6 | SEQ ID NO. 21 | SEQ ID NO. 22 | SEQ ID NO. 23 | SEQ ID NO. 24 |
| 1.7 | SEQ ID NO. 25 | SEQ ID NO. 26 | SEQ ID NO. 27 | SEQ ID NO. 28 |
| 1.8 | SEQ ID NO. 29 | SEQ ID NO. 30 | SEQ ID NO. 31 | SEQ ID NO. 32 |
| 1.9 | SEQ ID NO. 33 | SEQ ID NO. 34 | SEQ ID NO. 35 | SEQ ID NO. 36 |
| 1.10 | SEQ ID NO. 37 | SEQ ID NO. 38 | SEQ ID NO. 39 | SEQ ID NO. 40 |
| 1.11 | SEQ ID NO. 41 | SEQ ID NO. 42 | SEQ ID NO. 43 | SEQ ID NO. 44 |
| 1.12 | SEQ ID NO. 45 | SEQ ID NO. 46 | SEQ ID NO. 47 | SEQ ID NO. 48 |
| 1.13 | SEQ ID NO. 49 | SEQ ID NO. 50 | SEQ ID NO. 51 | SEQ ID NO. 52 |
| 1.14 | SEQ ID NO. 53 | SEQ ID NO. 54 | SEQ ID NO. 55 | SEQ ID NO. 56 |
| 1.15 | SEQ ID NO. 57 | SEQ ID NO. 58 | SEQ ID NO. 59 | SEQ ID NO. 60 |
| 1.16 | SEQ ID NO. 61 | SEQ ID NO. 62 | SEQ ID NO. 63 | SEQ ID NO. 64 |
| 1.17 | SEQ ID NO. 65 | SEQ ID NO. 66 | SEQ ID NO. 67 | SEQ ID NO. 68 |
| 1.18 | SEQ ID NO. 69 | SEQ ID NO. 70 | SEQ ID NO. 71 | SEQ ID NO. 72 |
| 1.19 | SEQ ID NO. 73 | SEQ ID NO. 74 | SEQ ID NO. 75 | SEQ ID NO. 76 |
| 1.20 | SEQ ID NO. 77 | SEQ ID NO. 78 | SEQ ID NO. 79 | SEQ ID NO. 80 |
| 1.21 | SEQ ID NO. 81 | SEQ ID NO. 82 | SEQ ID NO. 83 | SEQ ID NO. 84 |
| 1.22 | SEQ ID NO. 85 | SEQ ID NO. 86 | SEQ ID NO. 87 | SEQ ID NO. 88 |
| 1.23 | SEQ ID NO. 89 | SEQ ID NO. 90 | SEQ ID NO. 91 | SEQ ID NO. 92 |
| 1.24 | SEQ ID NO. 93 | SEQ ID NO. 94 | SEQ ID NO. 95 | SEQ ID NO. 96 |
| 1.25 | SEQ ID NO. 97 | SEQ ID NO. 98 | SEQ ID NO. 99 | SEQ ID NO. 100 |
| 1.26 | SEQ ID NO. 101 | SEQ ID NO. 102 | SEQ ID NO. 103 | SEQ ID NO. 104 |
| 1.27 | SEQ ID NO. 105 | SEQ ID NO. 106 | SEQ ID NO. 107 | SEQ ID NO. 108 |
| 1.28 | SEQ ID NO. 109 | SEQ ID NO. 110 | SEQ ID NO. 111 | SEQ ID NO. 112 |
| 1.29 | SEQ ID NO. 113 | SEQ ID NO. 114 | SEQ ID NO. 115 | SEQ ID NO. 116 |
| 1.30 | SEQ ID NO. 117 | SEQ ID NO. 118 | SEQ ID NO. 119 | SEQ ID NO. 120 |
| 1.31 | SEQ ID NO. 121 | SEQ ID NO. 122 | SEQ ID NO. 123 | SEQ ID NO. 124 |
| 1.32 | SEQ ID NO. 125 | SEQ ID NO. 126 | SEQ ID NO. 127 | SEQ ID NO. 128 |
| 1.33 | SEQ ID NO. 129 | SEQ ID NO. 130 | SEQ ID NO. 131 | SEQ ID NO. 132 |
| 1.34 | SEQ ID NO. 133 | SEQ ID NO. 134 | SEQ ID NO. 135 | SEQ ID NO. 136 |
| 1.35 | SEQ ID NO. 137 | SEQ ID NO. 138 | SEQ ID NO. 139 | SEQ ID NO. 140 |
| 1.36 | SEQ ID NO. 141 | SEQ ID NO. 142 | SEQ ID NO. 143 | SEQ ID NO. 144 |
| 1.37 | SEQ ID NO. 145 | SEQ ID NO. 146 | SEQ ID NO. 147 | SEQ ID NO. 148 |
| 1.38 | SEQ ID NO. 149 | SEQ ID NO. 150 | SEQ ID NO. 151 | SEQ ID NO. 152 |
| 1.39 | SEQ ID NO. 153 | SEQ ID NO. 154 | SEQ ID NO. 155 | SEQ ID NO. 156 |
| 1.40 | SEQ ID NO. 157 | SEQ ID NO. 158 | SEQ ID NO. 159 | SEQ ID NO. 160 |
| 1.41 | SEQ ID NO. 161 | SEQ ID NO. 162 | SEQ ID NO. 163 | SEQ ID NO. 164 |
| 1.42 | SEQ ID NO. 165 | SEQ ID NO. 166 | SEQ ID NO. 167 | SEQ ID NO. 168 |
| 1.43 | SEQ ID NO. 169 | SEQ ID NO. 170 | SEQ ID NO. 171 | SEQ ID NO. 172 |
| 1.44 | SEQ ID NO. 173 | SEQ ID NO. 174 | SEQ ID NO. 175 | SEQ ID NO. 176 |
| 1.45 | SEQ ID NO. 177 | SEQ ID NO. 178 | SEQ ID NO. 179 | SEQ ID NO. 180 |
| 1.46 | SEQ ID NO. 181 | SEQ ID NO. 182 | SEQ ID NO. 183 | SEQ ID NO. 184 |
| 1.47 | SEQ ID NO. 185 | SEQ ID NO. 186 | SEQ ID NO. 187 | SEQ ID NO. 188 |
| 1.48 | SEQ ID NO. 189 | SEQ ID NO. 190 | SEQ ID NO. 191 | SEQ ID NO. 192 |
| 1.49 | SEQ ID NO. 193 | SEQ ID NO. 194 | SEQ ID NO. 195 | SEQ ID NO. 196 |
| 1.50 | SEQ ID NO. 197 | SEQ ID NO. 198 | SEQ ID NO. 199 | SEQ ID NO. 200 |
| 1.51 | SEQ ID NO. 201 | SEQ ID NO. 202 | SEQ ID NO. 203 | SEQ ID NO. 204 |
| 1.52 | SEQ ID NO. 205 | SEQ ID NO. 206 | SEQ ID NO. 207 | SEQ ID NO. 208 |
| 1.53 | SEQ ID NO. 209 | SEQ ID NO. 210 | SEQ ID NO. 211 | SEQ ID NO. 212 |
| 1.54 | SEQ ID NO. 213 | SEQ ID NO. 214 | SEQ ID NO. 215 | SEQ ID NO. 216 |
| 1.55 | SEQ ID NO. 217 | SEQ ID NO. 218 | SEQ ID NO. 219 | SEQ ID NO. 220 |
| 1.56 | SEQ ID NO. 221 | SEQ ID NO. 222 | SEQ ID NO. 223 | SEQ ID NO. 224 |
| 1.57 | SEQ ID NO. 225 | SEQ ID NO. 226 | SEQ ID NO. 227 | SEQ ID NO. 228 |
| 1.58 | SEQ ID NO. 229 | SEQ ID NO. 230 | SEQ ID NO. 231 | SEQ ID NO. 232 |
| 1.59 | SEQ ID NO. 233 | SEQ ID NO. 234 | SEQ ID NO. 235 | SEQ ID NO. 236 |
| 1.60 | SEQ ID NO. 237 | SEQ ID NO. 238 | SEQ ID NO. 239 | SEQ ID NO. 240 |
| 1.61 | SEQ ID NO. 241 | SEQ ID NO. 242 | SEQ ID NO. 243 | SEQ ID NO. 244 |
| 1.62 | SEQ ID NO. 245 | SEQ ID NO. 246 | SEQ ID NO. 247 | SEQ ID NO. 248 |
| 1.63 | SEQ ID NO. 438 | SEQ ID NO. 439 | SEQ ID NO. 440 | SEQ ID NO. 441 |

TABLE 1-continued

This shows SEQ ID NOs. of family 1 CDR amino acid sequences and of family 1 full length V$_H$ sequences that are within the scope of the invention. Corresponding sequences are shown in FIG. 1A-B.

| Clone | CDR1 SEQ ID NO. | CDR2 SEQ ID NO. | CDR3 SEQ ID NO. | Full length V$_H$ sequence SEQ ID NO. |
|---|---|---|---|---|
| 1.64 | SEQ ID NO. 442 | SEQ ID NO. 443 | SEQ ID NO. 444 | SEQ ID NO. 445 |
| 1.65 | SEQ ID NO. 446 | SEQ ID NO. 447 | SEQ ID NO. 448 | SEQ ID NO. 449 |
| 1.66 | SEQ ID NO. 450 | SEQ ID NO. 451 | SEQ ID NO. 452 | SEQ ID NO. 453 |
| 1.67 | SEQ ID NO. 454 | SEQ ID NO. 455 | SEQ ID NO. 456 | SEQ ID NO. 457 |
| 1.68 | SEQ ID NO. 458 | SEQ ID NO. 459 | SEQ ID NO. 460 | SEQ ID NO. 461 |
| 1.69 | SEQ ID NO. 462 | SEQ ID NO. 463 | SEQ ID NO. 464 | SEQ ID NO. 466 |

In one aspect, the invention relates to a family 1 or family 1-like binding molecule comprising a human V$_H$ domain comprising a CDR3 sequence comprising SEQ ID NO. 3 or a sequence having at least 70%, at least 80%, at least 90%, or at least 95% homology to SEQ ID NO. 3.

In one embodiment, the family 1 or family-1 like binding molecule comprises at least one immunoglobulin single domain antibody directed against IL-17A wherein said domain is a human V$_H$ domain and wherein said human V$_H$ domain comprises at least one antigen binding site comprising a CDR3 sequence comprising SEQ ID NO. 3 or a sequence having at least 70%, at least 80%, at least 90%, or at least 95% homology to SEQ ID NO. 3.

In one embodiment of the aspects, homology is at least 90% homology to SEQ ID NO. 3.

In one embodiment, the V$_H$ domain comprises a CDR3 sequence comprising or consisting of an amino acid sequence selected from SEQ ID NO. 3, 7, 11, 15, 19, 23, 27, 31, 35, 39, 43, 47, 51, 55, 59, 63, 67, 71, 75, 79, 83, 87, 91, 95, 99, 103, 107, 111, 115, 119, 123, 127, 131, 135, 139, 143, 147, 151, 155, 159, 163, 167, 171, 175, 179, 183, 187, 191, 195, 199, 203, 207, 211, 215, 219, 223, 227, 231, 235, 239, 243 or 247, 440, 444, 448, 452, 456, 460 or 464.

In one embodiment, the family 1 or family 1-like binding molecule comprises at least one antigen binding site comprising CDR1, CDR2 and CDR3, said CDR1 comprising the amino acid sequence SEQ ID NO. 1 or a sequence with at least 70%, at least 80%, at least 90%, or at least 95% homology thereto, said CDR2 comprising the amino acid sequence SEQ ID NO. 2 or a sequence with at least 70%, at least 80%, at least 90%, or at least 95% homology thereto, and said CDR3 comprising the amino acid sequence SEQ ID NO. 3 or a sequence with at least 70%, at least 80%, at least 90%, or at least 95% homology thereto. For example, the CDR sequence may be a CDR sequence selected from one of the sequences shown in FIG. 1A-B.

In one embodiment, said CDR1 comprises or consists of the amino acid sequence as shown in SEQ ID NO. 1 or a sequence with at least 80%, 81%, 82%, 83%, 84%, 85%, 86%, 87%, 88%, 89%, 90%, 91%, 92%, 93%, 94%, 95%, 96%, 97%, 98%, 99% homology thereto. In one embodiment, said CDR2 comprises or consists of the amino acid sequence as shown in SEQ ID NO. 2 or a sequence with at least 80%, 81%, 82%, 83%, 84%, 85%, 87%, 88%, 89%, 90%, 91%, 92%, 93%, 94%, 95%, 96%, 97%, 98%, 99% homology thereto. In one embodiment, said CDR3 comprises or consists of the amino acid sequence as shown in SEQ ID NO. 3 or a sequence with at least 80%, 81%, 82%, 83%, 84%, 85%, 86% 87%, 88%, 89%, 90%, 91%, 92%, 93%, 94%, 95%, 96%, 97%, 98% or 99% homology thereto.

In one embodiment, the CDR sequences of the V$_H$ domain are as shown for clones 1.1 to 1.69 as in FIG. 1A-B or combinations thereof. In one embodiment, CDR1 comprises or consists of the amino acid sequence SEQ ID NO. 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 141, 145, 149, 153, 157, 161, 165, 169, 173, 177, 181, 185, 189, 193, 197, 201, 205, 209, 213, 217, 221, 225, 229, 233, 237, 241, 245, 438, 442, 446, 450, 454, 458 or 462, CDR2 comprises or consists of the amino acid sequence SEQ ID NO. 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158, 162, 166, 170, 174, 178, 182, 186, 190, 194, 198, 202, 206, 210, 214, 218, 222, 226, 230, 234, 238, 242, 246, 439, 443, 447, 451, 455, 459 or 463 and CDR3 comprises or consists of the amino acid sequence SEQ ID NO. 3, 7, 11, 15, 19, 23, 27, 31, 35, 39, 43, 47, 51, 55, 59, 63, 67, 71, 75, 79, 83, 87, 91, 95, 99, 103, 107, 111, 115, 119, 123, 127, 131, 135, 139, 143, 147, 151, 155, 159, 163, 167, 171, 175, 179, 183, 187, 191, 195, 199, 203, 207, 211, 215, 219, 223, 227, 231, 235, 239, 243, 247 440, 444, 448, 452, 456, 460 or 464.

In one embodiment, CDR1 comprises or consists of the amino acid sequence SEQ ID NO. 1, CDR2 comprises or consists of the amino acid sequence SEQ ID NO. 2 and CDR3 comprises or consists of the amino acid sequence SEQ ID NO. 3.

In one aspect, the invention also relates to a V$_H$ domain which has combinations of CDR1, CDR2 and CDR3 as shown for clones 1.1 to 1.69 in FIG. 1A-B. In one embodiment, the binding molecule has a combination of CDR1, CDR2 and CDR3 as shown for clones 1.1 to 1.22 in FIG. 1A. Thus, in one embodiment, the binding molecule comprises CDR1, 2 and 3 sequences wherein CDR1 is SEQ ID NO. 1, CDR2 is SEQ ID NO. 2 and CDR3 is SEQ ID NO. 3. In another embodiment, the binding molecule comprises CDR1, 2 and 3 sequences wherein CDR1 is SEQ ID NO. 5, CDR2 is SEQ ID NO. 6 and CDR3 is SEQ ID NO. 7. In another embodiment, the binding molecule comprises CDR1, 2 and 3 sequences wherein CDR1 is SEQ ID NO. 9, CDR2 is SEQ ID NO. 10 and CDR3 is SEQ ID NO. 11. In another embodiment, the binding molecule comprises CDR1, 2 and 3 sequences wherein CDR1 is SEQ ID NO. 13, CDR2 is SEQ ID NO. 14 and CDR3 is SEQ ID NO. 15. In another embodiment, the binding molecule comprises CDR1, 2 and 3 sequences wherein CDR1 is SEQ ID NO. 17, CDR2 is SEQ ID NO. 18 and CDR3 is SEQ ID NO. 19. In another embodiment, the binding molecule comprises CDR1, 2 and 3 sequences wherein CDR1 is SEQ ID NO. 21, CDR2 is SEQ ID NO. 22 and CDR3 is SEQ ID NO. 23. In another embodiment, the binding molecule comprises CDR1, 2 and 3 sequences wherein CDR1 is SEQ ID NO. 25, CDR2 is SEQ ID NO. 26 and CDR3 is SEQ ID NO. 27. In another embodiment, the binding molecule comprises CDR1, 2 and 3 sequences wherein CDR1 is SEQ ID NO. 29, CDR2 is SEQ ID NO. 30 and CDR3 is SEQ ID NO. 31. In another embodiment, the binding molecule comprises CDR1, 2 and 3 sequences wherein CDR1 is SEQ ID NO. 33, CDR2 is SEQ ID NO. 34 and CDR3 is SEQ ID NO. 35. In another embodiment, the binding molecule comprises CDR1, 2 and 3 sequences wherein CDR1 is SEQ ID NO. 37, CDR2 is SEQ ID NO. 38 and CDR3 is SEQ ID NO. 39. In another embodiment, CDR1 is SEQ ID NO. 41, CDR2 is SEQ ID NO. 42 and CDR3 is SEQ ID NO. 43. In another embodiment, the binding molecule comprises CDR1, 2 and 3 sequences wherein CDR1 is SEQ ID NO. 45, CDR2 is SEQ ID NO. 46 and CDR3 is SEQ ID NO. 47. In another embodiment, the binding molecule comprises CDR1, 2 and 3 sequences wherein CDR1 is SEQ ID NO. 49, CDR2 is SEQ ID NO. 50 and CDR3 is SEQ ID NO. 51. In another embodiment, the binding molecule comprises CDR1, 2 and 3 sequences wherein CDR1 is SEQ ID NO. 53, CDR2 is SEQ ID NO. 54 and CDR3 is SEQ ID NO. 55. In another embodiment, the binding molecule comprises CDR1, 2 and 3 sequences wherein CDR1 is SEQ ID NO. 57, CDR2 is SEQ ID NO. 58 and CDR3 is SEQ ID NO. 59. In another embodiment, the binding molecule comprises CDR1, 2 and 3 sequences wherein CDR1 is SEQ ID NO. 61, CDR2 is SEQ ID NO. 62 and CDR3 is SEQ ID NO. 63. In another embodiment, the binding molecule comprises CDR1, 2 and 3 sequences wherein CDR1 is SEQ ID NO. 65, CDR2 is SEQ ID NO. 66 and CDR3 is SEQ ID NO. 67. In another embodiment, the binding molecule comprises CDR1, 2 and 3 sequences wherein CDR1 is SEQ ID NO. 69, CDR2 is SEQ ID NO. 70 and CDR3 is SEQ ID NO. 71. In another embodiment, the binding molecule comprises CDR1, 2 and 3 sequences wherein CDR1 is SEQ ID NO. 73, CDR2 is SEQ ID NO. 74 and CDR3 is SEQ ID NO. 75. In another embodiment, the binding molecule comprises CDR1, 2 and 3 sequences wherein CDR1 is SEQ ID NO. 77, CDR2 is SEQ ID NO. 78 and CDR3 is SEQ ID NO. 79. In another embodiment, the binding molecule comprises CDR1, 2 and 3 sequences wherein CDR1 is SEQ ID NO. 81, CDR2 is SEQ ID NO. 82 and CDR3 is SEQ ID NO. 83. In another embodiment, the binding molecule comprises CDR1, 2 and 3 sequences wherein CDR1 is SEQ ID NO. 85, CDR2 is SEQ ID NO. 86 and CDR3 is SEQ ID NO. 87.

In one embodiment, the family 1 or family 1-like sequence has a $V_H$ domain that comprises or consists of SEQ ID NO. 4 or a sequence with at least 40%, 50%, 60%, 70%, 80%, 81%, 82%, 83%, 84%, 85%, 86%, 87%, 88%, 89%, 90%, 91%, 92%, 93%, 94%, 96%, 97%, 98%, 99% homology thereto. In one embodiment, homology is at least 70%, 80%, 81%, 82%, 83%, 84%, 85%, 87%, 88%, 89%, 90%, 91%, 92%, 93%, 94%, 95%, 96%, 97%, 98% or 99%. CDR sequences of such $V_H$ sequences are shown in FIG. 1A-B. For example, the $V_H$ domain comprises or consists of SEQ ID NO. 4, 8, 12, 16, 20, 24, 28, 32, 36, 40, 44, 48, 52, 56, 60, 64, 68, 72, 76, 80, 84, 88, 92, 96, 100, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244 or 248, 441, 445, 449, 453, 457, 461 or 466.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences. In one embodiment, the $V_H$ domain comprises or consists of SEQ ID NO. 4 or 8 or a sequence which comprises one or more amino acid substitutions, for example 1, 2, 3, 4, 5, 6, 7, 8, 9 or 10 amino acid substitutions.

In another aspect, the invention relates to a binding molecule comprising or consisting of at least one immunoglobulin single domain antibody directed against IL-17A wherein said domain is a human $V_H$ domain and wherein said $V_H$ domain comprises or consists of SEQ ID NO. 4, 8, 12, 16, 20, 24, 28, 32, 36, 40, 44, 48, 52, 56, 60, 64, 68, 72, 76, 80, 84, 88, 92, 96, 100, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244, 248, 441, 445, 449, 453, 457, 461 or 466 or a sequence with at least 40%, 50%, 60%, 70%, 80%, 81%, 82%, 83%, 84%, 85%, 87%, 88%, 89%, 90%, 91%, 92%, 93%, 94%, 96%, 97%, 98% or 99% homology thereto.

In another aspect, the invention relates to a binding molecule comprising or consisting of a $V_H$ domain as shown in SEQ ID NO. 4 or a variant thereof which has the following substitutions compared to SEQ ID NO. 4: residue 1 is Q, residue 11 is M or W, residue 13 is L or R, residue 24 is T, residue 33 is G, R, N or Q, residue 50 is, E, K, S, N, G or R, residue 52 is K, E, G, D or R, residue 53 is P, residue 54 is T, residue 57 is Q, E or K, residue 61 is A, residue 62 is S or G, residue 77 is K, and/or residue 13 is Y.

The family 1 or family 1-like binding molecules preferably have KD, Koff, KA, Kd and $IC_{50}$ values as further described herein and as shown in the examples and further set out below.

The term "KD" refers to the "equilibrium dissociation constant" and refers to the value obtained in a titration measurement at equilibrium, or by dividing the dissociation rate constant (Koff) by the association rate constant (Kon). "KA" refers to the affinity constant.

The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used.

In one aspect, the invention relates to a binding molecule capable of binding human IL-17A comprising a human $V_H$ domain comprising a family 2 or family-2 like sequence.

In one embodiment, the binding molecule comprises or consists of at least one immunoglobulin single domain antibody directed against IL-17A, preferably human IL-17A, wherein said domain is a human $V_H$ domain and wherein said IL-17A binding molecule comprises a family 2 or family 2-like sequence. These include the parent sequence (clone 2.1; SEQ ID NO.252) or a part thereof and sequences of clones that are derived from the parent clone (clone 2.1) or a part thereof, for example a CDR3 sequence, and to $V_H$ sequences of clones or parts thereof that are derived from the parent clone 2.1 through a process of optimization, for example as shown in FIG. 2A-B. CDR sequences and full length sequences of clones in family 2 are numbered according to table 2 as shown below.

TABLE 2

This shows SEQ ID NOs of family 2 CDR sequences and of family 2 full length V$_H$ sequences that are within the scope of the invention. Corresponding sequences are shown in FIG. 2A-B.

| Clone | CDR1 SEQ ID NO. | CDR2 SEQ ID NO. | CDR3 SEQ ID NO. | Full V$_H$ length sequence SEQ ID NO. |
|---|---|---|---|---|
| 2.1 | SEQ ID NO. 249 | SEQ ID NO. 250 | SEQ ID NO. 251 | SEQ ID NO. 252 |
| 2.2 | SEQ ID NO. 253 | SEQ ID NO. 254 | SEQ ID NO. 255 | SEQ ID NO. 256 |
| 2.3 | SEQ ID NO. 257 | SEQ ID NO. 258 | SEQ ID NO. 259 | SEQ ID NO. 260 |
| 2.4 | SEQ ID NO. 261 | SEQ ID NO. 262 | SEQ ID NO. 263 | SEQ ID NO. 264 |
| 2.5 | SEQ ID NO. 265 | SEQ ID NO. 266 | SEQ ID NO. 267 | SEQ ID NO. 268 |
| 2.6 | SEQ ID NO. 269 | SEQ ID NO. 270 | SEQ ID NO. 271 | SEQ ID NO. 272 |
| 2.7 | SEQ ID NO. 273 | SEQ ID NO. 274 | SEQ ID NO. 275 | SEQ ID NO. 276 |
| 2.8 | SEQ ID NO. 277 | SEQ ID NO. 278 | SEQ ID NO. 279 | SEQ ID NO. 280 |
| 2.9 | SEQ ID NO. 281 | SEQ ID NO. 282 | SEQ ID NO. 283 | SEQ ID NO. 284 |

In one aspect, the invention relates to a family 2 or family 2-like binding molecule comprising a human V$_H$ domain comprising a CDR3 sequence comprising SEQ ID NO. 251 or a sequence having at least 70%, at least 80%, at least 90%, or at least 95% homology to SEQ ID NO. 251.

In one embodiment, the family 2 or family-2 like binding molecule comprises at least one immunoglobulin single domain antibody directed against IL-17A wherein said domain is a human V$_H$ domain and wherein said human V$_H$ domain comprises at least one antigen binding site comprising a CDR3 sequence comprising SEQ ID NO. 251 or a sequence having at least 70%, at least 80%, at least 90%, or at least 95% homology to SEQ ID NO. 251.

In one embodiment of these aspects, homology is at least 90%.

In one embodiment, the V$_H$ domain comprises or consists of a CDR3 selected from SEQ ID NO. 251, 255, 259, 263, 267, 271, 275, 279 or 283.

In one embodiment, the family 2 or family 2-like sequence comprises a binding molecule comprising or consisting of at least one immunoglobulin single domain antibody directed against IL-17 wherein said domain is a human V$_H$ domain and wherein said IL-17 binding molecule comprises at least one antigen binding site comprising CDR1, CDR2 and CDR3, said CDR1 comprises or consists of the amino acid sequence SEQ ID NO. 249 or a sequence with at least 60%, at least 70%, at least 80%, at least 90%, or at least 95% homology thereto, said CDR2 comprises or consists of the amino acid sequence SEQ ID NO. 250 or a sequence with at least 70%, at least 80%, at least 90%, or at least 95% homology thereto, and said CDR3 comprises or consists of the amino acid sequence SEQ ID NO. 251 or a sequence with at least 70%, at least 80%, at least 90%, or at least 95% homology thereto.

In one embodiment, said CDR1 comprises or consists of the amino acid sequence SEQ ID NO. 249 or a sequence with at least 80%, 81%, 82%, 83%, 84%, 85%, 86%, 87%, 88%, 89%, 90%, 91%, 92%, 93%, 94%, 96%, 97%, 98% or 99% homology thereto. In one embodiment, said CDR2 comprises or consists of the amino acid sequence SEQ ID NO. 250 or a sequence with at least 80%, 81%, 82%, 83%, 84%, 85%, 87%, 88%, 89%, 90%, 91%, 92%, 93%, 94%, 95%, 96%, 97%, 98%, 99% homology thereto. In one embodiment, said CDR3 comprises or consists of the amino acid sequence SEQ ID NO. 251 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In embodiment, the CDR sequences of the V$_H$ domain are as shown for clones 2.1 to 2.9 as in FIG. 2A-B or combinations thereof. In one embodiment, CDR1 comprises or consists of the amino acid sequence SEQ ID NO. 249, 253, 257, 261, 265, 269, 273, 277 or 281, CDR2 comprises or consists of the amino acid sequence SEQ ID NO. 250, 254, 258, 262, 266, 270, 274, 278 or 282 and CDR3 comprises or consists of the amino acid sequence SEQ ID NO. 251, 255, 259, 263, 267, 271, 275, 279 or 283.

In one aspect, the invention relates to a V$_H$ domain which has combinations of CDR1, CDR2 and CDR3 as shown for 2.1 to 2.9 in FIG. 2A-B. Thus, in one embodiment, the binding molecule comprises CDR1, 2 and 3 sequences wherein CDR1 is SEQ ID NO. 249, CDR2 is SEQ ID NO. 250 and CDR3 is SEQ ID NO. 251. In one embodiment, the binding molecule comprises CDR1, 2 and 3 sequences wherein CDR1 is SEQ ID NO. 253, CDR2 is SEQ ID NO. 254 and CDR3 is SEQ ID NO. 255. Thus, in one embodiment, the binding molecule comprises CDR1, 2 and 3 sequences wherein CDR1 is SEQ ID NO. 257, CDR2 is SEQ ID NO. 258 and CDR3 is SEQ ID NO. 259. In one embodiment, the binding molecule comprises CDR1, 2 and 3 sequences wherein CDR1 is SEQ ID NO. 261, CDR2 is SEQ ID NO. 262 and CDR3 is SEQ ID NO. 263. In one embodiment, the binding molecule comprises CDR1, 2 and 3 sequences wherein CDR1 is SEQ ID NO. 265, CDR2 is SEQ ID NO. 266 and CDR3 is SEQ ID NO. 267. In one embodiment, the binding molecule comprises CDR1, 2 and 3 sequences wherein CDR1 is SEQ ID NO. 269, CDR2 is SEQ ID NO. 270 and CDR3 is SEQ ID NO. 271. In one embodiment, the binding molecule comprises CDR1, 2 and 3 sequences wherein CDR1 is SEQ ID NO. 273, CDR2 is SEQ ID NO. 274 and CDR3 is SEQ ID NO. 275. In one embodiment, the binding molecule comprises CDR1, 2 and 3 sequences wherein CDR1 is SEQ ID NO. 277, CDR2 is SEQ ID NO. 278 and CDR3 is SEQ ID NO. 279. In one embodiment, the binding molecule comprises CDR1, 2 and 3 sequences wherein CDR1 is SEQ ID NO. 281, CDR2 is SEQ ID NO. 282 and CDR3 is SEQ ID NO. 283.

In one embodiment, the family 2 or family 2-like sequence has a V$_H$ domain that comprises or consists of SEQ ID NO. 252 or a sequence with at least 40%, 50%, 60%, 70%, 80%, 81%, 82%, 83%, 84%, 85%, 87%, 86%, 88%, 89%, 90%, 91%, 92%, 93%, 94%, 96%, 97%, 98% or 99% homology thereto. In one embodiment, homology is at least 70%, 80%, 81%, 82%, 83%, 84%, 85%, 87%, 88%, 89%, 90%, 91%, 92%, 93%, 94%, 95%, 96%, 97%, 98% or 99%. CDR sequences of such sequences are shown in FIG. 2A-B. For example, the V$_H$ domain comprises or consists of SEQ ID NO. 252, 256, 260, 264, 268, 272, 276, 280 or 284.

In one embodiment, the family 2 or family 2-like sequence has a V$_H$ domain that comprises or consists of SEQ ID NO. 252, 256, 260, 264, 268, 272, 276, 280 or 284, or a sequence with at least 70%, 80%, 81%, 82%, 83%, 84%, 85%, 87%, 88%, 89%, 90%, 91%, 92%, 93%, 94%, 96%, 97%, 98%, 99% homology thereto. CDR sequences of such sequences are listed below.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences. In one embodiment, the $V_H$ domain comprises or consists of SEQ ID NO. 252 or a sequence which comprises one or more amino acid substitutions, for example 1, 2, 3, 4, 5, 6, 7, 8, 9 or 10 amino acid substitutions.

In another aspect, the invention relates to a binding molecule comprising or consisting of a $V_H$ domain as shown in SEQ ID NO. 252 or a variant thereof which has the following substitutions compared to SEQ ID NO. 252 residue 1 is Q, 31 is A or G, residue is W, residue 43 is A, residue 50 is N, residue 77 is N and/or residue 78 is A.

The family 2 or family 2-like binding molecules have KD, Koff, KA, Kd and $IC_{50}$ values as further described herein and as shown in the examples and further discussed below.

In one aspect, the invention relates to a binding molecule capable of binding human IL-17A comprising a human $V_H$ domain comprising a family 3 or family-3 like sequence.

In one embodiment, the binding molecule comprises or consists of at least one immunoglobulin single domain antibody directed against IL-17, preferably human IL-17, wherein said domain is a human $V_H$ domain and wherein said IL-17 binding molecule comprises a family 3 or family 3-like sequence. These include the parent clone sequence (SEQ ID NO. 288) or a part thereof and sequences of clones that are derived from the parent clone 3.1 or a part thereof, for example a CDR3 sequence, and to $V_H$ sequences of clones or parts thereof that are derived from the parent clone 3.1 through a process of optimization, for example as shown in FIG. 3. CDR sequences and full length sequences of clones in family 3 are numbered according to table 3 as shown below.

In one aspect, the invention relates to a family 3 or family 3-like binding molecule comprises a human $V_H$ domain comprising a CDR3 sequence comprising SEQ ID NO. 287 or a sequence having at least 70%, at least 80%, at least 90%, or at least 95% homology to SEQ ID NO. 287.

In one embodiment, the family 3 or family-3 like binding molecule comprises at least one immunoglobulin single domain antibody directed against IL-17A wherein said domain is a human $V_H$ domain and wherein said human $V_H$ domain comprises at least one antigen binding site comprising a CDR3 sequence comprising SEQ ID NO. 287 or a sequence having at least 70%, at least 80%, at least 90%, or at least 95% homology to SEQ ID NO. 287.

In one embodiment of these aspects, homology is at least 90%.

In one aspect, the CDR3 sequence comprises or consists of an amino acid sequence selected from SEQ ID NO. 287, 291, 295, 299, 303, 307, 311, 315, 319, 323, 327, 335 or 339.

In one embodiment, the family 3 or family 3-like sequence comprises a binding molecule comprising or consisting of at least one immunoglobulin single domain antibody directed against IL-17A wherein said domain is a human $V_H$ domain and wherein said IL-17A binding molecule comprises at least one antigen binding site comprising CDR1, CDR2 and CDR3, said CDR1 comprises or consists of the amino acid sequence SEQ ID NO. 285 or a sequence with at least 40%, at least 50%, at least 60%, at least 70%, at least 80%, at least 90%, at least 95% homology thereto, said CDR2 comprises or consists of the amino acid sequence SEQ ID NO. 286 or a sequence with at least 70%, at least 80%, at least 90%, at least 95% homology thereto, and said CDR3 comprises or consists of the amino acid sequence SEQ ID NO. 287 or a sequence with least 70, at least 80%, at least 90%, at least 95% homology thereto.

In one embodiment, said CDR1 comprises or consists of the amino acid sequence SEQ ID NO. 285 or a sequence with at least 80%, 81%, 82%, 83%, 84%, 85%, 86%, 87%, 88%, 89%, 90%, 91%, 92%, 93%, 94%, 96%, 97%, 98% or 99% homology thereto. In one embodiment, said CDR2 comprises or consists of the amino acid sequence SEQ ID NO. 286 or a sequence with at least 80%, 81%, 82%, 83%, 84%, 85%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 287 or a sequence with at least

TABLE 3

This shows SEQ ID NOs of family 3 CDR sequences and of family 3 full length $V_H$ sequences that are within the scope of the invention. Corresponding sequences are shown in FIG. 3.

| Clone | CDR1 SEQ ID NO. | CDR2 SEQ ID NO. | CDR3 SEQ ID NO. | Full length $V_H$ SEQ ID NO. |
|---|---|---|---|---|
| 3.1 | SEQ ID NO. 285 | SEQ ID NO. 286 | SEQ ID NO. 287 | SEQ ID NO. 288 |
| 3.2 | SEQ ID NO. 289 | SEQ ID NO. 290 | SEQ ID NO. 291 | SEQ ID NO. 292 |
| 3.3 | SEQ ID NO. 293 | SEQ ID NO. 294 | SEQ ID NO. 295 | SEQ ID NO. 296 |
| 3.4 | SEQ ID NO. 297 | SEQ ID NO. 298 | SEQ ID NO. 299 | SEQ ID NO. 300 |
| 3.5 | SEQ ID NO. 301 | SEQ ID NO. 302 | SEQ ID NO. 303 | SEQ ID NO. 304 |
| 3.6 | SEQ ID NO. 305 | SEQ ID NO. 306 | SEQ ID NO. 307 | SEQ ID NO. 308 |
| 3.7 | SEQ ID NO. 309 | SEQ ID NO. 310 | SEQ ID NO. 311 | SEQ ID NO. 312 |
| 3.8 | SEQ ID NO. 313 | SEQ ID NO. 314 | SEQ ID NO. 315 | SEQ ID NO. 316 |
| 3.9 | SEQ ID NO. 317 | SEQ ID NO. 318 | SEQ ID NO. 319 | SEQ ID NO. 320 |
| 3.10 | SEQ ID NO. 321 | SEQ ID NO. 322 | SEQ ID NO. 323 | SEQ ID NO. 324 |
| 3.11 | SEQ ID NO. 325 | SEQ ID NO. 326 | SEQ ID NO. 327 | SEQ ID NO. 328 |
| 3.12 | SEQ ID NO. 329 | SEQ ID NO. 330 | SEQ ID NO. 331 | SEQ ID NO. 332 |
| 3.13 | SEQ ID NO. 333 | SEQ ID NO. 334 | SEQ ID NO. 335 | SEQ ID NO. 366 |
| 3.14 | SEQ ID NO. 337 | SEQ ID NO. 338 | SEQ ID NO. 339 | SEQ ID NO. 340 |

80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, the CDR sequences of the $V_H$ domain are as shown for clones 3.1 to 3.14 as in FIG. 3 or combinations thereof.

In one aspect, the invention relates to a $V_H$ domain which has combinations of CDR1, CDR2 and CDR3 as shown for clones 3.1 to 3.14 in FIG. 3.

In one embodiment, CDR1 comprises or consists of the amino acid sequence SEQ ID NO. 285, 289, 293, 297, 301, 305, 309, 313, 317, 321, 325, 329, 333 or 337, CDR2 comprises or consists of the amino acid sequence 286, 290, 294, 298, 302, 306, 310, 314, 318, 322, 326, 330, 334 or 338 and CDR3 comprises or consists of the amino acid sequence 287, 291, 295, 299, 303, 307, 311, 315, 319, 323, 327, 335 or 339.

In one aspect, the invention relates to a $V_H$ domain which has combinations of CDR1, CDR2 and CDR3 as shown for 3.1 to 3.14 in FIG. 3. Thus, in one embodiment, the binding molecule comprises CDR1, 2 and 3 sequences wherein CDR1 is SEQ ID NO. 285, CDR2 is SEQ ID NO. 286 and CDR3 is SEQ ID NO. 287. In one embodiment, the binding molecule comprises CDR1, 2 and 3 sequences wherein CDR1 is SEQ ID NO. 289, CDR2 is SEQ ID NO. 290 and CDR3 is SEQ ID NO. 291. Thus, in one embodiment, the binding molecule comprises CDR1, 2 and 3 sequences wherein CDR1 is SEQ ID NO. 293, CDR2 is SEQ ID NO. 294 and CDR3 is SEQ ID NO. 295. In one embodiment, the binding molecule comprises CDR1, 2 and 3 sequences wherein CDR1 is SEQ ID NO. 297, CDR2 is SEQ ID NO. 298 and CDR3 is SEQ ID NO. 299. In one embodiment, the binding molecule comprises CDR1, 2 and 3 sequences wherein CDR1 is SEQ ID NO. 301, CDR2 is SEQ ID NO. 302 and CDR3 is SEQ ID NO. 303. In one embodiment, the binding molecule comprises CDR1, 2 and 3 sequences wherein CDR1 is SEQ ID NO. 305, CDR2 is SEQ ID NO. 306 and CDR3 is SEQ ID NO. 307. In one embodiment, the binding molecule comprises CDR1, 2 and 3 sequences wherein CDR1 is SEQ ID NO. 309, CDR2 is SEQ ID NO. 310 and CDR3 is SEQ ID NO. 311. In one embodiment, the binding molecule comprises CDR1, 2 and 3 sequences wherein CDR1 is SEQ ID NO. 313, CDR2 is SEQ ID NO. 314 and CDR3 is SEQ ID NO. 315. In one embodiment, the binding molecule comprises CDR1, 2 and 3 sequences wherein CDR1 is SEQ ID NO. 317, CDR2 is SEQ ID NO. 318 and CDR3 is SEQ ID NO. 319. In one embodiment, the binding molecule comprises CDR1, 2 and 3 sequences wherein CDR1 is SEQ ID NO. 321, CDR2 is SEQ ID NO. 322 and CDR3 is SEQ ID NO. 323. In one embodiment, the binding molecule comprises CDR1, 2 and 3 sequences wherein CDR1 is SEQ ID NO. 325, CDR2 is SEQ ID NO. 326 and CDR3 is SEQ ID NO. 327. In one embodiment, the binding molecule comprises CDR1, 2 and 3 sequences wherein CDR1 is SEQ ID NO. 329, CDR2 is SEQ ID NO. 330 and CDR3 is SEQ ID NO. 331. In one embodiment, the binding molecule comprises CDR1, 2 and 3 sequences wherein CDR1 is SEQ ID NO. 333, CDR2 is SEQ ID NO. 334 and CDR3 is SEQ ID NO. 335. In one embodiment, the binding molecule comprises CDR1, 2 and 3 sequences wherein CDR1 is SEQ ID NO. 337, CDR2 is SEQ ID NO. 338 and CDR3 is SEQ ID NO. 339.

In one embodiment, the family 3 or family 3-like sequence has a $V_H$ domain that comprises or consists of SEQ ID NO. 288 or a sequence with at least 80%, 81%, 82%, 83%, 84%, 85%, 87%, 88%, 89%, 90%, 91%, 92%, 93%, 94%, 96%, 97%, 98% or 99% homology thereto. CDR sequences of such sequences are shown in FIG. 3. For example, $V_H$ domain comprises or consists of SEQ ID NO. 292, 296, 300, 304, 308, 312, 316, 320, 324, 328, 332, 336 or 340.

In one embodiment, the family 3 or family 3-like sequence has a $V_H$ domain that comprises or consists of SEQ ID NO. 288, 292, 296, 300, 304, 308, 312, 316, 320, 324, 328, 332, 336 or 340, or a sequence with at least at least 40%, 50%, 60%, 70%, 80% or 90% homology thereto. In one embodiment, homology is at least 70%, 80%, 81%, 82%, 83%, 84%, 86%, 85%, 87%, 88%, 89%, 90%, 91%, 92%, 93%, 94%, 96%, 97%, 98% or 99%. CDR sequences of such sequences are listed below.

In another embodiment, the $V_H$ domain is selected from one of the sequences above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDR regions. In one embodiment, the amino acid substitutions are in the framework and CDR sequences. In one embodiment, the $V_H$ domain comprises or consists of SEQ ID NO. 288 or a sequence which comprises one or more amino acid substitutions, for example 1, 2, 3, 4, 5, 6, 7, 8, 9 or 10 amino acid substitutions.

In another aspect, the invention relates to a binding molecule comprising or consisting of a $V_H$ domain as shown in SEQ ID NO. 288 or a variant thereof which has the following substitutions compared to SEQ ID NO. 288 residue 23 is A, residue 28 is N, residue 29 is A or L, residue 31 is A or D, residue 33 is H, residue 34 is I or L, residue 35 is N, residue 50 is S, residue 52 is K, residue 55 is T, residue 57 is A or T, residue 58 is K, residue 62 is R, residue 63 is E, residue 65 is E, residue 50 is I or T, residue 99 is L, residue 103 is T, Q, residue 104 is R, F or W, residue 105 is Y, S, or D, residue 106 is P or F, residue 107 is H, N or G, residue 108 is D or S and/or residue 110 is Y or A or W.

The family 3 or family 3-like binding molecules have KD, Koff, KA, Kd and $IC_{50}$ values as further described herein and as shown in the examples.

In one aspect, the invention relates to a binding molecule capable of binding human IL-17A comprising a human $V_H$ domain comprising a family 4 or family-4 like sequence.

In one embodiment, the binding molecule comprises or consists of at least one immunoglobulin single domain antibody directed against IL-17A, preferably human IL-17A, wherein said domain is a human $V_H$ domain and wherein said IL-17A binding molecule comprises a family 4 or family 4-like sequence. These include the parent clone sequence (4.1; SEQ ID NO. 288) as shown in FIG. 4 or a part thereof, for example a CDR3 sequence, and $V_H$ sequences of clones or parts thereof that are derived from the parent clone 4 through a process of optimization, for example as shown in FIG. 4. CDR sequences and full length sequences of clones in family 4 are numbered according to table 4 as shown below.

TABLE 4

Family 4 CDR sequences and $V_H$ sequences that are within the scope of the invention. Corresponding sequences are shown in FIG. 4.

| Clone | CDR1 | CDR2 | CDR3 | Full length |
|---|---|---|---|---|
| 4.1 | SEQ ID NO. 341 | SEQ ID NO. 342 | SEQ ID NO. 343 | SEQ ID NO. 344 |

In aspect, the invention relates to a family 4 or family 4-like binding molecule that comprises a human $V_H$ domain comprising a CDR3 sequence comprising SEQ ID NO. 343 or a sequence having at least 70%, at least 80%, at least 90%, or at least 95% homology to SEQ ID NO. 343.

In one embodiment, the family 4 or family-4 like binding molecule comprises at least one immunoglobulin single domain antibody directed against IL-17A wherein said domain is a human $V_H$ domain and wherein said human $V_H$ domain comprises at least one antigen binding site comprising a CDR3 sequence comprising SEQ ID NO. 343 or a sequence having at least 70%, at least 80%, at least 90%, or at least 95% homology to SEQ ID NO. 343.

In one embodiment, the family 4 or family 4-like sequence comprises a binding molecule comprising or consisting of at least one immunoglobulin single domain antibody directed against IL-17A wherein said domain is a human $V_H$ domain and wherein said IL-17A binding molecule comprises at least one antigen binding site comprising hypervariable regions CDR1, CDR2 and CDR3, said CDR1 comprises or consists of the amino acid sequence SEQ ID NO. 341 or a sequence with at least 70%, at least 80%, at least 90%, at least 95% homology thereto, said CDR2 comprises or consists of the amino acid sequence SEQ ID NO. 342 or a sequence with at least 70%, at least 80%, at least 90%, or at least 95% homology thereto, and said CDR3 comprises or consists of the amino acid sequence SEQ ID NO. 343, or a sequence with at least 80%, at least 90% or at least 95% homology thereto.

In one embodiment, said CDR1 comprises or consists of the amino acid sequence SEQ ID NO. 341 or a sequence with at least 80%, 81%, 82%, 83%, 84%, 85%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 342 or a sequence with at least 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR3 comprises or consists of the amino acid sequence SEQ ID NO. 343 or a sequence with at least 80%, 81%, 82%, 83%, 84%, 85%, 86% 87%, 88%, 89%, 90%, 91%, 92%, 93%, 94%, 95%, 96%, 97%, 98% or 99% homology thereto.

In one embodiment, the family 4 or family 4-like sequence has a $V_H$ domain that comprises or consists of SEQ ID NO. 344 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. CDR sequences of such sequences are listed below. In one embodiment, homology is at least 70%, 80%, 81%, 82%, 83%, 84%, 85%, 86%, 87%, 88%, 89%, 90%, 91%, 92%, 93%, 94%, 95%, 96%, 97%, 98% or 99%. In another embodiment, the $V_H$ domain comprises a sequence as shown above, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences. In one embodiment, the $V_H$ domain comprises or consists of SEQ ID NO. 344 or a sequence which comprises one or more amino acid substitutions, for example 1, 2, 3, 4, 5, 6, 7, 8, 9 or 10 amino acid substitutions.

The family 4 or family 4-like binding molecules have KD, Koff, KA, Kd and $IC_{50}$ values as further described herein and as shown in the examples.

In one aspect, the invention relates to a binding molecule capable of binding human IL-17A comprising a human $V_H$ domain comprising a family 5 or family-5 like sequence.

In one aspect the invention relates to a binding molecule comprises or consists of at least one immunoglobulin single domain antibody directed against IL-17A, preferably human IL-17A, wherein said domain is a human $V_H$ domain and wherein said IL-17 binding 5 or family 5-like sequence. These include the parent clone sequence (5.1; SEQ ID NO. 348) as shown in FIG. 5 or a part thereof and sequences of clones that are can derived from the parent clone 5 or a part thereof, for example a CDR3 sequence, and to $V_H$ sequences of clones or parts thereof that are derived from parent clone 5 through a process of optimization, for example as shown in FIG. 5. CDR sequences and full length sequences of clones in family 5 are numbered according to table 5 as shown below.

TABLE 5

Family 5 CDR sequences and $V_H$ sequences that are within the scope of the invention. Corresponding sequences are shown in FIG. 5.

| Clone | CDR1 SEQ ID NO. | CDR2 SEQ ID NO. | CDR3 SEQ ID NO. | Full length $V_H$ SEQ ID NO. |
|---|---|---|---|---|
| 5.1 | SEQ ID NO. 345 | SEQ ID NO. 346 | SEQ ID NO. 347 | SEQ ID NO. 348 |

In one embodiment, the family 5 or family 5-like binding molecule comprises a human $V_H$ domain comprising a CDR3 sequence comprising SEQ ID NO. 287 or a sequence having at least 70%, at least 80%, at least 90%, or at least 95% homology to SEQ ID NO. 347.

In one embodiment, the family 5 or family-5 like binding molecule comprises at least one immunoglobulin single domain antibody directed against IL-17A wherein said domain is a human $V_H$ domain and wherein said human $V_H$ domain comprises at least one antigen binding site comprising a CDR3 sequence comprising SEQ ID NO. 347 or a sequence having at least 70%, at least 80%, at least 90%, or at least 95% homology to SEQ ID NO. 287.

In one embodiment, the family 5 or family 5-like sequence comprises a binding molecule comprising or consisting of at least one immunoglobulin single domain antibody directed against IL-17A wherein said domain is a human $V_H$ domain and wherein said IL-17A binding molecule comprises at least one antigen binding site comprising hypervariable regions CDR1, CDR2 and CDR3, said CDR1 comprises or consists of the amino acid sequence SEQ ID NO. 345 or a sequence with at least 70%, at least 80%, at least 90%, or at least 95% homology thereto, said CDR2 comprises or consists of the amino acid sequence SEQ ID NO. 345 or a sequence with at least 70%, at least 80%, at least 90%, or at least 95% homology thereto, and said CDR3 comprises or consists of the amino acid sequence SEQ ID NO. 347, or a sequence with at least 70%, at least 80%, at least 90%, or at least 95% homology thereto.

In one embodiment, said CDR1 comprises or consists of the amino acid sequence SEQ ID NO. 345 or a sequence with at least 80%, 81%, 82%, 83%, 84%, 86%, 85%, 87%, 88%, 89%, 90%, 91%, 92%, 93%, 94%, 96%, 97%, 98% or 99% homology thereto. In one embodiment, said CDR2 comprises or consists of the amino acid sequence SEQ ID NO. 346 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR3 comprises or consists of the amino acid sequence SEQ ID NO. 347 or a sequence with at least 80%, 81%, 82%, 83%, 84%, 85%, 87%, 88%, 89%, 90%, 91%, 92%, 93%, 94%, 95%, 96%, 97%, 98% or 99% homology thereto.

In one embodiment, the family 5 or family 5-like sequence has a $V_H$ domain that comprises or consists of SEQ ID NO. 348 or a sequence with at least 40%, 50%, 60%, 70%, 80% or 90% homology thereto. In one embodiment, homology is at least 70%, 80%, 81%, 82%, 83%, 84%, 85%, 87%, 88%, 89%, 90%, 91%, 92%, 93%, 94%, 96%, 97%, 98% or 99%. CDR sequences of such sequences are listed below. In another embodiment, the $V_H$ domain comprises SEQ ID NO. 348, but comprises one or more amino acid substitutions, for example 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs.

The family 5 or family 5-like binding molecules have KD, Koff, KA, Kd and $IC_{50}$ values as further described herein and as shown in the examples.

In one aspect, the binding molecule according to the invention comprises a CDR3 sequence selected from a family 1 or family 1-like, a family 2 or family 2-like, a family 3 or family 3-like, a family 4 or family 4-like or a family 5 or family 5-like CDR3 sequence combined with a CDR1 and/or CDR2 sequence from another family listed herein.

For example, the binding molecule according to the invention comprises a family 1 or family 1-like CDR3 sequence, for example as shown in FIG. 1A-B, combined with a CDR1 and/or a CDR2 sequence from one or two other families as shown in Table 2, 3, 4 or 5.

In another aspect, the binding molecule according to the invention comprises a family 2 or family 2-like CDR3 sequence, for example as shown in FIG. 2A-B, combined with a CDR1 and/or a CDR2 sequence from one or two other families as shown in Table 1, 3, 4 or 5. Various combinations are possible as would be appreciated by a skilled person.

In another aspect, the binding molecule according to the invention comprises a family 3 or family 3-like CDR3 sequence, for example as shown in FIG. 3, combined with a CDR1 and/or a CDR2 sequence from one or two other families as shown in Table 1, 2, 4 or 5. Various combinations are possible as would be appreciated by a skilled person.

In another aspect, the binding molecule according to the invention comprises a family 4 or family 4-like CDR3 sequence, for example as shown in FIG. 4, combined with a CDR1 and/or a CDR2 sequence from one or two other families as shown in Table 1, 2, 3, or 5. Various combinations are possible as would be appreciated by a skilled person.

In another aspect, the binding molecule according to the invention comprises a family 5 or family 5-like CDR3 sequence, for example as shown in FIG. 5, combined with a CDR1 and/or a CDR2 sequence from one or two other families as shown in Table 1, 2, 3 or 4. Various combinations are possible as would be appreciated by a skilled person.

A binding molecule described herein may be provided as a fusion protein with one or more additional protein moiety. For example, the binding molecule described herein may be provided as a fusion with a second moiety.

The second moiety may comprise a $V_H$ domain that is also specific for human IL-17A thus providing a bivalent binding molecule. In one embodiment, the binding molecule is biparatopic. Biparatopic binding molecules bind to different epitopes. Biparatopic binding molecules of the present invention can be constructed using methods known art.

For example, to generate a bivalent binding molecule, a family 1 or family 1-like binding molecule may be linked to a family 2, 3, 4 or 5 or family 2-, 3-, 4- or 5-like binding molecule. This is further illustrated in the examples and in FIGS. 29-33A-B. In one embodiment of the invention, a $V_H$ as defined for clone 1.2 is connected to another $V_H$ from family 2 or family 3, for example to the $V_H$ as defined for clone 3.2. Two or more $V_H$ are connected by a linker, for example a polypeptide linker. Suitable linkers, for example comprising linker include GS residues such as $(Gly_4Ser)_n$, where n=from 1 to 10, e.g., 2, 3, 4, 5, 6, 7, 8, 9 or 10.

In one embodiment, the invention relates to one of the following biparatopic binding molecules 3.2-2($G_4S$)-1.2, 3.2-6($G_4S$)-1.2, 3.2-4($G_4S$)-1.2. Thus, the invention also relates to a binding molecule comprising SEQ ID No. 430, 432, 434 or 436 and nucleic acids encoding such a binding molecule.

In another embodiment, the second moiety comprises a $V_H$ domain or another antibody fragment that is specific for a different antigen to provide a bispecific binding molecule. As used herein, the term "bispecific binding molecule" thus refers to a polypeptide that comprises a binding molecule as described herein which has a binding site that has binding specificity for IL-17A, and a second polypeptide domain which has a binding site that has binding specificity for a second target, i.e., the agent has specificity for two targets. The first target and the second target are not the same, i.e. are different targets e.g., proteins, but are both present on a cell. Accordingly, a bispecific polypeptide agent as described herein can selectively and specifically bind to a cell that expresses (or displays on its cell surface) the first target and the second target. In another embodiment, the binding molecule comprises more than two protein moieties.

In another embodiment, more than two moieties are joined together providing a multispecific binding molecule. A multispecific polypeptide agent as described herein can in addition bind one or more additional targets, i.e., a multispecific polypeptide can bind at least two, at least three, at least four, at least five, at least six, or more targets, wherein the multispecific polypeptide agent has at least two, at least, at least three, at least four, at least five, at least six, or more target binding sites respectively.

As used herein, the term "target" refers to a biological molecule (e.g., peptide, polypeptide, protein, lipid, carbohydrate) to which a polypeptide domain which has a binding site can selectively bind. The target can be, for example, an intracellular target (e.g., an intracellular protein target) or a cell surface target (e.g., a membrane protein, a receptor protein). Preferably, a target is a cell surface target, such as a cell surface protein. Preferably, the first cell surface target and second cell surface target are both present on a cell.

Multispecific antibodies of the present invention can be constructed using methods known art.

In biparatopic or multispecific binding molecules, the moieties are generally joined by a linker, for example a polypeptide linker. Suitable linkers, for example comprising linker including GS residues such as $(Gly_4Ser)_n$, where n=from 1 to 10, e.g., 2, 3, 4, 5, 6, 7, 8, 9 or 10, are known in the art.

If desired, bispecific or multispecific binding molecules can be linked to an antibody Fc region or a fragment thereof, comprising one or both of $C_H2$ and $C_H3$ domains, and optionally a hinge region. For example, vectors encoding bispecific or multispecific binding molecules linked as a single nucleotide sequence to an Fc region or a fragment thereof can be used to prepare such polypeptides.

Exemplary second antigen targets include leukocyte receptors, e.g., MHC, CD2, CD3, CD4, CD7, CD8, CD25, CD28, CD4, CD45, CD58, CD80, CD86 or their ligands; TNF, IL-1 IL-15, IL-23, IL-6 or CD20. This list is not limited to the agents mentioned.

In one embodiment, a second (or third, fourth, fifth etc) moiety may serve to prolong the half-life of the binding molecule. The second or third moiety may comprise a protein, for example an antibody, or part thereof that binds a serum albumin, e.g., human serum albumin (HSA). The second moiety may comprise a $V_H$ domain that binds serum albumin, e.g. human serum albumin (HSA).

The second moiety may comprise a serum albumin, e.g. a human serum albumin (HSA) or a variant thereof such as C34S. Further provided is a binding molecule as described herein comprising a $V_H$ domain and an Fc domain or a fragment thereof, e.g., wherein the $V_H$ domain is connected to an Fc domain or a fragment thereof. Further provided is a binding molecule that comprises a second variable domain that specifically binds a second antigen, where the second antigen is an antigen other than human IL-17A. The second antigen may be a cluster of differentiation (CD) molecule or a Major Histocompatibility Complex (MHC) Class II molecule.

The present invention further provides an isolated nucleic acid encoding a binding member of the present invention. Nucleic acid may include DNA and/or RNA. In one aspect, the present invention provides an isolated nucleic acid that codes for a CDR, a set of CDRs, a $V_H$ domain or a binding molecule as defined above. In one aspect, the invention also relates to nucleic acid sequences comprising or consisting of SEQ ID NOs. 349 to 410 which encode $V_H$ domains of family 1 wherein said $V_H$ domain comprises or consists of SEQ ID NO. 4, 8, 12, 16, 20, 24, 28, 32, 36, 40, 44, 48, 52, 56, 60, 64, 68, 72, 76, 80, 84, 88, 92, 96, 100, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244 or 248 440, 444, 448, 452, 456, 460 or 464 respectively.

Examples of such nucleic acids are shown below.

nucleic acid encoding $V_H$ 1.1
SEQ ID No. 349
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATTCGATGTACTGGGTCCGCCAGGCTCCAGGGAAG

GGGCTGGAGTGGGTGGCCAACATAAAGCAAGATGGAAGTGAGA

AATACTATGTGGACTCTGTGAAGGGCCGATTCACCATCTCCAG

AGACAACGCCAAGAACTCACTGTTTCTGCAAATGAATAGCCTG

AGAGCCGAGGACACGGCTGTGTATTACTGTGCGAAAGGGGAAA

TACTACCCCTCCACTTTGACTACTGGGGCCAGGGAACCCTGGT

CACTGTCTCCTCA nucleic acid encoding $V_H$ 1.2
SEQ ID No. 350
GAGGTTCAGTTGGTGGAAAGCGGCGGTGGCCTGGTCCAGCCGG

GTGGTAGCCTGCGCCTGTCCTGCGCGGCTAGCGGTTTCACGTT

TAGCAGCTACAGCATGTACTGGGTGCGTCAAGCGCCAGGCAAA

GGTCTGGAATGGGTTGCCGAGATTAAGCAAGACGGTTCTGTTC

AGTATTATGTCAGCGACGTGAAGGGTCGTTTTACCATCAGCCG

TGACAACGCGAAAAACAGCCTGTATTTGCAGATGAATTCCCTG

CGCGCTGAAGATACCGCGGTGTATTACTGTGCGAAAGGTGAGA

TTCTGCCGCTGTACTTCGATTACTGGGGCCAAGGCACCCTGGT

TACTGTCTCGAGC nucleic acid encoding $V_H$ 1.3
SEQ ID No. 351
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATAGCATGTACTGGGTCCGCCAGGCTCCAGGGAAG

GGGCTGGAGTGGGTGGCCGAGATAAAGCAAGATGGAAGTGTGC

AATACTATGTGGACTCTGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGG

TCACTGTCTCTTCA nucleic acid encoding $V_H$ 1.4
SEQ ID No. 352
GAGGTTCAGTTGGTGGAAAGCGGCGGTGGCCTGGTCCAGCCGG

GTGGTAGCCTGCGCCTGTCCTGCGCGGCTAGCGGTTTCACGTT

TAGCAGCTACAGCATGTACTGGGTGCGTCAAGCGCCAGGCAAA

GGTCTGGAATGGGTTGCCGAGATTAAGCAAACCGGTTCTGTTC

AGTATTATGTCGACAGCGTGAAGGGTCGTTTTACCATCAGCCG

TGACAACGCGAAAAACAGCCTGTATTTGCAGATGAATTCCCTG

CGCGCTGAAGATACCGCGGTGTATTACTGTGCGAAAGGTGAGA

-continued
TTCTGCCGCTGTACTTCGATTACTGGGGCCAAGGCACCCTGGT

TACTGTCTCGAGC nucleic acid encoding V_H 1.5
SEQ ID No. 353
GAGGTTCAGTTGGTGGAAAGCGGCGGTGGCCTGGTCCAGCCGG

GTGGTAGCCTGCGCCTGTCCTGCGCGGCTAGCGGTTTCACGTT

TAGCAGCTACAGCATGTACTGGGTGCGTCAAGCGCCAGGCAAA

GGTCTGGAATGGGTTGCCGAGATTAAGCCGACCGGTTCTGTTC

AGTATTATGTCGACAGCGTGAAGGGTCGTTTTACCATCAGCCG

TGACAACGCGAAAAACAGCCTGTATTTGCAGATGAATTCCCTG

CGCGCTGAAGATACCGCGGTGTATTACTGTGCGAAAGGTGAGA

TTCTGCCGCTGTACTTCGATTACTGGGGCCAAGGCACCCTGGT

TACTGTCTCGAGC nucleic acid encoding V_H 1.6
SEQ ID No. 354
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATAGCATGTACTGGGTCCGCCAGGCTCCAGGGAAG

GGGCTGGAGTGGGTGGCCGAGATAAAGCAAGATGGAAGTGAGC

AATACTATGTGGACTCTGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACCGTCTCCTCA nucleic acid encoding V_H 1.7
SEQ ID No. 355
CAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATGGGATGTACTGGGTCCGCCAGGCTCCAGGGAAG

GGGCTGGAGTGGGTGGCCAAGATAGAGCAAGATGGAAGTGAGG

AATACTATGTGGACTCTGTGAAGGGCCGATTCACCATCTCCAG

AGACAACGCCAAGAAGTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACCGTCTCCTCA nucleic acid encoding V_H 1.8
SEQ ID No. 356
CAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATGGTATGTACTGGGTCCGCCAGGCTCCAGGGAAG

GGGCTGGAGTGGGTGGCCAAGATAGAGCAAGATGGAAGTGAGA

AATACTATGTGGACTCTGTGAAGGGCCGATTCACCATCTCCAG

AGACAACGCCAAGAACTCACTGTTTCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACCGTCTCCTCA nucleic acid encoding V_H 1.9
SEQ ID No. 357
CAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATGGAATGTACTGGGTCCGCCAGGCTCCAGGGAAG

GGGCTGGAGTGGGTGGCCGAGATAAAACAAGATGGAAGTGAGA

AATACTATGTGGACTCTGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACTGTCTCTTCA nucleic acid encoding V_H 1.10
SEQ ID No. 358
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATCGCATGTACTGGGTCCGCCAGGCTCCAGGGAAG

GGGCTGGAGTGGGTGGCCAGCATAGAACAAGATGGAAGTGAGG

AATACTATGTGGACTCTGTGAAGGGCCGATTCACCATCTCCAG

AGACAACGCCAAGAAGTCACTGTTTCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACTGTCTCTTCA nucleic acid encoding V_H 1.11
SEQ ID No. 359
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATCAGATGTACTGGGTCCGCCAGGCTCCAGGGAAG

GGGCTGGAGTGGGTGGCCAGCATAAAACAAGATGGAAGTGAGG

AATACTATGTGGACTCTGTGAAGGGCCGATTCACCATCTCCAG

AGACAACGCCAAGAACTCACTGTTTCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACTGTCTCTTCA nucleic acid encoding V_H 1.12
SEQ ID No. 360
CAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATGGGATGTACTGGGTCCGCCAGGCTCCAGGGAAG

GGGCTGGAGTGGGTGGCCAAGATAGAGCAAGATGGAAGTGAGG

AATACTATGTGGACTCTGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

-continued

TACTACCCCTCTACTTTGACTACTGGGGCCAGGGAACCCTGGT

CACTGTCTCCTCA nucleic acid encoding V<sub>H</sub> 1.13
SEQ ID No. 361
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATGGGATGTACTGGGTCCGCCAGGCTCCAGGGAAG

GGGCTGGAGTGGGTGGCCAGCATAGAACAAGATGGAAGTGAGA

AATACTATGTGGACTCTGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACCGTCTCCTCA nucleic acid encoding V<sub>H</sub> 1.14
SEQ ID No. 362
GAGGTGCAGCTGGTGGAGTCTGGGGGAGGCTTGGTCCAGCGTG

GGGGGTCCCTGAGACTCTCCTGTGCAGCCTCTGGATTCACCTT

TAGTAGTTATCGGATGTACTGGGTCCGCCAGGCTCCAGGGAAG

GGGCTGGAGTGGGTGGCCAGCATAGAACAAGATGGAAGTGAGG

AATACTATGTGGACTCTGTGAAGGGCCGATTCACCATCTCCAG

AGACAACGCCAAGAAGTCACTGTTTCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACTGTCTCTTCA nucleic acid encoding V<sub>H</sub> 1.15
SEQ ID No. 363
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATAGCATGTACTGGGTCCGCCAGGCTCCAGGGAAG

GGGCTGGAGTGGGTGGCCGAGATAAGGCAAGATGGAAGTGAGC

AATACTATGTGGACTCTGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACTGTCTCTTCA nucleic acid encoding V<sub>H</sub> 1.16
SEQ ID No. 364
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATAGCATGTACTGGGTCCGCCAGGCTCCAGGGAAG

GGGCTGGAGTGGGTGGCCGAGATAAAGCAAGATGGAAGTGAGC

AATACTATGTGGACTCTGTGAAGGGCCGATTCACCATCTCCAG

AGACAACGCCAAGAACTCACTGTATCTGCAAATGAATGGCCTG

AGAGCCGAGGACACGGCTGTGTATTACTGTGCGAAAGGGGAAA

TACTGCCCCTCTACTTCGACTACTGGGGCCAGGGAACCCTGG

TCACTGTCTCTTCA nucleic acid encoding V<sub>H</sub> 1.17
SEQ ID No. 365
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATAGCATGTACTGGGTCCGCCAGGCTCCAGGGAAG

GGGCTGGAGTGGGTGGCCGAGATAAAGCCAACCGGGAGTGTGC

AATACTATGTGTCCGACGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTG

GTCACTGTCTCTTCA nucleic acid encoding V<sub>H</sub> 1.18
SEQ ID No. 366
GAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGTTATAGCATGTACTGGGTCCGCCAGGCTCCAGGGAAG

GGGCTGGAGTGGGTGGCCGAGATAAAGCAAGACGGCAGTGTGC

AATACTATGTGGGGGCGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACTGTCTCTTCA nucleic acid encoding V<sub>H</sub> 1.19
SEQ ID No. 367
GAGGTGCAGCTGGTGGAGTCTGGGGGAGGCTTGGTCCAGCCTG

GGGGGTCCCTGAGACTCTCCTGTGCAACCTCTGGATTCACCTT

TAGTAGTTATGGAATGTACTGGGTCCGCCAGGCTCCAGGGAAG

GGGCTGGAGTGGGTGGCCGAGATAAAACAAGATGGAAGTGAGA

AATACTATGTGGACTCCGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGG

TCACTGTCTCTTCA nucleic acid encoding V<sub>H</sub> 1.20
SEQ ID No. 368
GAGGTGCAGCTGGTGGAGTCTGGGGGAGGCCTGGTCCAGCCTG

GGGGGTCCCTGAGACTCTCCTGTGCAGCCTCTGGATTCACCTT

TAGTAGTTATGGGATGTACTGGGTCCGCCAGGCTCCAGGGAAG

GGGCTGGAGTGGGTGGCCAAGATAGAGCAAGATGGAAGTGAGG

AATACTATGCGGACTCTGTGAAGGGCCGATTCACCATCTCCAG

AGACAACGCCAAGAAGTCACTGTATCTGCAAATGAATAGCCTG

AGAGCCGAGGACACGGCTGTGTATTACTGTGCGAAAGGGGAAA

```
TACTACCCCTCTACTTTGACTACTGGGGCCAGGGAACCCTGGT

CACTGTCTCTTCA
nucleic acid encoding V_H 1.21
                                    SEQ ID No. 369
GAGGTGCAGCTGGTGGAGTCTGGGGGAGGCTTGGTCCTGCCTG

GGGGGTCCCTGAGACTCTCCTGTGCGGCCTCTGGATTCACCTT

TAGTAGTTATAGCATGTACTGGGTCCGCCAGGCTCCAGGGAAG

GGGCTGGAGTGGGTGGCCGAGATAAAGCAAGATGGAAGTGAGC

AATACTATGTGGACTCTGTGAAGGGCCGATTCACCATCTCCAG

AGACAACGCCAAGAACTCACTGTATCTGCAAATGAATAGCCTG

AGAGCCGAGGACACGGCTGTGTATTACTGTGCGAAAGGGGAAA

TACTACCCCTCTACTTTGACTACTGGGGCCAGGGAACCCTGGT

CACTGTCTCTTCA
nucleic acid encoding V_H 1.22
                                    SEQ ID No. 370
GAGGTGCAGCTGGTGGAGTCTGGGGGAGGCTTGGTCCGGCCTG

GGGGGTCCCTGAGACTCTCCTGTGCAGCCTCTGGATTCACCTT

TAGTAGTTATGGGATGTACTGGGTCCGCCAGGCTCCAGGGAAG

GGGCTGGAGTGGGTGGCCAAGATAGAGCAAGATGGAAGTGAGG

AATACTATGTGGACTCTGTGAAGGGCCGATTCACCATCTCCAG

AGACAACGCCAAGAAGTCACTGTATCTGCAAATGAATAGCCTG

AGAGCCGAGGACACGGCCGTGTATTACTGTGCGAAAGGGGAAA
```

```
TACTACCCCTCTACTTTGACTACTGGGGCCAGGGAACCCTGGT

CACTGTCTCTTCA
```

In one aspect, the invention also relates to nucleic acid sequences comprising a sequence, for example SEQ ID NO. 371, which encodes a $V_H$ domain of family 2 wherein said $V_H$ domain comprises or consists of SEQ ID NO. 252, 256, 260, 264, 268, 272, 276, 280 or 284.

```
nucleic acid encoding V_H 2.1
                                    SEQ ID No. 371
CAGGTGCAGCTGGTGGAGTCTGGGGGAGGCTTGGTCCAGCCTG

GGGGGTCCCTGAGACTCTCCTGTGCAGCCTCTGGATTCACCTT

TAGTAGCTATGGGATGGGCTGGGTCCGCCAGGCTCCAGGGAAG

GGGCTGGAGTGGGTGGCCAAAATAAAACAAGATGGAAGTGAGA

AAGACTATGTGGACTCTGTGAAGGGCCGATTCACCATCTCCAG

AGACAACGCCAAGAAGTCACTGTTTCTGCAAATGAACAGCCTG

AGAGCCGAGGACACGGCTGTGTATTATTGTGCGAGAGAGAGTA

TATTTGGAATCCCCGAGGACTGGGGCCAGGGAACCCTGGTC

ACCGTCTCCTCA
```

In one aspect, the invention also relates to nucleic acid sequences, for example comprising a sequence selected from SEQ ID NO. 372 to 381, which encode $V_H$ domains of family 3 wherein said $V_H$ domain comprises or consists of SEQ ID NO. 288, 292, 296, 300, 304, 308, 312, 316, 320, 324, 328, 332, 336 or 340.

```
nucleic acid encoding V_H 3.1
                                    SEQ ID No. 372
CAGGTGCAGCTGGTGCAGTCTGGGGCTGAGGTGAAGAAGCCTGGGGCCTCAGTGAA

GGTCTCCTGCAAGGCTTCTGGATACACCTTCACCGGCTACTATATGCACTGGGTGCGA

CAGGCCCCTGGACAAGGGCTTGAGTGGATGGGATGGATCAACCCTAACAGTGGTGGC

ACAAACTATGCACAGAAGTTTCAGGGCAGGGTCACCATGACCAGGGACACGTCCATC

AGCACAGCCTACATGGAGCTGAGCAGGCTGAGATCTGACGACACGGCCGTGTATTAC

TGTGCGAGTATGGATCGGGATTATTATGATACTAGTGGTTACTTTGGCTGGTTCGACTC

CTGGGGCCAGGGAACCCTGGTCACCGTCTCTTCA
nucleic acid encoding V_H 3.2
                                    SEQ ID No. 373
CAGGTTCAGCTGGTGCAGTCTGGAGCTGAGGTAAAGAAGCCTGGGGCCTCGGTGAAG

GTCTCCTGTAAGGCTTCCGGATATAACGCGGACGCCTATTATATAAATTGGGTGCGAC

AGGCCCCTGGACAAGGTCTTGAGTGGATGGGAAGTATCAAGCCTAATACCGGTGCCA

CAAAATATGCACAGAAGTTTCAGGGCAGAGTCACCATAACCAGGGACACGTCCATCAG

CACAGCCTACATGGAGCTGAGCAGGCTGAGATCTGACGACACGGCCGTGTATTACTG

TGCGAGTCTGGATCGGGATACGTGGTACCCGCACTCCTACGCGGGGTGGTTCGACGC

GTGGGGCCAGGGAACCCTGGTCACCGTCTCTTCA
acid encoding V_H 3.3
                                    SEQ ID No. 374
CAGGTGCAGCTGGTGCAGTCTGGGGCTGAGGTGAAGAAGCCTGGGGCCTCAGTGAA

GGTCTCCTGCGCAGCTTCCGGATACACCTTCACCGACTACTATCTGCACTGGGTGCGA
```

```
CAGGCCCCTGGACAAGGGCTTGAGTGGATGGGGTGGATCAACCCTAACACTGGCACC

ACAAAGTATGCACGGGAGTTTGAGGGCAGAGTCACCATGACCAGGGACACGTCCATC

AGCACAGCCTACATGGAGCTGAGCAGGCTGAGATCTGACGACACGGCCGTGTATTAC

TGTGCGAGTATGGATCGGGATTATTATGATACTAGTGGTTACTTTGGCTGGTTCGACTC

CTGGGGCCAGGGAACCCTGGTCACCGTCTCTTCA
``` nucleic acid encoding V<sub>H</sub> 3.5

SEQ ID No. 375

```
CAGGTCCAGCTGGTGCAGTCTGGGGCTGAGGTGAAGAAGCCTGGGGCCTCAGTGAA

GGTCTCCTGCGCAGCTTCCGGATACACCTTCACCGACTACTATCTGCACTGGGTGCGA

CAGGCCCCTGGACAAGGGCTTGAGTGGATGGGGTGGATCAACCCTAACACTGGCACC

ACAAAGTATGCACGGGAGTTTGAGGGCAGAGTCACCATGACCAGGGACACGTCCATC

AGCACAGCCTACATGGAGCTGAGCAGGCTGAGATCTGACGACACGGCCGTGTATTAC

TGTGCGAGTCTGGATCGGGATTGGCGCTCGCCCAACGACTACTTTGGCTGGTTCGAC

TCGTGGGGCCAGGGAACCCTGGTCACCGTCTCTTCA
``` nucleic acid encoding V<sub>H</sub> 3.6

SEQ ID No. 376

```
CAGGTCCAGCTGGTGCAGTCTGGGGCTGAGGTGAAGAAGCCTGGGGCCTCAGTGAA

GGTCTCCTGCGCAGCTTCCGGATACACCTTCACCGACTACTATCTGCACTGGGTGCGA

CAGGCCCCTGGACAAGGGCTTGAGTGGATGGGGTGGATCAACCCTAACACTGGCACC

ACAAAGTATGCACGGGAGTTTGAGGGCAGAGTCACCATGACCAGGGACACGTCCATC

AGCACAGCCTACATGGAGCTGAGCAGGCTGAGATCTGACGACACGGCCGTGTATTAC

TGTGCGAGTCTGGATCGGGATTGGCGCTCGCCCAACGACTACTACGGGTGGTTCGAC

TCGTGGGGCCAGGGAACCCTGGTCACCGTCTCTTCA
``` nucleic acid encoding V<sub>H</sub> 3.9

SEQ ID No. 377

```
CAGGTGCAGCTGGTGCAGTCTGGGGCTGAGGTGAAGAAGCCTGGGGCCTCAGTGAA

GGTCTCCTGTAAGGCTTCCGGATATAACTTCGACGCCTATCATATAAATTGGGTGCGA

CAGGCCCCTGGACAAGGGCTTGAGTGGATGGGAAGTATCAAGCCTAATAGTGGTGCC

ACAAAATATGCACAGAAGTTTCAGGGCAGAGTCACCATAACCAGGGACACGTCCATCA

GCACAGCCTACATGGAGCTGAGCAGGCTGAGATCTGACGACACGGCCGTGTATTACT

GTGCGAGTATGGATCGGGATTACTATGATACTAGTGGTTACTTTGGCTGGTTCGACTC

CTGGGGCCAGGGAACCCTGGTCACCGTCTCCTCA
``` nucleic acid encoding V<sub>H</sub> 3.11

SEQ ID No. 378

```
CAGGTGCAGCTGGTGCAGTCTGGGGCTGAGGTGAAGAAGCCTGGGGCCTCAGTGAA

GGTCTCCTGTAAGGCTTCCGGATATAACTTCGACGCCTATCATATAAATTGGGTGCGA

CAGGCCCCTGGACAAGGTCTTGAGTGGATGGGAAGTATCAAGCCTAATAGTGGTGCC

ACAAAATATGCACAGAAGTTTCAGGGCAGAGTCACCATAACCAGGGACACGTCCATCA

GCACAGCCTACATGGAGCTGAGCAGGCTGAGATCTGACGACACGGCCGTGTATTACT

GTGCGAGTCTGGATCGGGATACGTGGTACCCGCACTCCTACTTTGGCTGGTTCGACT

CGTGGGGCCAGGGAACCCTGGTCACCGTCTCTTCA
``` nucleic acid encoding V<sub>H</sub> 3.13

SEQ ID No. 379

```
CAGGTCCAGCTGGTGCAGTCTGGGGCTGAGGTGAAGAAGCCTGGGGCCTCAGTGAA

GGTCTCCTGTAAGGCTTCCGGATATAACTTCGACGCCTATCATATAAATTGGGTGCGA

CAGGCCCCTGGACAAGGTCTTGAGTGGATGGGAAGTATCAAGCCTAATAGTGGTGCC
```

```
-continued
ACAAAATATGCACAGAAGTTTCAGGGCAGAGTCACCATAACCAGGGACACGTCCATCA

GCACAGCCTACATGGAGCTGAGCAGGCTGAGATCTGACGACACGGCCGTGTATTACT

GTGCGAGTCTGGATCGGGATACGTGGTACCCGCACTCCTACGCGGGGTGGTTCGACT

CGTGGGGCCAGGGAACCCTGGTCACCGTCTCTTCA
```

In one aspect, the invention also relates to nucleic acid sequences, for example comprising sequence SEQ ID NO. 380 which encodes $V_H$ domains of family 4 wherein said $V_H$ domain comprises or consists of SEQ ID NO. 344.

```
nucleic acid encoding V_H 4.1
                                       SEQ ID No.: 380
CAGGTGCAGCTGGTGGAGTCTGGGGGAGGCTTGGTCCAGCCTGGGGGGTCC

CTGAGACTCTCCTGTGCAGCCTCTGGATTCACCTTTAGTAGCTATTGGATG

AACTGGGTCCGCCAGGCTCCAGGGAAGGGGCTGGAATGGGTGGCCACCATA

AAACAAGATGGAAGTGAGAAATACTATGTGGACTCTGTGAAGGGCCGATTC

ACCATCTCCAGAGACAACGCCACGAACTCACTGTTTCTGCAAATGAACAGC

CTGAGAGCCGAGGACACGGCTGTGTATTACTGTGCGAGGGGAGATACGATT

TTCGACGGTGCTTTTGATATCTGGGGCCAAGGGACAATGGTCACTGTCTCC

TCA
```

In one aspect, the invention also relates to nucleic acid sequences, for example comprising sequence SEQ ID NO. 381 which encodes a $V_H$ domain of family 5 wherein said $V_H$ domain comprises or consists of SEQ ID NO. 348.

```
nucleic acid encoding V_H 5.1
                                        SEQ ID No. 381
GAGGTGCAGCTGGTGGAGTCTGGGGGAGGCTTGGTCCAGCCTGGGGGG

TCCCTGAGACTCTCCTGTGCAGCCTCTGGATTCACCTTTAGTAGCTAT

TGGATGAGCTGGGTCCGCCAGGCTCCAGGGAAGGGGCTGGAGTGGGTG

GCCAACATAAAGCAAGATGGAAGTGAGAAATACTATGTGGACTCTGTG

AAGGGCCGATTCACCATCTCCAGAGACAACGCCAAGAACTCACTGTAT

CTGCAAATGAACAGCCTGAGAGCCGAGGACACGGCTGTGTATTACTGT

GCGCATCAGTGGCCCTTCTTTGACTACTGGGGCCAAGGGACAATGGTC

ACTGTCTCCTCA
```

Nucleic acid according to the present invention may comprise DNA or RNA and may be wholly or partially synthetic or recombinantly produced. Reference to a nucleotide sequence as set out herein encompasses a DNA molecule with the specified sequence, and encompasses a RNA molecule with the specified sequence in which U is substituted for T, unless context requires otherwise.

Furthermore, the invention relates to a nucleic acid construct comprising at least one nucleic acid defined above. The construct may be in the form of plasmids, vectors, transcription or expression cassettes.

The invention also relates to an isolated recombinant host cell comprising one or more nucleic acid constructs as above.

The invention also relates to a binding agent capable of binding to IL-17A that competes for binding to IL-17A with a binding molecule of the invention as described above in a competitive assay.

The binding molecules of the invention have certain functional properties as described below.

In particular, the binding molecules of the invention block the effects of IL-17A on its target cells and are thus indicated for use in the treatment of IL-17A-mediated diseases, for example as described herein. These and other pharmacological activities of the binding molecules of the invention may be demonstrated in standard test methods for example as described in the art: Neutralization of IL-17A dependent production of interleukin-6 by primary human fibroblasts: The production of IL-6 in primary human (dermal) fibroblasts is dependent on IL-17 (Hwang S Y et al., (2004) Arthritis Res Ther; 6:R120-128)) and in the examples herein. Thus, as described in more detail in the examples, binding members according to the invention neutralize IL-17A with high potency. The term "neutralizing" thus refers to neutralization of a biological activity of IL-17 when a binding protein specifically binds IL-17. Inhibition of a biological activity of IL-17 by a neutralizing binding protein can be assessed by measuring one or more indicators of IL-17 biological activity well known in the art, as described in the examples.

For example, neutralisation of IL-17A binding to its receptor may be measured as cellular release of a biological molecule, e.g., MMP13, PGE2 or a cytokine such as IL-6 or IL-8, in a biological assay, since IL-17A binding to its receptor induces cellular release of these molecules, which can be determined using appropriate assays, e.g., in HT1080 cells, chondrocytes or other suitable cell or tissue types.

Inhibition of biological activity may be partial or total. In specific embodiments, binding members are provided that inhibit IL-17A biological activity by at least 95%, at least 90%, at least 85%, at least 80%, at least 75%, at least 70%, at least 60%, or at least 50% of the activity in absence of the binding member. The degree to which a binding member neutralises IL-17A is referred to as its neutralising potency. Potency may be determined or measured using one or more assays known to the skilled person and/or as described or referred to herein. For example, potency may be assayed in:
  HTRF® (Homogeneous Time-Resolved Fluorescence) receptor-ligand binding assay
    HT1080 cell assay using synergised IL-6 release in response to IL-17 and TNFα
    Chondrocyte IL-6/IL-8/MMP13/PGE2-release assay
    IL-6 release assay in cartilage explants
    IL-6 release assay in synovial fibroblasts (e.g., from RA or OA patients), e.g., using synergised IL-6 response to IL-17 and TNFα.

Assays methods are described in detail in the examples.

Neutralising potency of a binding member as calculated in an assay using IL-17A from a first species (e.g., human) may be compared with neutralising potency of the binding member in the same assay using IL-17 from a second species (e.g., cynomolgus), in order to assess the extent of cross-reactivity of the binding member for IL-17 of the two species.

Potency is normally expressed as an $IC_{50}$ value, in nM unless otherwise stated. In functional assays, $IC_{50}$ is the concentration of a binding member that reduces a biological response by 50% of its maximum. $IC_{50}$ may be calculated by plotting % of maximal biological response as a function of the log of the binding member concentration, and using a software program to fit a sigmoidal function to the data to generate $IC_{50}$ values.

In another aspect, the invention thus relates to a binding molecule comprising at least one $V_H$ domain directed against human IL-17A, or comprising or comprising or consisting of at least one immunoglobulin single $V_H$ domain antibody, wherein said $V_H$ domain has an $IC_{50}$ for inhibition of IL-6 production of about 0.2 to about 1000 nM or more, for example 0.2 to 900, 0.2 to 800, 0.2 to 700, 0.2 to 600, 0.2 to 500, 0.2 to 400, 0.2 to 300, 0.2 to 200, 0.2 to 100, 0.2 to 50, 0.2 to 40, 0.2 to 30, 0.2 to 20, 0.2 to 10, 0.2 to 9, 0.2 to 8, 0.2 to 7, 0.2 to 6, 0.2 to 5, 0.2 to 4.0, 0.2 to 3, 0.2 to 2 or 0.2 to 1 when tested as described in the examples, i.e. by measuring the ability of IL-17 binding $V_H$ to inhibit IL-17 induced IL-6 release from the cell line HT1080. For example, the binding molecules of the invention typically have $IC_{50}$ for inhibition of IL-6 production of about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4 3.5, 3.6, 3.7, 3.8, 3.9 or 4.0 nM. The binding molecules of the invention may have an $IC_{50}$ for inhibition of IL-6 production of less than about 4 nM, preferably less than about 2 nM assessed by measuring the ability of IL-17 binding $V_H$ to inhibit IL-17 induced IL-6 release from the cell line HT1080. This assay measures IL-6 release in response to and a detailed method is given in the examples. The binding molecule, for example a $V_H$ domain, having these binding characteristics may be selected from one of the sequences disclosed herein.

In another embodiment, the $V_H$ domain comprises a CDR3 sequence or $V_H$ sequence as described herein.

For example, in one embodiment, said IL-17A binding molecule comprises a family 1-like sequence that has an $IC_{50}$ for inhibition of IL-6 production of about 0.2 to about 13, for example 0.2 to 4.0 nM when tested as described in the examples, i.e. by measuring the ability of IL-17 binding $V_H$ to inhibit IL-17 induced IL-6 release from the cell line HT1080. The binding molecules of the invention may have an $IC_{50}$ for inhibition of IL-6 production of less than about 13, preferably less than about 10, 9, 8, 7, 6, or 4 nM, preferably less than about 2 nM. In one embodiment, the $IC_{50}$ is 0.2-2.0 nM, for example 0.2-1.0 nM, for example about 0.4 nM. In one embodiment, the $IC_{50}$ is as shown in the examples.

In one embodiment, the family 1 or family 1-like sequence comprises CDR3 sequence SEQ ID NO. 3, or a sequence with at least 80%, 85%, 90%, 95% homology thereto. In one embodiment, said CDR3 comprises or consists of the amino acid sequence SEQ ID NO. 3 or a sequence with at least 80%, 81%, 82%, 83%, 84%, 85%, 86%, 87%, 88%, 89%, 90%, 91%, 92%, 93%, 94%, 96%, 97%, 98% or 99% homology thereto.

In one embodiment, CDR1 comprises or consists of the amino acid sequence SEQ ID NO. 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 141, 145, 149, 153, 157, 161, 165 169, 173, 177, 181, 185, 189, 193, 197, 201, 205, 209, 213, 217, 221, 225, 229, 233, 237, 241, 245, 438, 442, 446, 450, 454, 458 or 462, CDR2 comprises or consists of the amino acid sequence SEQ ID NO. 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158, 162, 166, 170, 174, 178, 182, 186, 190, 194, 198, 202, 206, 210, 214, 218, 222, 226, 230, 234, 238, 242, 246, 439, 443, 447, 451, 455, 459, 463 and CDR3 comprises or consists of the amino acid sequence SEQ ID NO. 3, 7, 11, 15, 19, 23, 27, 31, 35, 39, 43, 47, 51, 55, 59, 63, 67, 71, 75, 79, 83, 87, 91, 95, 99, 103, 107, 111, 115, 119, 123, 127, 131, 135, 139, 143, 147, 151, 155, 159, 163, 167, 171, 175, 179, 183, 187, 191, 195, 199, 203, 207, 211, 215, 219, 223, 227, 231, 235, 239, 243, 247 440, 444, 448, 452, 456, 460 or 464.

In one embodiment, the binding molecule has combinations of CDR1, CDR2 and CDR3 as shown for clones 1.1 to 1.69 in FIG. 1A-B. In one embodiment, the binding molecule has a combination of a CDR1, CDR2 and CDR3 as shown for clones 1.1 to 1.22 in FIG. 1A.

In one embodiment, the family 1 or family 1-like sequence has a $V_H$ domain that comprises or consists of SEQ ID NO. 4 or a sequence with at least 40%, 50%, 60%, 70%, 80%, 81%, 82%, 83%, 84%, 86%, 85%, 87%, 88%, 89%, 90%, 91%, 92%, 93%, 94%, 96%, 97%, 98% or 99% homology thereto. Examples are shown in FIG. 1A-B. In one embodiment, the $V_H$ domain comprises or consists of SEQ ID NO. 8, 12, 16, 20, 24, 28, 32, 36, 40, 44, 48, 52, 56, 60, 64, 68, 72, 76, 80, 84, 88, 92, 96, 100, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244, 248, 441, 445, 449, 453, 457, 461 or 466.

In another embodiment, said IL-17 binding molecule comprises a family 2 or family 2-like sequence. In one embodiment, said family 2-like has an $IC_{50}$ for inhibition of IL-6 production of about 9 nM or less when tested as described in the examples, i.e., by measuring the ability of an IL-17-binding molecule comprising a $V_H$ to inhibit IL-17 induced IL-6 release from the cell line HT1080.

In one embodiment, the family 2 or family 2-like sequence comprises CDR3 sequence SEQ ID NO. SEQ ID NO. 251 or a sequence with at least 80%, 85%, 90%, 95% homology thereto. In one embodiment, said CDR3 comprises or consists of the amino acid sequence SEQ ID NO. 251 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, said CDR1 comprises or consists of the amino acid sequence SEQ ID NO. 249 or a sequence with at least 60%, 70%, 80%, 81%, 82%, 83%, 84%, 85%, 86% 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. SEQ ID NO. 250 or a sequence with at least 80%, 81%, 82%, 83%, 84%, 85%, 86%, 87%, 88%, 89%, 90%, 91%, 92%, 93%, 94%, 95%, 96%, 97%, 98%, 99% homology thereto.

In one embodiment, CDR1 comprises or consists of the amino acid sequence SEQ ID NO. 249, 253, 257, 261, 265, 269, 273, 277 or 281, CDR2 comprises or consists of the amino acid sequence SEQ ID NO. 250, 254, 258, 262, 266, 270, 274, 278 or 282 and CDR3 comprises or consists of the amino acid sequence SEQ ID NO. 251, 255, 259, 263, 267, 271, 275, 279 or 283.

In one embodiment, the binding molecule has a combination of a CDR1, CDR2 and CDR3 as shown for clones 2.1 to 2.9 in FIG. 2A-B.

In one embodiment, the family 2 or family 2-like sequence has a $V_H$ domain that comprises or consists of SEQ ID NO. 252 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. Examples are shown in table 2. In one embodiment, the family 2 sequence has a $V_H$ domain that comprises or consists of SEQ ID NO. 256, 260, 264, 268, 272, 276, 280 or 284.

In another embodiment, said IL-17A binding molecule comprises a family 3-like sequence that has an $IC_{50}$ for inhibition of IL-6 production of about 0.2 to about 1000 nM, for example 0.2 to 200 when tested as described in the examples, i.e. by measuring the ability of an IL-17-binding molecule comprising a $V_H$ to inhibit IL-17 induced IL-6 release from the cell line HT1080. The binding molecules of the invention may have an $IC_{50}$ for inhibition of IL-6 production of less than about 200 nM, preferably less than about 100 nM, preferably less than about 10 nM assessed by measuring the ability of IL-17 binding $V_H$ to inhibit IL-17 induced IL-6 release from the cell line HT1080. In one embodiment, the $IC_{50}$ is 0.2-2.5 nM.

In one embodiment, the family 3 or family 3-like sequence comprises CDR3 sequence SEQ ID NO. 287 or a sequence with at least 60%, 70% 80%, 85%, 90%, 95% homology thereto. In one embodiment, said CDR3 comprises or consists of the amino acid sequence SEQ ID NO. 287 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, said CDR1 comprises or consists of the amino acid sequence SEQ ID NO. 285 or a sequence with at least 40%, 50%, 60%, 70%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR2 comprises or consists of the amino acid sequence SEQ ID NO. 286 or a sequence with at least 70%, 80%, 81%, 82%, 83%, 84%, 85%, 87%, 88%, 89%, 90%, 91%, 92%, 93%, 94%, 95%, 96%, 97%, 98% or 99% homology thereto.

In one embodiment, CDR1 comprises or consists of the amino acid sequence SEQ ID NO. 285, 289, 293, 297, 301, 305, 309, 313, 317, 321, 325, 329, 333 or 337, CDR2 comprises or consists of the amino acid sequence 286, 290, 294, 298, 302, 306, 310, 314, 318, 322, 326, 330, 334 or 338 and CDR3 comprises or consists of the amino acid sequence 287, 291, 295, 299, 303, 307, 311, 315, 319, 323, 327, 335 or 339.

In one embodiment, the binding molecule has a combination of a CDR1, CDR2 and CDR3 as shown for clones 3.1 to 3.14 in FIG. 3.

In one embodiment, the family 3 or family 3-like sequence has a $V_H$ domain that comprises or consists of SEQ ID NO. 288 or a sequence with at least 40%, 50%, 60%, 70%, 80%, 81%, 82%, 83%, 84%, 86%, 85%, 87%, 88%, 89%, 90%, 91%, 92%, 93%, 94%, 95%, 96%, 97%, 98%, 99% homology thereto. CDR sequences of such sequences are shown in FIG. 3. For example, the $V_H$ domain comprises or consists of SEQ ID NO. 292, 296, 300, 304, 308, 312, 316, 320, 324, 328, 332, 336 or 340.

In another embodiment, the invention also relates to a binding molecule comprising at least one immunoglobulin single domain antibody directed against IL-17A wherein said domain is a human $V_H$ domain and wherein said IL-17A binding molecule comprises a family 4 or family 4-like sequence.

In one embodiment, the family 4 or family 4-like sequence comprises CDR3 sequence SEQ ID NO. 343, or a sequence with at least 70%, 80%, 85%, 90%, 95% homology thereto. In one embodiment, said CDR3 comprises or consists of the amino acid sequence SEQ ID NO. 343 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, said CDR1 comprises or consists of the amino acid sequence SEQ ID NO. 341 or a sequence with at least 70%, 80%, 81%, 82%, 83%, 84%, 85%, 86%, 87%, 88%, 89%, 90%, 91%, 92%, 93%, 94%, 95% 96%, 97%, 98% or 99% homology thereto. In one embodiment, said CDR2 comprises or consists of the amino acid sequence SEQ ID NO. 342 or a sequence with at least 70%, 80%, 81%, 82%, 83%, 84%, 85%, 87%, 88%, 89%, 90%, 91%, 92%, 93%, 94%, 95%, 96%, 97%, 98% or 99% homology thereto.

In one embodiment, the family 4 or family 4-like sequence has a $V_H$ domain that comprises or consists of SEQ ID NO. 344 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. Examples are shown in FIG. 4.

In another embodiment, said IL-17A binding molecule comprises a family 5 or family 5-like sequence.

In one embodiment, the family 5 or family 5-like sequence comprises CDR3 sequence SEQ ID NO. 347, or a sequence with at least 80%, 85%, 90%, 95% homology thereto. In one embodiment, said CDR3 comprises or consists of the amino acid sequence SEQ ID NO. 347 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, said CDR1 comprises or consists of the amino acid sequence SEQ ID NO. 345 or a sequence with at least 80%, 81%, 82%, 83%, 84%, 85%, 86% 87%, 88%, 89%, 90%, 91%, 92%, 93%, 95%, 94%, 96%, 97%, 98% or 99% homology thereto. In one embodiment, said CDR2 comprises or consists of the amino acid sequence SEQ ID NO. 346 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, the family 5 or family 5-like sequence has a $V_H$ domain that comprises or consists of SEQ ID NO. 348 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. Examples are shown in FIG. 5.

Additionally, binding kinetics and affinity (expressed as the equilibrium dissociation constant, KD) of IL-17A binding molecules of the invention for binding IL-17A may be determined, e.g., using surface plasmon resonance such as BIAcore®, or KD may be estimated from pA2 analysis.

In another aspect, the invention relates to a binding molecule that has a KD (M) value of 5×10−9 to 1×10−11, for example 5×10−9 to 2×10−10 wherein said KD is calculated using BIAcore®. The term "KD" refers to the "equilibrium dissociation constant" and refers to the value obtained in a titration measurement at equilibrium, or by dividing the dissociation rate constant (Koff) by the association rate constant (Kon). In one embodiment, the KD may be as shown in the examples.

In one embodiment, the binding molecule is a family 1 or family 1-like sequence. In one embodiment, the family 1 or family 1-like sequence comprises CDR3 sequence SEQ ID NO. 3, or a sequence with at least 80%, 85%, 90%, 95% homology thereto. In one embodiment, said CDR3 comprises or consists of the amino acid sequence SEQ ID NO. 3 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, CDR1 comprises or consists of the amino acid sequence SEQ ID NO. 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 141, 145, 149, 153, 157, 161, 165 169, 173, 177,181, 185, 189, 193, 197, 201, 205, 209, 213, 217, 221, 225, 229, 233, 237, 241, 245 438, 442, 446, 450, 454, 458 or 462, CDR2 comprises or consists of the amino acid sequence SEQ ID NO. 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158, 162, 166, 170, 174, 178, 182, 186, 190, 194, 198, 202, 206, 210, 214, 218, 222, 226, 230, 234, 238, 242, 246 439, 443, 447, 451, 455, 459, 463 and CDR3 comprises or consists of the amino acid sequence SEQ ID NO. 3, 7, 11, 15, 19, 23, 27, 31, 35, 39, 43, 47, 51, 55, 59, 63, 67, 71, 75, 79, 83, 87, 91, 95, 99, 103, 107, 111, 115, 119, 123, 127, 131, 135, 139, 143, 147, 151, 155, 159, 163, 167, 171, 175, 179, 183, 187, 191, 195, 199, 203, 207, 211, 215, 219, 223, 227, 231, 235, 239, 243, 247 440, 444, 448, 452, 456, 460 or 464.

In one embodiment, the binding molecule has combinations of CDR1, CDR2 and CDR3 as shown for clones 1.1 to 1.62 in FIG. 1A-B. In one embodiment, the binding molecule has combinations of CDR1, CDR2 and CDR3 as shown for clones 1.1 to 1.22 in FIG. 1A.

In one embodiment, the family 1 or family 1-like sequence has a $V_H$ domain that comprises or consists of SEQ ID NO. 4 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. Examples are shown in FIG. 1A-B. For example, $V_H$ domain comprises or consists of SEQ ID NO. 8, 12, 16, 20, 24, 28, 32, 36, 40, 44, 48, 52, 56, 60, 64, 68, 72, 76, 80, 84, 88, 92, 96, 100, 104, 108, 112, 116, 120, 124, 128, 132, 136, 140, 144, 148, 152, 156, 160, 164, 168, 172, 176, 180, 184, 188, 192, 196, 200, 204, 208, 212, 216, 220, 224, 228, 232, 236, 240, 244 or 248.

In one embodiment, the binding molecule is a family 2 or family 2-like sequence. In one embodiment, the family 2-like sequence comprises CDR3 sequence SEQ ID NO. 251 or a sequence with at least 80%, 85%, 90%, 95% homology thereto. In one embodiment, said CDR3 comprises or consists of the amino acid sequence SEQ ID NO. 251 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, said CDR1 comprises or consists of the amino acid sequence SEQ ID NO. 249 or a sequence with at least 60,%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 250 or a sequence with at least 80%, 81%, 82%, 83%, 84%, 85%, 86%, 87%, 88%, 89%, 90%, 91%, 92%, 93%, 94%, 95%, 96%, 97%, 98%, 99% homology thereto.

In one embodiment, CDR1 comprises or consists of the amino acid sequence SEQ ID NO. 249, 253, 257, 261, 265, 269, 273, 277 or 281, CDR2 comprises or consists of the amino acid sequence SEQ ID NO. 250, 254, 258, 262, 266, 270, 274, 278 or 282 and CDR3 comprises or consists of the amino acid sequence SEQ ID NO. 251, 255, 259, 263, 267, 271, 275, 279 or 283.

In one embodiment, the binding molecule has a combination of a CDR1, CDR2 and CDR3 as shown for clones 2.1 to 2.9 in FIG. 2A-B.

In one embodiment, the family 2 or family 2-like sequence has a $V_H$ domain that comprises or consists of SEQ ID NO. 252 or a sequence with at least 40%, 50%, 60%, 70%, 80%, 81%, 82%, 83%, 84%, 85%, 86%, 87%, 88%, 89%, 90%, 91%, 92%, 93%, 94%, 96%, 95%, 97%, 98%, 99% homology thereto. Examples are shown in table 2. In one embodiment, the family 2 sequence has a $V_H$ domain that comprises or consists of SEQ ID NO. 256, 260, 264, 268, 272, 276, 280 or 284.

In one embodiment, the binding molecule is a family 3-like sequence. In one embodiment, the family 3 or family 3-like sequence comprises CDR3 sequence SEQ ID NO. 287 or a sequence with at least 60%, 70%, 80%, 85%, 90%, 95% homology thereto. In one embodiment, said CDR3 comprises or consists of the amino acid sequence SEQ ID NO.: SEQ ID NO. 287 or a sequence with at least 81%, 82%, 83%, 84%, 85%, 86%, 87%, 88%, 89%, 90%, 91%, 92%, 93%, 94%, 95%, 96%, 97%, 98% or 99% homology thereto.

In one embodiment, said CDR1 comprises or consists of the amino acid sequence SEQ ID NO. 285 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 286 or a sequence with at least 70%, 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, CDR1 comprises or consists of the amino acid sequence SEQ ID NO. 285, 289, 293, 297, 301, 305, 309, 313, 317, 321, 325, 329, 333 or 337, CDR2 comprises or consists of the amino acid sequence 286, 290, 294, 298, 302, 306, 310, 314, 318, 322, 326, 330, 334 or 338 and CDR3 comprises or consists of the amino acid sequence 287, 291, 295, 299, 303, 307, 311, 315, 319, 323, 327, 335 or 339.

In one embodiment, the binding molecule has combinations of CDR1, CDR2 and CDR3 as shown for clones 3.1 to 3.14 in FIG. 3.

In one embodiment, the family 3 or family 3-like sequence has a $V_H$ domain that comprises or consists of SEQ ID NO. 288 or a sequence with at least 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% homology thereto. CDR sequences of such sequences are shown in FIG. 3. For example, $V_H$ domain comprises or consists of SEQ ID NO. 292, 296, 300, 304, 308, 312, 316, 320, 324, 328, 332, 336 or 340.

In one embodiment, the binding molecule is a family 4 or family 4-like sequence. In one embodiment, this comprises CDR3 sequence SEQ ID NO. 343, or a sequence with at least 80%, 85%, 90%, 95% homology thereto. In one embodiment, said CDR3 comprises or consists of the amino acid sequence SEQ ID NO. 343 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, said CDR1 comprises or consists of the amino acid sequence SEQ ID NO. 341 or a sequence with at least 80%, 81%, 82%, 83%, 84%, 85%, 87%, 88%, 89%, 90%, 91%, 92%, 93%, 94%, 96%, 97%, 98%, 99% homology thereto. In one embodiment, said CDR2 comprises or consists of the amino acid sequence SEQ ID NO. 342 or a sequence with at least 80%, 81%, 82%, 83%, 84%, 85%, 87%, 88%, 89%, 90%, 91%, 92%, 93%, 94%, 96%, 97%, 98%, 99% homology thereto.

In one embodiment, the family 4 sequence has a $V_H$ domain that comprises or consists of SEQ ID NO. 344 or a sequence with at least 40%, 50%, 60%, 70%, 80%, 81%, 82%, 83%, 84%, 85%, 87%, 88%, 89%, 90%, 91%, 92%, 93%, 94%, 96%, 97%, 98%, 99% homology thereto. Examples are shown in FIG. 4.

In another embodiment, said IL-17 binding molecule comprises a family 5 or family 5-like sequence.

In one embodiment, the family 5 or family 5-like sequence comprises CDR3 sequence SEQ ID NO. 347, or a sequence with at least 80%, 85%, 90%, 95% homology thereto. In one embodiment, said CDR3 comprises or consists of the amino acid sequence SEQ ID NO. 347 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, said CDR1 comprises or consists of the amino acid sequence SEQ ID NO. 345 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto. In one embodiment, said CDR2 comprises or consists of the amino acid sequence SEQ ID NO. 346 or a sequence with at least 80%, 81%, 82%, 83%, 84%, 85%, 86%, 87%, 88%, 89%, 90%, 91%, 92%, 93%, 94%, 95%, 96%, 97%, 98% or 99% homology thereto.

In one embodiment, the family 5 sequence has a $V_H$ domain that comprises or consists of SEQ ID NO. 348 or a sequence with at least 40%, 50%, 60%, 70%, 80%, 81%, 82%, 83%, 84%, 85%, 87%, 88%, 89%, 90%, 91%, 92%, 93%, 94%, 96%, 97%, 98%, 99% homology thereto. Examples are shown in FIG. 5.

In one embodiment, the binding molecule has a KD as defined above and an $IC_{50}$ for inhibition of IL-6 production as defined above.

The invention also relates to an isolated $V_H$ domain comprising an amino acid product of or derived from a human $V_H$ germline sequence, for example a human $V_H$ 3-07 or $V_H$ 1-02 germline sequence.

A skilled person will know that there are different ways to identify and obtain the antigen binding molecules as described herein, including in vitro and in vivo expression libraries. This is further described in the examples. Optimisation techniques known in the art, such as display (e.g., ribosome and/or phage display) and/or mutagenesis (e.g., error-prone mutagenesis) can be used.

Methods for preparing or generating the polypeptides, nucleic acids, host cells, products and compositions described herein using in vitro expression libraries can comprise the steps of:
a) providing a set, collection or library of nucleic acid sequences encoding amino acid sequences; and
b) screening said set, collection or library for amino acid sequences that can bind to/have affinity for IL-17A and
c) isolating the amino acid sequence(s) that can bind to/have affinity for IL-17A.

In the above methods, the set, collection or library of sequences may be displayed on a phage, phagemid, ribosome or suitable micro-organism (such as yeast), such as to facilitate screening. Suitable methods, techniques and host organisms for displaying and screening (a set, collection or library of) sequences will be clear to the person skilled in the art (see for example Phage Display of Peptides and Proteins: A Laboratory Manual, Academic Press; 1st edition (Oct. 28, 1996) Brian K. Kay, Jill Winter, John McCafferty).

The binding molecule described herein, including $V_H$ domains, can be expressed in a transgenic rodent. The transgenic rodent, for example a mouse, has a reduced capacity to express endogenous antibody genes. Thus, in one embodiment, the rodent has a reduced capacity to express endogenous light and/or heavy chain antibody genes. The rodent may therefore comprise additional modifications to disrupt expression of endogenous light and/or heavy chain antibody genes so that no functional light and/or heavy chains are produced.

The invention also relates to a method for producing a binding molecule comprising at least one human immunoglobulin single domain antibody capable of binding human IL-17A wherein said domain is a human $V_H$ domain said method comprising
d) immunising a transgenic mouse with an IL-17A antigen wherein said mouse expresses a nucleic acid construct comprising human heavy chain V genes and is not capable of making functional endogenous light or heavy chains,
e) generating a library of sequences comprising $V_H$ domain sequences from said mouse and
f) isolating sequences comprising $V_H$ domain sequences from said libraries.

The invention also relates to a binding molecule comprising a $V_H$ domain obtained or obtainable from a mouse that is not capable of making functional endogenous light or heavy chains, for example through the method described above.

In one embodiment, the rodent is a mouse. The mouse may comprise a non-functional lambda light chain locus. Thus, the mouse does not make a functional endogenous lambda light chain. In one embodiment, the lambda light chain locus is deleted in part or completely or rendered non-functional through insertion, inversion, a recombination event, gene editing or gene silencing. For example, at least the constant region genes C1, C2 and C3 may be rendered non-functional. In one embodiment, the locus is functionally silenced so that mouse does not make a functional endogenous lambda light chain.

Furthermore, the mouse may comprise a non-functional kappa light chain locus. Thus, the mouse does not make a functional endogenous kappa light chain. In one embodiment, the kappa light chain locus is deleted in part or completely or rendered non-functional through insertion inversion, a recombination event, gene editing or gene silencing. In one embodiment, the locus is functionally silenced so that the mouse does not make a functional endogenous kappa light chain.

The mouse having functionally silenced endogenous lambda and kappa L-chain loci may, for example, be made as disclosed in WO 2003/000737, which is hereby incorporated by reference in its entirety.

Furthermore, the mouse may comprise a non-functional heavy chain locus. Thus, the mouse does not make a functional endogenous heavy chain. In one embodiment, the heavy chain locus is deleted in part or completely or rendered non-functional through insertion inversion, a recombination event, gene editing or gene silencing.

For example, as described in WO 2004/076618 (hereby incorporated by reference in its entirety), all 8 endogenous heavy chain constant region immunoglobulin genes (μ, δ, γ3, γ1, γ2a, γ2b, ε and α) are absent in the mouse, or partially absent to the extent that they are non-functional, or genes δ, γ3, γ1, γ2a, γ2b and ε are absent and the flanking genes μ and α are partially absent to the extent that they are rendered non-functional, or genes μ, δ, γ3, γ1, γ2a, γ2b and ε are absent and α is partially absent to the extent that it is rendered non-functional, or δ, γ3, γ1, γ2a, γ2b, ε and α are absent and μ is partially absent to the extent that it is rendered non-functional. In one embodiment, the locus is functionally silenced so that mouse does not make a functional endogenous heavy light chain.

By deletion in part is meant that the endogenous locus gene sequence has been deleted or disrupted, for example by an insertion, to the extent that no functional endogenous gene product is encoded by the locus, i.e. that no functional product is expressed from the locus. In another embodiment, the locus is functionally silenced.

In one embodiment, the mouse comprises a non-functional endogenous heavy chain locus, a non-functional endogenous lambda light chain locus and a non-functional endogenous kappa light chain locus. The mouse therefore does not produce any functional endogenous light or heavy chains. Thus, the mouse is a triple knockout (TKO) mouse.

The transgenic mouse comprises a vector, for example a Yeast Artificial Chromosome (YAC) for expressing a heterologous heavy chain locus. YACs are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopaedia of Life Sciences 2002 Macmillan Publishers Ltd, Nature Publishing Group/www.els.net).

For example, the YAC may comprise a plethora of human $V_H$, D and J genes in combination with mouse immunoglobulin constant region genes lacking $C_H1$ domains, mouse enhancer and regulatory regions. An example of such a YAC is provided in the example section.

Alternative methods known in the art may be used for deletion or inactivation of endogenous mouse or rat immunoglobulin genes and introduction of human $V_H$, D and J genes in combination with mouse immunoglobulin constant region genes lacking $C_H1$ domains, mouse enhancer and regulatory regions.

Transgenic mice can be created according to standard techniques as illustrated in the examples. The two most characterised routes for creating transgenic mice are via pronuclear microinjection of genetic material into freshly fertilised oocytes or via the introduction of stably transfected embryonic stem cells into morula or blastocyst stage embryos. Regardless of how the genetic material is introduced, the manipulated embryos are transferred to pseudopregnant female recipients where pregnancy continues and candidate transgenic pups are born.

The main differences between these broad methods are that ES clones can be screened extensively before their use to create a transgenic animal. In contrast, pronuclear microinjection relies on the genetic material integrating to the host genome after its introduction and, generally speaking, the successful incorporation of the transgene cannot be confirmed until after pups are born.

There are many methods known in the art to both assist with and determine whether successful integration of transgenes occurs. Transgenic animals can be generated by multiple means including random integration of the construct into the genome, site-specific integration, or homologous recombination. There are various tools and techniques that can be used to both drive and select for transgene integration and subsequent modification including the use of drug resistance markers (positive selection), recombinases, recombination-mediated cassette exchange, negative selection techniques, and nucleases to improve the efficiency of recombination. Most of these methods are commonly used in the modification of ES cells. However, some of the techniques may have utility for enhancing transgenesis mediated via pronuclear injection.

Further refinements can be used to give more efficient generation of the transgenic line within the desired background. As described above, in preferred embodiments, the endogenous mouse immunoglobulin expression is silenced to permit sole use of the introduced transgene for the expression of the heavy-chain only repertoire that can be exploited for drug discovery. Genetically-manipulated mice, for example TKO mice that are silenced for all endogenous immunoglobulin loci (mouse heavy chain, mouse kappa chain and mouse lambda chain) can be used as described above. The transfer of any introduced transgene to this TKO background can be achieved via breeding, (either conventional or with the inclusion of an IVF step to give efficient scaling of the process). However, it is also possible to include the TKO background during the transgenesis procedure. For example, for microinjection, the oocytes may be derived from TKO donors. Similarly, ES cells from TKO embryos can be derived for use in transgenesis.

The binding molecule of the invention may be conjugated to another moiety. This can be selected from a toxin, enzyme, radioisotope, other detectable label, peptide, protein and chemical moiety of interest.

For example, the binding molecule of the invention may be labelled with a detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Half-life of the binding molecule of the invention can be increased by a chemical modification, especially by PEGylation or linking to a serum albumin, e.g., HAS, or an anti-HAS binding molecule, or by incorporation in a liposome.

In one embodiment, the binding molecule of the invention is covalently modified. The term "covalently modified/covalent modification" includes modifications of an antibody and binding molecule according to the present invention, e.g., of a specified sequence; with an organic proteinaceous or non-proteinaceous derivatizing agent, fusions to heterologous polypeptide sequences, and post-translational modifications. Covalent modified polypeptides, e.g., of a specified sequence, still have the functional properties described herein, for example the ability to bind the human IL-17 or e.g., neutralize IL-6 production of IL-17 induced human dermal fibroblasts by crosslinking. Covalent modifications are generally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally de-amidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the [alpha]-amino groups of lysine, arginine, and histidine side chains. Covalent modifications e.g., include fusion proteins comprising a binding molecule according to the present invention, e.g., of a specified sequence and their amino acid sequence variants, such as immunoadhesins, and N-terminal fusions to heterologous signal sequences.

In another aspect of the present invention, there is provided a pharmaceutical composition comprising an IL-17A binding molecule according to the present invention and optionally a pharmaceutically acceptable carrier. The binding molecule of the present invention or compositions can be administered by any convenient route and examples of the administration form of the binding molecule or composition of the present invention include without limitation topical, in particular dermal, parenteral, and intranasal. Parenteral administration includes subcutaneous injections, intravenous, intramuscular, intrasternal injection or infusion techniques. Compositions can take the form of one or more dosage units.

The composition of the invention can be in the form of a liquid, e.g., a solution, emulsion or suspension. The liquid can be useful for delivery by injection. The liquid compositions of the invention, whether they are solutions, suspensions or other like form, can also include one or more of the following: sterile diluents such as water, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A composition can be enclosed in an ampoule, a disposable syringe or a multiple-dose vial made of glass, plastic or other material.

In specific embodiments, it can be desirable to administer one or more binding molecule of the present invention or compositions locally to the area in need of treatment.

Thus, in a preferred embodiment of all aspects of the invention, administration of the composition or binding molecule of the invention is by topical administration to healthy or diseased skin. The binding molecule is capable of penetrating at least the outer layer of the skin and can therefore be delivered dermally or transdermally. Accordingly, in one embodiment of the various aspects of the invention, topical delivery of the the composition or binding molecule of the invention to the skin is direct delivery into the skin for local non-systemic exposure. In another embodiment, topical delivery of the the composition or binding molecule of the invention to the skin is direct delivery to the skin to provide systemic exposure following penetration through all layers of the skin.

The skin that is treated may be diseased or healthy skin. In a preferred embodiment, the skin disease is psoriasis or atopic dermatitis.

Preferably, the surface area to which it is applied is 1%-30% of the body surface area, for example 1%-10% or 1-20%. Administration may thus be to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 27%, 26%, 28%, 29% or 30% of body surface area. In one embodiment, the disease state is mild. In another embodiment, the disease state is moderate. In another embodiment, the disease state is severe. For the treatment of psoriasis, administration is to areas affected, typically one or more area selected from elbows, knees, palms of hands, scalp, soles of feet, genitals, upper thighs, groin, buttocks, face and torso.

For the treatment of atopic dermatitis administration is to areas affected, typically one or more area selected from face, forearms and wrists.

The binding molecule can be directly applied to diseased or healthy skin in the form of cream, lotion, sprays, solution, gel, ointment, paste, plaster, patch, bioadhesive, suspension or the like, and/or may be prepared so as to contain liposomes, micelles, and/or microspheres. In one embodiment, the binding molecule is directly applied to diseased skin in the form of a liquid (e.g., a spray), plaster, patch or bioadhesive. In one embodiment, the binding molecule is directly applied to diseased skin in the form of a microemulsion.

Microemulsions are generally defined as having a droplet diameter within the range of 2-500 nm thus allowing effective delivery of actives into the skin. Microemulsions have been proposed for use in enhancing transdermal delivery of a range of compounds. This is described in US2007/0243132, incorporated herein in its entirety.

Specifically, as used herein, the term microemulsion refers to a formulation that comprises an oil phase, a water phase and a surfactant, wherein the microemulsion is capable of transdermal delivery of a binding molecule, for example comprising a human $V_H$ domain as described herein. Preferably, the microemulsion of the invention has a droplet diameter within the range of 2-500 nm. In one embodiment, the microemulsion further comprises a co-surfactant, a co-solvent, or a combination thereof.

The microemulsions of the present invention may be oil-in-water microemulsion, wherein the surfactant is preferentially soluble in water; water-in-oil microemulsion, wherein the surfactant is mainly in the oil phase; a three-phase microemulsion wherein a surfactant-rich middle phase coexists with water and oil phases; a bicontinuous monophase; a single-phase micellar solution that forms upon addition of a sufficient quantity of amphiphile (surfactant plus alcohol); or a swollen micellar solution.

The microemulsions of the present invention may be produced by methods known in the art. In general, microemulsions are produced by emulsifying components under conditions including typically sufficient force or the required temperature to generate the required dispersion level, conductivity, viscosity, percolativity or other dispersion characteristics.

Microemulsion formation can be assessed using scattering and spectroscopic techniques such as neutron scattering, time-average scattering, quasi-electric light scattering, i.e., high-resolution ultrasonic spectroscopy or photon correlation spectroscopy. The partition coefficients of microemulsions may also be measured chromatographically. The selection of particular formulations is based on a number of different paradigms depending upon the desired application. Illustrative paradigms include the hydrophilic-lipophilic balance, the phase-inversion temperature, or the cohesive-energy ratio. Microemulsions may be formulated using a wide range of immiscible liquids and other additional agents.

The microemulsion of the present invention may comprise an oil phase in the range of from 50 to 99% by weight, most preferably from 50 to 90% by weight; a water phase in the range of from 2 and 50% by weight, most preferably from 1 and 50 by weight; from 0.1 to 90% by weight surfactant, preferably from 1 to 90% by weight surfactant. The microemulsion may further comprise 0.1 to 90% by weight cosurfactant or cosolvent; preferably 1 to 90% by weight cosurfactant or cosolvent.

The oil phase may comprise natural oils derived from plants or animals, such as vegetable oils, sunflower oils, coconut oils, almond oils; purified synthetic or natural di or triglycerides (such as Crodamol GTCC® and Capmul MCM®); phospholipids and their derivatives (such as lecithin or lysolecithin); fatty acid esters (such as isopropyl myristate, isopropyl palmitate, ethyl oleate, oleic acid ethyl ester); hydrocarbons (such as hexane, the n-decane through n-octadecane series); and/or glycerolysed fats and oils (such as glyceryl monooleate, glyceryl monocaprylate, glycerol monocaprate, propylene glycol monocaprylate, propyleme glycol monolaurate).

Other oil phase ingredients include, but are not limited to, Labrafil M 1944 CS®, benzene, tetrahydrofuran, and n-methyl pyrrolidone, or halogenated hydrocarbons, such as methylene chloride, or chloroform. In a particular embodiment, the oil phase comprises Crodamol GTCC® and Capmul MCM®, at 3:1 ratio. The oil component is either used alone or in combination with another oil component or components. Each oil or unique mixture of oils may require a different surfactant or mixture of surfactants or surfactants and co-surfactants to form a microemulsion with the water phase, as can routinely be determined by those of skill in the art. Water phase ingredients may comprise water and any water-soluble components in water, including one or more pharmaceutical agent.

The microemulsion of the present invention may further comprise solvents or other agents to enhance emulsion formation or stability. Other agents may be introduced to provide functions such as pH, ionic content, polymerisation, taste, fragrance, sterility, colour, viscosity etc.

The microemulsions of the present invention may also be generated using any suitable synthetic plastic or polymeric, monomeric or hybrid colloidal material.

According to the methods and uses set out above, the binding molecule can be administered together with one or more chemical skin penetration enhancer. Examples of skin penetration enhancers are set out below.

In another embodiment, the binding molecule is administered using occlusion. In one embodiment, the binding molecule is administered to healthy or diseased skin together with a chemical skin penetration enhancer and using occlusion. In one embodiment, the binding molecule is administered to healthy or diseased skin as a microemulsion and using occlusion.

In another embodiment of the various aspects of the invention, administration may be improved using non-chemical skin penetration enhancers, for example phonophoresis, sonophoresis, electroporation or using the microneedle technique. This uses small needles (10-200 μm height and 10-50 μm width) which are connected with the drug reservoir. The microneedle delivery device is applied to the skin surface without reaching the nerve endings of the upper dermis.

A binding molecule administered as set out above is capable of penetrating at least the outer layer of the skin and thus delivers an effective therapeutic amount of the binding molecule to treat the disease. A binding molecule administered as set out herein is capable of penetrating the skin in preferably 6 hours or less, for example 1 hour or less.

In one aspect, the invention relates to a pharmaceutical composition comprising a binding molecule of the invention and a skin penetration enhancer that facilitates or improves skin penetration. Unless otherwise, specified, the term skin penetration enhancer as used herein refers to a chemical skin penetration enhancer. Numerous chemical penetration enhancers are known in the art and can be used in the composition of the invention. These include, but are not limited to: water, alcohols, preferably alcohols with up to six carbon atoms, for example ethanol, glycols, for example alcohol diethylene glycol (Transcutol®), alkyl-N,N-disubstituted aminoacetates, for example dodecyl-N,N-dimethylaminoacetate, esters, for example ethylacetate, Azone® and derivatives, surfactants, for example sodium dodecyl sulphate, terpenes and terpenoids, for example d-Limonene, fatty acids, for example oleic acid, urea and derivatives, for example 1,3-Diphenyl-urea, pyrrolidones, for example N-Methyl-2-pyrrolidone, and 2-pyrrolidone-5-carboxylic acid, cyclodextrins, for example beta-cyclodextrin, sulphoxides, for example dimethylsulphoxide. Other skin penetration enhancers are known to the skilled person. In one embodiment, the enhancer is not water. In one embodiment, the skin penetration enhancers are selected from one or more of Propylene Glycol, Isopropyl Myristate and Azone. Preferred penetration enhancers are DMSO, azone, Transcutol®, isopropyl myristate, oleic acid or combinations thereof, for example as set out in tables 13 and 14 and in the examples.

In one embodiment, the penetration enhancer is not one or more of water, ethanol, polyethylene glycol derivatives, polyoxyethylene derivatives such as polysorbate, a fatty alcohol such as cetyl alcohol, stearyl alcohol, or cerostearyl alcohol, glycerol and propylene glycol.

The amount of the binding molecule of the present invention that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions of the invention comprise an effective amount of a binding molecule of the present invention such that a suitable dosage will be obtained. The correct dosage of the compounds will vary according to the particular formulation, the mode of application, and its particular site, host and the disease being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Typically, this amount is at least about 0.01% of a binding molecule of the present invention by weight of the composition.

Preferred compositions of the present invention are prepared so that a parenteral dosage unit contains from about 0.01% to about 2% by weight of the binding molecule of the present invention.

For intravenous administration, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight.

The present compositions can take the form of suitable carriers, such aerosols, sprays, suspensions, or any other form suitable for use. Other examples of suitable pharmaceutical carriers are described in "Remington's Pharmaceutical Sciences" by E. W. Martin.

Liposomes and micelles can also be used according to the invention.

Liposomes are microscopic vesicles having a lipid wall comprising a lipid bilayer, and, in the present context, encapsulate heavy chain only antibody or composition of the invention. Liposomal preparations herein include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename Lipofectin (GIBCO BRL, Grand Island, N.Y.). Similarly, anionic and neutral liposomes are readily available as well or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Microspheres, similarly, may be incorporated into the present formulations. Like liposomes and micelles, microspheres essentially encapsulate one or more components of the present formulations. They are generally although not necessarily formed from lipids, preferably charged lipids such as phospholipids. Preparation of lipidic microspheres is well known in the art and described in the pertinent texts and literature.

The pharmaceutical compositions can be prepared using methodology well known in the pharmaceutical art. For example, a composition intended to be administered by injection can be prepared by combining a binding molecule of the present invention with water so as to form a solution. A surfactant can be added to facilitate the formation of a homogeneous solution or suspension.

The invention furthermore relates to a method for the prevention and/or treatment of a disease comprising administering a binding molecule of the invention to a patient, said method comprising administering, to a subject in need thereof, a pharmaceutically active amount of a binding molecule and/or of a pharmaceutical composition of the invention. More in particular, the invention relates to a method for the prevention and/or treatment of a disease selected from the non-limiting group consisting of the diseases and disorders listed herein, said method comprising administering, to a subject in need thereof, a pharmaceutically active amount of a binding molecule or a pharmaceutical composition of the invention. Examples of the immune related diseases that can be treated according to the invention will be clear to the skilled person based on the disclosure herein, and for example include autoimmune diseases, inflammatory conditions, allergies and allergic conditions, hypersensitivity reactions, severe infections, and organ or tissue transplant rejection.

The invention also relates to a binding molecule of the invention for use in the treatment of disease. In another aspect, the invention relates to a binding molecule of the invention for use in the treatment of a disease, for example autoimmune disease, inflammatory conditions, allergies and allergic conditions, hypersensitivity reactions, severe infections, and organ or tissue transplant rejection.

In another aspect, the invention relates to the use of a binding molecule of the invention in the manufacture of a medicament for the treatment of a disease, for example autoimmune disease, inflammatory conditions, allergies and allergic conditions, hypersensitivity reactions, severe infections, and organ or tissue transplant rejection. According to the different aspects above, the disease may be selected from the following non-limiting list: psoriasis, systemic lupus erythematosis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, and Whipple's disease, autoimmune or immune-mediated skin diseases including bullous skin diseases, erythema multiforme and contact dermatitis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, autoimmune haematological disorders (including e.g., hemolytic anaemia, aplastic anaemia, pure red cell anaemia and idiopathic thrombocytopenia), autoimmune inflammatory bowel disease (including e.g., ulcerative colitis, Crohn's disease and Irritable Bowel Syndrome), transplantation associated diseases including graft rejection and graft-versus-host-disease.

The binding molecules of the invention are also useful for the treatment, prevention, or amelioration of asthma, bronchitis, pneumoconiosis, pulmonary emphysema, and other obstructive or inflammatory diseases of the airways.

In a preferred embodiment, the disease is selected from psoriasis, spondyloarthropathies, uveitis, atopic dermatitis and asthma.

Antibodies of the invention are useful for treating undesirable acute and hyperacute inflammatory reactions which are mediated by IL-17, or involve IL-17 production, or the promotion of TNF release by IL-17, e.g., acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

The binding molecules of the invention are particularly useful for treating diseases of bone metabolism including osteoarthritis, osteoporosis and other inflammatory arthritis, and bone loss in general, including age-related bone loss, and in particular periodontal disease.

The binding molecule of the invention may be administered as the sole active ingredient or in combination with one or more other drug, e.g., an immunosuppressive or immunomodulating agent or other anti-inflammatory agent, e.g., for the treatment or prevention of diseases mentioned above. For example, the binding molecule of the invention maybe used in combination with immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g., a recombinant binding molecule having at least a portion of the extracellular domain of CTLA4 or a mutant thereof, e.g., an at least extracellular portion of CTLA4 or a mutant thereof joined to a non-CTLA4 protein sequence, e.g., CTLA4Ig (e.g., designated ATCC 68629) or a mutant thereof, e.g., LEA29Y; adhesion molecule inhibitors, e.g., LFA-I antagonists, ICAM-I or -3 antagonists, VCAM-4 antagonists or VLA-4 antagonists; or a chemotherapeutic agent, e.g., paclitaxel, gemcitabine, cisplatinum, doxorubicin or 5-fluorouracil; anti TNF agents, e.g., monoclonal antibodies to TNF, e.g., infliximab, adalimumab, CDP870, or receptor constructs to TNF-RI or TNF-RII, e.g., Etanercept®, PEG-TNF-RI; blockers of proinflammatory cytokines, IL-I blockers, e.g., Anakinra or IL-I trap, AAL160, ACZ 885, IL-6 blockers; chemokines blockers, e.g., inhibitors or activators of proteases, e.g., metalloproteases, anti-IL-15 antibodies, anti-IL-6 antibodies, anti-CD20 antibodies, NSAIDs, such as aspirin or an anti-infectious agent. This list is not limited to the agents mentioned.

The binding molecule of the invention may be administered at the same time or at a different time as the other drug e.g., simultaneously, separately or sequentially.

The invention also relates to methods for diagnosing a disease. Exemplary diseases are listed above. In one embodiment, the disease is psoriasis. The method comprises determining the level of IL-17A expression by detecting binding of a binding molecule described herein in a sample and comparing the level of expression of IL-17A in the test sample with the level of expression in a control sample from a non-psoriatic subject or with a standard value or standard value range for a non-psoriatic subject. An elevation in IL-17A expression in the test sample relative to the control or standard indicates presence of the disease.

In another aspect, the invention provides a kit containing a binding molecule of the invention useful for the treatment of a disease described above and optionally instructions for use.

The invention also relates to detection methods using the binding molecule of the invention. Given their ability to bind to human IL-17A, the human-IL-17A-binding molecules, disclosed herein can be used to detect IL-17A (e.g., in a biological sample, such as serum or plasma), using a conventional immunoassay, such as an enzyme linked immunosorbent assays (ELISA), an radioimmunoassay (RIA) or tissue immunohistochemistry. A method for detecting IL-17A in a biological sample is provided comprising contacting a biological sample with a binding molecule, disclosed herein and detecting either the binding molecule bound to IL-17A or unbound binding molecule, to thereby detect IL-17A in the biological sample. The binding molecule is directly or indirectly labeled with a detectable substance to facilitate detection of the bound or unbound antibody. Suitable detectable substances include various enzymes, prosthetic groups, fluorescent materials, luminescent materials and radioactive materials.

Alternative to labeling the binding protein, human IL-17A can be assayed in biological fluids by a competition immunoassay utilizing IL-17 standards labeled with a detectable substance and an unlabeled human IL-17 binding molecule. In this assay, the biological sample, the labeled IL-17 standards and the human IL-17A binding molecule are combined and the amount of labeled IL-17 standard bound to the unlabeled binding molecule is determined. The amount of human IL-17A in the biological sample is inversely proportional to the amount of labeled IL-17 standard bound to the IL-17 binding molecule. Similarly, human IL-17 can also be assayed in biological fluids by a competition immunoassay utilizing IL-17 standards labeled with a detectable substance and an unlabeled human IL-17 binding molecule.

As explained herein, the binding molecules of the invention are capable of neutralizing IL-17 activity, e.g., human IL-17 activity, both in vitro and in vivo.

Accordingly, such binding molecule disclosed herein can be used to inhibit IL-17 activity, e.g., in a cell culture containing IL-17, in human subjects or in other mammalian subjects having IL-17 with which a binding molecule disclosed herein cross-reacts. In one embodiment, a method for inhibiting or increasing IL-17 activity is provided comprising contacting IL-17 with a binding molecule disclosed herein such that IL-17 activity is inhibited or increased. For example, in a cell culture containing, or suspected of containing IL-17, a binding molecule disclosed herein can be added to the culture medium to inhibit IL-17 activity in the culture.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including references to gene accession numbers.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

EXAMPLES

Example 1. Construction of Tg/TKO Mice

Mice carrying a heavy-chain antibody transgenic locus in germline configuration within a background that is silenced for endogenous heavy and light chain antibody expression (triple knock-out, or TKO) were created as previously described (WO2004/076618 and WO2003/000737, Ren et al. Genomics, 84, 686, 2004; Zou et al., J. Immunol., 170, 1354, 2003). Briefly, transgenic mice were derived following pronuclear microinjection of freshly fertilised oocytes with a yeast artificial chromosome (YAC) comprising a plethora of human $V_H$, D and J genes in combination with mouse immunoglobulin constant region genes lacking $C_H1$ domains, mouse enhancer and regulatory regions. Yeast artificial chromosomes (YACs) are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, ENCYCLOPEDIA OF LIFE SCIENCES 2002 Macmillan Publishers Ltd, Nature Publishing Group/www.els.net).

The YAC used was about 340 kb comprises 10 human heavy chain V genes in their natural configuration, human heavy chain D and J genes, a murine Cy1 gene and a murine 3' enhancer gene. It lacks the $C_H1$ exon. Specifically, the YAC comprised (from 5' to 3'): telomere-yeast TRP1 marker gene-Centromere-10 human V genes-human D genes-human J genes-mouse μ enhancer and switch-mouse Cyt ($C_H14$) gene-mouse 3' enhancer-Hygromycin resistant gene-yeast marker gene H/S3-telomere.

The transgenic founder mice were back-crossed with animals that lacked endogenous immunoglobulin expression to create the Tg/TKO lines used in the immunisation studies described.

Example 2. Antigen for Immunisation

The immunisations used recombinant purified protein. Recombinant human IL-17A was purchased from Peprotech (Peprotech, cat #AF-200-17).

Example 3. Immunisation Protocol

In the present case, recombinant protein was administered to the Tg/TKO. Briefly, mice aged 8-12 weeks of age each received a total of 10 ug of recombinant protein, emulsified in Complete Freund's Adjuvant and delivered subcutaneously, followed by boosts of 1-10 ug of recombinant protein, emulsified in Incomplete Freund's Adjuvant, also administered subcutaneously, given at various intervals following the initial priming. A final dose of antigen was administered intraperitoneally, in phosphate buffered saline, in the absence of adjuvant.

Alternative immunisation routes and procedures can also be employed. For example, different adjuvants or immune potentiating procedures may be used instead of Freund's adjuvant. DNA immunisations are often delivered intramuscularly or via a Genegun. Transfected cells or membrane preparations from such cells are often, although not exclusively, administered intraperitoneally.

Example 4. Serum ELISA

During and following immunisation, serum was collected from mice and checked for the presence of heavy-chain antibody responses to the immunogen by ELISA. Nunc Maxisorp plates (Nunc Cat. No. 443404) were coated overnight at 4° C. with 50 μl/well of a 5 μg recombinant antigen/ml of PBS solution. Following decanting of the antigen solution, plates were washed using PBS (prepared from PBS tablets, Oxoid cat no. BR0014G) supplemented with 0.05% Tween® 20 (sigma P1379), followed by washes with PBS without added Tween®. To block non-specific protein interactions, a solution of 3% skimmed milk powder (Marvel) in PBS was added to the wells and the plate was incubated for at least one hour at room temperature. Dilutions of serum in 3% skimmed milk powder/PBS were prepared in polypropylene tubes or plates and incubated for at least one hour at room temperature prior to transfer to the blocked ELISA plate where a further incubation of at least one hour took place. Unbound protein was then washed away using repetitive washes with PBS/Tween® followed by PBS. A solution of biotin-conjugated, goat anti mouse IgG, Fcgamma subclass 1 specific antibody (Jackson 115-065-205), prepared in PBS/3% μ was then added to each well and a further incubation at room temperature for at least one hour took place. Unbound detection antibody was removed by repeated washing using PBS/Tween® and PBS. Neutravidin-HRP solution (Pierce 31030) in 3% Marvel/PBS was then added to the ELISA plates and allowed to bind for at least 30 minutes. Following further washing, the ELISA was developed using TMB substrate (Sigma cat. no. T0440) and the reaction was stopped after 10 minutes by the addition of 0.5M $H_2SO_4$ solution (Sigma cat. no. 320501). Absorbances were determined by reading at 450 nm. Examples of Serum ELISA data are shown in FIG. 7. Alternative assays, such as ELISPOT assays, may also be used to check for immunisation-induced heavy-chain antibody responses.

Example 5. Generation of Libraries from Immunised Mice a. Processing Tissues, RNA Extraction and cDNA Manufacture Spleen, inguinal and brachial lymph nodes were collected into RNAlater from each immunised animal. For each animal, ⅓ of the spleen and 4 lymph nodes were processed separately. Initially, the tissues were homogenised; following transfer of tissues to Lysing matrix D bead tubes (MP Bio cat #116913100), 600 μl of RLT buffer containing β-mercaptoethanol (from Qiagen RNeasy® kit cat #74104) was added before homogenisation in a MP Bio Fastprep homogeniser (cat #116004500) using 6 m/s 40 seconds cycles. The tubes containing the homogenised tissues were transferred to ice and debris was pelleted by microcentrifugation at 10 g for 5 minutes. 400 μl of the supernatant was removed and used for RT-PCR.

Initially, RNA was extracted using Qiagen RNeasy® kit cat #74104 following the manufacturer's protocol. Each RNA sample was then used to make cDNA using Superscript III RT-PCR high-fidelity kit (Invitrogen cat #12574-035). For each spleen and LN RNA sample, 5 RT-PCR reactions were performed, each with $V_{H\_}J/F$ (long) primer in combination with a primer for $V_H1$, $V_H2$, $V_H3$, $V_H4$ or $V_H6$ family. Details of the primers are below;

TABLE 6

Primers

| | |
|---|---|
| V1a/pelB (long) | GCCGCTGGATTGTTATTACTCGCGGCCCAGCCGGCCAT GGCCCAGGTBCAGCTGGTGCAGTCTGGGGCTGAGG SEQ ID No. 382 |

TABLE 6-continued

| Primers | |
|---|---|
| V2/pelB (long) | GCCGCTGGATTGTTATTACTCGCGGCCCAGCCGGCCAT GGGCCCAGATCACCTTGAAGGAGTCTGG SEQ ID No. 383 |
| V3/pelB (long) | GCCGCTGGATTGTTATTACTCGCGGCCCAGCCGGCCAT GGCCSAGGTGCAGCTGGTGGAGTCTGGGGGAGG SEQ ID No. 384 |
| V4-4/pelB (long) | GCCGCTGGATTGTTATTACTCGCGGCCCAGCCGGCCAT GGCCCAGGTGCAGCTGCAGGAGTCGGG SEQ ID No. 385 |
| V6/pelB (long) | GCCGCTGGATTGTTATTACTCGCGGCCCAGCCGGCCAT GGCCCAGGTACAGCTGCAGCAGTCAGG SEQ ID No. 386 |
| VH_J/F (long) | CCGTGGTGATGGTGGTGATGGCTACCGCCACCCTCGAG TGARGAGACRGTGACC SEQ ID No. 387 |

Residues in Bold have Homology with pUCG3

Mastermixes were prepared for the RT-PCR reactions, based on the following tube reaction components.

12.5 µl 2× reaction mix
0.5 µl forward primer (10 uM)
0.5 µl reverse primer (10 uM)
0.5 µl enzyme mix
500 ng-1 µg RNA
Up to 25 µl with water The RT-PCR reactions were carried out in a thermal cycler using the following conditions;

| | |
|---|---|
| 50° C. 20 min | |
| 94° C. 2 min | |
| 35 cycles of | 94° C. 15 sec |
| | 58° C. 30 sec |
| | 68° C. 30 sec |
| 68° C. 5 min | |
| Hold at 4° C. | |

Products in the range of 370 bp were confirmed by gel electrophoresis.

For each mouse, the $V_H$ products amplified for a given family from the ⅓ spleen and each of the 4 lymph nodes were then pooled for purification using Thermo/Fermentas GeneJet PCR purification kit (cat #K0702) which was used according to the Manufacturer's instructions, with the products eluted in 50 µl of water.

b. Cloning into Phagemid Vector

The phagemid vector, pUCG3, was employed in these studies. As indicated, $V_H$ may be cloned into pUCG3, using conventional methods involving restriction enzyme digestions with NcoI and XhoI, ligation and transformation. Alternatively, a PCR-based method may be used to construct the $V_H$ phagemid libraries. Both of these procedures were used to generate libraries from the amplified $V_H$ sequences. The former method is widely used in the art. For the PCR-based method, the following procedure was used:

A linearised version of pUCG3 was created using PCR; with the following primers:

pUCG3-F3
SEQ ID No. 388
CTCGAGGGTGGCGGTAGCCATCACCACCATC pUCG3-R3
SEQ ID No. 389
TCCATGGCCATCGCCGGCTGGGCCGCGAG

Phusion High fidelity PCR master mix with GC buffer (cat #F532L, NEB) was used for the PCR reactions which comprised the following reagents;

| | |
|---|---|
| Phusion GC 2x mix | 25 µl |
| pUCG3 | 5-10 ng |
| Primers (10 uM) | 1.25 µl of each |
| DMSO | 1.5 µl |
| Nuclease-free H₂O | to final volume of 50 µl |

The cycling conditions used were

| | |
|---|---|
| 98° C. | 30 seconds |
| 10 cycles of | |
| 98° C. | 10 seconds |
| 58° C. | 20 seconds |
| 68° C. | 2 minutes, 30 seconds |
| 20 cycles of | |
| 98° C. | 10 seconds |
| 58° C. | 20 seconds |
| 68° C. | 3 minutes |
| 68° C. | 5 minutes |
| 4° C. | hold |

The PCR product (3152 bp) was gel purified using Fermentas GeneJet Gel purification kit (cat #K0691), according to the manufacturer's instructions, with final elution in 40 µl of elution buffer. The purified $V_H$ RT-PCR products were employed as megaprimers with the linearised pUCG3 to give phagemid products for transformation and library creation, based on the following reactions;

| | |
|---|---|
| Phusion GC 2x mix | 25 µl |
| Linearised pUCG3 | 700 ng |
| $V_H$ PCR product | 250 ng |
| DMSO | 1.5 µl |
| Nuclease-free H₂O | to 50 µl final volume |

PCR was performed as follows;

| | |
|---|---|
| 98° C. 30 sec | |
| 98° C. 10 sec | |
| 58° C. 20 sec | 10 cycles |
| 72° C. 2 min | |
| 72° C. 5 min | |
| Hold at 10° C. | |

The products of PCR were analysed on a 1% agarose gel.

The various family $V_H$/phagemid products were purified using Ferment as PCR purification kit (cat #K0702) according to the manufacturer's instructions with the final elution being in 25 µl H₂O and used for transformations of TG1 *E. coli* (Lucigen, Cat: 60502-2) by electroporation using Bio-Rad® 10×1 mm cuvettes (BioRad® cat #165-2089, a Eppendorf® Eporator and pre-warmed recovery medium (Lucigen, proprietary mix). 41 of the purified products were added to 25 ul of cells for the electroporation, with up to 10 electroporations being performed for each $V_H$/phagemid product at 1800v. Electroporated cells were pooled and recovered in 50 ml Falcon tubes incubated for 1 hour at 37°

C. with shaking at 150 rpm. A 10-fold dilution series of an aliquot of the transformations was performed and plated in petri dishes containing 2×TY agar supplemented with 2% (w/v) glucose and 100 ug/ml ampicillin. Resulting colonies on these dishes were used to estimate the library size. The remainder of the transformation was plated on large format Bioassay dishes containing 2×TY agar supplemented with 2% (w/v) glucose and 100 ug/ml ampicillin. All agar plates were incubated overnight at 30° C. 10 ml of 2×TY broth was added to the large format bioassay dishes and colonies were scraped and OD600 measured (OD of 1.0=5×10$^8$ cells/ml). Aliquots were stored at −80° C. in cryovials after addition of 50% v/v glycerol solution (50%) or used directly in a phage selection process.

In some instances, clones were picked directly and sequence was determined to give an estimate of the diversity of the library. Typically, for each mouse a phage display library with greater than 1e8 recombinants was constructed to fully capture the $V_H$ diversity in that mouse.

Example 6. Naive $V_H$ Libraries

Construction of Naive In Vitro Human $V_H$1 Library

The human $V_H$1-02 scaffold was amplified by PCR (Finnzymes F-531L) as follows: 25 ul 2 xPhusion PCR mix; 2.5 μl V1a/B (10 uM); 2.5 ul $V_H$3-93/F/C- (10 uM); 10 ng of plasmid encoding $V_H$ 1-02 and dH$_2$O to 50 μl final volume. Reactions were then heated to 95° C. for 1 minute followed by 30 cycles of PCR: 98° C. 10 seconds, 54° C. 30 seconds, 72° C. 30 seconds. Products of PCR were then analysed by electrophoresis on 1% (w/v) agarose gels followed by staining with ethidium bromide. PCR amplification products were observed at the correct size of approximately 300 bp (FIG. 6A).

Human cDNA from spleen, lymph node, bone marrow and peripheral blood lymphocytes was purchased from commercial sources (Invitrogen, Clontech). Oligonucleotide primers $V_H$ CDR3/B/G- and VHJ/F were synthesised to facilitate PCR amplification of $V_H$-CDR3 plus $V_H$ framework 4 sequences from B cell cDNA as follows: 25 μl 2 xPhusion PCR mix (Finnzymes F-531L); 2.5 μl VHCDR3/B/G- (10 uM); 2.5 ul $V_H$ J/F (10 uM); 3 ng cDNA and dH$_2$O to 50 ul final. Reactions were then heated to 95° C. for 1 minute followed by 30 cycles of PCR: 98° C. 10 seconds, 54° C. 30 seconds, 72° C. 30 seconds. After 30 cycles PCR reactions were then heated at 72° C. for 8 minutes followed by holding at 10° C. Products of PCR were then analysed by electrophoresis on 1% (w/v) agarose gels followed by staining with ethidium bromide. PCR amplification products were observed at the correct size of approximately 50-100 bp (FIG. 6B).

Human $V_H$-CDR3 PCR products were then assembled with the $V_H$ 1-02 scaffold to generate DNA products encoding full length $V_H$ binding molecules. The $V_H$ 1-02 scaffold was assembled with amplified human $V_H$-CDR3 sequences by adding the following: 12.5 ul 2× Phusion PCR mix (Finnzymes F-531L); 40 ng of $V_H$ 1-02 PCR product; 10 ng of each $V_H$-CDR3 PCR product and dH$_2$O to 25 ul final. The reaction was then heated to 95° C. for 1 minute followed by 8 cycles of PCR: 98° C. 10 seconds, 54° C. 30 seconds, 72° C. 30 seconds. After 8 cycles PCR reactions were then heated at 72° C. for 8 minutes followed by holding at 10° C. Full-length $V_H$ products were then amplified from the assembly products by pull-through PCR: 100 ul 2× Phusion PCR mix (Finnzymes F-531L); 10 ul of oligonucleotide V1a/B (10 uM); 10 ul of oligonucleotide VHJ/F (10 uM); 10 ul of $V_H$ 1-02 assembly products and dH$_2$O to 200 ul final volume. Reactions were then heated to 95° C. for 1 minute followed by 30 cycles of PCR: 98° C. 10 seconds, 54° C. 30 seconds, 72° C. 30 seconds. After 30 cycles PCR reactions were then heated at 72° C. for 8 minutes followed by holding at 10° C. Products of PCR were then analysed by electrophoresis on 1% (w/v) agarose gels followed by staining with ethidium bromide. Full length $V_H$ products were observed at the expected size of approximately 400 bp (FIG. 6C). The PCR products were purified using Fermentas PCR purification columns (K0701) and resuspended in dH$_2$O.

To prepare libraries for phage display, full-length $V_H$ products were cloned into phagemid vector pUCG3 by restriction digest and ligation. pUCG3 DNA and $V_H$ 1-02 pull-through PCR products were digested with NcoI (Fermentas FD0574) and XhoI (Fermentas FD0694) restriction enzymes overnight at 37° C. All digests were heated to 80° C. for 5 minutes and then each product purified using Fermentas PCR purification columns (K0701) and finally resuspended in dH$_2$O.

The digested $V_H$ products were ligated with similarly digested pUCG3 using NEB T4 DNA ligase (M0202M) following the manufacturer's instructions. Briefly, NcoI/XhoI double-digested pUCG3 DNA and $V_H$ products were mixed at a molar ratio of 1:2 and incubated overnight with T4 ligase at 16° C. Following incubation at 70° C. for 30 minutes, the products of ligation were purified using using Fermentas PCR purification columns and finally resuspended in dH$_2$O. Then, using Biorad® cuvettes (165-2089) and a Biorad® Micropulser, 2 ul of the purified ligation products were electroporated into 25 μl of electrocompetent TG1 cells (Lucigen 60502-1) following the manufacturer's instructions. Electroporated TG1 cells were plated onto 2×TY agar plates supplemented with ampicillin at 100 ug/ml and glucose at 20% (w/v) and incubated overnight at 30° C. Also a dilution series of electroporated TG1 cells were plated to determine the library size which was calculated to be 7.7e9 recombinants.

TABLE 7

| Sequences |
|---|
| Oligonucleotide primers (5' to 3') |

| | |
|---|---|
| VH_J/F | GCTACCGCCACCCTCGAGTGARGAGACRGTGACC SEQ ID No. 390 |
| V1a/B | GGAACAGACCACCATGGCCCAGGTBCAGCTGGTG CAGTCTGGGGCTGAGG SEQ ID No. 391 |
| VHCDR3/B/G- | GACACGGCCGTGTATTACTGTGC SEQ ID No. 392 |
| VHCDR3/F/C- | GCACAGTAATACACGGCCGTGTC SEQ ID No. 393 |

| Scaffold sequences |
|---|

$V_H$ 1-02 amino acid sequence SEQ ID No. 394

QVQLVQSGAEVKKPGASVKVSCKASGYTFTGYYMHWVRQAPGQGLEW

MGWINPNSGGTNYAQKFQGRVTMTRDTSISTAYMEISRLRSDDTAVY

YCAR $V_H$ 1-02 nucleic acid sequence SEQ ID No. 395
CAGGTGCAGCTGGTGCAGTCTGGGGCTGAGGTGAAGAAGCCTGGGGC

CTCAGTGAAGGTCTCCTGCAAGGCTTCTGGATACACCTTCACCGGCT

ACTATATGCACTGGGTGCGACAGGCCCCTGGACAAGGGCTTGAGTGG

TABLE 7-continued

Sequences

ATGGGATGGATCAACCCTAACAGTGGTGGCACAAACTATGCACAGAA

GTTTCAGGGCAGGGTCACCATGACCAGGGACACGTCCATCAGCACAG

CCTACATGGAGCTGAGCAGGCTGAGATCTGACGACACGGCCGTGTAT

TACTGTGCGAGA

Example 7. Selection Strategies for Isolation of IL-17A-Binding $V_H$

Preparation of library phage stocks and phage display selections were performed according to published methods (Antibody Engineering, Edited by Benny Lo, chapter 8, p161-176, 2004). In most cases, phage display combined with a panning approach was used to isolate binding $V_H$ domains. However, a variety of different selection methods may be employed including: (a) soluble selections; (b) selections performed under stress, where phage are heated at 70° C. for 2 hours prior to selection; and (c) competitive selections, where excess antigen or antigen-reactive $V_H$ domains are added as competition to encourage the recovery of high affinity $V_H$ domains or to skew selections away from a particular epitope. For the libraries from immunised mice, one round of selection was carried out. However, for the naive libraries 2-3 rounds of selection were performed.

Example 8. Assays for Target Binding $V_H$ from the different selections were screened in one or more of the following assays to identify specific $V_H$ with neutralising properties.

a) Binding ELISA

Following selections of the libraries, specific $V_H$ antibodies were identified by phage ELISA following published methods (Antibody Engineering, Edited by Benny Lo, chapter 8, p 161-176, 2004). Phage ELISAs were performed against target protein and an unrelated antigen as control. In some cases, purified or crude extracts of $V_H$ domains were assayed by ELISA instead of using a phage ELISA. In these cases, bacterial periplasmic extracts or purified $V_H$ were used.

Small-scale bacterial periplasmic extracts were prepared from 1 ml cultures, grown in deep well plates. Starter cultures were used to inoculate 96-well deep well plates (Fisher, cat #MPA-600-030X) containing 2×TY broth (Melford, M2130), supplemented with 0.1% (w/v) glucose+100 ug/ml ampicillin at 37° C. with 250 rpm shaking. When OD600 had achieved 0.6-1, $V_H$ production was induced by adding 100 ul of 2×TY, supplemented with IPTG (final concentration 1 mM) and ampicillin and the cultures were grown overnight at 30° C. with shaking at 250 rpm. E. coli were pelleted by centrifugation at 3200 rpm for 10 mins and supernatants discarded. Cell pellets were resuspended in 30-100 μl of ice cold extraction buffer (20% (w/v) sucrose, 1 mM EDTA & 50 mM Tris-HCl pH8.0) by gently pipetting. Cells were incubated on ice for 30 minutes and then centrifuged at 4500 rpm for 15 mins at 4° C. Supernatants were transferred to polypropylene plates and used, following incubation in skimmed milk powder/PBS blocking solution, in the ELISA.

The purified $V_H$ were obtained by using the $V_H$ C-terminal 6×HIS tag for nickel-agarose affinity chromatographic purification of the periplasmic extracts. A starter culture of each $V_H$ was grown overnight in 5 ml 2×TY broth (Melford, M2103) supplemented with 2% (w/v) glucose+100 ug/ml ampicillin at 30° C. with 250 rpm shaking. 50 μl of this overnight culture was then used to inoculate 50 ml 2×TY supplemented with 2% (w/v) glucose+100 μg/ml ampicillin and incubated at 37° C. with 250 rpm shaking for approximately 6-8 hours (until OD600=0.6-1.0). Cultures were then centrifuged at 3200 rpm for 10 mins and the cell pellets resuspended in 50 ml fresh 2×TY broth containing 100 ug/ml ampicillin+1 mM IPTG. Shake flasks were then incubated overnight at 30° C. and 250 rpm. Cultures were again centrifuged at 3200 rpm for 10 mins and supernatants discarded. Cell pellets were resuspended in 1 ml ice cold extraction buffer (20% (w/v) sucrose, 1 mM EDTA & 50 mM Tris-HCl pH8.0) by gently pipetting and then a further 1.5 ml of 1:5 diluted ice cold extraction buffer added. Cells were incubated on ice for 30 minutes and then centrifuged at 4500 rpm for 15 mins at 4° C. Supernatants were transferred to 50 ml Falcon tubes containing imidazole (Sigma, I2399—final concentration 10 mM) and 0.5 ml of nickel agarose beads (Qiagen, Ni-NTA 50% soln, 30210) pre-equilibrated with PBS buffer. $V_H$ binding to the nickel agarose beads was allowed to proceed for 2 hours at 4° C. with gentle shaking. The nickel agarose beads were then transferred to a polyprep column (BioRad®, 731-1550) and the supernatant discarded by gravity flow. The columns were then washed 3 times with 5 ml of PBS+0.05% Tween® followed by 3 washes with 5 ml of PBS containing imidazole at a concentration of 20 mM. $V_H$ were then eluted from the columns by the addition of 250 ul of PBS containing imidazole at a concentration of 250 mM. Imidazole was then removed from the purified $V_H$ preparations by buffer exchange with NAP-5 columns (GE Healthcare, 17-0853-01) and then eluting with 1 ml of PBS. Yields of purified $V_H$ were estimated spectrophotemetrically and purity was assessed using SDS PAGE.

The binding ELISA for crude or purified $V_H$ was similar to the serum ELISA and phage ELISA, previously described, mostly differing in the final detection steps. Briefly, antigen was immobilised on maxisorb plates (Nunc 443404) by adding 50 ul volumes at 0.1-1 ug/ml in PBS and incubating at 4° C. overnight. Following coating, the antigen solution was aspirated and the plates were washed using PBS (prepared from PBS tablets, Oxoid cat no. BR0014G) supplemented with 0.05% Tween® 20 (sigma P1379), followed by washes with PBS without added Tween®. To block non-specific protein interactions, a solution of 3% skimmed milk powder (Marvel) in PBS was added to the wells and the plate was incubated for at least one hour at room temperature. Dilutions of periplasmic extract or purified $V_H$ in 3% skimmed milk powder/PBS were prepared in polypropylene tubes or plates and incubated for at least one hour at room temperature prior to transfer to the blocked ELISA plate where a further incubation of at least one hour took place. Unbound protein was then washed away using repetitive washes with PBS/Tween® followed by PBS. A solution of HRP-conjugated anti-His Ab (Miltenyi Biotec, 130-092-785), prepared at 1:1000 dilution in PBS/3% skimmed milk powder was then added to each well and a further incubation at room temperature for at least one hour took place. Unbound detection antibody was removed by repeated washing using PBS/Tween® and PBS. The ELISA was then developed using TMB substrate (Sigma cat. no. T0440) and the reaction was stopped after 10 minutes by the addition of 0.5M H₂SO₄ solution (Sigma cat. no. 320501). Absorbances were determined by reading at 450 nm. Example ELISA data is shown in FIG. 8A-B.

b) R/L Biochemical Inhibition Assay $V_H$, both purified and crude periplasmic extracts, were also tested for their ability to inhibit the interaction of IL-17A with recombinant IL-17RA-Fc. Maxisorb 96F well mictrotitre plates were incubated with 50 µl solution of 2 nM IL-17-RA (R & D systems, cat #177-IR-100) and incubated overnight at 4° C. Following washing of excess coating antigen, as described above, the wells of the plate were incubated with 3% skimmed milk powder/PBS to block non-specific protein interactions. $V_H$ preparations, crude periplasmic extracts or purified $V_H$, or suitable controls, were incubated at room temperature for at least 1 hour with 1 nM recombinant IL-17A (Peprotech, cat #AF-200-17) in 3% marvel/PBS solution in polypropylene plates or tubes. The mixture was then transferred to the assay plate and incubated for 1 hour at room temperature. Excess protein was removed by washing and bound IL-17A was detected by incubation with biotinylated anti-IL-17A Mab (R & D Systems, cat BAF317) followed by the addition of neutravidin-HRP (Pierce, cat #31030) and TMB substrate (Sigma, cat #T0440). The TMB reaction was stopped by addition of 0.5M H2504 and absorbances were measured at 450 nm in a plate reader.

Where appropriate, curve fitting in PRISM was used to determine the $EC_{50}$ of inhibiting $V_H$. Example data illustrating inhibition of IL-17A responses in the biochemical assay are shown in FIG. 9A-B. $V_H$ were expressed from phagemid vector and have the following C terminal extension LEGGGS HHHHHH (SEQ ID No. 396).

c) R/L Cell Based Inhibition Assay

An assay was developed to measure the ability of IL-17A-binding $V_H$ to inhibit IL-17A-induced IL6 release from the cell line, HT1080 (ECACC cat #85111505). The cell line was maintained in exponential growth in MEM with Earles's salts, supplemented with non-essential amino acids, 10% FBS, 2 mM L-Glutamine and penicillin/streptomycin and incubated in a humidified incubator at 37° C., 5% CO₂. For the assay, 50,000 cells/well were seeded into a 96 flat bottomed tissue culture plate and cultured overnight. Serial dilution of purified $V_H$ were prepared and incubated at 37° C. for 1 hour with culture medium/PBS supplemented with 10 ng/ml IL-17A (Peprotech cat #AF200-17). Following incubation, the $V_H$/IL-17A mixture (or suitable controls) were transferred to the HT1080 cells (from which culture medium had been aspirated) and incubated for a further 5 hours in the CO₂ incubator. The cell culture supernatant was collected and assayed for IL6 using the IL-6 Duoset (R & D Systems, cat #DY206), following manufacturer's instructions. Example data illustrating inhibition of IL-17A responses in the cell based assay are shown in FIG. 10A-B. $V_H$ were expressed from phagemid vector and have the following C terminal extension LEGGGS HHHHHH (SEQ ID No. 396).

d) Biacore®.

Binding kinetics of anti-IL-17A $V_H$ antibodies were measured on a BIAcore® T200 instrument. Recombinant IL-17A (Peprotech AF-200-17) was diluted to 1 ug/ml in acetate buffer, pH 5.5 (BIAcore®, cat #BR-100-52) and coupled to a CM5 Series S chip (cat #BR-1006-68) using amine coupling chemistry (NHS-EDC amine coupling kit, cat #BR-1000-50) and the BIAcore® immobilization Wizard® software. In this way 100RU of IL-17A was immobilised plus a blank surface (no IL-17A) was also prepared for reference subtraction.

Binding kinetics of anti-IL-17A $V_H$ antibodies were determined by single-cycle kinetics. $V_H$ antibodies were prepared in dilution series (typically 1:3 dilution series starting with 100 nM $V_H$ at the highest concentration), and then injected over the antigen coated surfaces and also a blank surface, starting with the lowest concentration of $V_H$ and then working progressively up to the highest concentration. $V_H$ binding kinetics were then determined from the (blank subtracted) sensorgram traces using 1:1 binding models and BIAevaluation software. Example BIAcore® binding traces are shown in FIG. 11A-D. $V_H$ were expressed from phagemid vector and have the following C terminal extension LEGGGS HHHHHH (SEQ ID No. 396).

Following the above screening cascade, a number of $V_H$ to IL-17A were identified that demonstrated inhibitory properties. These are summarised below in table 8. The clones are the parent clones for optimisation.

TABLE 8

| Target antigen | $V_H$ Source | Family name | CDR3 sequence | Biochem IC50 (nM) | Cell assay IC50 (nM) | BIAcore® (Affinity) ka (1/Ms) | kd (1/s) | KD (M) |
| --- | --- | --- | --- | --- | --- | --- | --- | --- |
| IL-17A | Naive in vitro library | Family 3 (clone 3.1) | MDRDYYDTS GYFGWFDS SEQ ID No. 287 | 230 | >1000 | 3.427 E+04 | 5.94 E−03 | 1.73 E−07 |
| | Immunised mouse | Family 1 (clone 1.1) | GEILPLHFDY SEQ ID No. 3 | 53 | 13 | 2.96 E+05 | 1.49 E−03 | 5.0 E−09 |
| | | Family 2 (clone 2.1) | ESIFGIPED SEQ ID No. 251 | 32 | 8.3 | 1.22 E+06 | 2.47 E−03 | 2.0 E−09 |
| | | Family 4 (clone 4.1) | GDTIFDGAFDI SEQ ID No. 343 | 3140 | nd | 5856 | 2.89 E−03 | 4.93 E−07 |
| | | Family 5 (clone 5.1) | QWPFFDY SEQ ID No. 347 | 337 | nd | 3.04 E+05 | 5.05 E−02 | 1.66 E+07 |

Example 9. Lead Optimisation of $V_H$ a. Optimisation of $V_H$ Isolated from Immunised Mice Where appropriate, a novel optimisation strategy was used to increase binding affinities of $V_H$ isolated from immunised mice. Lead $V_H$ were aligned with other members of the same lineage to identify somatic hypermutation hot-spots targeted during the immune response (FIG. 9A-B).

The choice of amino acids at these positions formed the basis of a new recombination library approach, and led to the design of new libraries aimed at selecting higher affinity $V_H$ with optimal amino acids at each mutation hot-spot.

As an example for IL-17A, clone 1.1 was isolated directly from immunised mouse. This $V_H$ was shown to bind IL-17A with high affinity (FIG. 11A-D) and shown to block IL-17A binding to receptor. Alignment of clone 1.1 with other members of the same lineage identified a number of amino acid positions that had been mutated during the immune response, and both $V_H$-CDRs and $V_H$-framework regions were affected (FIG. 12A-B). This information was then utilised to design a new clone 1.1 recombination library with the aim of identifying a higher affinity variant of clone 1.1.

TABLE 9

| PCR | Primer | Sequence | Amino acid changes (Kabat position) | PCR product size |
|---|---|---|---|---|
| 1 | V3/pEIB (long) | GCCGCTGGATTGTTA TTACTCGCGGCCCAG CCGGCCATGGCCSAG GTGCAGCTGGTGGAG TCTGGGGGAGG SEQ ID No. 397 | none | 160 bp |
|  | 53F9-33S-R | TGGCGGACCCAGTAC ATNYBATAACTACTA AAGGTG SEQ ID No. 398 | S33 to S, G, E, R |  |
| 2 | 53F9-33S-F | CACCTTTAGTAGTTA TVRNATGTACTGGGT CCGCCA SEQ ID No. 52 | S33 to S, G, E, R | 100 bp |
|  | 53F9-57K-R | CACATAGTATTBCTC ACTTCCATCTTGNTY TATSYYGGCCACCCA CTCCAG SEQ ID No. 399 | N50 to N, S, D, K K52 to K, E, N K57 to K, Q, E |  |
| 3 | 53F9-57K-F | CAAGATGGAAGTGAG VAATACTATGTGGAC TCTGTGA SEQ ID No. 400 | K57 to K, Q, E | 100 bp |
|  | 53F9-76/79-R | AGGCTATTCATTTGC AGAWACAGTGASTTC TTGGCGTTGTCTCTG SEQ ID No. 401 | N76 to N, K F79 to F, Y |  |
| 4 | 53F9-76/79-F | CAGAGACAACGCCAA GAASTCACTGTVVTC TGCAAATGAATAGCC T SEQ ID No. 402 | N76 to N, K F79 to F, Y | 90 bp |
|  | 53F9-89V-R | AGTATTTCCCCTTTC GCACAGTAATACACA GCCGTG SEQ ID No. 403 | none |  |
| 5 | 53F9-89V-F (long) | CACGGCTGTGTATTA CTGTGCGAAAGGGGA AATACTACCCCTCYA STTTGACYACTGGGG CCAGGGA SEQ ID No. 404 | H100A to H, Y, Q Y100D to Y, H | 130 bp |
|  | VH_J/F (long) | CCGTGGTGATGGTGG TGATGGCTACCGCCA CCCTCGAGTGARGAG ACRGTGACC SEQ ID No. 405 | none |  |

Phusion High fidelity PCR master mix with HF buffer (cat #F531L, NEB) was used for the PCR reactions which were set up for each primer pairing as follows:

| Phusion HF 2x mix | 25 µl |
|---|---|
| Primers (10 uM) | 1.25 µl each (pairings as in table) |
| 53F9 plasmid DNA (34 ng/ul) | 0.5 µl |
| Nuclease-free H₂O | to 50 µl final volume |

PCR was performed as follows;

98° C. 30 sec
98° C. 10 sec
58° C. 20 sec  } 31 cycles
72° C. 20 sec
72° C. 10 min
Hold at 10° C.

The products of each PCR were analysed on a 1% agarose gel. Each product was then purified using Fermentas PCR purification kit (K0701) into 40 ul elution buffer. Assembly PCRs were then set up to rebuild the full $V_H$ sequence:

| Phusion HF 2x mix | 25 µl |
|---|---|
| Purified PCR product 1 | 5 µl |
| Purified PCR product 2 | 5 µl |
| Purified PCR product 3 | 5 µl |
| Purified PCR product 4 | 5 µl |
| Purified PCR product 5 | 5 µl |

PCR was performed as follows;

98° C. 30 sec
98° C. 10 sec
58° C. 20 sec  } 5 cycles
72° C. 20 sec

Added 0.5 ul of primers V3/pelB (long) and $V_H$_J/F (long) (both 10 uM) to the reaction and then continued for a further 10 PCR cycles at the above conditions. The PCR product was analysed on a 1% agarose gel and purified using Fermentas PCR purification kit into 40 ul elution buffer. The PCR product was then used as a megaprimer for library construction as described above in Example 5, part b. Phage display selections and $V_H$ screening was then performed as described in examples 7 and 8, following which several new variants of clone 1.1 were isolated with up to 10-fold improved affinities (clones 1.10, 1.6, 1.7).

b. Optimisation of $V_H$ Isolated from Naive In Vitro Libraries

For anti-IL-17A $V_H$ isolated from naive in vitro phage display libraries, a number of different strategies were employed to increase $V_H$ affinity for antigen, the choice and combination of which was driven by the starting potency of the $V_H$ in question. Several of the optimisation strategies used are already described in the art and include:

a) shuffling (Antibody Engineering, Edited by Benny Lo, chapter 19, p 327-343, 2004), although in our case CDR1 and CDR2 domains were shuffled whilst retaining the $V_H$ CDR3 sequence. $V_H$ CDR1 and CDR2 domains were amplified from human cDNA (Clontech) by PCR, and then assembled with the $V_H$ sequence to generate a library of $V_H$ with identical CDR3 domains but diversified CDR1 and CDR2 regions. Phage display technology was then utilised to isolate higher affinity $V_H$, typically following the same selection processes as described in section 7 above.

b) Targeted randomisation of CDR3 regions using randomised oligonucleotides and phage display technology (Main et al., J Pharmacol Exp Ther. 2006 December; 319(3): 1395-404.)

c. Optimisation of $V_H$ by Error-Prone Mutagenesis and Ribosome Display

Error-prone mutagenesis and ribosome display was used to optimise affinities of $V_H$ isolated from naive in vitro phage display libraries and, where appropriate, $V_H$ from immunised mice. Error-prone PCR reactions, assembly with the cK fragment and preparation of RNA templates for ribosome display was performed as described previously (Edwards B M, He M, Methods Mol. Biol. 2012; 907: 281-92). The method was then adapted to facilitate in solution selections and give greater control of antigen concentration during selections.

TABLE 10

| | Primers |
|---|---|
| CKF/f | GCACTCTCCCCTGTTGAAGCTCTTTGTGACGGGCGAGCTCA GGCCCTGATGGGTGACTTCGCAGGCGTAGAC SEQ ID No. 406 |
| Gaga2 G | GCAGCTAATACGACTCACTATAGGGAGACAGACCACCATGG SEQ ID No. 407 |
| CK/f | GCACTCTCCCCTGTTGAAGCT SEQ ID No. 408 |

Solution based ribosome display selections were performed with streptavidin magnetic beads (Dynabeads M280, Invitrogen) that were pre-blocked as follows. The required volume of beads (typically 100 ul per selection) was transferred to a siliconised 1.5 ml tube (Sigma T3406) and then washed in wash buffer (PBS containing 0.05% Tween® 20 and 5 mM MgAc, stored at 4° C.), then again in PBS before finally resuspending in 100 ul 1% BSA in PBS+2 ul S. cerevisiae RNA (Sigma 83847, prepared at 10 mg/ml in RNase free water, stored at −20° C.)+20 ul heparin (Sigma, Cat. No. H3393, 250 mg/ml stock solution, stored at −20° C.) and incubating by mixing on a turntable at 4° C. for >1 hour.

In vitro translation of the library RNA template to prepare the ribosome complexes was carried out as described (Edwards B M, He M, Methods Mol. Biol. 2012; 907: 281-92), using 5 ug mRNA template per selection. After completion of the in vitro translation step, reactions were diluted into blocking buffer to help stabilise ribosome complexes prior to selection. Blocking buffer was prepared by the addition of 100 ul 10×BPM (10% BSA, 10 mM MgAc in 10×PBST) to 400 ul dilution buffer (5 mM reduced glutathione, 5 mM oxidised glutathione and 13 mM MgAc), containing 10 ul heparin stock solution and 1 ul S. cerevisae RNA stock solution.

After incubation with the blocking buffer for 5 mins on ice, the reaction was then centrifuged at 14000 g for 5 mins at 4° C. and the supernatant transferred to a pre-chilled 0.5 ml siliconised tube for selection. For the first round of selection, biotinylated antigen was added to the mix for a final concentration of 200 mM and incubated by mixing on a turntable at 4° C. for 2 hours.

Antigen-bound complexes were recovered from the selection mix by addition of the pre-blocked streptavidin beads, incubating by rotation for 15 mins at 4° C., and then bound complexes pulled down using a magnet. Magnetic beads were then washed 5 times with wash buffer, 400 ul per wash, incubating up to 30 mins at 4° C. A final rapid wash of 400 ul ice cold 5 mM MgAc was carried out before resuspending the beads in 100 ul 5 mM MgAc. Elution and purification of RNA from the beads was carried out using a RNeasy® Minelute kit (Qiagen 74204), adding 350 ul buffer RLT to the beads, mixing well, then adding 100% ethanol and mixing well by pipetting. The beads were then pulled to one side with a magnet and the remaining supernatant was added to the minielute column in a 2 ml collection tube, and immediately centrifuged at 8000 g for 15 sec. The column was placed in a new collection tube and the remaining steps from the addition of buffer RPE to the column onwards carried out according to the manufacturer's instructions.

The eluted RNA was converted to cDNA using Revertaid H Minus reverse transcriptase (Fermentas EP0451):

| Eluate | 6 μl |
|---|---|
| CKF/f primer (10 uM) | 1.6 μl |
| dNTP (10 mM) | 2 μl |
| water | 2.9 μl |

The reaction was incubated at 65° C. for 5 mins, before transferring to ice for >3 mins. 8 ul of the following mixture was then added to the mix:

| 5 x reaction buffer | 4 μl |
|---|---|
| Water | 2 μl |
| Rnasein Plus | 1 μl (Promega, Cat. No. N2611) |
| RevertAid H Minus RT | 1 μl |

The reaction was mixed and spun down briefly before incubating at 42° C. for 60 mins, followed by 10 mins at 70° C. PCR recovery of the cDNA was then carried out using Taq polymerase PCR kit (Qiagen 201203) as follows:

| 10 x buffer | 80 μl |
|---|---|
| 5 x Q | 160 μl |
| dNTPS (2.5 mM) | 64 μl |
| Gaga2G primer | 38.4 μl |
| Ck/F primer | 38.4 μl |
| RT | 8 μl |
| Taq polymerase | 4 μl |
| Water | 407.2 μl |

The reaction was spilt between 16 PCR tubes of 50 μl each and the reaction cycled as follows:

94° C. 5 min
94° C. 30 sec ⎫
59° C. 30 sec ⎬ 20-30 cycles
72° C. 1 min ⎭
72° C. 8min
Hold at 4° C.

Products in the range of 700 bp were confirmed by gel electrophoresis and the PCR reactions pooled and purified using Wizard® SV PCR purification columns (Promega A9281). PCR products were used directly to prepare RNA templates for subsequent rounds of selection, as described above.

Subsequent rounds of selection were performed with increasing stringency, for example by decreasing antigen concentration and shortening the length of time complexes were incubated with biotinylated antigen. In addition, washing steps increased in either duration or number, or both. Off-rate selections were also used following the wash steps, where the complexes and beads were incubated with a 100- to 1000-fold molar excess of unbiotinylated antigen at 4° C. for >2 hours.

Other modifications to the protocol for subsequent rounds of selection included a pre-selection step to eliminate ribosome complexes binding non-specifically to streptavidin beads. This was accomplished by incubating the in vitro translation mixes with streptavidin beads prior to selection (beads prepared as above, binding for 1 hour at 4° C.). Beads were then captured and the translation mix transferred to a clean 1.5 ml siliconised tube and biotinylated antigen added for selection.

Following the lead optimisation steps, the potencies of improved $V_H$ were as follows:

TABLE 11 a) $V_H$ produced following optimisation of anti-IL-17A $V_H$ family 3 (parent clone 3.1 derived from in vitro naive library)

| $V_H$ name | CDR3 sequence | Bio-chem IC$_{50}$ (nM) | Cell assay IC$_{50}$ (nM) | BIAcore (Affinity) ka (1/Ms) | kd (1/s) | KD (M) |
|---|---|---|---|---|---|---|
| parent Clone 3.1 | MDRDYYDTS GYFGWFDS SEQ ID NO. 287 | 230 | >1000 | 3.427E+04 | 5.94E-03 | 1.73E-07 |
| Clone 3.3 | MDRDYYDTS GYFGWFDS SEQ ID NO. 295 | 271 | 106 | 9.981E+04 | 2.85E-03 | 2.90E-08 |

TABLE 11-continued a) $V_H$ produced following optimisation of anti-IL-17A $V_H$ family 3 (parent clone 3.1 derived from in vitro naive library)

| $V_H$ name | CDR3 sequence | Bio-chem IC$_{50}$ (nM) | Cell assay IC$_{50}$ (nM) | BIAcore (Affinity) ka (1/Ms) | kd (1/s) | KD (M) |
|---|---|---|---|---|---|---|
| Clone 3.5 | LDRDWRSPN DYFGWFDS SEQ ID NO. 303 | 4 | 26 | 2.81E+05 | 6.19E-04 | 2.20E-09 |
| Clone 3.6 | LDRDWRSPN DYYGWFDS SEQ ID NO. 307 | 3 | 28 | 5.73E+05 | 4.80E-04 | 8.38E-10 |
| Clone 3.9 | MDRDYYDTS GYFGWFDS SEQ ID NO. 319 | 43 | 182 | 9.643E+04 | 0.002.01E-03 | 2.10E-08 |
| 3.11 | LDRDTWYPH SYFGWFDS SEQ ID NO. 327 | 8 | 17 | 5.38E+05 | 2.37E-04 | 4.40E-10 |
| Clone 3.13 | LDRDTWYPH SYAGWFDS SEQ ID NO. 335 | 2 | 5 | 1.02E+06 | 2.01E-04 | 1.97E-10 |
| Clone 3.2 | LDRDTWYPH SYAGWFDA SEQ ID NO. 291 | 2.5 | 2.5 | 1.10E+06 | 2.52E-04 | 2.30E-10 |

TABLE 12 b) $V_H$ produced following optimisation of anti-IL-17A $V_H$ family 1 (parent derived from immunised TKO mouse as described above)

| VH name | CDR3 sequence | Cell assay IC50 (nM) | BIAcore ® (Affinity) ka (1/Ms) | kd (1/s) | KD (M) |
|---|---|---|---|---|---|
| Clone 1.1 | GEILPLHFDY SEQ ID NO. 3 | 13 | 2.96E+05 | 1.49E-03 | 5.0E-09 |
| Clone 1.6 | GEILPLYFDY SEQ ID NO. 23 | 1.3 | 7.70E+05 | 4.82E-04 | 6.27E-10 |
| Clone 1.7 | GEILPLYFDY SEQ ID NO. 27 | 2.0 | 7.65E+05 | 4.66E-04 | 6.09E-10 |
| Clone 1.8 | GEILPLYFDY SEQ ID NO. 31 | 1.2 | 6.97E+05 | 4.29E-04 | 6.16E-10 |
| Clone 1.9 | GEILPLYFDY SEQ ID NO. 35 | 2.4 | 8.77E+05 | 4.64E-04 | 5.29E-10 |
| Clone 1.10 | GEILPLYFDY SEQ ID NO. 39 | 1.9 | 6.64E+05 | 9.66E-04 | 1.46E-09 |
| Clone 1.11 | GEILPLYFDY SEQ ID NO. 43 | 1.5 | 6.17E+05 | 5.21E-04 | 8.45E-10 |
| Clone 1.12 | GEILPLYFDY SEQ ID NO. 47 | 1.4 | 7.32E+05 | 5.30E-04 | 7.24E-10 |
| Clone 1.13 | GEILPLYFDY SEQ ID NO. 51 | 1.2 | 6.14E+05 | 5.15E-04 | 8.40E-10 |

TABLE 12-continued b) $V_H$ produced following optimisation of anti-IL-17A $V_H$ family 1 (parent derived from immunised TKO mouse as described above)

| VH name | CDR3 sequence | Cell assay IC50 (nM) | BIAcore ® (Affinity) ka (1/Ms) | kd (1/s) | KD (M) |
|---|---|---|---|---|---|
| Clone 1.14 | GEILPLYFDY SEQ ID NO. 55 | 2.9 | 7.53E+05 | 6.88E-04 | 9.13E-10 |
| Clone 1.3 prep 1 | GEILPLYFDY SEQ ID NO. 11 | 1.8 | 9.64E+05 | 2.22E-04 | 2.30E-10 |
| Clone 1.15 | GEILPLYFDY SEQ ID NO. 59 | 2.5 | 1.04E+06 | 2.42E-04 | 2.32E-10 |
| Clone 1.16 | GEILPLYFDY SEQ ID NO. 63 | 1.4 | 9.86E+05 | 2.13E-04 | 2.16E-10 |
| Clone 1.17 | GEILPLYFDY SEQ ID NO. 67 | 1.91 | 9.23E+05 | 4.62E-04 | 15.00E-10 |
| Clone 1.18 | GEILPLYFDY SEQ ID NO. 71 | 1.04 | 1.31E+06 | 4.79E-04 | 3.66E-10 |
| Clone 1.19 | GEILPLYFDY SEQ ID NO. 75 | 1.2 | 7.14E+05 | 1.53E-04 | 2.15E-10 |
| Clone 1.20 | GEILPLYFDY SEQ ID NO. 79 | 2.03 | 8.51E+05 | 2.08E-04 | 2.44E-10 |
| Clone 1.21 | GEILPLYFDY SEQ ID NO. 83 | 2.05 | 7.92E+05 | 2.05E-04 | 2.59E-10 |
| Clone 1.22 | GEILPLYFDY SEQ ID NO. 87 | 3.25 | 5.65E+05 | 1.26E-04 | 2.23E-10 |
| Clone 1.3 prep 2 | GEILPLYFDY SEQ ID NO. 11 | 0.57 | 7.99E+05 | 5.01E-04 | 6.27E-10 |
| Clone 1.2 | GEILPLYFDY SEQ ID NO. 6 | 0.4 | 8.74E+05 | 4.85E-04 | 5.55E-10 |

Optimised $V_H$ show improved affinities to IL-17 and improved potencies in the IL-17 cell based assay due to slower off-rates (FIG. 11A-D). $V_H$ were expressed from phagemid vector and have the following C terminal extension LEGGGS HHHHHH (SEQ ID No.396).

Example 10—Characterisation of $V_H$ a. Specificity of Anti-IL-17A

The specificity of individual $V_H$ for target antigen was confirmed by ELISA, following the methods described in Example 8(a). $V_H$ were tested for binding to IL-17A and shown not to cross-react with close relatives such as IL-17C and IL-17F. In addition, binding to species homolog's (murine IL-17A) was also demonstrated (FIG. 13A-B). $V_H$ were expressed from phagemid vector and have the following C terminal extension LEGGGS HHHHHH (SEQ ID No. 396).

b. Epitope Mapping $V_H$ were shown to bind to unique epitopes of IL-17A using a BIAcore® T200 instrument. Manual sensorgrams were initiated at 30 ul/min in HBS buffer and $V_H$ injected as appropriate over the IL-17A coupled CM5 chip coupled CM5 chip, plus a blank surface for reference subtraction (FIG. 14). $V_H$ expressed from phagemid vector and have the following C terminal extension LEGGGS HHHHHH (SEQ ID No. 396).

For IL-17A, $V_H$ samples were prepared at 4 ug/ml in HBS buffer and then the first $V_H$ was injected over the IL-17A coupled surface for 120 seconds. Following binding of the first $V_H$, HBS buffer only was injected over the surface for 60 seconds, following which the second $V_H$ was injected for 120 seconds. If the $V_H$ competed for the same epitope, then no binding would be observed with the second v antibody. Non-competing $V_H$ would both be able to bind simultaneously to the IL-17A coupled surface. Epitope competition data is shown (FIG. 14). The surface was regenerated by injecting glycine pH 1.5 for 10 seconds and then the process repeated for different antibody pairs.

c. HPLC Size Exclusion Chromatography

Purified $V_H$ were subjected to size exclusion chromatography. Briefly, purified $V_H$ were analysed using a Waters® 2795 Separation Module with a Waters® 2487 Dual A #absorbance Detector—(Detected at 280 nM) and a TSKgel G2000SWXL (TOSOH) column. Samples were injected in 10-50 ul volumes and run in mobile phases of either 10% isopropanol/90% PBS or 100 mM Phosphate buffer, pH 6.8, 150 mM NaCl at a flow rate of 0.5 ml/min-0.7 ml/min. Data were collected for up to 35 minutes and the size of the $V_H$ fraction compared with known standards (see FIG. 15A-K). $V_H$ analysed were expressed from phagemid vector and have the following C terminal extension LEGGGS HHHHHH (SEQ ID No. 396).

Example 11

Skin Penetration Study

The $v_H$ domain used in the experiments was clone 1.10.2. Clone 1.10.2 has a $v_H$ sequence as shown in FIG. 1A-B but includes additional C terminal residues (SEQ ID No. 409). Using a standard *E. coli* recombinant expression vector, protein expression was carried out under standard batch mode conditions in rich media in a 25 L fermenter. Expression was driven by an IPTG induced promoter and secreted into the media by an OmpA signal sequence. The $v_H$ was modified to carry a C-terminal His-tag (6×His) which was used for purification and detection in subsequent IHC imaging and western blots.

The $v_H$ in the fermentation media was clarified by centrifugation and purified using $Ni^{2+}$-affinity chromatography followed by protein concentration and a final SEC purification step on Superdex® 75. The $v_H$ was buffer exchanged into PBS, pH 7.4 and concentrated to 20 mg/ml.

In a pre-study, the quality of the skin disks to be used in subsequent studies (in particular, to evaluate any potential impact of the freezing process) was assessed. Each of two potential vehicle formulations (PBS and 35% DMSO) were incubated on intact and abraded (tape-stripped) skin disks for 24 hours at 32° C., then fixed in 10% formalin and stored in 70% ethanol at room temperature. In addition, one sample each of intact and tape-stripped skin was fixed (as above) without prior incubation with any vehicle. The structure of the fixed skin samples was subsequently assessed by IHC.

Protocols:
Formalin Fixation of Tissues
To make 1 L 10% Formalin (v/v):
100 ml 37% Formaldehyde
900 ml PBSc
To make 1 L PBSc (PBS, 0.5 mM MgCl2, 0.9 mM $CaCl_2$)):
1 L PBS
0.5 ml 1M MgCl2
0.9 ml 1M $CaCl_2$)
Fixation protocol:
1) Each sample was placed into a vial and covered to a height of at least 1 cm above the specimen with 10% formalin.
2) The sample was then allowed to fix at room temperature for a set period of time depending on its size (see below).
<1 cm3 18 hours
1-3 cm3 48 hours
3) Immediately after fixation the fixative was replaced with the same volume of 70% ethanol. At this stage the tissue could be stored indefinitely if immediate processing was not be required.

Immunohistochemistry (IHC)
To expose the incubated area of the skin disk, each disk was cut in half and both halves put into an embedding cassette (Cell Path, #EAD-0107-03A and #EAD-0102-03A). The samples were dehydrated by passing them through a series of alcohols (70% and 100% Ethanol (VWR #20821.330), 100% propan-2-ol (Fisher #P/7500/PB17)) and xylene (100% xylene (Fisher #X/0250/PB17)) and subsequently infiltrated with paraffin wax. The samples were embedded in paraffin wax, orientated so that the cut edge of each half would be the first exposed tissue. 5 μm sections of each block were cut onto glass slides. A 5 μm section of the commercially supplied normal human skin (AMSBio #500041022) was also cut. This sample was not frozen prior to fixation. The tissue structure of the previously frozen test samples was compared against this control skin. Sections were stained with haematoxylin and eosin (H&E) using the protocol below to visualise the tissue structure. Images of the skin samples were taken at two magnifications.

Haematoxylin and Eosin Staining Protocol
Slide sections were deparaffinised and rehydrated in a series of xylene and ethanol washes as follows:

| | |
|---|---|
| Xylene | 10 min |
| Xylene | 10 min |
| Xylene | 1 min |
| Xylene | 1 min |
| 100% ethanol | 1 min |
| 100% ethanol | 1 min |
| 100% ethanol | 1 min |
| 70% ethanol | 1 min |

The slides were washed in running tap water for 1 min then transferred to Mayer's haematoxylin for 2 min and washed in running tap water for 1 min. Slides were "blued" by placing them in Scott's water for 1 min and washed in running tap water for 1 min. Slides were subsequently transferred into Eosin (Raymond A Lamb; LAMB/100-D) for 30 secs and washed in running tap water for 1 min after which they were dehydrated and cleared through a series of ethanol and xylene washes as follows:

| | |
|---|---|
| 70% ethanol | 1 min |
| Abs ethanol | 1 min |
| Abs ethanol | 1 min |
| Abs ethanol | 1 min |
| Xylene | 1 min |
| Xylene | 1 min |

The slides were dipped in Histoclear (Fisher Scientific; H/0468/17) and mounted immediately in DPX mounting medium (Cell Path; SEA-0304-00A)

Mayer's Haematoxylin:
Solution 1: 3 g Haematoxylin (BDH; 340374T) in 20 mls of absolute ethanol Solution 2: 0.3 g Sodium Iodate (Sigma S-4007) 1 g Citric acid (Fisher Scientific C/6200/53) 50 g Chloral Hydrate (Fisher Scientific C/4280/53) 50 g Aluminium Potassium Sulphate (Sigma 237086) 850 ml $dH_2O$. Reagents were added sequentially, mixed well to ensure all have dissolved. Solution 1 was added to Solution 2 and mixed well. Finally 120 ml of glycerol was added (Fisher Scientific G/0650/17), mixed well and stored in a darkened bottle. The final mix was always filtered immediately prior to use. Scotts' Tap Water: Tap water with 2% MgSO4 (Sigma M7506) and 0.35% $NaHCO_3$ (Sigma S-6297).

Results:
Sample 1 Intact control
Sample 2 Tape-stripped control
Sample 3 Intact PBS
Sample 4 Tape-stripped PBS
Sample 5 Intact DMSO
Sample 6 Tape-stripped DMSO At both low and high power, the structure of the epidermis and dermis did not appear to differ significantly between the previously frozen samples and the non-frozen control sample. There was no separation of the epidermis from the dermis and the collagen was observed to be densely packed within the dermis of the frozen samples as in the non-frozen control.

The skin samples not incubated with vehicle and those incubated with PBS or DMSO (samples 3 to 6) all showed normal architecture when compared with the non-frozen control sample. IHC of the tape-stripped skin clearly identified the expected reduction in the extent of the stratum corneum compared to the intact samples.

The above results suggested that the treatments to be used in the skin penetration study were suitable for retaining intact tissue architecture.

The penetration experiments used a Bronaugh flow-through diffusion cell system. In this system a small disk of dermatomed human skin was clamped between an upper ('donor') chamber and lower ('receiver') chamber (the latter containing a receiver fluid which remains in contact with the underside the skin sample). Test formulation containing $V_H$ applied to the upper (stratum corneum) surface of the skin was only able to move from the donor chamber into the receiver chamber if it had first entered and then traversed the full thickness of the skin sample. The benefit of using the Bronaugh system over other similar apparatus (e.g., the Franz cell) is that it offers the advantages of continuous perfusion of the underside of the skin sample, with fresh receptor fluid to maintain sink conditions when evaluating drugs penetrating the skin.

Assessment of the ability of various prototype formulations to facilitate penetration of $V_H$ into skin samples (intact and tape-stripped). The primary deliverable of this study was IHC images showing $V_H$ in the skin.

All human skin was obtained following elective surgery and was prepared within 24 hours of excision. The prepared tissue was subsequently stored frozen (minus 20° C.) in sealed vacuum packages prior to use. Actual thickness of the dermatomed skin was measured and recorded at time of use with a snap gauge micrometer. One potential clinical indication of interest for a topically applied $V_H$ is the treatment of patients with psoriasis. Patients with psoriasis routinely have their plaques treated with a keratolytic agent (e.g., salicylic acid) either as a monotherapy or compounded with other therapies such as topical steroids. Keratolytics assist in removing scale or hyperkeratosis and can facilitate the penetration of other topical agents. The best way to mimic psoriatic skin pre-treated with a keratolytic agent is to lightly abrade (tape-strip) the skin in order to remove part of the stratum corneum. This was achieved by repeatedly applying and removing pieces of cellophane tape (20-30 times) to the skin in order to compromise the stratum corneum barrier function.

The in vitro skin penetration study assessed the relative ability of each of the formulations in the table below to facilitate the penetration of $V_H$ into intact or tape-stripped skin using Bronaugh flow through cells.

The study was conducted with dermatomed human skin from a single donor. Skin was obtained and prepared as detailed below. Samples of each formulation were prepared immediately prior to use in the study.

TABLE 13

Composition of prototype formulations used in the In Vitro skin penetration study

| | % w/w | | | | | | | | | |
|---|---|---|---|---|---|---|---|---|---|---|
| | 2% $V_H$ soln in buffer | | | | | | | | | |
| | 100 | 10 | 65.0 | | | | | | — | |
| | Formulation | | | | | | | | | |
| Ingredients | C1 4077-18A | C2 4077-18B | C3 4077-18C | 1 4077-19A | 2 4077-19B | 3 4077-19C | 4 4077-20A | 5 4077-20B | 6 4077-21 (placebo) | category |
| Microemulsion | — | 90.0 | — | — | — | — | — | — | — | Penetration enhancer |
| DMSO | — | — | 35.0 | — | — | — | — | — | | |
| Propylene Glycol | — | — | — | 35.0 | — | 25.0 | 20.0 | — | 25.0 | |
| Transcutol ® | — | — | — | — | 24.0 | — | — | — | — | |
| Ethanol | — | — | — | — | — | 10.0 | — | — | 10.0 | |
| Isopropyl Myristate | — | — | — | — | — | — | 10.0 | — | — | |
| Azone* (laurocapram) | — | — | — | — | — | — | — | 10.0 | — | |
| Steareth-21 (Brij ® 721) | — | | — | | | — | 3.0 | 3.0 | — | Non-ionic surfactant water insoluble |
| Steareth-2 (Brij ® 72) | — | — | — | — | — | — | 2.0 | 2.0 | — | |
| PBS pH 7.4 (q.s) | — | — | — | — | 11.0 | — | — | 20.0 | 65.0 | |
| Observations | Clear | Cloudy | Clear | Clear | Clear | Clear | White; thick | White; runny | Clear | |
| Prototype | | Control | | | Solution | | | Emulsion | Solution | |

Study Design/Formulation

Tissue Type: Dermatomed human skin from a single donor

Cell Type: 54 Flow-Thru diffusion cells (Bronaugh design with 0.9 cm diameter or 0.64 cm2 area)

Cell Temperature: 32° C.

Receiver Phase (RP): PBS, pH 7.4, with 0.1% (w/v) sodium azide

RP Collection Points: 0-6, 6-12, 12-18, and 18-24 hours

RP Flow Rate: 0.25 mL/hr.

Dose Level: Infinite dose: 500 mg of formulation per cell

TABLE 14

| | Test Formulation | Number of Bronaugh Cells |
|---|---|---|
| Intact Skin | A: Vehicle 1: PBS | 1 |
| | B: Vehicle 2: DMSO | 1 |
| | C: Vehicle 3: Prototype 3 Vehicle | 1 |
| | D: IgG Control | 2 |
| | E: C1-VH PBS Control | 2 |
| | F: C2-VH Microemulsion Control | 3 |
| | G: C3-VH DMSO Control | 2 |
| | H: Prototype 1 | 3 |
| | I: Prototype 2 | 3 |
| | J: Prototype 3 | 3 |
| | K: Prototype 4 | 3 |

TABLE 14-continued

| | Test Formulation | Number of Bronaugh Cells |
|---|---|---|
| | L: Prototype 5 | 3 |
| Tape- | M: Vehicle 1: PBS | 1 |
| Stripped | N: Vehicle 2: DMSO | 1 |
| Skin (TS) | O: Vehicle 3: Prototype 3 Vehicle | 1 |
| | P: IgG Control | 2 |
| | Q: C1-VH PBS Control | 2 |
| | R: C2-VH Microemulsion Control | 3 |
| | S: C3-VH DMSO Control | 2 |
| | T: Prototype 1 | 3 |
| | U: Prototype 2 | 3 |
| | V: Prototype 3 | 3 |
| | W: Prototype 4 | 3 |
| | X: Prototype 5 | 3 |

Tissue Preparation

Normal Skin:

The human skin was obtained following elective surgery and was prepared within 24 hours of excision. The prepared tissue was subsequently stored frozen (at minus 20° C.) in sealed vacuum packages prior to use. Actual thickness of the dermatomed skin was measured and recorded at time of use at multiple random sites with a snap gauge micrometer in order to determine the range of skin thickness.

Tape Stripped Skin:

Samples of the normal skin, prepared as above, was repetitively tape stripped (thirty times) with individual pieces of cellophane tape to compromise the stratum corneum barrier function.

Immediately prior to use, skin samples were cut into disks of the correct size and assembled in the Bronaugh cells with the stratum corneum uppermost.

Experimental Details

Dosing of Test Material:

Samples of each test formulation and controls (detailed in Table 13) were prepared immediately prior to use in the study. Dosing of the prototype formulations was staggered across the diffusion cell manifold systems. Approximately 500 mg of each formulation was dispensed onto the skin, exact mass was determined by weight. After dosing, the cells were occluded with Parafilm and remained undisturbed at 32° C. for the 24-hour exposure period.

Sample Preparation and Analysis:

The skin sample in each Bronaugh cell was maintained with its lower surface in contact with receiver fluid comprised of PBS, pH 7.4, with 0.1% (w/v) sodium azide. Receiver fluid was pumped to flow through each receiver chamber at 0.25 ml/hr. Receiver phase samples were collected automatically with continuous collection at intervals of six hours. Every 6 hours the automatic fraction collector rotated to align a new 20 mL scintillation vial under the cell collecting the next six hours of sample. All samples were collected in pre-weighed scintillation vials, the post-collection weights were taken and the difference recorded as the weight of the receiver phase collected.

Following the 24-hour exposure period, the Bronaugh chambers were disassembled following removal of donor solution without contaminating the receiver fluid with the donor fluid, the skin samples removed from their respective Bronaugh Chambers and each fixed in formalin as described in the pre-study.

All receiver phase samples were packaged in plastic scintillation vials and frozen at −80° C. until subsequent ELISA analysis.

ELISA:

The ELISA method used was the same as used in the pre-formulation studies, except that each sample of receiver fluid was prepared at 2 concentrations: (a) neat (50 μl of receiver fluid plus 10 μl of 18% Marvel, 6×PBS), and (b) 1:100 dilution (41 receiver fluid plus 198 μl 3% Marvel/PBS).

Results of Receiver Fluid Analysis

Receiver fluid was sampled at four time points from each Bronaugh cell during the penetration study (at 6 hrs, 12 hrs, 18 hrs and 24 hrs). All were tested by ELISA to determine whether or not the $V_H$ applied to the top surface (stratum corneum) of the skin had entered and passed through the skin sample. The results of the ELISA are shown in FIG. 17A-B for intact skin and FIG. 18 for tape-stripped skin. Where a positive ELISA signal was recorded, variations in the size of the ELISA signal derived from cells containing $V_H$ in different formulations indicated that the ability of the different penetration enhancers in each prototype formulation to facilitate the penetration of the $V_H$ across the stratum corneum and further into the epidermis and dermis varied.

Results of IHC Imaging of $V_H$ in the Skin Samples

Examples of IHC images from skin treated with $V_H$ in the prototype formulations are shown in FIG. 19 to FIG. 28. It was possible to see labeling of $V_H$ throughout the depth of the skin sample. In addition, there was a general positive correlation between the scale of $V_H$ labeling observed on the IHC images and the ELISA signal measured in the receiver fluids derived from the corresponding Bronaugh cells. Importantly, the size control IgG did not cross the stratum corneum and penetrate further into the skin at all, neither in the normal intact nor the tape stripped skin, supporting the fact that only the much smaller $V_H$ domain was able to penetrate across the stratum corneum into the epidermis.

Example 12

Two identical or two different anti-IL-17A $V_H$ can be joined together in tandem directly or via a protein linker. If the two joined $V_H$s each act on the same epitope of IL17A, the joined $V_H$—$V_H$ is termed bivalent. If the joined two $V_H$s each act on different epitopes of IL-1A7, the joined $V_H$-$V_H$ is termed biparatopic.

Standard molecular biology cloning techniques are used to clone the coding DNA sequences of the two $V_H$s and the linker in $V_H$-linker-$V_H$ format with C-terminal HIS6 tag into *E. coli* or yeast (*Pichia Pastoris*) expression vector. Expression and purification of the HIS6 tagged $V_H$-$V_H$ products follows standard protein expression and purification methods. A number of constructs were made and results are shown in the figures. The constructs use clones 1.1, 1.10, 1.2 and 3.2.

```
Bivalent:
1.10-3(G4S)-1.1 linker sequence:
                                        (SEQ ID NO. 426)
GGGGSGGGGSGGGGS DNA sequence:
Biparatopic:
3.2-2(G4S)-1.2; 3.2-4(G4S)-1.2; 3.2-6(G4S)-1.2;

linker sequences:
                                        (SEQ ID NO. 427)
AAGGGGSGGGGS
```

-continued

AAGGGGSGGGGSGGGGSGGGGS (SEQ ID NO. 428)

AAGGGGSGGGGSGGGGSGGGGSGGGGSGGGGS (SEQ ID NO: 429)

The purified V$_H$-V$_H$s have been tested on BIAcore® for IL1A7 binding affinity. The functionality has been analysed on IL6 release assay.

Sequence Information 1.10.2 (clone 1.10 with C terminal extension and His tag)
SEQ ID No. 409
EVQLVESGGGLVQPGGSLRLSCAASGFTFSSYRMYWVRQAPGKGLEWVASIEQDGSEE
YYVDSVKGRFTISRDNAKKSLFLQMNSLRAEDTAVYYCAK GEILPLYFDY
WGQGTLVTVSSAAA HHHHHH 1.2.2 (clone 1.2 with C terminal extension and His tag)
SEQ ID No. 410
EVQLVESGGGLVQPGGSLRLSCAASGFTFSSYSMYWVRQAPGKGLEWVAEIKQDGSVQ
YYVSDVKGRFTISRDNAKNSLYLQMNSLRAEDTAVYYCAKGEILPLYFDYWGQGTLVTVS
SAAA HHHHHH 1.2.3 (clone 1.2 with C terminal extension)
SEQ ID No. 411
EVQLVESGGGLVQPGGSLRLSCAASGFTFSSYSMYWVRQAPGKGLEWVAEIKQDGSVQ
YYVSDVKGRFTISRDNAKNSLYLQMNSLRAEDTAVYYCAKGEILPLYFDYWGQGTLVTVS
SA 1.3.2 (clone 1.3 with C terminal extension and His tag)
SEQ ID No. 412
EVQLVESGGGLVQPGGSLRLSCAASGFTFSSYSMYWVRQAPGKGLEWVAEIKQDGSVQ
YYVDSVKGRFTISRDNAKNSLYLQMNSLRAEDTAVYYCAKGEILPLYFDYWGQGTLVTVS
S AAA HHHHHH 1.3.3 (clone 1.3 with C terminal extension)
SEQ ID No. 413
EVQLVESGGGLVQPGGSLRLSCAASGFTFSSYSMYWVRQAPGKGLEWVAEIKQDGSVQ
YYVDSVKGRFTISRDNAKNSLYLQMNSLRAEDTAVYYCAKGEILPLYFDYWGQGTLVTVS
SA 1.6.1 (clone 1.6 expressed from phagemid vector: with linker residues and His tag)
SEQ ID No. 414
EVQLVESGGGLVQPGGSLRLSCAASGFTFSSYSMYWVRQAPGKGLEWVAEIKQDGSEQ
YYVDSVKGRFTISRDNAKNSLYLQMNSLRAEDTAVYYCAKGEILPLYFDYWGQGTLVTVS
SLEGGGS HHHHHH 1.7.1 (clone 1.7 expressed from phagemid vector: with linker residues and His tag)
SEQ ID No. 415
QVQLVESGGGLVQPGGSLRLSCAASGFTFSSYGMYWVRQAPGKGLEWVAKIEQDGSEE
YYVDSVKGRFTISRDNAKKSLYLQMNSLRAEDTAVYYCAKGEILPLYFDYWGQGTLVTVSS
LEGGGS HHHHHH 1.10.1 (clone 1.10 expressed from phagemid vector: with linker residues and His tag)
SEQ ID No. 416
EVQLVESGGGLVQPGGSLRLSCAASGFTFSSYRMYWVRQAPGKGLEWVASIEQDGSEE
YYVDSVKGRFTISRDNAKKSLFLQMNSLRAEDTAVYYCAKGEILPLYFDYWGQGTLVTVSS
LEGGGS HHHHHH 1.3.1 (clone 1.3 expressed from phagemid vector: with linker residues and His tag)
SEQ ID No. 417
EVQLVESGGGLVQPGGSLRLSCAASGFTFSSYSMYWVRQAPGKGLEWVAEIKQDGSVQ -continued

YYVDSVKGRFTISRDNAKNSLYLQMNSLRAEDTAVYYCAKGEILPLYFDYWGQGTLVTVS

S LEGGGS HHHHHH 3.2.1 (clone 3.2 expressed from phagemid vector: with linker residues and His tag)

SEQ ID No. 418

QVQLVQSGAEVKKPGASVKVSCKASGYNADAYYINWVRQAPGQGLEWMGSIKPNTGAT

KYAQKFQGRVTITRDTSISTAYMEISRLRSDDTAVYYCASLDRDTWYPHSYAGWFDAWG

QGTLVTVSS LEGGGS HHHHHH 1.1.1 (clone 1.1 expressed from phagemid vector: with linker residues and His tag)

SEQ ID No. 419

EVQLVESGGGLVQPGGSLRLSCAASGFTFSSYSMYWVRQAPGKGLEWVANIKQDGSEK

YYVDSVKGRFTISRDNAKNSLFLQMNSLRAEDTAVYYCAKGEILPLHFDYWGQGTLVTVS

S LEGGGS HHHHHH 1.16.1 (clone 1.16 expressed from phagemid vector: with linker residues and His tag)

SEQ ID No. 420

EVQLVESGGGLVQPGGSLRLSCAASGFTFSSYSMYWVRQAPGKGLEWVAEIKQDGSEQ

YYVDSVKGRFTISRDNAKNSLYLQMNGLRAEDTAVYYCAKGEILPLYFDYWGQGTLVTVS

S LEGGGS HHHHHH 1.20.1 (clone 1.20 expressed from phagemid vector: with linker residues and His tag)

SEQ ID No. 421

EVQLVESGGGLVQPGGSLRLSCAASGFTFSSYGMYWVRQAPGKGLEWVAKIEQDGSEE

YYADSVKGRFTISRDNAKKSLYLQMNSLRAEDTAVYYCAKGEILPLYFDYWGQGTLVTVSS

LEGGGS HHHHHH 1.19.1 (clone 1.19 expressed from phagemid vector: with linker residues and His tag)

SEQ ID No. 422

EVQLVESGGGLVQPGGSLRLSCATSGFTFSSYGMYWVRQAPGKGLEWVAEIKQDGSEK

YYVDSVKGRFTISRDNAKNSLYLQMNSLRAEDTAVYYCAKGEILPLYFDYWGQGTLVTVS

S LEGGGS HHHHHH 1.17.1 (clone 1.17 expressed from phagemid vector: with linker residues and His tag)

SEQ ID No. 423

EVQLVESGGGLVQPGGSLRLSCAASGFTFSSYSMYWVRQAPGKGLEWVAEIKPTGSVQY

YVSDVKGRFTISRDNAKNSLYLQMNSLRAEDTAVYYCAKGEILPLYFDYWGQGTLVTVSS

LEGGGS HHHHHH 1.18.1 (clone 1.18 expressed from phagemid vector: with linker residues and His tag)

SEQ ID No. 424

EVQLVESGGGLVQPGGSLRLSCAASGFTFSSYSMYWVRQAPGKGLEWVAEIKQDGSVQ

YYVGGVKGRFTISRDNAKNSLYLQMNSLRAEDTAVYYCAKGEILPLYFDYWGQGTLVTVS

SLEGGGS HHHHHH 1.21.1 (clone 1.21 expressed from phagemid vector: with linker residues and His tag)

SEQ ID No. 425

EVQLVESGGGLVLPGGSLRLSCAASGFTFSSYSMYWVRQAPGKGLEWVAEIKQDGSEQY

YVDSVKGRFTISRDNAKNSLYLQMNSLRAEDTAVYYCAKGEILPLYFDYWGQGTLVTVSS

LEGGGS HHHHHH

Bivalent: 1.10-3(G$_4$S)-1.1(E1/6Q)

SEQ ID No. 430

EVQLVESGGGLVQPGGSLRLSCAASGFTFSSYRMYWVRQAPGKGLEWVASIEQDGSEE

YYVDSVKGRFTISRDNAKKSLFLQMNSLRAEDTAVYYCAKGEILPLYFDYWGQGTLVTVSS

```
GGGGSGGGGSGGGGSQVQLVQSGGGLVQPGGSLRLSCAASGFTFSSYSMYWVRQAP
GKGLEWVANIKQDGSEKYYVDSVKGRFTISRDNAKNSLFLQMNSLRAEDTAVYYCAKGEI
LPLHFDYWGQGTLVTVSS
```

SEQ ID No. 431

```
GAGGTGCAGCTGGTGGAGTCTGGGGGAGGCTTGGTCCAGCCTGGGGGGTCCCTGAG
ACTCTCCTGTGCAGCCTCTGGATTCACCTTTAGTAGTTATCGCATGTACTGGGTCCGC
CAGGCTCCAGGGAAGGGGCTGGAGTGGGTGGCCAGCATAGAACAAGATGGAAGTGA
GGAATACTATGTGGACTCTGTGAAGGGCCGATTCACCATCTCCAGAGACAACGCCAAG
AAGTCACTGTTTCTGCAAATGAATAGCCTGAGAGCCGAGGACACGGCTGTGTATTACT
GTGCGAAAGGGGAAATACTACCCCTCTACTTTGACTACTGGGGCCAGGGAACCCTGG
TCACCGTCTCCTCAGGTGGAGGAGGTAGTGGTGGAGGAGGTAGTGGTGGAGGAGGT
AGTCAGGTGCAGCTGGTGCAGTCTGGGGGAGGCTTGGTCCAGCCTGGGGGGTCCCT
GAGACTCTCCTGTGCAGCCTCTGGATTCACCTTTAGTAGTTATTCGATGTACTGGGTC
CGCCAGGCTCCAGGGAAGGGGCTGGAGTGGGTGGCCAACATAAAGCAAGATGGAAG
TGAGAAATACTATGTGGACTCTGTGAAGGGCCGATTCACCATCTCCAGAGACAACGCC
AAGAACTCACTGTTTCTGCAAATGAATAGCCTGAGAGCCGAGGACACGGCTGTGTATT
ACTGTGCGAAAGGGGAAATACTACCCCTCCACTTTGACTACTGGGGCCAGGGAACCC
TGGTCACCGTCTCTTCA
```

Biparatopic: 3.2-2(G$_4$S)-1.2

SEQ ID No. 432

```
QVQLVQSGAEVKKPGASVKVSCKASGYNADAYYINWVRQAPGQGLEWMGSIKPNTGAT
KYAQKFQGRVTITRDTSISTAYMEISRLRSDDTAVYYCASLDRDTWYPHSYAGWFDAWG
QGTLVTVSSAAGGGGSGGGGSEVQLVESGGGLVQPGGSLRLSCAASGFTFSSYSMYWV
RQAPGKGLEWVAEIKQDGSVQYYVSDVKGRFTISRDNAKNSLYLQMNSLRAEDTAVYYC
AKGEILPLYFDYWGQGTLVTVSS
```

SEQ ID No. 433

```
CAGGTTCAGCTGGTGCAGTCTGGAGCTGAGGTAAAGAAGCCTGGGGCCTCGGTGAAG
GTCTCCTGTAAGGCTTCCGGATATAACGCGGACGCCTATTATATAAATTGGGTGCGAC
AGGCCCCTGGACAAGGTCTTGAGTGGATGGGAAGTATCAAGCCTAATACCGGTGCCA
CAAAATATGCACAGAAGTTTCAGGGCAGAGTCACCATAACCAGGGACACGTCCATCAG
CACAGCCTACATGGAGCTGAGCAGGCTGAGATCTGACGACACGGCCGTGTATTACTG
TGCGAGTCTGGATCGGGATACGTGGTACCCGCACTCCTACGCGGGGTGGTTCGACGC
GTGGGGCCAGGGAACCCTGGTCACCGTCTCTTCAGCGGCCGGTGGTGGCGGTTCAG
GTGGAGGTGGTAGTGAGGTTCAGTTGGTGGAAAGCGGCGGTGGCCTGGTCCAGCCG
GGTGGTAGCCTGCGCCTGTCCTGCGCGGCTAGCGGTTTCACGTTTAGCAGCTACAGC
ATGTACTGGGTGCGTCAAGCGCCAGGCAAAGGTCTGGAATGGGTTGCCGAGATTAAG
CAAGACGGTTCTGTTCAGTATTATGTCAGCGACGTGAAGGGTCGTTTTACCATCAGCC
GTGACAACGCGAAAAACAGCCTGTATTTGCAGATGAATTCCCTGCGCGCTGAAGATAC
CGCCGTGTATTACTGTGCGAAAGGTGAGATTCTGCCGCTGTACTTCGATTACTGGGGC
CAAGGCACCCTGGTTACTGTCTCGAGC
```

Biparatopic 3.2-4(G$_4$S)-1.2

SEQ ID No. 434

```
QVQLVQSGAEVKKPGASVKVSCKASGYNADAYYINWVRQAPGQGLEWMGSIKPNTGAT
```

-continued

KYAQKFQGRVTITRDTSISTAYMEISRLRSDDTAVYYCASLDRDTWYPHSYAGWFDAWG
QGTLVTVSSAAGGGGSGGGGSGGGGSGGGGSEVQLVESGGGLVQPGGSLRLSCAASG
FTFSSYSMYWVRQAPGKGLEWVAEIKQDGSVQYYVSDVKGRFTISRDNAKNSLYLQMNS
LRAEDTAVYYCAKGEILPLYFDYWGQGTLVTVSS

SEQ ID No. 435

CAGGTTCAGCTGGTGCAGTCTGGAGCTGAGGTAAAGAAGCCTGGGGCCTCGGTGAAG
GTCTCCTGTAAGGCTTCCGGATATAACGCGGACGCCTATTATATAAATTGGGTGCGAC
AGGCCCCTGGACAAGGTCTTGAGTGGATGGGAAGTATCAAGCCTAATACCGGTGCCA
CAAAATATGCACAGAAGTTTCAGGGCAGAGTCACCATAACCAGGGACACGTCCATCAG
CACAGCCTACATGGAGCTGAGCAGGCTGAGATCTGACGACACGGCCGTGTATTACTG
TGCGAGTCTGGATCGGGATACGTGGTACCCGCACTCCTACGCGGGGTGGTTCGACGC
GTGGGGCCAGGGAACCCTGGTCACCGTCTCTTCAGCGGCCGGTGGTGGCGGTTCAG
GAGGTGGAGGTTCAGGAGGTGGTGTTCTGGTGGAGGTGGTAGTGAGGTTCAGTTG
GTGGAAAGCGGCGGTGGCCTGGTCCAGCCGGGTGGTAGCCTGCGCCTGTCCTGCGC
GGCTAGCGGTTTCACGTTTAGCAGCTACAGCATGTACTGGGTGCGTCAAGCGCCAGG
CAAAGGTCTGGAATGGGTTGCCGAGATTAAGCAAGACGGTTCTGTTCAGTATTATGTC
AGCGACGTGAAGGGTCGTTTTACCATCAGCCGTGACAACGCGAAAAACAGCCTGTATT
TGCAGATGAATTCCCTGCGCGCTGAAGATACCGCGGTGTATTACTGTGCGAAAGGTGA
GATTCTGCCGCTGTACTTCGATTACTGGGGCCAAGGCACCCTGGTTACTGTCTCGAGC

Biparatopic 3.2-6(G₄S)-1.2

SEQ ID No. 436

QVQLVQSGAEVKKPGASVKVSCKASGYNADAYYINWVRQAPGQGLEWMGSIKPNTGAT
KYAQKFQGRVTITRDTSISTAYMEISRLRSDDTAVYYCASLDRDTWYPHSYAGWFDAWG
QGTLVTVSSAAGGGGSGGGGSGGGGSGGGGSGGGGSEVQLVESGGGLVQPG
GSLRLSCAASGFTFSSYSMYWVRQAPGKGLEWVAEIKQDGSVQYYVSDVKGRFTISRDN
AKNSLYLQMNSLRAEDTAVYYCAKGEILPLYFDYWGQGTLVTVSS

SEQ ID No. 437

CAGGTTCAGCTGGTGCAGTCTGGAGCTGAGGTAAAGAAGCCTGGGGCCTCGGTGAAG
GTCTCCTGTAAGGCTTCCGGATATAACGCGGACGCCTATTATATAAATTGGGTGCGAC
AGGCCCCTGGACAAGGTCTTGAGTGGATGGGAAGTATCAAGCCTAATACCGGTGCCA
CAAAATATGCACAGAAGTTTCAGGGCAGAGTCACCATAACCAGGGACACGTCCATCAG
CACAGCCTACATGGAGCTGAGCAGGCTGAGATCTGACGACACGGCCGTGTATTACTG
TGCGAGTCTGGATCGGGATACGTGGTACCCGCACTCCTACGCGGGGTGGTTCGACGC
GTGGGGCCAGGGAACCCTGGTCACCGTCTCTTCAGCGGCCGGTGGTGGCGGTTCAG
GCGGAGGTGGCTCTGGAGGTGGAGGTTCAGGAGGTGGTGTTCTGGCGGCGGTGGA
TCGGGTGGAGGTGGTAGTGAGGTTCAGTTGGTGGAAAGCGGCGGTGGCCTGGTCCA
GCCGGGTGGTAGCCTGCGCCTGTCCTGCGCGGCTAGCGGTTTCACGTTTAGCAGCTA
CAGCATGTACTGGGTGCGTCAAGCGCCAGGCAAAGGTCTGGAATGGGTTGCCGAGAT
TAAGCAAGACGGTTCTGTTCAGTATTATGTCAGCGACGTGAAGGGTCGTTTTACCATC
AGCCGTGACAACGCGAAAAACAGCCTGTATTTGCAGATGAATTCCCTGCGCGCTGAAG
ATACCGCGGTGTATTACTGTGCGAAAGGTGAGATTCTGCCGCTGTACTTCGATTACTG
GGGCCAAGGCACCCTGGTTACTGTCTCGAGC

The invention claimed is:

1. A binding molecule comprising a single domain antibody that binds human IL-17A, said single domain antibody comprising a human heavy chain variable immunoglobulin domain ($V_H$) that comprises a CDR1, a CDR2, and a CDR3 sequence,
wherein said CDR1 sequence comprises the amino acid sequence of SEQ ID NO. 5;
wherein said CDR2 sequence comprises the amino acid sequence of SEQ ID NO. 6; and
wherein said CDR3 sequence comprises the amino acid sequence of SEQ ID NO. 7.

2. The binding molecule according to claim 1, wherein said human heavy chain variable immunoglobulin domain ($V_H$) comprises the amino acid sequence of SEQ ID NO. 85.

3. A pharmaceutical composition comprising
a pharmaceutical carrier; and
a binding molecule that binds human IL-17A, said binding molecule comprising a human heavy chain variable immunoglobulin domain ($V_H$) that comprises a CDR1, a CDR2, and a CDR3 sequence,
wherein said CDR1 sequence comprises the amino acid sequence of SEQ ID NO. 5;
wherein said CDR2 sequence comprises the amino acid sequence of SEQ ID NO. 6; and
wherein said CDR3 sequence comprises the amino acid sequence of SEQ ID NO. 7.

4. The pharmaceutical composition according to claim 3, wherein said composition is formulated for topical administration to the skin.

5. The pharmaceutical composition according to claim 3, wherein said human heavy chain variable immunoglobulin domain ($V_H$) comprises the amino acid sequence of SEQ ID NO. 8.

6. A method for treating at least one disease or condition selected from the group consisting of an autoimmune disease, inflammatory conditions, allergies, allergic conditions, hypersensitivity reactions, and organ or tissue transplant rejection, said method comprising:
administering an effective amount of the pharmaceutical composition according to claim 3.

7. The method according to claim 6, wherein said disease is selected from psoriasis, systemic lupus erythematosis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems multiple sclerosis, idiopathic demyelinating polyneuropathy or Guillain Barre syndrome, chronic inflammatory demyelinating polyneuropathy, hepatobiliary diseases, autoimmune chronic active hepatitis, primary biliary cirrhosis, granulomatous hepatitis, sclerosing cholangitis, inflammatory bowel disease, gluten-sensitive enteropathy, Whipple's disease, autoimmune or immune-mediated skin diseases, bullous skin diseases, erythema multiforme, contact dermatitis, allergic diseases, asthma, allergic rhinitis, atopic dermatitis, food hypersensitivity, urticaria, immunologic diseases of the lung, eosinophilic pneumonia, idiopathic pulmonary fibrosis, hypersensitivity pneumonitis, autoimmune haematological disorders, hemolytic anaemia, aplastic anaemia, pure red cell anaemia, idiopathic thrombocytopenia, autoimmune inflammatory bowel disease, ulcerative colitis, Crohn's disease, Irritable Bowel Syndrome, uveitis, transplantation associated diseases, graft rejection, and graft-versus-host-disease.

* * * * *

SEQUENCE LISTING

<160> NUMBER OF SEQ ID NOS: 466

<210> SEQ ID NO 1
<211> LENGTH: 5
<212> TYPE: PRT
<213> ORGANISM: Artificial Sequence
<220> FEATURE:
<223> OTHER INFORMATION: clone

<400> SEQUENCE: 1

Ser Tyr Ser Met Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: clone

<400> SEQUENCE: 2

Asn Ile Lys Gln Asp Gly Ser Glu Lys Tyr Tyr Val Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: clone

<400> SEQUENCE: 3

Gly Glu Ile Leu Pro Leu His Phe Asp Tyr
1               5                   10

<210> SEQ ID NO 4
<211> LENGTH: 119
<212> TYPE: PRT
<213> ORGANISM: Artificial Sequence
<220> FEATURE:
<223> OTHER INFORMATION: clone

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
        115

<210> SEQ ID NO 5

```
<211> LENGTH: 5
<212> TYPE: PRT
<213> ORGANISM: Artificial Sequence
<220> FEATURE:
<223> OTHER INFORMATION: clone

<400> SEQUENCE: 5

Ser Tyr Ser Met Tyr
1               5

<210> SEQ ID NO 6
<211> LENGTH: 17
<212> TYPE: PRT
<213> ORGANISM: Artificial Sequence
<220> FEATURE:
<223> OTHER INFORMATION: clone

<400> SEQUENCE: 6

Glu Ile Lys Gln Asp Gly Ser Val Gln Tyr Tyr Val Ser Asp Val Lys
1               5                   10                  15

Gly

<210> SEQ ID NO 7
<211> LENGTH: 10
<212> TYPE: PRT
<213> ORGANISM: Artificial Sequence
<220> FEATURE:
<223> OTHER INFORMATION: clone

<400> SEQUENCE: 7

Gly Glu Ile Leu Pro Leu Tyr Phe Asp Tyr
1               5                   10

<210> SEQ ID NO 8
<211> LENGTH: 119
<212> TYPE: PRT
<213> ORGANISM: Artificial Sequence
<220> FEATURE:
<223> OTHER INFORMATION: clone

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Val Gln Tyr Tyr Val Ser Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 9
<211> LENGTH: 5
<212> TYPE: PRT
<213> ORGANISM: Artificial Sequence
<220> FEATURE:
```

-continued

<223> OTHER INFORMATION: clone

<400> SEQUENCE: 9

Ser Tyr Ser Met Tyr
1               5

<210> SEQ ID NO 10
<211> LENGTH: 17
<212> TYPE: PRT
<213> ORGANISM: Artificial Sequence
<220> FEATURE:
<223> OTHER INFORMATION: clone

<400> SEQUENCE: 10

Glu Ile Lys Gln Asp Gly Ser Val Gln Tyr Tyr Val Asp Ser Val Lys
1               5                   10                  15

Gly

<210> SEQ ID NO 11
<211> LENGTH: 10
<212> TYPE: PRT
<213> ORGANISM: Artificial Sequence
<220> FEATURE:
<223> OTHER INFORMATION: clone

<400> SEQUENCE: 11

Gly Glu Ile Leu Pro Leu Tyr Phe Asp Tyr
1               5                   10

<210> SEQ ID NO 12
<211> LENGTH: 119
<212> TYPE: PRT
<213> ORGANISM: Artificial Sequence
<220> FEATURE:
<223> OTHER INFORMATION: clone

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Val Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 13
<211> LENGTH: 5
<212> TYPE: PRT
<213> ORGANISM: Artificial Sequence
<220> FEATURE:
<223> OTHER INFORMATION: clone

<400> SEQUENCE: 13

```
Ser Tyr Ser Met Tyr
1               5
```

<210> SEQ ID NO 14
<211> LENGTH: 17
<212> TYPE: PRT
<213> ORGANISM: Artificial Sequence
<220> FEATURE:
<223> OTHER INFORMATION: clone

<400> SEQUENCE: 14

```
Glu Ile Lys Gln Thr Gly Ser Val Gln Tyr Tyr Val Asp Ser Val Lys
1               5                   10                  15

Gly
```

<210> SEQ ID NO 15
<211> LENGTH: 10
<212> TYPE: PRT
<213> ORGANISM: Artificial Sequence
<220> FEATURE:
<223> OTHER INFORMATION: clone

<400> SEQUENCE: 15

```
Gly Glu Ile Leu Pro Leu Tyr Phe Asp Tyr
1               5                   10
```

<210> SEQ ID NO 16
<211> LENGTH: 119
<212> TYPE: PRT
<213> ORGANISM: Artificial Sequence
<220> FEATURE:
<223> OTHER INFORMATION: clone

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Thr Gly Ser Val Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115
```

<210> SEQ ID NO 17
<211> LENGTH: 5
<212> TYPE: PRT
<213> ORGANISM: Artificial Sequence
<220> FEATURE:
<223> OTHER INFORMATION: clone

<400> SEQUENCE: 17

```
Ser Tyr Ser Met Tyr
1               5
```

```
<210> SEQ ID NO 18
<211> LENGTH: 17
<212> TYPE: PRT
<213> ORGANISM: Artificial Sequence
<220> FEATURE:
<223> OTHER INFORMATION: clone

<400> SEQUENCE: 18

Glu Ile Lys Pro Thr Gly Ser Val Gln Tyr Tyr Val Asp Ser Val Lys
1               5                   10                  15
Gly

<210> SEQ ID NO 19
<211> LENGTH: 10
<212> TYPE: PRT
<213> ORGANISM: Artificial Sequence
<220> FEATURE:
<223> OTHER INFORMATION: clone

<400> SEQUENCE: 19

Gly Glu Ile Leu Pro Leu Tyr Phe Asp Tyr
1               5                   10

<210> SEQ ID NO 20
<211> LENGTH: 119
<212> TYPE: PRT
<213> ORGANISM: Artificial Sequence
<220> FEATURE:
<223> OTHER INFORMATION: clone

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Pro Thr Gly Ser Val Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 21
<211> LENGTH: 5
<212> TYPE: PRT
<213> ORGANISM: Artificial Sequence
<220> FEATURE:
<223> OTHER INFORMATION: clone

<400> SEQUENCE: 21

Ser Tyr Ser Met Tyr
1               5

<210> SEQ ID NO 22
<211> LENGTH: 17
<212> TYPE: PRT
<213> ORGANISM: Artificial Sequence
```

<220> FEATURE:
<223> OTHER INFORMATION: clone

<400> SEQUENCE: 22

Glu Ile Lys Gln Asp Gly Ser Glu Gln Tyr Tyr Val Asp Ser Val Lys
1               5                   10                  15
Gly

<210> SEQ ID NO 23
<211> LENGTH: 10
<212> TYPE: PRT
<213> ORGANISM: Artificial Sequence
<220> FEATURE:
<223> OTHER INFORMATION: clone

<400> SEQUENCE: 23

Gly Glu Ile Leu Pro Leu Tyr Phe Asp Tyr
1               5                   10

<210> SEQ ID NO 24
<211> LENGTH: 119
<212> TYPE: PRT
<213> ORGANISM: Artificial Sequence
<220> FEATURE:
<223> OTHER INFORMATION: clone

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 25
<211> LENGTH: 5
<212> TYPE: PRT
<213> ORGANISM: Artificial Sequence
<220> FEATURE:
<223> OTHER INFORMATION: clone

<400> SEQUENCE: 25

Ser Tyr Gly Met Tyr
1               5

<210> SEQ ID NO 26
<211> LENGTH: 17
<212> TYPE: PRT
<213> ORGANISM: Artificial Sequence
<220> FEATURE:
<223> OTHER INFORMATION: clone

<400> SEQUENCE: 26

Lys Ile Glu Gln Asp Gly Ser Glu Glu Tyr Tyr Val Asp Ser Val Lys
1               5                   10                  15

Gly

<210> SEQ ID NO 27
<211> LENGTH: 10
<212> TYPE: PRT
<213> ORGANISM: Artificial Sequence
<220> FEATURE:
<223> OTHER INFORMATION: clone

<400> SEQUENCE: 27

Gly Glu Ile Leu Pro Leu Tyr Phe Asp Tyr
1               5                   10

<210> SEQ ID NO 28
<211> LENGTH: 119
<212> TYPE: PRT
<213> ORGANISM: Artificial Sequence
<220> FEATURE:
<223> OTHER INFORMATION: clone

<400> SEQUENCE: 28

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Lys Ile Glu Gln Asp Gly Ser Glu Glu Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 29
<211> LENGTH: 5
<212> TYPE: PRT
<213> ORGANISM: Artificial Sequence
<220> FEATURE:
<223> OTHER INFORMATION: clone

<400> SEQUENCE: 29

Ser Tyr Gly Met Tyr
1               5

<210> SEQ ID NO 30
<211> LENGTH: 17
<212> TYPE: PRT
<213> ORGANISM: Artificial Sequence
<220> FEATURE:
<223> OTHER INFORMATION: clone

<400> SEQUENCE: 30

Lys Ile Glu Gln Asp Gly Ser Glu Lys Tyr Tyr Val Asp Ser Val Lys
1               5                   10                  15

Gly

<210> SEQ ID NO 31
<211> LENGTH: 10
<212> TYPE: PRT
<213> ORGANISM: Artificial Sequence
<220> FEATURE:
<223> OTHER INFORMATION: clone

<400> SEQUENCE: 31

Gly Glu Ile Leu Pro Leu Tyr Phe Asp Tyr
1               5                   10

<210> SEQ ID NO 32
<211> LENGTH: 119
<212> TYPE: PRT
<213> ORGANISM: Artificial Sequence
<220> FEATURE:
<223> OTHER INFORMATION: clone

<400> SEQUENCE: 32

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Lys Ile Glu Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 33
<211> LENGTH: 5
<212> TYPE: PRT
<213> ORGANISM: Artificial Sequence
<220> FEATURE:
<223> OTHER INFORMATION: clone

<400> SEQUENCE: 33

Ser Tyr Gly Met Tyr
1               5

<210> SEQ ID NO 34
<211> LENGTH: 17
<212> TYPE: PRT
<213> ORGANISM: Artificial Sequence
<220> FEATURE:
<223> OTHER INFORMATION: clone

<400> SEQUENCE: 34

Glu Ile Lys Gln Asp Gly Ser Glu Lys Tyr Tyr Val Asp Ser Val Lys
1               5                   10                  15

Gly

<210> SEQ ID NO 35

```
<211> LENGTH: 10
<212> TYPE: PRT
<213> ORGANISM: Artificial Sequence
<220> FEATURE:
<223> OTHER INFORMATION: clone

<400> SEQUENCE: 35

Gly Glu Ile Leu Pro Leu Tyr Phe Asp Tyr
1               5                   10

<210> SEQ ID NO 36
<211> LENGTH: 119
<212> TYPE: PRT
<213> ORGANISM: Artificial Sequence
<220> FEATURE:
<223> OTHER INFORMATION: clone

<400> SEQUENCE: 36

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 37
<211> LENGTH: 5
<212> TYPE: PRT
<213> ORGANISM: Artificial Sequence
<220> FEATURE:
<223> OTHER INFORMATION: clone

<400> SEQUENCE: 37

Ser Tyr Arg Met Tyr
1               5

<210> SEQ ID NO 38
<211> LENGTH: 17
<212> TYPE: PRT
<213> ORGANISM: Artificial Sequence
<220> FEATURE:
<223> OTHER INFORMATION: clone

<400> SEQUENCE: 38

Ser Ile Glu Gln Asp Gly Ser Glu Glu Tyr Tyr Val Asp Ser Val Lys
1               5                   10                  15

Gly

<210> SEQ ID NO 39
<211> LENGTH: 10
<212> TYPE: PRT
<213> ORGANISM: Artificial Sequence
<220> FEATURE:
```

<223> OTHER INFORMATION: clone

<400> SEQUENCE: 39

Gly Glu Ile Leu Pro Leu Tyr Phe Asp Tyr
1               5                   10

<210> SEQ ID NO 40
<211> LENGTH: 119
<212> TYPE: PRT
<213> ORGANISM: Artificial Sequence
<220> FEATURE:
<223> OTHER INFORMATION: clone

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Glu Gln Asp Gly Ser Glu Glu Tyr Tyr Val Asp Ser Val
    50                  55                  60

Lys Gly Arg Phe Thr Ile Ser Arg Asp Asn Ala Lys Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 41
<211> LENGTH: 5
<212> TYPE: PRT
<213> ORGANISM: Artificial Sequence
<220> FEATURE:
<223> OTHER INFORMATION: clone

<400> SEQUENCE: 41

Ser Tyr Gln Met Tyr
1               5

<210> SEQ ID NO 42
<211> LENGTH: 17
<212> TYPE: PRT
<213> ORGANISM: Artificial Sequence
<220> FEATURE:
<223> OTHER INFORMATION: clone

<400> SEQUENCE: 42

Ser Ile Lys Gln Asp Gly Ser Glu Glu Tyr Tyr Val Asp Ser Val Lys
1               5                   10                  15

Gly

<210> SEQ ID NO 43
<211> LENGTH: 10
<212> TYPE: PRT
<213> ORGANISM: Artificial Sequence
<220> FEATURE:
<223> OTHER INFORMATION: clone

<400> SEQUENCE: 43

```
Gly Glu Ile Leu Pro Leu Tyr Phe Asp Tyr
1               5                   10

<210> SEQ ID NO 44
<211> LENGTH: 119
<212> TYPE: PRT
<213> ORGANISM: Artificial Sequence
<220> FEATURE:
<223> OTHER INFORMATION: clone

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Tyr Trp Val Arg Gln Ala Pro Gly Lys Gly Leu Glu Trp Val
        35                  40                  45

Ala Ser Ile Lys Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 45
<211> LENGTH: 5
<212> TYPE: PRT
<213> ORGANISM: Artificial Sequence
<220> FEATURE:
<223> OTHER INFORMATION: clone

<400> SEQUENCE: 45

Ser Tyr Gly Met Tyr
1               5

<210> SEQ ID NO 46
<211> LENGTH: 17
<212> TYPE: PRT
<213> ORGANISM: Artificial Sequence
<220> FEATURE:
<223> OTHER INFORMATION: clone

<400> SEQUENCE: 46

Lys Ile Glu Gln Asp Gly Ser Glu Glu Tyr Tyr Val Asp Ser Val Lys
1               5                   10                  15

Gly

<210> SEQ ID NO 47
<211> LENGTH: 10
<212> TYPE: PRT
<213> ORGANISM: Artificial Sequence
<220> FEATURE:
<223> OTHER INFORMATION: clone

<400> SEQUENCE: 47

Gly Glu Ile Leu Pro Leu Tyr Phe Asp Tyr
1               5                   10
```

```
<210> SEQ ID NO 48
<211> LENGTH: 10
<212> TYPE: PRT
<213> ORGANISM: Artificial Sequence
<220> FEATURE:
<223> OTHER INFORMATION: clone

<400> SEQUENCE: 48

Gly Glu Ile Leu Pro Leu Tyr Phe Asp Tyr
1               5                   10

<210> SEQ ID NO 49
<211> LENGTH: 5
<212> TYPE: PRT
<213> ORGANISM: Artificial Sequence
<220> FEATURE:
<223> OTHER INFORMATION: clone

<400> SEQUENCE: 49

Ser Tyr Gly Met Tyr
1               5

<210> SEQ ID NO 50
<211> LENGTH: 17
<212> TYPE: PRT
<213> ORGANISM: Artificial Sequence
<220> FEATURE:
<223> OTHER INFORMATION: clone

<400> SEQUENCE: 50

Ser Ile Glu Gln Asp Gly Ser Glu Lys Tyr Tyr Val Asp Ser Val Lys
1               5                   10                  15

Gly

<210> SEQ ID NO 51
<211> LENGTH: 10
<212> TYPE: PRT
<213> ORGANISM: Artificial Sequence
<220> FEATURE:
<223> OTHER INFORMATION: clone

<400> SEQUENCE: 51

Gly Glu Ile Leu Pro Leu Tyr Phe Asp Tyr
1               5                   10

<210> SEQ ID NO 52
<211> LENGTH: 119
<212> TYPE: PRT
<213> ORGANISM: Artificial Sequence
<220> FEATURE:
<223> OTHER INFORMATION: clone

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met Tyr Trp Val Arg Gln Ala Pro Gly Lys Gly Leu Glu Trp Val
            35                  40                  45

Ala Ser Ile Glu Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                    85                  90                  95
Ala Lys Gly Glu Ile Leu Pro Leu Tyr Phe Asp Tyr Trp Gly Gln Gly
                100                 105                 110
Thr Leu Val Thr Val Ser Ser
        115
```

<210> SEQ ID NO 53
<211> LENGTH: 5
<212> TYPE: PRT
<213> ORGANISM: Artificial Sequence
<220> FEATURE:
<223> OTHER INFORMATION: clone

<400> SEQUENCE: 53

```
Ser Tyr Arg Met Tyr
1               5
```

<210> SEQ ID NO 54
<211> LENGTH: 17
<212> TYPE: PRT
<213> ORGANISM: Artificial Sequence
<220> FEATURE:
<223> OTHER INFORMATION: clone

<400> SEQUENCE: 54

```
Ser Ile Glu Gln Asp Gly Ser Glu Glu Tyr Tyr Val Asp Ser Val Lys
1               5                   10                  15
Gly
```

<210> SEQ ID NO 55
<211> LENGTH: 10
<212> TYPE: PRT
<213> ORGANISM: Artificial Sequence
<220> FEATURE:
<223> OTHER INFORMATION: clone

<400> SEQUENCE: 55

```
Gly Glu Ile Leu Pro Leu Tyr Phe Asp Tyr
1               5                   10
```

<210> SEQ ID NO 56
<211> LENGTH: 119
<212> TYPE: PRT
<213> ORGANISM: Artificial Sequence
<220> FEATURE:
<223> OTHER INFORMATION: clone

<400> SEQUENCE: 56

```
Glu Val Gln Leu Val Glu Ser Gly Gly Leu Val Gln Arg Gly Gly
1               5                   10                  15
Ser Leu Arg Leu Ser Cys Ala Ala Ser Gly Phe Thr Phe Ser Ser Tyr
                20                  25                  30
Arg Met Tyr Trp Val Arg Gln Ala Pro Gly Lys Gly Leu Glu Trp Val
            35                  40                  45
Ala Ser Ile Glu Gln Asp Gly Ser Glu Glu Tyr Tyr Val Asp Ser Val
        50                  55                  60
Lys Gly Arg Phe Thr Ile Ser Arg Asp Asn Ala Lys Lys Ser Leu Phe
65                  70                  75                  80
Leu Gln Met Asn Ser Leu Arg Ala Glu Asp Thr Ala Val Tyr Tyr Cys
                85                  90                  95
Ala Lys Gly Glu Ile Leu Pro Leu Tyr Phe Asp Tyr Trp Gly Gln Gly
                100                 105                 110
```

```
Thr Leu Val Thr Val Ser Ser
        115

<210> SEQ ID NO 57
<211> LENGTH: 5
<212> TYPE: PRT
<213> ORGANISM: Artificial Sequence
<220> FEATURE:
<223> OTHER INFORMATION: clone

<400> SEQUENCE: 57

Ser Tyr Ser Met Tyr
1               5

<210> SEQ ID NO 58
<211> LENGTH: 17
<212> TYPE: PRT
<213> ORGANISM: Artificial Sequence
<220> FEATURE:
<223> OTHER INFORMATION: clone

<400> SEQUENCE: 58

Glu Ile Arg Gln Asp Gly Ser Glu Gln Tyr Tyr Val Asp Ser Val Lys
1               5                   10                  15

Gly

<210> SEQ ID NO 59
<211> LENGTH: 10
<212> TYPE: PRT
<213> ORGANISM: Artificial Sequence
<220> FEATURE:
<223> OTHER INFORMATION: clone

<400> SEQUENCE: 59

Gly Glu Ile Leu Pro Leu Tyr Phe Asp Tyr
1               5                   10

<210> SEQ ID NO 60
<211> LENGTH: 119
<212> TYPE: PRT
<213> ORGANISM: Artificial Sequence
<220> FEATURE:
<223> OTHER INFORMATION: clone

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Arg Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115
```

```
<210> SEQ ID NO 61
<211> LENGTH: 5
<212> TYPE: PRT
<213> ORGANISM: Artificial Sequence
<220> FEATURE:
<223> OTHER INFORMATION: clone

<400> SEQUENCE: 61

Ser Tyr Ser Met Tyr
1               5

<210> SEQ ID NO 62
<211> LENGTH: 17
<212> TYPE: PRT
<213> ORGANISM: Artificial Sequence
<220> FEATURE:
<223> OTHER INFORMATION: clone

<400> SEQUENCE: 62

Glu Ile Lys Gln Asp Gly Ser Glu Gln Tyr Tyr Val Asp Ser Val Lys
1               5                   10                  15

Gly

<210> SEQ ID NO 63
<211> LENGTH: 10
<212> TYPE: PRT
<213> ORGANISM: Artificial Sequence
<220> FEATURE:
<223> OTHER INFORMATION: clone

<400> SEQUENCE: 63

Gly Glu Ile Leu Pro Leu Tyr Phe Asp Tyr
1               5                   10

<210> SEQ ID NO 64
<211> LENGTH: 119
<212> TYPE: PRT
<213> ORGANISM: Artificial Sequence
<220> FEATURE:
<223> OTHER INFORMATION: clone

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Tyr Trp Val Arg Gln Ala Pro Gly Lys Gly Leu Glu Trp Val
            35                  40                  45

Ala Glu Ile Lys Gln Asp Gly Ser Glu Gln Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Gly Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 65
<211> LENGTH: 5
<212> TYPE: PRT
```

```
<213> ORGANISM: Artificial Sequence
<220> FEATURE:
<223> OTHER INFORMATION: clone

<400> SEQUENCE: 65

Ser Tyr Ser Met Tyr
1               5

<210> SEQ ID NO 66
<211> LENGTH: 17
<212> TYPE: PRT
<213> ORGANISM: Artificial Sequence
<220> FEATURE:
<223> OTHER INFORMATION: clone

<400> SEQUENCE: 66

Glu Ile Lys Pro Thr Gly Ser Val Gln Tyr Tyr Val Ser Asp Val Lys
1               5                   10                  15

Gly

<210> SEQ ID NO 67
<211> LENGTH: 10
<212> TYPE: PRT
<213> ORGANISM: Artificial Sequence
<220> FEATURE:
<223> OTHER INFORMATION: clone

<400> SEQUENCE: 67

Gly Glu Ile Leu Pro Leu Tyr Phe Asp Tyr
1               5                   10

<210> SEQ ID NO 68
<211> LENGTH: 119
<212> TYPE: PRT
<213> ORGANISM: Artificial Sequence
<220> FEATURE:
<223> OTHER INFORMATION: clone

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Pro Thr Gly Ser Val Gln Tyr Tyr Val Ser Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 69
<211> LENGTH: 5
<212> TYPE: PRT
<213> ORGANISM: Artificial Sequence
<220> FEATURE:
<223> OTHER INFORMATION: clone
```

```
<400> SEQUENCE: 69

Ser Tyr Ser Met Tyr
1               5

<210> SEQ ID NO 70
<211> LENGTH: 17
<212> TYPE: PRT
<213> ORGANISM: Artificial Sequence
<220> FEATURE:
<223> OTHER INFORMATION: clone

<400> SEQUENCE: 70

Glu Ile Lys Gln Asp Gly Ser Val Gln Tyr Tyr Val Gly Gly Val Lys
1               5                   10                  15

Gly

<210> SEQ ID NO 71
<211> LENGTH: 10
<212> TYPE: PRT
<213> ORGANISM: Artificial Sequence
<220> FEATURE:
<223> OTHER INFORMATION: clone

<400> SEQUENCE: 71

Gly Glu Ile Leu Pro Leu Tyr Phe Asp Tyr
1               5                   10

<210> SEQ ID NO 72
<211> LENGTH: 119
<212> TYPE: PRT
<213> ORGANISM: Artificial Sequence
<220> FEATURE:
<223> OTHER INFORMATION: clone

<400> SEQUENCE: 72

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Val Gln Tyr Tyr Val Gly Gly Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 73
<211> LENGTH: 5
<212> TYPE: PRT
<213> ORGANISM: Artificial Sequence
<220> FEATURE:
<223> OTHER INFORMATION: clone

<400> SEQUENCE: 73

Ser Tyr Gly Met Tyr
1               5
```

```
<210> SEQ ID NO 74
<211> LENGTH: 17
<212> TYPE: PRT
<213> ORGANISM: Artificial Sequence
<220> FEATURE:
<223> OTHER INFORMATION: clone

<400> SEQUENCE: 74

Glu Ile Lys Gln Asp Gly Ser Glu Lys Tyr Tyr Val Asp Ser Val Lys
1               5                   10                  15
Gly

<210> SEQ ID NO 75
<211> LENGTH: 10
<212> TYPE: PRT
<213> ORGANISM: Artificial Sequence
<220> FEATURE:
<223> OTHER INFORMATION: clone

<400> SEQUENCE: 75

Gly Glu Ile Leu Pro Leu Tyr Phe Asp Tyr
1               5                   10

<210> SEQ ID NO 76
<211> LENGTH: 119
<212> TYPE: PRT
<213> ORGANISM: Artificial Sequence
<220> FEATURE:
<223> OTHER INFORMATION: clone

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 77
<211> LENGTH: 5
<212> TYPE: PRT
<213> ORGANISM: Artificial Sequence
<220> FEATURE:
<223> OTHER INFORMATION: clone

<400> SEQUENCE: 77

Ser Tyr Gly Met Tyr
1               5

<210> SEQ ID NO 78
<211> LENGTH: 17
```

```
<212> TYPE: PRT
<213> ORGANISM: Artificial Sequence
<220> FEATURE:
<223> OTHER INFORMATION: clone

<400> SEQUENCE: 78

Lys Ile Glu Gln Asp Gly Ser Glu Glu Tyr Tyr Ala Asp Ser Val Lys
1               5                   10                  15

Gly

<210> SEQ ID NO 79
<211> LENGTH: 10
<212> TYPE: PRT
<213> ORGANISM: Artificial Sequence
<220> FEATURE:
<223> OTHER INFORMATION: clone

<400> SEQUENCE: 79

Gly Glu Ile Leu Pro Leu Tyr Phe Asp Tyr
1               5                   10

<210> SEQ ID NO 80
<211> LENGTH: 119
<212> TYPE: PRT
<213> ORGANISM: Artificial Sequence
<220> FEATURE:
<223> OTHER INFORMATION: clone

<400> SEQUENCE: 80

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met Tyr Trp Val Arg Gln Ala Pro Gly Lys Gly Leu Glu Trp Val
            35                  40                  45

Ala Lys Ile Glu Gln Asp Gly Ser Glu Glu Tyr Tyr Ala Asp Ser Val
        50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 81
<211> LENGTH: 5
<212> TYPE: PRT
<213> ORGANISM: Artificial Sequence
<220> FEATURE:
<223> OTHER INFORMATION: clone

<400> SEQUENCE: 81

Ser Tyr Ser Met Tyr
1               5

<210> SEQ ID NO 82
<211> LENGTH: 17
<212> TYPE: PRT
<213> ORGANISM: Artificial Sequence
<220> FEATURE:
<223> OTHER INFORMATION: clone
```

-continued

<400> SEQUENCE: 82

Glu Ile Lys Gln Asp Gly Ser Glu Gln Tyr Tyr Val Asp Ser Val Lys
1               5                   10                  15

Gly

<210> SEQ ID NO 83
<211> LENGTH: 10
<212> TYPE: PRT
<213> ORGANISM: Artificial Sequence
<220> FEATURE:
<223> OTHER INFORMATION: clone

<400> SEQUENCE: 83

Gly Glu Ile Leu Pro Leu Tyr Phe Asp Tyr
1               5                   10

<210> SEQ ID NO 84
<211> LENGTH: 119
<212> TYPE: PRT
<213> ORGANISM: Artificial Sequence
<220> FEATURE:
<223> OTHER INFORMATION: clone

<400> SEQUENCE: 84

Glu Val Gln Leu Val Glu Ser Gly Gly Gly Leu Val Leu Pro Gly Gly
1               5                   10                  15

Ser Leu Arg Leu Ser Cys Ala Ala Ser Gly Phe Thr Phe Ser Ser Tyr
                20                  25                  30

Ser Met Tyr Trp Val Arg Gln Ala Pro Gly Lys Gly Leu Glu Trp Val
            35                  40                  45

Ala Glu Ile Lys Gln Asp Gly Ser Glu Gln Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 85
<211> LENGTH: 5
<212> TYPE: PRT
<213> ORGANISM: Artificial Sequence
<220> FEATURE:
<223> OTHER INFORMATION: clone

<400> SEQUENCE: 85

Ser Tyr Gly Met Tyr
1               5

<210> SEQ ID NO 86
<211> LENGTH: 17
<212> TYPE: PRT
<213> ORGANISM: Artificial Sequence
<220> FEATURE:
<223> OTHER INFORMATION: clone

<400> SEQUENCE: 86

Lys Ile Glu Gln Asp Gly Ser Glu Glu Tyr Tyr Val Asp Ser Val Lys

Gly

<210> SEQ ID NO 87
<211> LENGTH: 10
<212> TYPE: PRT
<213> ORGANISM: Artificial Sequence
<220> FEATURE:
<223> OTHER INFORMATION: clone

<400> SEQUENCE: 87

```
Gly Glu Ile Leu Pro Leu Tyr Phe Asp Tyr
1               5                   10
```

<210> SEQ ID NO 88
<211> LENGTH: 119
<212> TYPE: PRT
<213> ORGANISM: Artificial Sequence
<220> FEATURE:
<223> OTHER INFORMATION: clone

<400> SEQUENCE: 88

```
Glu Val Gln Leu Val Glu Ser Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Lys Ile Glu Gln Asp Gly Ser Glu Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115
```

<210> SEQ ID NO 89
<211> LENGTH: 5
<212> TYPE: PRT
<213> ORGANISM: Artificial Sequence
<220> FEATURE:
<223> OTHER INFORMATION: clone

<400> SEQUENCE: 89

```
Ser Tyr Gly Met Tyr
1               5
```

<210> SEQ ID NO 90
<211> LENGTH: 17
<212> TYPE: PRT
<213> ORGANISM: Artificial Sequence
<220> FEATURE:
<223> OTHER INFORMATION: clone

<400> SEQUENCE: 90

```
Glu Ile Lys Gln Asp Gly Ser Glu Lys Tyr Tyr Val Asp Ser Val Lys
1               5                   10                  15

Gly
```

```
<210> SEQ ID NO 91
<211> LENGTH: 10
<212> TYPE: PRT
<213> ORGANISM: Artificial Sequence
<220> FEATURE:
<223> OTHER INFORMATION: clone

<400> SEQUENCE: 91

Gly Glu Ile Leu Pro Leu Tyr Phe Asp Tyr
1               5                   10

<210> SEQ ID NO 92
<211> LENGTH: 119
<212> TYPE: PRT
<213> ORGANISM: Artificial Sequence
<220> FEATURE:
<223> OTHER INFORMATION: clone

<400> SEQUENCE: 92

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 93
<211> LENGTH: 5
<212> TYPE: PRT
<213> ORGANISM: Artificial Sequence
<220> FEATURE:
<223> OTHER INFORMATION: clone

<400> SEQUENCE: 93

Ser Tyr Gly Met Tyr
1               5

<210> SEQ ID NO 94
<211> LENGTH: 17
<212> TYPE: PRT
<213> ORGANISM: Artificial Sequence
<220> FEATURE:
<223> OTHER INFORMATION: clone

<400> SEQUENCE: 94

Glu Ile Lys Gln Asp Gly Ser Glu Gln Tyr Tyr Val Asp Ser Val Lys
1               5                   10                  15

Gly

<210> SEQ ID NO 95
<211> LENGTH: 10
<212> TYPE: PRT
```

<213> ORGANISM: Artificial Sequence
<220> FEATURE:
<223> OTHER INFORMATION: clone

<400> SEQUENCE: 95

Gly Glu Ile Leu Pro Leu Tyr Phe Asp Tyr
1               5                   10

<210> SEQ ID NO 96
<211> LENGTH: 119
<212> TYPE: PRT
<213> ORGANISM: Artificial Sequence
<220> FEATURE:
<223> OTHER INFORMATION: clone

<400> SEQUENCE: 96

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 97
<211> LENGTH: 5
<212> TYPE: PRT
<213> ORGANISM: Artificial Sequence
<220> FEATURE:
<223> OTHER INFORMATION: clone

<400> SEQUENCE: 97

Ser Tyr Glu Met Tyr
1               5

<210> SEQ ID NO 98
<211> LENGTH: 17
<212> TYPE: PRT
<213> ORGANISM: Artificial Sequence
<220> FEATURE:
<223> OTHER INFORMATION: clone

<400> SEQUENCE: 98

Ser Ile Lys Gln Asp Gly Ser Glu Gln Tyr Tyr Val Asp Ser Val Lys
1               5                   10                  15

Gly

<210> SEQ ID NO 99
<211> LENGTH: 10
<212> TYPE: PRT
<213> ORGANISM: Artificial Sequence
<220> FEATURE:
<223> OTHER INFORMATION: clone

<400> SEQUENCE: 99

Gly Glu Ile Leu Pro Leu Tyr Phe Asp Tyr
1               5                   10

<210> SEQ ID NO 100
<211> LENGTH: 119
<212> TYPE: PRT
<213> ORGANISM: Artificial Sequence
<220> FEATURE:
<223> OTHER INFORMATION: clone

<400> SEQUENCE: 100

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Tyr Trp Val Arg Gln Ala Pro Gly Lys Gly Leu Glu Trp Val
        35                  40                  45

Ala Ser Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 101
<211> LENGTH: 5
<212> TYPE: PRT
<213> ORGANISM: Artificial Sequence
<220> FEATURE:
<223> OTHER INFORMATION: clone

<400> SEQUENCE: 101

Ser Tyr Gly Met Tyr
1               5

<210> SEQ ID NO 102
<211> LENGTH: 17
<212> TYPE: PRT
<213> ORGANISM: Artificial Sequence
<220> FEATURE:
<223> OTHER INFORMATION: clone

<400> SEQUENCE: 102

Arg Ile Gly Gln Asp Gly Ser Glu Glu Tyr Tyr Val Asp Ser Val Lys
1               5                   10                  15

Gly

<210> SEQ ID NO 103
<211> LENGTH: 10
<212> TYPE: PRT
<213> ORGANISM: Artificial Sequence
<220> FEATURE:
<223> OTHER INFORMATION: clone

<400> SEQUENCE: 103

Gly Glu Ile Leu Pro Leu Tyr Phe Asp Tyr
1               5                   10

<210> SEQ ID NO 104
<211> LENGTH: 119
<212> TYPE: PRT
<213> ORGANISM: Artificial Sequence
<220> FEATURE:
<223> OTHER INFORMATION: clone

<400> SEQUENCE: 104

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Arg Ile Gly Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 105
<211> LENGTH: 5
<212> TYPE: PRT
<213> ORGANISM: Artificial Sequence
<220> FEATURE:
<223> OTHER INFORMATION: clone

<400> SEQUENCE: 105

Ser Tyr Arg Met Tyr
1               5

<210> SEQ ID NO 106
<211> LENGTH: 17
<212> TYPE: PRT
<213> ORGANISM: Artificial Sequence
<220> FEATURE:
<223> OTHER INFORMATION: clone

<400> SEQUENCE: 106

Ser Ile Glu Gln Asp Gly Ser Glu Glu Tyr Tyr Val Asp Ser Val Lys
1               5                   10                  15

Gly

<210> SEQ ID NO 107
<211> LENGTH: 10
<212> TYPE: PRT
<213> ORGANISM: Artificial Sequence
<220> FEATURE:
<223> OTHER INFORMATION: clone

<400> SEQUENCE: 107

Gly Glu Ile Leu Pro Leu Tyr Phe Asp Tyr
1               5                   10

<210> SEQ ID NO 108
<211> LENGTH: 119

```
<212> TYPE: PRT
<213> ORGANISM: Artificial Sequence
<220> FEATURE:
<223> OTHER INFORMATION: clone

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Glu Gln Asp Gly Ser Glu Glu Tyr Tyr Val Asp Ser Val
    50                  55                  60

Lys Gly Arg Phe Thr Ile Ser Arg Asp Asn Ala Lys Lys Ser Leu Phe
65                  70                  75                  80

Leu Gln Met Asn Ser Leu Arg Ala Gly Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 109
<211> LENGTH: 5
<212> TYPE: PRT
<213> ORGANISM: Artificial Sequence
<220> FEATURE:
<223> OTHER INFORMATION: clone

<400> SEQUENCE: 109

Ser Tyr Arg Met Tyr
1               5

<210> SEQ ID NO 110
<211> LENGTH: 17
<212> TYPE: PRT
<213> ORGANISM: Artificial Sequence
<220> FEATURE:
<223> OTHER INFORMATION: clone

<400> SEQUENCE: 110

Ser Ile Glu Gln Asp Gly Ser Glu Glu Tyr Tyr Val Asp Ser Val Lys
1               5                   10                  15

Gly

<210> SEQ ID NO 111
<211> LENGTH: 10
<212> TYPE: PRT
<213> ORGANISM: Artificial Sequence
<220> FEATURE:
<223> OTHER INFORMATION: clone

<400> SEQUENCE: 111

Gly Glu Ile Leu Pro Leu Tyr Phe Asp Tyr
1               5                   10

<210> SEQ ID NO 112
<211> LENGTH: 119
<212> TYPE: PRT
<213> ORGANISM: Artificial Sequence
<220> FEATURE:
<223> OTHER INFORMATION: clone
```

-continued

```
<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Glu Gln Asp Gly Ser Glu Gly Tyr Tyr Val Asp Ser Val
    50                  55                  60

Lys Gly Arg Phe Thr Ile Ser Arg Asp Asn Ala Lys Lys Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Ala Val Ser Ser
        115

<210> SEQ ID NO 113
<211> LENGTH: 5
<212> TYPE: PRT
<213> ORGANISM: Artificial Sequence
<220> FEATURE:
<223> OTHER INFORMATION: clone

<400> SEQUENCE: 113

Ser Tyr Ser Met Tyr
1               5

<210> SEQ ID NO 114
<211> LENGTH: 17
<212> TYPE: PRT
<213> ORGANISM: Artificial Sequence
<220> FEATURE:
<223> OTHER INFORMATION: clone

<400> SEQUENCE: 114

Ser Ile Asp Gln Asp Gly Ser Glu Glu Tyr Tyr Val Asp Ser Val Lys
1               5                   10                  15

Gly

<210> SEQ ID NO 115
<211> LENGTH: 10
<212> TYPE: PRT
<213> ORGANISM: Artificial Sequence
<220> FEATURE:
<223> OTHER INFORMATION: clone

<400> SEQUENCE: 115

Gly Glu Ile Leu Pro Leu Tyr Phe Asp Tyr
1               5                   10

<210> SEQ ID NO 116
<211> LENGTH: 119
<212> TYPE: PRT
<213> ORGANISM: Artificial Sequence
<220> FEATURE:
<223> OTHER INFORMATION: clone

<400> SEQUENCE: 116

Glu Val Gln Leu Val Glu Ser Gly Gly Gly Leu Val Gln Pro Gly Gly
```

```
                1               5                   10                  15
        Ser Leu Arg Leu Ser Cys Ala Ala Ser Gly Phe Thr Phe Ser Ser Tyr
                        20                  25                  30

Ser Met Tyr Trp Val Arg Gln Ala Pro Gly Lys Gly Leu Glu Trp Val
                        35                  40                  45

Ala Ser Ile Asp Gln Asp Gly Ser Glu Glu Tyr Tyr Val Asp Ser Val
                        50                  55                  60

Lys Gly Arg Phe Thr Ile Ser Arg Asp Asn Ala Lys Lys Ser Leu Tyr
        65                      70                  75                  80

Leu Gln Met Asn Ser Leu Arg Ala Glu Asp Thr Ala Val Tyr Tyr Cys
                        85                  90                  95

Ala Lys Gly Glu Ile Leu Pro Leu Tyr Phe Asp Tyr Trp Gly Gln Gly
                        100                 105                 110

Thr Leu Val Thr Val Ser Ser
                        115

<210> SEQ ID NO 117
        <211> LENGTH: 5
        <212> TYPE: PRT
        <213> ORGANISM: Artificial Sequence
        <220> FEATURE:
        <223> OTHER INFORMATION: clone

<400> SEQUENCE: 117

Ser Tyr Arg Met Tyr
        1               5

<210> SEQ ID NO 118
        <211> LENGTH: 17
        <212> TYPE: PRT
        <213> ORGANISM: Artificial Sequence
        <220> FEATURE:
        <223> OTHER INFORMATION: clone

<400> SEQUENCE: 118

Ser Ile Asp Gln Asp Gly Ser Glu Glu Tyr Tyr Val Asp Ser Val Lys
        1               5                   10                  15

Gly

<210> SEQ ID NO 119
        <211> LENGTH: 10
        <212> TYPE: PRT
        <213> ORGANISM: Artificial Sequence
        <220> FEATURE:
        <223> OTHER INFORMATION: clone

<400> SEQUENCE: 119

Gly Glu Ile Leu Pro Leu Tyr Phe Asp Tyr
        1               5                   10

<210> SEQ ID NO 120
        <211> LENGTH: 119
        <212> TYPE: PRT
        <213> ORGANISM: Artificial Sequence
        <220> FEATURE:
        <223> OTHER INFORMATION: clone

<400> SEQUENCE: 120

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Thr Phe Ser Ser Tyr
                        20                  25                  30
```

```
Arg Met Tyr Trp Val Arg Gln Ala Pro Gly Lys Gly Leu Glu Trp Val
        35                  40                  45

Ala Ser Ile Asp Gln Asp Gly Ser Glu Glu Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 121
<211> LENGTH: 5
<212> TYPE: PRT
<213> ORGANISM: Artificial Sequence
<220> FEATURE:
<223> OTHER INFORMATION: clone

<400> SEQUENCE: 121

Ser Tyr Asn Met Tyr
 1               5

<210> SEQ ID NO 122
<211> LENGTH: 5
<212> TYPE: PRT
<213> ORGANISM: Artificial Sequence
<220> FEATURE:
<223> OTHER INFORMATION: clone

<400> SEQUENCE: 122

Ser Tyr Asn Met Tyr
 1               5

<210> SEQ ID NO 123
<211> LENGTH: 10
<212> TYPE: PRT
<213> ORGANISM: Artificial Sequence
<220> FEATURE:
<223> OTHER INFORMATION: clone

<400> SEQUENCE: 123

Gly Glu Ile Leu Pro Leu Tyr Phe Asp Tyr
 1               5                  10

<210> SEQ ID NO 124
<211> LENGTH: 119
<212> TYPE: PRT
<213> ORGANISM: Artificial Sequence
<220> FEATURE:
<223> OTHER INFORMATION: clone

<400> SEQUENCE: 124

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asn Met Tyr Trp Val Arg Gln Ala Pro Gly Lys Gly Leu Glu Trp Val
        35                  40                  45

Ala Asn Ile Glu Gln Asp Gly Ser Glu Glu Tyr Tyr Val Asp Ser Val
 50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 125
<211> LENGTH: 5
<212> TYPE: PRT
<213> ORGANISM: Artificial Sequence
<220> FEATURE:
<223> OTHER INFORMATION: clone

<400> SEQUENCE: 125

Ser Tyr Arg Met Tyr
1               5

<210> SEQ ID NO 126
<211> LENGTH: 17
<212> TYPE: PRT
<213> ORGANISM: Artificial Sequence
<220> FEATURE:
<223> OTHER INFORMATION: clone

<400> SEQUENCE: 126

Gly Ile Glu Gln Asp Gly Ser Glu Glu Tyr Tyr Val Asp Ser Val Lys
1               5                   10                  15

Gly

<210> SEQ ID NO 127
<211> LENGTH: 10
<212> TYPE: PRT
<213> ORGANISM: Artificial Sequence
<220> FEATURE:
<223> OTHER INFORMATION: clone

<400> SEQUENCE: 127

Gly Glu Ile Leu Pro Leu Tyr Phe Asp Tyr
1               5                   10

<210> SEQ ID NO 128
<211> LENGTH: 119
<212> TYPE: PRT
<213> ORGANISM: Artificial Sequence
<220> FEATURE:
<223> OTHER INFORMATION: clone

<400> SEQUENCE: 128

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Gly Ile Glu Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
 65                 70                  75                  80
```

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 129
<211> LENGTH: 5
<212> TYPE: PRT
<213> ORGANISM: Artificial Sequence
<220> FEATURE:
<223> OTHER INFORMATION: clone

<400> SEQUENCE: 129

Ser Tyr Gly Met Tyr
1               5

<210> SEQ ID NO 130
<211> LENGTH: 17
<212> TYPE: PRT
<213> ORGANISM: Artificial Sequence
<220> FEATURE:
<223> OTHER INFORMATION: clone

<400> SEQUENCE: 130

Gly Ile Glu Gln Asp Gly Ser Glu Lys Tyr Tyr Val Asp Ser Val Lys
1               5                   10                  15

Gly

<210> SEQ ID NO 131
<211> LENGTH: 10
<212> TYPE: PRT
<213> ORGANISM: Artificial Sequence
<220> FEATURE:
<223> OTHER INFORMATION: clone

<400> SEQUENCE: 131

Gly Glu Ile Leu Pro Leu Tyr Phe Asp Tyr
1               5                   10

<210> SEQ ID NO 132
<211> LENGTH: 119
<212> TYPE: PRT
<213> ORGANISM: Artificial Sequence
<220> FEATURE:
<223> OTHER INFORMATION: clone

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Gly Ile Glu Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

```
            100                 105                 110

Thr Leu Val Thr Val Ser Ser
        115

<210> SEQ ID NO 133
<211> LENGTH: 5
<212> TYPE: PRT
<213> ORGANISM: Artificial Sequence
<220> FEATURE:
<223> OTHER INFORMATION: clone

<400> SEQUENCE: 133

Ser Tyr Gly Met Tyr
1               5

<210> SEQ ID NO 134
<211> LENGTH: 17
<212> TYPE: PRT
<213> ORGANISM: Artificial Sequence
<220> FEATURE:
<223> OTHER INFORMATION: clone

<400> SEQUENCE: 134

Gly Ile Glu Gln Asp Gly Ser Glu Lys Tyr Tyr Val Asp Ser Val Lys
1               5                   10                  15

Gly

<210> SEQ ID NO 135
<211> LENGTH: 10
<212> TYPE: PRT
<213> ORGANISM: Artificial Sequence
<220> FEATURE:
<223> OTHER INFORMATION: clone

<400> SEQUENCE: 135

Gly Glu Ile Leu Pro Leu Tyr Phe Asp Tyr
1               5                   10

<210> SEQ ID NO 136
<211> LENGTH: 119
<212> TYPE: PRT
<213> ORGANISM: Artificial Sequence
<220> FEATURE:
<223> OTHER INFORMATION: clone

<400> SEQUENCE: 136

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Gly Ile Glu Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115
```

<210> SEQ ID NO 137
<211> LENGTH: 5
<212> TYPE: PRT
<213> ORGANISM: Artificial Sequence
<220> FEATURE:
<223> OTHER INFORMATION: clone

<400> SEQUENCE: 137

Ser Tyr Gly Met Tyr
1               5

<210> SEQ ID NO 138
<211> LENGTH: 17
<212> TYPE: PRT
<213> ORGANISM: Artificial Sequence
<220> FEATURE:
<223> OTHER INFORMATION: clone

<400> SEQUENCE: 138

Gly Ile Glu Gln Asp Gly Ser Glu Lys Tyr Tyr Val Asp Ser Val Lys
1               5                   10                  15

Gly

<210> SEQ ID NO 139
<211> LENGTH: 10
<212> TYPE: PRT
<213> ORGANISM: Artificial Sequence
<220> FEATURE:
<223> OTHER INFORMATION: clone

<400> SEQUENCE: 139

Gly Glu Ile Leu Pro Leu Tyr Phe Asp Tyr
1               5                   10

<210> SEQ ID NO 140
<211> LENGTH: 119
<212> TYPE: PRT
<213> ORGANISM: Artificial Sequence
<220> FEATURE:
<223> OTHER INFORMATION: clone

<400> SEQUENCE: 140

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met Tyr Trp Val Arg Gln Ala Pro Gly Lys Gly Leu Glu Trp Val
            35                  40                  45

Ala Gly Ile Glu Gln Asp Gly Ser Glu Lys Tyr Tyr Val Asp Ser Val
        50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 141
<211> LENGTH: 5

```
<212> TYPE: PRT
<213> ORGANISM: Artificial Sequence
<220> FEATURE:
<223> OTHER INFORMATION: clone

<400> SEQUENCE: 141

Ser Tyr Gly Met Tyr
1               5

<210> SEQ ID NO 142
<211> LENGTH: 17
<212> TYPE: PRT
<213> ORGANISM: Artificial Sequence
<220> FEATURE:
<223> OTHER INFORMATION: clone

<400> SEQUENCE: 142

Gly Ile Glu Gln Asp Gly Ser Glu Glu Tyr Tyr Val Asp Ser Val Lys
1               5                   10                  15

Gly

<210> SEQ ID NO 143
<211> LENGTH: 10
<212> TYPE: PRT
<213> ORGANISM: Artificial Sequence
<220> FEATURE:
<223> OTHER INFORMATION: clone

<400> SEQUENCE: 143

Gly Glu Ile Leu Pro Leu Tyr Phe Asp Tyr
1               5                   10

<210> SEQ ID NO 144
<211> LENGTH: 119
<212> TYPE: PRT
<213> ORGANISM: Artificial Sequence
<220> FEATURE:
<223> OTHER INFORMATION: clone

<400> SEQUENCE: 144

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met Tyr Trp Val Arg Gln Ala Pro Gly Lys Gly Leu Glu Trp Val
            35                  40                  45

Ala Gly Ile Glu Gln Asp Gly Ser Glu Glu Tyr Tyr Val Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 145
<211> LENGTH: 5
<212> TYPE: PRT
<213> ORGANISM: Artificial Sequence
<220> FEATURE:
<223> OTHER INFORMATION: clone
```

<400> SEQUENCE: 145

Ser Tyr Gly Met Tyr
1               5

<210> SEQ ID NO 146
<211> LENGTH: 17
<212> TYPE: PRT
<213> ORGANISM: Artificial Sequence
<220> FEATURE:
<223> OTHER INFORMATION: clone

<400> SEQUENCE: 146

Arg Ile Glu Gln Asp Gly Ser Glu Gln Tyr Tyr Val Asp Ser Val Lys
1               5                   10                  15
Gly

<210> SEQ ID NO 147
<211> LENGTH: 10
<212> TYPE: PRT
<213> ORGANISM: Artificial Sequence
<220> FEATURE:
<223> OTHER INFORMATION: clone

<400> SEQUENCE: 147

Gly Glu Ile Leu Pro Leu Tyr Phe Asp Tyr
1               5                   10

<210> SEQ ID NO 148
<211> LENGTH: 119
<212> TYPE: PRT
<213> ORGANISM: Artificial Sequence
<220> FEATURE:
<223> OTHER INFORMATION: clone

<400> SEQUENCE: 148

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Arg Ile Glu Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 149
<211> LENGTH: 5
<212> TYPE: PRT
<213> ORGANISM: Artificial Sequence
<220> FEATURE:
<223> OTHER INFORMATION: clone

<400> SEQUENCE: 149

Ser Tyr Gly Met Tyr

```
<210> SEQ ID NO 150
<211> LENGTH: 17
<212> TYPE: PRT
<213> ORGANISM: Artificial Sequence
<220> FEATURE:
<223> OTHER INFORMATION: clone

<400> SEQUENCE: 150

Asn Ile Lys Gln Asp Gly Ser Glu Glu Tyr Tyr Val Asp Ser Val Lys
1               5                   10                  15

Gly

<210> SEQ ID NO 151
<211> LENGTH: 10
<212> TYPE: PRT
<213> ORGANISM: Artificial Sequence
<220> FEATURE:
<223> OTHER INFORMATION: clone

<400> SEQUENCE: 151

Gly Glu Ile Leu Pro Leu Tyr Phe Asp Tyr
1               5                   10

<210> SEQ ID NO 152
<211> LENGTH: 119
<212> TYPE: PRT
<213> ORGANISM: Artificial Sequence
<220> FEATURE:
<223> OTHER INFORMATION: clone

<400> SEQUENCE: 152

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 153
<211> LENGTH: 5
<212> TYPE: PRT
<213> ORGANISM: Artificial Sequence
<220> FEATURE:
<223> OTHER INFORMATION: clone

<400> SEQUENCE: 153

Ser Tyr Gly Met Tyr
1               5

<210> SEQ ID NO 154
```

```
<211> LENGTH: 17
<212> TYPE: PRT
<213> ORGANISM: Artificial Sequence
<220> FEATURE:
<223> OTHER INFORMATION: clone

<400> SEQUENCE: 154

Asn Ile Lys Gln Asp Gly Ser Glu Glu Tyr Tyr Val Asp Ser Val Lys
1               5                   10                  15

Gly

<210> SEQ ID NO 155
<211> LENGTH: 10
<212> TYPE: PRT
<213> ORGANISM: Artificial Sequence
<220> FEATURE:
<223> OTHER INFORMATION: clone

<400> SEQUENCE: 155

Gly Glu Ile Leu Pro Leu Tyr Phe Asp Tyr
1               5                   10

<210> SEQ ID NO 156
<211> LENGTH: 119
<212> TYPE: PRT
<213> ORGANISM: Artificial Sequence
<220> FEATURE:
<223> OTHER INFORMATION: clone

<400> SEQUENCE: 156

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 157
<211> LENGTH: 5
<212> TYPE: PRT
<213> ORGANISM: Artificial Sequence
<220> FEATURE:
<223> OTHER INFORMATION: clone

<400> SEQUENCE: 157

Ser Tyr Gly Met Tyr
1               5

<210> SEQ ID NO 158
<211> LENGTH: 17
<212> TYPE: PRT
<213> ORGANISM: Artificial Sequence
<220> FEATURE:
```

```
<223> OTHER INFORMATION: clone

<400> SEQUENCE: 158

Asn Ile Glu Gln Asp Gly Ser Glu Lys Tyr Tyr Val Asp Ser Val Lys
1               5                   10                  15

Gly

<210> SEQ ID NO 159
<211> LENGTH: 10
<212> TYPE: PRT
<213> ORGANISM: Artificial Sequence
<220> FEATURE:
<223> OTHER INFORMATION: clone

<400> SEQUENCE: 159

Gly Glu Ile Leu Pro Leu His Phe Asp Tyr
1               5                   10

<210> SEQ ID NO 160
<211> LENGTH: 119
<212> TYPE: PRT
<213> ORGANISM: Artificial Sequence
<220> FEATURE:
<223> OTHER INFORMATION: clone

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Met Phe Ser Ser Tyr
            20                  25                  30

Gly Met Tyr Trp Val Arg Gln Ala Pro Gly Lys Gly Leu Glu Trp Val
        35                  40                  45

Ala Asn Ile Glu Gln Asp Gly Ser Glu Lys Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
        115

<210> SEQ ID NO 161
<211> LENGTH: 5
<212> TYPE: PRT
<213> ORGANISM: Artificial Sequence
<220> FEATURE:
<223> OTHER INFORMATION: clone

<400> SEQUENCE: 161

Ser Tyr Gly Met Tyr
1               5

<210> SEQ ID NO 162
<211> LENGTH: 17
<212> TYPE: PRT
<213> ORGANISM: Artificial Sequence
<220> FEATURE:
<223> OTHER INFORMATION: clone

<400> SEQUENCE: 162
```

Asn Ile Glu Gln Asp Gly Ser Glu Lys Tyr Tyr Val Asp Ser Val Lys
1               5                   10                  15

Gly

<210> SEQ ID NO 163
<211> LENGTH: 10
<212> TYPE: PRT
<213> ORGANISM: Artificial Sequence
<220> FEATURE:
<223> OTHER INFORMATION: clone

<400> SEQUENCE: 163

Gly Glu Ile Leu Pro Leu His Phe Asp Tyr
1               5                   10

<210> SEQ ID NO 164
<211> LENGTH: 119
<212> TYPE: PRT
<213> ORGANISM: Artificial Sequence
<220> FEATURE:
<223> OTHER INFORMATION: clone

<400> SEQUENCE: 164

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Met Phe Ser Ser Tyr
            20                  25                  30

Gly Met Tyr Trp Val Arg Gln Ala Pro Gly Lys Gly Leu Glu Trp Val
        35                  40                  45

Ala Asn Ile Glu Gln Asp Gly Ser Glu Lys Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
        115

<210> SEQ ID NO 165
<211> LENGTH: 5
<212> TYPE: PRT
<213> ORGANISM: Artificial Sequence
<220> FEATURE:
<223> OTHER INFORMATION: clone

<400> SEQUENCE: 165

Ser Tyr Gly Met Tyr
1               5

<210> SEQ ID NO 166
<211> LENGTH: 17
<212> TYPE: PRT
<213> ORGANISM: Artificial Sequence
<220> FEATURE:
<223> OTHER INFORMATION: clone

<400> SEQUENCE: 166

Asn Ile Lys Gln Asp Gly Ser Glu Gln Tyr Tyr Val Asp Ser Val Lys
1               5                   10                  15

Gly

<210> SEQ ID NO 167
<211> LENGTH: 10
<212> TYPE: PRT
<213> ORGANISM: Artificial Sequence
<220> FEATURE:
<223> OTHER INFORMATION: clone

<400> SEQUENCE: 167

Gly Glu Ile Leu Pro Leu His Phe Asp Tyr
1               5                   10

<210> SEQ ID NO 168
<211> LENGTH: 119
<212> TYPE: PRT
<213> ORGANISM: Artificial Sequence
<220> FEATURE:
<223> OTHER INFORMATION: clone

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Asn Ile Lys Gln Asp Gly Ser Glu Gln Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
        115

<210> SEQ ID NO 169
<211> LENGTH: 5
<212> TYPE: PRT
<213> ORGANISM: Artificial Sequence
<220> FEATURE:
<223> OTHER INFORMATION: clone

<400> SEQUENCE: 169

Ser Tyr Ser Met Tyr
1               5

<210> SEQ ID NO 170
<211> LENGTH: 17
<212> TYPE: PRT
<213> ORGANISM: Artificial Sequence
<220> FEATURE:
<223> OTHER INFORMATION: clone

<400> SEQUENCE: 170

Asn Ile Lys Gln Asp Gly Ser Glu Lys Tyr Tyr Val Asp Ser Val Lys
1               5                   10                  15

Gly

<210> SEQ ID NO 171
<211> LENGTH: 10

```
<212> TYPE: PRT
<213> ORGANISM: Artificial Sequence
<220> FEATURE:
<223> OTHER INFORMATION: clone

<400> SEQUENCE: 171

Gly Glu Ile Leu Pro Leu His Phe Asp Tyr
1               5                   10

<210> SEQ ID NO 172
<211> LENGTH: 119
<212> TYPE: PRT
<213> ORGANISM: Artificial Sequence
<220> FEATURE:
<223> OTHER INFORMATION: clone

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
        115

<210> SEQ ID NO 173
<211> LENGTH: 5
<212> TYPE: PRT
<213> ORGANISM: Artificial Sequence
<220> FEATURE:
<223> OTHER INFORMATION: clone

<400> SEQUENCE: 173

Ser Tyr Ser Met Tyr
1               5

<210> SEQ ID NO 174
<211> LENGTH: 17
<212> TYPE: PRT
<213> ORGANISM: Artificial Sequence
<220> FEATURE:
<223> OTHER INFORMATION: clone

<400> SEQUENCE: 174

Asn Ile Lys Gln Asp Gly Ser Glu Lys Tyr Tyr Val Asp Ser Val Lys
1               5                   10                  15

Gly

<210> SEQ ID NO 175
<211> LENGTH: 10
<212> TYPE: PRT
<213> ORGANISM: Artificial Sequence
<220> FEATURE:
<223> OTHER INFORMATION: clone
```

```
<400> SEQUENCE: 175

Gly Glu Ile Leu Pro Leu Tyr Phe Asp His
1               5                   10

<210> SEQ ID NO 176
<211> LENGTH: 119
<212> TYPE: PRT
<213> ORGANISM: Artificial Sequence
<220> FEATURE:
<223> OTHER INFORMATION: clone

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
        115

<210> SEQ ID NO 177
<211> LENGTH: 5
<212> TYPE: PRT
<213> ORGANISM: Artificial Sequence
<220> FEATURE:
<223> OTHER INFORMATION: clone

<400> SEQUENCE: 177

Ser Tyr Trp Met Tyr
1               5

<210> SEQ ID NO 178
<211> LENGTH: 17
<212> TYPE: PRT
<213> ORGANISM: Artificial Sequence
<220> FEATURE:
<223> OTHER INFORMATION: clone

<400> SEQUENCE: 178

Lys Ile Lys Gln Asp Gly Ser Glu Lys Tyr Tyr Val Asp Ser Val Lys
1               5                   10                  15

Gly

<210> SEQ ID NO 179
<211> LENGTH: 10
<212> TYPE: PRT
<213> ORGANISM: Artificial Sequence
<220> FEATURE:
<223> OTHER INFORMATION: clone

<400> SEQUENCE: 179

Gly Glu Ile Leu Pro Leu Gln Phe Asp Tyr
```

1               5                    10

<210> SEQ ID NO 180
<211> LENGTH: 119
<212> TYPE: PRT
<213> ORGANISM: Artificial Sequence
<220> FEATURE:
<223> OTHER INFORMATION: clone

<400> SEQUENCE: 180

Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Ser
        115

<210> SEQ ID NO 181
<211> LENGTH: 5
<212> TYPE: PRT
<213> ORGANISM: Artificial Sequence
<220> FEATURE:
<223> OTHER INFORMATION: clone

<400> SEQUENCE: 181

Ser Tyr Trp Met Tyr
1               5

<210> SEQ ID NO 182
<211> LENGTH: 17
<212> TYPE: PRT
<213> ORGANISM: Artificial Sequence
<220> FEATURE:
<223> OTHER INFORMATION: clone

<400> SEQUENCE: 182

Lys Ile Asn Gln Asp Gly Ser Glu Lys Tyr Tyr Val Asp Ser Val Lys
1               5                   10                  15

Gly

<210> SEQ ID NO 183
<211> LENGTH: 10
<212> TYPE: PRT
<213> ORGANISM: Artificial Sequence
<220> FEATURE:
<223> OTHER INFORMATION: clone

<400> SEQUENCE: 183

Gly Glu Ile Leu Pro Leu Gln Phe Asp Tyr
1               5                   10

<210> SEQ ID NO 184

<211> LENGTH: 119
<212> TYPE: PRT
<213> ORGANISM: Artificial Sequence
<220> FEATURE:
<223> OTHER INFORMATION: clone

<400> SEQUENCE: 184

```
Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Ser
        115
```

<210> SEQ ID NO 185
<211> LENGTH: 5
<212> TYPE: PRT
<213> ORGANISM: Artificial Sequence
<220> FEATURE:
<223> OTHER INFORMATION: clone

<400> SEQUENCE: 185

```
Ser Tyr Trp Met Tyr
1               5
```

<210> SEQ ID NO 186
<211> LENGTH: 17
<212> TYPE: PRT
<213> ORGANISM: Artificial Sequence
<220> FEATURE:
<223> OTHER INFORMATION: clone

<400> SEQUENCE: 186

```
Lys Ile Asn Gln Asp Gly Ser Glu Lys Tyr Tyr Val Asp Ser Val Lys
1               5                   10                  15

Gly
```

<210> SEQ ID NO 187
<211> LENGTH: 10
<212> TYPE: PRT
<213> ORGANISM: Artificial Sequence
<220> FEATURE:
<223> OTHER INFORMATION: clone

<400> SEQUENCE: 187

```
Gly Glu Ile Leu Pro Leu Gln Phe Asp Tyr
1               5                   10
```

<210> SEQ ID NO 188
<211> LENGTH: 119
<212> TYPE: PRT
<213> ORGANISM: Artificial Sequence
<220> FEATURE:

<223> OTHER INFORMATION: clone

<400> SEQUENCE: 188

Gln Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Ser
        115

<210> SEQ ID NO 189
<211> LENGTH: 5
<212> TYPE: PRT
<213> ORGANISM: Artificial Sequence
<220> FEATURE:
<223> OTHER INFORMATION: clone

<400> SEQUENCE: 189

Ser Tyr Trp Met Tyr
1               5

<210> SEQ ID NO 190
<211> LENGTH: 17
<212> TYPE: PRT
<213> ORGANISM: Artificial Sequence
<220> FEATURE:
<223> OTHER INFORMATION: clone

<400> SEQUENCE: 190

Lys Ile Asn Gln Asp Gly Ser Glu Lys Tyr Tyr Val Asp Ser Val Lys
1               5                   10                  15

Gly

<210> SEQ ID NO 191
<211> LENGTH: 10
<212> TYPE: PRT
<213> ORGANISM: Artificial Sequence
<220> FEATURE:
<223> OTHER INFORMATION: clone

<400> SEQUENCE: 191

Gly Glu Ile Leu Pro Leu Gln Phe Asp Tyr
1               5                   10

<210> SEQ ID NO 192
<211> LENGTH: 119
<212> TYPE: PRT
<213> ORGANISM: Artificial Sequence
<220> FEATURE:
<223> OTHER INFORMATION: clone

<400> SEQUENCE: 192

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu Gln Phe Asp Tyr Trp Gly Gln Gly
        100                 105                 110

Thr Leu Val Thr Val Ser Pro
            115
```

```
<210> SEQ ID NO 193
<211> LENGTH: 5
<212> TYPE: PRT
<213> ORGANISM: Artificial Sequence
<220> FEATURE:
<223> OTHER INFORMATION: clone

<400> SEQUENCE: 193

Ser Tyr Gln Met Tyr
1               5
```

```
<210> SEQ ID NO 194
<211> LENGTH: 17
<212> TYPE: PRT
<213> ORGANISM: Artificial Sequence
<220> FEATURE:
<223> OTHER INFORMATION: clone

<400> SEQUENCE: 194

Glu Ile Lys Gln Asp Gly Ser Glu Gln Tyr Tyr Val Asp Ser Val Lys
1               5                   10                  15

Gly
```

```
<210> SEQ ID NO 195
<211> LENGTH: 10
<212> TYPE: PRT
<213> ORGANISM: Artificial Sequence
<220> FEATURE:
<223> OTHER INFORMATION: clone

<400> SEQUENCE: 195

Gly Glu Ile Leu Pro Leu Tyr Phe Asp His
1               5                   10
```

```
<210> SEQ ID NO 196
<211> LENGTH: 119
<212> TYPE: PRT
<213> ORGANISM: Artificial Sequence
<220> FEATURE:
<223> OTHER INFORMATION: clone

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30
Gln Met Tyr Trp Val Arg Gln Ala Pro Gly Lys Gly Leu Glu Trp Val
        35                  40                  45

Ala Glu Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
            115

<210> SEQ ID NO 197
<211> LENGTH: 5
<212> TYPE: PRT
<213> ORGANISM: Artificial Sequence
<220> FEATURE:
<223> OTHER INFORMATION: clone

<400> SEQUENCE: 197

Ser Tyr Ser Met Ile
1               5

<210> SEQ ID NO 198
<211> LENGTH: 17
<212> TYPE: PRT
<213> ORGANISM: Artificial Sequence
<220> FEATURE:
<223> OTHER INFORMATION: clone

<400> SEQUENCE: 198

Asp Ile Lys Gln Asp Gly Ser Glu Lys Tyr Tyr Val Asp Ser Val Lys
1               5                   10                  15

Gly

<210> SEQ ID NO 199
<211> LENGTH: 10
<212> TYPE: PRT
<213> ORGANISM: Artificial Sequence
<220> FEATURE:
<223> OTHER INFORMATION: clone

<400> SEQUENCE: 199

Gly Glu Val Leu Pro Leu Tyr Phe Asp Tyr
1               5                   10

<210> SEQ ID NO 200
<211> LENGTH: 119
<212> TYPE: PRT
<213> ORGANISM: Artificial Sequence
<220> FEATURE:
<223> OTHER INFORMATION: clone

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ile Trp Val Arg Gln Ala Pro Gly Lys Gly Leu Glu Trp Val
        35                  40                  45
```

-continued

```
Ala Asp Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Val Leu Pro Leu Tyr Phe Asp Tyr Trp Gly Gln Gly
            100                 105                 110

Thr Leu Val Thr Val Ser Ser
            115

<210> SEQ ID NO 201
<211> LENGTH: 5
<212> TYPE: PRT
<213> ORGANISM: Artificial Sequence
<220> FEATURE:
<223> OTHER INFORMATION: clone

<400> SEQUENCE: 201

Ser Tyr Ser Met Ile
1               5

<210> SEQ ID NO 202
<211> LENGTH: 17
<212> TYPE: PRT
<213> ORGANISM: Artificial Sequence
<220> FEATURE:
<223> OTHER INFORMATION: clone

<400> SEQUENCE: 202

Asp Ile Lys Gln Asp Gly Ser Glu Lys Tyr Tyr Val Asp Ser Val Lys
1               5                  10                  15

Gly

<210> SEQ ID NO 203
<211> LENGTH: 10
<212> TYPE: PRT
<213> ORGANISM: Artificial Sequence
<220> FEATURE:
<223> OTHER INFORMATION: clone

<400> SEQUENCE: 203

Gly Glu Val Leu Pro Leu Tyr Phe Asp Tyr
1               5                  10

<210> SEQ ID NO 204
<211> LENGTH: 119
<212> TYPE: PRT
<213> ORGANISM: Artificial Sequence
<220> FEATURE:
<223> OTHER INFORMATION: clone

<400> SEQUENCE: 204

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ser Met Ile Trp Val Arg Gln Ala Pro Gly Lys Gly Leu Glu Trp Val
         35                  40                  45

Ala Asp Ile Lys Gln Asp Gly Ser Glu Lys Tyr Tyr Val Asp Ser Val
    50                  55                  60
```

-continued

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Val Leu Pro Leu Tyr Phe Asp Tyr Trp Gly Gln Gly
            100                 105                 110

Thr Leu Val Thr Val Ser Ser
            115

<210> SEQ ID NO 205
<211> LENGTH: 5
<212> TYPE: PRT
<213> ORGANISM: Artificial Sequence
<220> FEATURE:
<223> OTHER INFORMATION: clone

<400> SEQUENCE: 205

Ser Tyr Asn Met Tyr
1               5

<210> SEQ ID NO 206
<211> LENGTH: 17
<212> TYPE: PRT
<213> ORGANISM: Artificial Sequence
<220> FEATURE:
<223> OTHER INFORMATION: clone

<400> SEQUENCE: 206

Glu Ile Asp Gln Asp Gly Ser Glu Lys Tyr Tyr Val Asp Ser Val Lys
1               5                   10                  15

Gly

<210> SEQ ID NO 207
<211> LENGTH: 10
<212> TYPE: PRT
<213> ORGANISM: Artificial Sequence
<220> FEATURE:
<223> OTHER INFORMATION: clone

<400> SEQUENCE: 207

Gly Glu Ile Leu Pro Leu Tyr Phe Asp His
1               5                   10

<210> SEQ ID NO 208
<211> LENGTH: 119
<212> TYPE: PRT
<213> ORGANISM: Artificial Sequence
<220> FEATURE:
<223> OTHER INFORMATION: clone

<400> SEQUENCE: 208

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asn Met Tyr Trp Val Arg Gln Ala Pro Gly Lys Gly Leu Glu Trp Val
        35                  40                  45

Ala Glu Ile Asp Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys

```
                    85                  90                  95
Ala Lys Gly Glu Ile Leu Pro Leu Tyr Phe Asp His Trp Gly Gln Gly
                100                 105                 110

Thr Leu Val Thr Val Ser Ser
        115

<210> SEQ ID NO 209
<211> LENGTH: 5
<212> TYPE: PRT
<213> ORGANISM: Artificial Sequence
<220> FEATURE:
<223> OTHER INFORMATION: clone

<400> SEQUENCE: 209

Ser Tyr Arg Met Tyr
1               5

<210> SEQ ID NO 210
<211> LENGTH: 17
<212> TYPE: PRT
<213> ORGANISM: Artificial Sequence
<220> FEATURE:
<223> OTHER INFORMATION: clone

<400> SEQUENCE: 210

Ser Ile Glu Gln Asp Gly Ser Glu Glu Tyr Tyr Val Asp Ser Val Lys
1               5                   10                  15

Gly

<210> SEQ ID NO 211
<211> LENGTH: 10
<212> TYPE: PRT
<213> ORGANISM: Artificial Sequence
<220> FEATURE:
<223> OTHER INFORMATION: clone

<400> SEQUENCE: 211

Gly Glu Ile Leu Pro Leu Tyr Phe Asp Tyr
1               5                   10

<210> SEQ ID NO 212
<211> LENGTH: 119
<212> TYPE: PRT
<213> ORGANISM: Artificial Sequence
<220> FEATURE:
<223> OTHER INFORMATION: clone

<400> SEQUENCE: 212

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Glu Gln Asp Gly Ser Glu Glu Tyr Tyr Val Asp Ser Val
    50                  55                  60

Lys Gly Arg Phe Thr Ile Ser Arg Asp Asn Ala Lys Arg Ser Leu Phe
65                  70                  75                  80

Leu Gln Met Ser Ser Leu Arg Ala Glu Asp Ser Ala Val Tyr Tyr Cys
                85                  90                  95

Ala Lys Gly Glu Ile Leu Pro Leu Tyr Phe Asp Tyr Trp Gly Gln Gly
                100                 105                 110
```

Thr Leu Val Thr Val Ser Ser
        115

<210> SEQ ID NO 213
<211> LENGTH: 5
<212> TYPE: PRT
<213> ORGANISM: Artificial Sequence
<220> FEATURE:
<223> OTHER INFORMATION: clone

<400> SEQUENCE: 213

Ser Tyr Gln Met Tyr
1               5

<210> SEQ ID NO 214
<211> LENGTH: 17
<212> TYPE: PRT
<213> ORGANISM: Artificial Sequence
<220> FEATURE:
<223> OTHER INFORMATION: clone

<400> SEQUENCE: 214

Gly Ile Glu Gln Asp Gly Ser Glu Glu Tyr Tyr Val Asp Ser Val Lys
1               5                   10                  15

Gly

<210> SEQ ID NO 215
<211> LENGTH: 10
<212> TYPE: PRT
<213> ORGANISM: Artificial Sequence
<220> FEATURE:
<223> OTHER INFORMATION: clone

<400> SEQUENCE: 215

Gly Glu Ile Leu Pro Leu Tyr Phe Asp His
1               5                   10

<210> SEQ ID NO 216
<211> LENGTH: 119
<212> TYPE: PRT
<213> ORGANISM: Artificial Sequence
<220> FEATURE:
<223> OTHER INFORMATION: clone

<400> SEQUENCE: 216

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Tyr Trp Val Arg Gln Ala Pro Gly Lys Gly Leu Glu Trp Val
        35                  40                  45

Ala Gly Ile Glu Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
        115

```
<210> SEQ ID NO 217
<211> LENGTH: 5
<212> TYPE: PRT
<213> ORGANISM: Artificial Sequence
<220> FEATURE:
<223> OTHER INFORMATION: clone

<400> SEQUENCE: 217

Ser Tyr Glu Met Tyr
1               5

<210> SEQ ID NO 218
<211> LENGTH: 17
<212> TYPE: PRT
<213> ORGANISM: Artificial Sequence
<220> FEATURE:
<223> OTHER INFORMATION: clone

<400> SEQUENCE: 218

Asn Ile Lys Gln Asp Gly Ser Glu Lys Tyr Tyr Val Asp Ser Val Lys
1               5                   10                  15

Gly

<210> SEQ ID NO 219
<211> LENGTH: 17
<212> TYPE: PRT
<213> ORGANISM: Artificial Sequence
<220> FEATURE:
<223> OTHER INFORMATION: clone

<400> SEQUENCE: 219

Asn Ile Lys Gln Asp Gly Ser Glu Lys Tyr Tyr Val Asp Ser Val Lys
1               5                   10                  15

Gly

<210> SEQ ID NO 220
<211> LENGTH: 119
<212> TYPE: PRT
<213> ORGANISM: Artificial Sequence
<220> FEATURE:
<223> OTHER INFORMATION: clone

<400> SEQUENCE: 220

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Glu Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Lys Gly Glu Ile Leu Pro Leu His Phe Asp Tyr Arg Gly Gln Gly
            100                 105                 110

Thr Leu Val Thr Val Ser Ser
        115

<210> SEQ ID NO 221
```

<211> LENGTH: 5
<212> TYPE: PRT
<213> ORGANISM: Artificial Sequence
<220> FEATURE:
<223> OTHER INFORMATION: clone

<400> SEQUENCE: 221

Ser Tyr Ser Met Tyr
1               5

<210> SEQ ID NO 222
<211> LENGTH: 17
<212> TYPE: PRT
<213> ORGANISM: Artificial Sequence
<220> FEATURE:
<223> OTHER INFORMATION: clone

<400> SEQUENCE: 222

Asn Ile Lys Gln Asp Gly Ser Glu Lys Tyr Tyr Val Asp Ser Val Lys
1               5                   10                  15

Gly

<210> SEQ ID NO 223
<211> LENGTH: 10
<212> TYPE: PRT
<213> ORGANISM: Artificial Sequence
<220> FEATURE:
<223> OTHER INFORMATION: clone

<400> SEQUENCE: 223

Gly Glu Ile Leu Pro Leu Tyr Phe Asp Tyr
1               5                   10

<210> SEQ ID NO 224
<211> LENGTH: 119
<212> TYPE: PRT
<213> ORGANISM: Artificial Sequence
<220> FEATURE:
<223> OTHER INFORMATION: clone

<400> SEQUENCE: 224

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Leu Leu Tyr
65                  70                  75                  80

Leu Gln Met Asn Ser Leu Arg Val Glu Asp Thr Ala Val Tyr Tyr Cys
                85                  90                  95

Ala Lys Gly Glu Ile Leu Pro Leu Tyr Phe Asp Tyr Arg Gly Gln Gly
            100                 105                 110

Thr Leu Val Thr Val Ser Ser
        115

<210> SEQ ID NO 225
<211> LENGTH: 5
<212> TYPE: PRT
<213> ORGANISM: Artificial Sequence
<220> FEATURE:

<223> OTHER INFORMATION: clone

<400> SEQUENCE: 225

Ser Tyr Arg Met Tyr
1               5

<210> SEQ ID NO 226
<211> LENGTH: 17
<212> TYPE: PRT
<213> ORGANISM: Artificial Sequence
<220> FEATURE:
<223> OTHER INFORMATION: clone

<400> SEQUENCE: 226

Ser Ile Asn Gln Asp Gly Ser Glu Lys Tyr Tyr Val Asp Ser Val Lys
1               5                   10                  15

Gly

<210> SEQ ID NO 227
<211> LENGTH: 10
<212> TYPE: PRT
<213> ORGANISM: Artificial Sequence
<220> FEATURE:
<223> OTHER INFORMATION: clone

<400> SEQUENCE: 227

Gly Glu Ile Leu Pro Leu His Phe Asp Tyr
1               5                   10

<210> SEQ ID NO 228
<211> LENGTH: 119
<212> TYPE: PRT
<213> ORGANISM: Artificial Sequence
<220> FEATURE:
<223> OTHER INFORMATION: clone

<400> SEQUENCE: 228

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Lys Gly Glu Ile Leu Pro Leu His Phe Asp Tyr Arg Gly Gln Gly
            100                 105                 110

Thr Leu Val Thr Val Ser Ser
        115

<210> SEQ ID NO 229
<211> LENGTH: 5
<212> TYPE: PRT
<213> ORGANISM: Artificial Sequence
<220> FEATURE:
<223> OTHER INFORMATION: clone

<400> SEQUENCE: 229

```
Ser Tyr Arg Met Tyr
1               5
```

<210> SEQ ID NO 230
<211> LENGTH: 17
<212> TYPE: PRT
<213> ORGANISM: Artificial Sequence
<220> FEATURE:
<223> OTHER INFORMATION: clone

<400> SEQUENCE: 230

```
Ser Ile Asn Gln Asp Gly Ser Glu Lys Tyr Tyr Val Asp Ser Val Lys
1               5                   10                  15

Gly
```

<210> SEQ ID NO 231
<211> LENGTH: 17
<212> TYPE: PRT
<213> ORGANISM: Artificial Sequence
<220> FEATURE:
<223> OTHER INFORMATION: clone

<400> SEQUENCE: 231

```
Ser Ile Asn Gln Asp Gly Ser Glu Lys Tyr Tyr Val Asp Ser Val Lys
1               5                   10                  15

Gly
```

<210> SEQ ID NO 232
<211> LENGTH: 119
<212> TYPE: PRT
<213> ORGANISM: Artificial Sequence
<220> FEATURE:
<223> OTHER INFORMATION: clone

<400> SEQUENCE: 232

```
Gln Val Gln Leu Val Glu Ser Gly Gly Met Val Gln Pro Gly Gly
1               5                   10                  15

Ser Leu Arg Leu Ser Cys Ala Val Ser Gly Phe Thr Phe Ser Ser Tyr
                20                  25                  30

Arg Met Tyr Trp Val Arg Gln Ala Pro Gly Lys Gly Leu Glu Trp Val
            35                  40                  45

Ala Ser Ile Asn Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Lys Gly Glu Ile Leu Pro Leu His Phe Asp Tyr Arg Gly Gln Gly
            100                 105                 110

Thr Leu Val Thr Val Ser Ser
        115
```

<210> SEQ ID NO 233
<211> LENGTH: 5
<212> TYPE: PRT
<213> ORGANISM: Artificial Sequence
<220> FEATURE:
<223> OTHER INFORMATION: clone

<400> SEQUENCE: 233

```
Ser Tyr Trp Met Tyr
1               5
```

<210> SEQ ID NO 234
<211> LENGTH: 17
<212> TYPE: PRT
<213> ORGANISM: Artificial Sequence
<220> FEATURE:
<223> OTHER INFORMATION: clone

<400> SEQUENCE: 234

Lys Ile Lys Gln Asp Gly Thr Glu Lys Tyr Tyr Val Asp Ser Val Lys
1               5                   10                  15

Gly

<210> SEQ ID NO 235
<211> LENGTH: 10
<212> TYPE: PRT
<213> ORGANISM: Artificial Sequence
<220> FEATURE:
<223> OTHER INFORMATION: clone

<400> SEQUENCE: 235

Gly Glu Ile Leu Pro His Tyr Phe Asp Tyr
1               5                   10

<210> SEQ ID NO 236
<211> LENGTH: 119
<212> TYPE: PRT
<213> ORGANISM: Artificial Sequence
<220> FEATURE:
<223> OTHER INFORMATION: clone

<400> SEQUENCE: 236

Gln Val Gln Leu Gln Glu Ser Gly Gly Asp Trp Val Gln Pro Gly Gly
1               5                   10                  15

Ser Leu Arg Leu Ser Cys Gly Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Lys Gln Asp Gly Thr Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro His Tyr Phe Asp Tyr Trp Gly Gln Gly
            100                 105                 110

Thr Leu Val Thr Val Ser Ser
        115

<210> SEQ ID NO 237
<211> LENGTH: 5
<212> TYPE: PRT
<213> ORGANISM: Artificial Sequence
<220> FEATURE:
<223> OTHER INFORMATION: clone

<400> SEQUENCE: 237

Asn Tyr Ser Met Tyr
1               5

<210> SEQ ID NO 238
<211> LENGTH: 17

<212> TYPE: PRT
<213> ORGANISM: Artificial Sequence
<220> FEATURE:
<223> OTHER INFORMATION: clone

<400> SEQUENCE: 238

Asn Ile Lys Gln Asp Gly Ser Glu Glu Tyr Tyr Val Asp Ser Val Lys
1               5                   10                  15
Gly

<210> SEQ ID NO 239
<211> LENGTH: 10
<212> TYPE: PRT
<213> ORGANISM: Artificial Sequence
<220> FEATURE:
<223> OTHER INFORMATION: clone

<400> SEQUENCE: 239

Gly Glu Ile Leu Pro Leu Tyr Phe Asp His
1               5                   10

<210> SEQ ID NO 240
<211> LENGTH: 119
<212> TYPE: PRT
<213> ORGANISM: Artificial Sequence
<220> FEATURE:
<223> OTHER INFORMATION: clone

<400> SEQUENCE: 240

Glu Val Gln Leu Val Glu Ser Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Arg Asn Ser Leu Tyr
65                  70                  75                  80

Leu Gln Met Ile Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
        115

<210> SEQ ID NO 241
<211> LENGTH: 5
<212> TYPE: PRT
<213> ORGANISM: Artificial Sequence
<220> FEATURE:
<223> OTHER INFORMATION: clone

<400> SEQUENCE: 241

Asn Tyr Ser Met Tyr
1               5

<210> SEQ ID NO 242
<211> LENGTH: 17
<212> TYPE: PRT
<213> ORGANISM: Artificial Sequence
<220> FEATURE:
<223> OTHER INFORMATION: clone

<400> SEQUENCE: 242

Asn Ile Lys Gln Asp Gly Ser Glu Glu Tyr Tyr Val Asp Ser Val Lys
1               5                   10                  15

Gly

<210> SEQ ID NO 243
<211> LENGTH: 10
<212> TYPE: PRT
<213> ORGANISM: Artificial Sequence
<220> FEATURE:
<223> OTHER INFORMATION: clone

<400> SEQUENCE: 243

Gly Glu Ile Leu Pro Leu Tyr Phe Asp His
1               5                   10

<210> SEQ ID NO 244
<211> LENGTH: 119
<212> TYPE: PRT
<213> ORGANISM: Artificial Sequence
<220> FEATURE:
<223> OTHER INFORMATION: clone

<400> SEQUENCE: 244

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Arg Asn Ser Leu Tyr
65                  70                  75                  80

Leu Gln Met Ile Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
        115

<210> SEQ ID NO 245
<211> LENGTH: 5
<212> TYPE: PRT
<213> ORGANISM: Artificial Sequence
<220> FEATURE:
<223> OTHER INFORMATION: clone

<400> SEQUENCE: 245

Asn Tyr Ser Met Tyr
1               5

<210> SEQ ID NO 246
<211> LENGTH: 17
<212> TYPE: PRT
<213> ORGANISM: Artificial Sequence
<220> FEATURE:
<223> OTHER INFORMATION: clone

<400> SEQUENCE: 246

Asn Ile Lys Gln Asp Gly Ser Glu Glu Tyr Tyr Val Asp Ser Val Lys

```
                1               5                  10                  15
Gly

<210> SEQ ID NO 247
<211> LENGTH: 10
<212> TYPE: PRT
<213> ORGANISM: Artificial Sequence
<220> FEATURE:
<223> OTHER INFORMATION: clone

<400> SEQUENCE: 247

Gly Glu Ile Leu Pro Leu Tyr Phe Asp His
1               5                  10

<210> SEQ ID NO 248
<211> LENGTH: 119
<212> TYPE: PRT
<213> ORGANISM: Artificial Sequence
<220> FEATURE:
<223> OTHER INFORMATION: clone

<400> SEQUENCE: 248

Gln Val Gln Leu Val Glu Ser Gly Gly Gly Leu Val Gln Pro Gly Gly
1               5                  10                  15

Ser Leu Arg Leu Ser Cys Thr Ala Ser Gly Phe Thr Phe Ser Asn Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Arg Asn Ser Leu Tyr
65                  70                  75                  80

Leu Gln Met Ile Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
        115

<210> SEQ ID NO 249
<211> LENGTH: 5
<212> TYPE: PRT
<213> ORGANISM: Artificial Sequence
<220> FEATURE:
<223> OTHER INFORMATION: clone

<400> SEQUENCE: 249

Ser Tyr Gly Met Gly
1               5

<210> SEQ ID NO 250
<211> LENGTH: 17
<212> TYPE: PRT
<213> ORGANISM: Artificial Sequence
<220> FEATURE:
<223> OTHER INFORMATION: clone

<400> SEQUENCE: 250

Lys Ile Lys Gln Asp Gly Ser Glu Lys Asp Tyr Val Asp Ser Val Lys
1               5                  10                  15

Gly
```

-continued

<210> SEQ ID NO 251
<211> LENGTH: 17
<212> TYPE: PRT
<213> ORGANISM: Artificial Sequence
<220> FEATURE:
<223> OTHER INFORMATION: clone

<400> SEQUENCE: 251

Lys Ile Lys Gln Asp Gly Ser Glu Lys Asp Tyr Val Asp Ser Val Lys
1               5                   10                  15

Gly

<210> SEQ ID NO 252
<211> LENGTH: 118
<212> TYPE: PRT
<213> ORGANISM: Artificial Sequence
<220> FEATURE:
<223> OTHER INFORMATION: clone

<400> SEQUENCE: 252

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Gly Trp Val Arg Gln Ala Pro Gly Lys Gly Leu Glu Trp Val
        35                  40                  45

Ala Lys Ile Lys Gln Asp Gly Ser Glu Lys Asp Tyr Val Asp Ser Val
    50                  55                  60

Lys Gly Arg Phe Thr Ile Ser Arg Asp Asn Ala Lys Ser Leu Phe
65                  70                  75                  80

Leu Gln Met Asn Ser Leu Arg Ala Glu Asp Thr Ala Val Tyr Tyr Cys
                85                  90                  95

Ala Arg Glu Ser Ile Phe Gly Ile Pro Glu Asp Trp Gly Gln Gly Thr
            100                 105                 110

Leu Val Thr Val Ser Ser
        115

<210> SEQ ID NO 253
<211> LENGTH: 5
<212> TYPE: PRT
<213> ORGANISM: Artificial Sequence
<220> FEATURE:
<223> OTHER INFORMATION: clone

<400> SEQUENCE: 253

Ala Tyr Trp Met Gly
1               5

<210> SEQ ID NO 254
<211> LENGTH: 17
<212> TYPE: PRT
<213> ORGANISM: Artificial Sequence
<220> FEATURE:
<223> OTHER INFORMATION: clone

<400> SEQUENCE: 254

Lys Ile Lys Gln Asp Gly Ser Glu Lys Asp Tyr Val Asp Ser Val Lys
1               5                   10                  15

Gly

<210> SEQ ID NO 255

<211> LENGTH: 9
<212> TYPE: PRT
<213> ORGANISM: Artificial Sequence
<220> FEATURE:
<223> OTHER INFORMATION: clone

<400> SEQUENCE: 255

Glu Ser Ile Phe Gly Ile Pro Glu Asp
1               5

<210> SEQ ID NO 256
<211> LENGTH: 118
<212> TYPE: PRT
<213> ORGANISM: Artificial Sequence
<220> FEATURE:
<223> OTHER INFORMATION: clone

<400> SEQUENCE: 256

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Ala Tyr
            20                  25                  30

Trp Met Gly Trp Val Arg Gln Ala Pro Gly Lys Gly Leu Glu Trp Val
        35                  40                  45

Ala Lys Ile Lys Gln Asp Gly Ser Glu Lys Asp Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Glu Ser Ile Phe Gly Ile Pro Glu Asp Trp Gly Gln Gly Thr
            100                 105                 110

Leu Val Thr Val Ser Ser
        115

<210> SEQ ID NO 257
<211> LENGTH: 5
<212> TYPE: PRT
<213> ORGANISM: Artificial Sequence
<220> FEATURE:
<223> OTHER INFORMATION: clone

<400> SEQUENCE: 257

Ala Tyr Trp Met Gly
1               5

<210> SEQ ID NO 258
<211> LENGTH: 17
<212> TYPE: PRT
<213> ORGANISM: Artificial Sequence
<220> FEATURE:
<223> OTHER INFORMATION: clone

<400> SEQUENCE: 258

Lys Ile Lys Gln Asp Gly Ser Glu Lys Asp Tyr Val Asp Ser Val Lys
1               5                   10                  15

Gly

<210> SEQ ID NO 259
<211> LENGTH: 9
<212> TYPE: PRT
<213> ORGANISM: Artificial Sequence
<220> FEATURE:

<223> OTHER INFORMATION: clone

<400> SEQUENCE: 259

Glu Ser Ile Phe Gly Thr Pro Glu Asp
1               5

<210> SEQ ID NO 260
<211> LENGTH: 118
<212> TYPE: PRT
<213> ORGANISM: Artificial Sequence
<220> FEATURE:
<223> OTHER INFORMATION: clone

<400> SEQUENCE: 260

Gln Val Gln Leu Val Glu Ser Gly Gly Gly Leu Val Gln Pro Gly Gly
1               5                   10                  15

Ser Leu Arg Leu Ser Cys Thr Thr Ser Gly Phe Thr Phe Ser Ala Tyr
            20                  25                  30

Trp Met Gly Trp Val Arg Gln Ala Pro Gly Lys Gly Leu Glu Trp Val
        35                  40                  45

Ala Lys Ile Lys Gln Asp Gly Ser Glu Lys Asp Tyr Val Asp Ser Val
    50                  55                  60

Lys Gly Arg Phe Thr Ile Ser Arg Asp Asn Ala Lys Lys Ser Leu Phe
65                  70                  75                  80

Leu Gln Met Asn Ser Leu Arg Ala Glu Asp Thr Ala Val Tyr Tyr Cys
                85                  90                  95

Ala Arg Glu Ser Ile Phe Gly Thr Pro Glu Asp Trp Gly Gln Gly Thr
            100                 105                 110

Leu Val Thr Val Ser Ser
        115

<210> SEQ ID NO 261
<211> LENGTH: 5
<212> TYPE: PRT
<213> ORGANISM: Artificial Sequence
<220> FEATURE:
<223> OTHER INFORMATION: clone

<400> SEQUENCE: 261

Ser Tyr Trp Met Ser
1               5

<210> SEQ ID NO 262
<211> LENGTH: 17
<212> TYPE: PRT
<213> ORGANISM: Artificial Sequence
<220> FEATURE:
<223> OTHER INFORMATION: clone

<400> SEQUENCE: 262

Lys Ile Lys Gln Asp Gly Ser Glu Lys Asp Tyr Val Asp Ser Val Lys
1               5                   10                  15

Gly

<210> SEQ ID NO 263
<211> LENGTH: 9
<212> TYPE: PRT
<213> ORGANISM: Artificial Sequence
<220> FEATURE:
<223> OTHER INFORMATION: clone

<400> SEQUENCE: 263

Glu Ser Ile Phe Gly Ile Pro Glu Asp
1               5

<210> SEQ ID NO 264
<211> LENGTH: 118
<212> TYPE: PRT
<213> ORGANISM: Artificial Sequence
<220> FEATURE:
<223> OTHER INFORMATION: clone

<400> SEQUENCE: 264

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Lys Ile Lys Gln Asp Gly Ser Glu Lys Asp Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Glu Ser Ile Phe Gly Ile Pro Glu Asp Trp Gly Gln Gly Thr
            100                 105                 110

Leu Val Thr Val Ser Ser
        115

<210> SEQ ID NO 265
<211> LENGTH: 5
<212> TYPE: PRT
<213> ORGANISM: Artificial Sequence
<220> FEATURE:
<223> OTHER INFORMATION: clone

<400> SEQUENCE: 265

Gly Tyr Trp Met Gly
1               5

<210> SEQ ID NO 266
<211> LENGTH: 17
<212> TYPE: PRT
<213> ORGANISM: Artificial Sequence
<220> FEATURE:
<223> OTHER INFORMATION: clone

<400> SEQUENCE: 266

Lys Ile Lys Gln Asp Gly Ser Glu Lys Asp Tyr Val Asp Ser Val Lys
1               5                   10                  15

Gly

<210> SEQ ID NO 267
<211> LENGTH: 9
<212> TYPE: PRT
<213> ORGANISM: Artificial Sequence
<220> FEATURE:
<223> OTHER INFORMATION: clone

<400> SEQUENCE: 267

Glu Ser Ile Phe Gly Ile Pro Glu Asp
1               5

```
<210> SEQ ID NO 268
<211> LENGTH: 118
<212> TYPE: PRT
<213> ORGANISM: Artificial Sequence
<220> FEATURE:
<223> OTHER INFORMATION: clone

<400> SEQUENCE: 268

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met Gly Trp Val Arg Gln Ala Pro Gly Lys Gly Leu Glu Trp Val
        35                  40                  45

Ala Lys Ile Lys Gln Asp Gly Ser Glu Lys Asp Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Glu Ser Ile Phe Gly Ile Pro Glu Asp Trp Gly Gln Gly Thr
            100                 105                 110

Leu Val Thr Val Ser Ser
        115

<210> SEQ ID NO 269
<211> LENGTH: 5
<212> TYPE: PRT
<213> ORGANISM: Artificial Sequence
<220> FEATURE:
<223> OTHER INFORMATION: clone

<400> SEQUENCE: 269

Ala Tyr Trp Met Gly
1               5

<210> SEQ ID NO 270
<211> LENGTH: 17
<212> TYPE: PRT
<213> ORGANISM: Artificial Sequence
<220> FEATURE:
<223> OTHER INFORMATION: clone

<400> SEQUENCE: 270

Lys Ile Lys Gln Asp Gly Ser Glu Lys Asp Tyr Val Asp Ser Val Lys
1               5                   10                  15

Gly

<210> SEQ ID NO 271
<211> LENGTH: 9
<212> TYPE: PRT
<213> ORGANISM: Artificial Sequence
<220> FEATURE:
<223> OTHER INFORMATION: clone

<400> SEQUENCE: 271

Glu Ser Ile Phe Gly Thr Pro Glu Asp
1               5

<210> SEQ ID NO 272
<211> LENGTH: 118
<212> TYPE: PRT
<213> ORGANISM: Artificial Sequence
```

<220> FEATURE:
<223> OTHER INFORMATION: clone

<400> SEQUENCE: 272

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Trp Met Gly Trp Val Arg Gln Ala Pro Gly Lys Gly Leu Glu Trp Val
        35                  40                  45

Ala Lys Ile Lys Gln Asp Gly Ser Glu Lys Asp Tyr Val Asp Ser Val
    50                  55                  60

Lys Gly Arg Phe Thr Ile Ser Arg Asp Asn Ala Lys Lys Ala Leu Phe
65                  70                  75                  80

Leu Gln Met Asn Ser Leu Arg Ala Glu Asp Thr Ala Val Tyr Tyr Cys
                85                  90                  95

Ala Arg Glu Ser Ile Phe Gly Thr Pro Glu Asp Trp Gly Gln Gly Thr
            100                 105                 110

Leu Val Thr Val Ser Ser
        115

<210> SEQ ID NO 273
<211> LENGTH: 5
<212> TYPE: PRT
<213> ORGANISM: Artificial Sequence
<220> FEATURE:
<223> OTHER INFORMATION: clone

<400> SEQUENCE: 273

Ser Tyr Trp Met Ser
1               5

<210> SEQ ID NO 274
<211> LENGTH: 17
<212> TYPE: PRT
<213> ORGANISM: Artificial Sequence
<220> FEATURE:
<223> OTHER INFORMATION: clone

<400> SEQUENCE: 274

Asn Ile Lys Gln Asp Gly Ser Glu Lys Asp Tyr Val Asp Ser Val Lys
1               5                   10                  15

Gly

<210> SEQ ID NO 275
<211> LENGTH: 17
<212> TYPE: PRT
<213> ORGANISM: Artificial Sequence
<220> FEATURE:
<223> OTHER INFORMATION: clone

<400> SEQUENCE: 275

Asn Ile Lys Gln Asp Gly Ser Glu Lys Asp Tyr Val Asp Ser Val Lys
1               5                   10                  15

Gly

<210> SEQ ID NO 276
<211> LENGTH: 118
<212> TYPE: PRT
<213> ORGANISM: Artificial Sequence
<220> FEATURE:
<223> OTHER INFORMATION: clone

<400> SEQUENCE: 276

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Asp Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Glu Ser Ile Phe Gly Thr Pro Glu Asp Trp Gly Gln Gly Thr
            100                 105                 110

Leu Val Thr Val Ser Ser
        115

<210> SEQ ID NO 277
<211> LENGTH: 5
<212> TYPE: PRT
<213> ORGANISM: Artificial Sequence
<220> FEATURE:
<223> OTHER INFORMATION: clone

<400> SEQUENCE: 277

Gly Tyr Trp Met Gly
1               5

<210> SEQ ID NO 278
<211> LENGTH: 17
<212> TYPE: PRT
<213> ORGANISM: Artificial Sequence
<220> FEATURE:
<223> OTHER INFORMATION: clone

<400> SEQUENCE: 278

Lys Ile Lys Gln Asp Gly Ser Glu Lys Asp Tyr Val Asp Ser Val Lys
1               5                   10                  15

Gly

<210> SEQ ID NO 279
<211> LENGTH: 9
<212> TYPE: PRT
<213> ORGANISM: Artificial Sequence
<220> FEATURE:
<223> OTHER INFORMATION: clone

<400> SEQUENCE: 279

Glu Ser Ile Phe Gly Ile Pro Glu Asp
1               5

<210> SEQ ID NO 280
<211> LENGTH: 118
<212> TYPE: PRT
<213> ORGANISM: Artificial Sequence
<220> FEATURE:
<223> OTHER INFORMATION: clone

<400> SEQUENCE: 280

Glu Val Gln Leu Val Glu Ser Gly Gly Gly Leu Val Gln Pro Gly Gly

```
                1               5                   10                  15
            Ser Leu Arg Leu Ser Cys Ala Ala Ser Gly Phe Thr Phe Ser Gly Tyr
                            20                  25                  30

Trp Met Gly Trp Val Arg Gln Ala Pro Gly Lys Gly Leu Glu Trp Val
                        35                  40                  45

Ala Lys Ile Lys Gln Asp Gly Ser Glu Lys Asp Tyr Val Asp Ser Val
                    50                  55                  60

Lys Gly Arg Phe Thr Ile Ser Arg Asp Asn Ala Lys Asn Ser Leu Phe
            65                  70                  75                  80

Leu Gln Met Asn Ser Leu Arg Ala Glu Asp Thr Ala Val Tyr Tyr Cys
                            85                  90                  95

Ala Arg Glu Ser Ile Phe Gly Ile Pro Glu Asp Trp Gly Gln Gly Thr
                        100                 105                 110

Leu Val Thr Val Ser Ser
                    115
```

<210> SEQ ID NO 281
<211> LENGTH: 5
<212> TYPE: PRT
<213> ORGANISM: Artificial Sequence
<220> FEATURE:
<223> OTHER INFORMATION: clone

<400> SEQUENCE: 281

```
Ala Tyr Trp Met Gly
1               5
```

<210> SEQ ID NO 282
<211> LENGTH: 17
<212> TYPE: PRT
<213> ORGANISM: Artificial Sequence
<220> FEATURE:
<223> OTHER INFORMATION: clone

<400> SEQUENCE: 282

```
Lys Ile Lys Gln Asp Gly Ser Glu Lys Asp Tyr Val Asp Ser Val Lys
1               5                   10                  15

Gly
```

<210> SEQ ID NO 283
<211> LENGTH: 9
<212> TYPE: PRT
<213> ORGANISM: Artificial Sequence
<220> FEATURE:
<223> OTHER INFORMATION: clone

<400> SEQUENCE: 283

```
Glu Ser Ile Phe Gly Ile Pro Glu Asp
1               5
```

<210> SEQ ID NO 284
<211> LENGTH: 118
<212> TYPE: PRT
<213> ORGANISM: Artificial Sequence
<220> FEATURE:
<223> OTHER INFORMATION: clone

<400> SEQUENCE: 284

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
                20                  25                  30
```

Trp Met Gly Trp Val Arg Gln Ala Pro Gly Arg Gly Leu Glu Trp Val
        35                  40                  45

Ala Lys Ile Lys Gln Asp Gly Ser Glu Lys Asp Tyr Val Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Glu Ser Ile Phe Gly Ile Pro Glu Asp Trp Gly Gln Gly Thr
             100                 105                 110

Leu Val Thr Val Ser Ser
        115

<210> SEQ ID NO 285
<211> LENGTH: 5
<212> TYPE: PRT
<213> ORGANISM: Artificial Sequence
<220> FEATURE:
<223> OTHER INFORMATION: clone

<400> SEQUENCE: 285

Gly Tyr Tyr Met His
1               5

<210> SEQ ID NO 286
<211> LENGTH: 17
<212> TYPE: PRT
<213> ORGANISM: Artificial Sequence
<220> FEATURE:
<223> OTHER INFORMATION: clone

<400> SEQUENCE: 286

Trp Ile Asn Pro Asn Ser Gly Gly Thr Asn Tyr Ala Gln Lys Phe Gln
1               5                   10                  15

Gly

<210> SEQ ID NO 287
<211> LENGTH: 17
<212> TYPE: PRT
<213> ORGANISM: Artificial Sequence
<220> FEATURE:
<223> OTHER INFORMATION: clone

<400> SEQUENCE: 287

Met Asp Arg Asp Tyr Tyr Asp Thr Ser Gly Tyr Phe Gly Trp Phe Asp
1               5                   10                  15

Ser

<210> SEQ ID NO 288
<211> LENGTH: 126
<212> TYPE: PRT
<213> ORGANISM: Artificial Sequence
<220> FEATURE:
<223> OTHER INFORMATION: clone

<400> SEQUENCE: 288

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met

```
            35                  40                  45
Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Ser Met Asp Arg Asp Tyr Tyr Asp Thr Ser Gly Tyr Phe Gly Trp
            100                 105                 110

Phe Asp Ser Trp Gly Gln Gly Thr Leu Val Thr Val Ser Ser
        115                 120                 125
```

<210> SEQ ID NO 289
<211> LENGTH: 5
<212> TYPE: PRT
<213> ORGANISM: Artificial Sequence
<220> FEATURE:
<223> OTHER INFORMATION: clone

<400> SEQUENCE: 289

```
Ala Tyr Tyr Ile Asn
1               5
```

<210> SEQ ID NO 290
<211> LENGTH: 17
<212> TYPE: PRT
<213> ORGANISM: Artificial Sequence
<220> FEATURE:
<223> OTHER INFORMATION: clone

<400> SEQUENCE: 290

```
Ser Ile Lys Pro Asn Thr Gly Ala Thr Lys Tyr Ala Gln Lys Phe Gln
1               5                   10                  15

Gly
```

<210> SEQ ID NO 291
<211> LENGTH: 17
<212> TYPE: PRT
<213> ORGANISM: Artificial Sequence
<220> FEATURE:
<223> OTHER INFORMATION: clone

<400> SEQUENCE: 291

```
Leu Asp Arg Asp Thr Trp Tyr Pro His Ser Tyr Ala Gly Trp Phe Asp
1               5                   10                  15

Ala
```

<210> SEQ ID NO 292
<211> LENGTH: 126
<212> TYPE: PRT
<213> ORGANISM: Artificial Sequence
<220> FEATURE:
<223> OTHER INFORMATION: clone

<400> SEQUENCE: 292

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Ala Asp Ala Tyr
            20                  25                  30

Tyr Ile Asn Trp Val Arg Gln Ala Pro Gly Gln Gly Leu Glu Trp Met
        35                  40                  45
```

-continued

```
Gly Ser Ile Lys Pro Asn Thr Gly Ala Thr Lys Tyr Ala Gln Lys Phe
    50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Leu Asp Arg Asp Thr Trp Tyr Pro His Ser Tyr Ala Gly Trp
                100                 105                 110

Phe Asp Ala Trp Gly Gln Gly Thr Leu Val Thr Val Ser Ser
                115                 120                 125
```

<210> SEQ ID NO 293
<211> LENGTH: 5
<212> TYPE: PRT
<213> ORGANISM: Artificial Sequence
<220> FEATURE:
<223> OTHER INFORMATION: clone

<400> SEQUENCE: 293

```
Asp Tyr Tyr Leu His
1               5
```

<210> SEQ ID NO 294
<211> LENGTH: 17
<212> TYPE: PRT
<213> ORGANISM: Artificial Sequence
<220> FEATURE:
<223> OTHER INFORMATION: clone

<400> SEQUENCE: 294

```
Trp Ile Asn Pro Asn Thr Gly Thr Thr Lys Tyr Ala Arg Glu Phe Glu
1               5                   10                  15

Gly
```

<210> SEQ ID NO 295
<211> LENGTH: 17
<212> TYPE: PRT
<213> ORGANISM: Artificial Sequence
<220> FEATURE:
<223> OTHER INFORMATION: clone

<400> SEQUENCE: 295

```
Met Asp Arg Asp Tyr Tyr Asp Thr Ser Gly Tyr Phe Gly Trp Phe Asp
1               5                   10                  15

Ser
```

<210> SEQ ID NO 296
<211> LENGTH: 126
<212> TYPE: PRT
<213> ORGANISM: Artificial Sequence
<220> FEATURE:
<223> OTHER INFORMATION: clone

<400> SEQUENCE: 296

```
Gln Val Gln Leu Val Gln Ser Gly Ala Glu Val Lys Lys Pro Gly Ala
1               5                   10                  15

Ser Val Lys Val Ser Cys Ala Ala Ser Gly Tyr Thr Phe Thr Asp Tyr
                20                  25                  30

Tyr Leu His Trp Val Arg Gln Ala Pro Gly Gln Gly Leu Glu Trp Met
            35                  40                  45

Gly Trp Ile Asn Pro Asn Thr Gly Thr Thr Lys Tyr Ala Arg Glu Phe
        50                  55                  60
```

Glu Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Met Asp Arg Asp Tyr Tyr Asp Thr Ser Gly Tyr Phe Gly Trp
            100                 105                 110

Phe Asp Ser Trp Gly Gln Gly Thr Leu Val Thr Val Ser Ser
        115                 120                 125

<210> SEQ ID NO 297
<211> LENGTH: 5
<212> TYPE: PRT
<213> ORGANISM: Artificial Sequence
<220> FEATURE:
<223> OTHER INFORMATION: clone

<400> SEQUENCE: 297

Asp Tyr Tyr Leu His
1               5

<210> SEQ ID NO 298
<211> LENGTH: 17
<212> TYPE: PRT
<213> ORGANISM: Artificial Sequence
<220> FEATURE:
<223> OTHER INFORMATION: clone

<400> SEQUENCE: 298

Trp Ile Asn Pro Asn Thr Gly Thr Thr Lys Tyr Ala Arg Glu Phe Glu
1               5                   10                  15

Gly

<210> SEQ ID NO 299
<211> LENGTH: 17
<212> TYPE: PRT
<213> ORGANISM: Artificial Sequence
<220> FEATURE:
<223> OTHER INFORMATION: clone

<400> SEQUENCE: 299

Met Asp Arg Asp Trp Arg Ser Pro Asn Asp Tyr Phe Gly Trp Phe Asp
1               5                   10                  15

Ser

<210> SEQ ID NO 300
<211> LENGTH: 126
<212> TYPE: PRT
<213> ORGANISM: Artificial Sequence
<220> FEATURE:
<223> OTHER INFORMATION: clone

<400> SEQUENCE: 300

Gln Val Gln Leu Val Gln Ser Gly Ala Glu Val Lys Lys Pro Gly Ala
1               5                   10                  15

Ser Val Lys Val Ser Cys Ala Ala Ser Gly Tyr Thr Phe Thr Asp Tyr
                20                  25                  30

Tyr Leu His Trp Val Arg Gln Ala Pro Gly Gln Gly Leu Glu Trp Met
            35                  40                  45

Gly Trp Ile Asn Pro Asn Thr Gly Thr Thr Lys Tyr Ala Arg Glu Phe
        50                  55                  60

Glu Gly Arg Val Thr Met Thr Arg Asp Thr Ser Ile Ser Thr Ala Tyr

```
            65                   70                  75                  80
Met Glu Leu Ser Arg Leu Arg Ser Asp Thr Ala Val Tyr Tyr Cys
                    85                  90                  95

Ala Ser Met Asp Arg Asp Trp Arg Ser Pro Asn Asp Tyr Phe Gly Trp
            100                 105                 110

Phe Asp Ser Trp Gly Gln Gly Thr Leu Val Thr Val Ser Ser
            115                 120                 125
```

<210> SEQ ID NO 301
<211> LENGTH: 5
<212> TYPE: PRT
<213> ORGANISM: Artificial Sequence
<220> FEATURE:
<223> OTHER INFORMATION: clone

<400> SEQUENCE: 301

```
Asp Tyr Tyr Leu His
1               5
```

<210> SEQ ID NO 302
<211> LENGTH: 17
<212> TYPE: PRT
<213> ORGANISM: Artificial Sequence
<220> FEATURE:
<223> OTHER INFORMATION: clone

<400> SEQUENCE: 302

```
Trp Ile Asn Pro Asn Thr Gly Thr Thr Lys Tyr Ala Arg Glu Phe Glu
1               5                   10                  15

Gly
```

<210> SEQ ID NO 303
<211> LENGTH: 17
<212> TYPE: PRT
<213> ORGANISM: Artificial Sequence
<220> FEATURE:
<223> OTHER INFORMATION: clone

<400> SEQUENCE: 303

```
Leu Asp Arg Asp Trp Arg Ser Pro Asn Asp Tyr Phe Gly Trp Phe Asp
1               5                   10                  15

Ser
```

<210> SEQ ID NO 304
<211> LENGTH: 126
<212> TYPE: PRT
<213> ORGANISM: Artificial Sequence
<220> FEATURE:
<223> OTHER INFORMATION: clone

<400> SEQUENCE: 304

```
Gln Val Gln Leu Val Gln Ser Gly Ala Glu Val Lys Lys Pro Gly Ala
1               5                   10                  15

Ser Val Lys Val Ser Cys Ala Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asn Pro Asn Thr Gly Thr Thr Lys Tyr Ala Arg Glu Phe
    50                  55                  60

Glu Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                85                  90                  95

Ala Ser Leu Asp Arg Asp Trp Arg Ser Pro Asn Asp Tyr Phe Gly Trp
            100                 105                 110

Phe Asp Ser Trp Gly Gln Gly Thr Leu Val Thr Val Ser Ser
        115                 120                 125

<210> SEQ ID NO 305
<211> LENGTH: 5
<212> TYPE: PRT
<213> ORGANISM: Artificial Sequence
<220> FEATURE:
<223> OTHER INFORMATION: clone

<400> SEQUENCE: 305

Asp Tyr Tyr Leu His
1               5

<210> SEQ ID NO 306
<211> LENGTH: 17
<212> TYPE: PRT
<213> ORGANISM: Artificial Sequence
<220> FEATURE:
<223> OTHER INFORMATION: clone

<400> SEQUENCE: 306

Trp Ile Asn Pro Asn Thr Gly Thr Thr Lys Tyr Ala Arg Glu Phe Glu
1               5                   10                  15

Gly

<210> SEQ ID NO 307
<211> LENGTH: 17
<212> TYPE: PRT
<213> ORGANISM: Artificial Sequence
<220> FEATURE:
<223> OTHER INFORMATION: clone

<400> SEQUENCE: 307

Leu Asp Arg Asp Trp Arg Ser Pro Asn Asp Tyr Tyr Gly Trp Phe Asp
1               5                   10                  15

Ser

<210> SEQ ID NO 308
<211> LENGTH: 126
<212> TYPE: PRT
<213> ORGANISM: Artificial Sequence
<220> FEATURE:
<223> OTHER INFORMATION: clone

<400> SEQUENCE: 308

Gln Val Gln Leu Val Gln Ser Gly Ala Glu Val Lys Lys Pro Gly Ala
1               5                   10                  15

Ser Val Lys Val Ser Cys Ala Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asn Pro Asn Thr Gly Thr Thr Lys Tyr Ala Arg Glu Phe
    50                  55                  60

Glu Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Ser Leu Asp Arg Asp Trp Arg Ser Pro Asn Asp Tyr Tyr Gly Trp
            100                 105                 110

Phe Asp Ser Trp Gly Gln Gly Thr Leu Val Thr Val Ser Ser
        115                 120                 125

<210> SEQ ID NO 309
<211> LENGTH: 5
<212> TYPE: PRT
<213> ORGANISM: Artificial Sequence
<220> FEATURE:
<223> OTHER INFORMATION: clone

<400> SEQUENCE: 309

Asp Tyr Tyr Leu His
1               5

<210> SEQ ID NO 310
<211> LENGTH: 17
<212> TYPE: PRT
<213> ORGANISM: Artificial Sequence
<220> FEATURE:
<223> OTHER INFORMATION: clone

<400> SEQUENCE: 310

Trp Ile Asn Pro Asn Thr Gly Thr Thr Lys Tyr Ala Arg Glu Phe Glu
1               5                   10                  15

Gly

<210> SEQ ID NO 311
<211> LENGTH: 17
<212> TYPE: PRT
<213> ORGANISM: Artificial Sequence
<220> FEATURE:
<223> OTHER INFORMATION: clone

<400> SEQUENCE: 311

Leu Asp Arg Asp Trp Arg Ser Pro Asn Asp Tyr Tyr Gly Trp Phe Asp
1               5                   10                  15

Ser

<210> SEQ ID NO 312
<211> LENGTH: 126
<212> TYPE: PRT
<213> ORGANISM: Artificial Sequence
<220> FEATURE:
<223> OTHER INFORMATION: clone

<400> SEQUENCE: 312

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asn Pro Asn Thr Gly Thr Thr Lys Tyr Ala Arg Glu Phe
    50                  55                  60

Glu Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Leu Asp Arg Asp Trp Arg Ser Pro Asn Asp Tyr Tyr Gly Trp
```

```
                100             105             110
Phe Asp Ser Trp Gly Gln Gly Thr Leu Val Thr Val Ser Ser
        115                 120                 125

<210> SEQ ID NO 313
<211> LENGTH: 5
<212> TYPE: PRT
<213> ORGANISM: Artificial Sequence
<220> FEATURE:
<223> OTHER INFORMATION: clone

<400> SEQUENCE: 313

Asp Tyr Tyr Leu His
1               5

<210> SEQ ID NO 314
<211> LENGTH: 17
<212> TYPE: PRT
<213> ORGANISM: Artificial Sequence
<220> FEATURE:
<223> OTHER INFORMATION: clone

<400> SEQUENCE: 314

Trp Ile Asn Pro Asn Thr Gly Thr Thr Lys Tyr Ala Arg Glu Phe Glu
1               5                   10                  15

Gly

<210> SEQ ID NO 315
<211> LENGTH: 17
<212> TYPE: PRT
<213> ORGANISM: Artificial Sequence
<220> FEATURE:
<223> OTHER INFORMATION: clone

<400> SEQUENCE: 315

Leu Asp Arg Asp Trp Arg Ser Pro Asn Asp Tyr Phe Gly Trp Phe Asp
1               5                   10                  15

Ser

<210> SEQ ID NO 316
<211> LENGTH: 126
<212> TYPE: PRT
<213> ORGANISM: Artificial Sequence
<220> FEATURE:
<223> OTHER INFORMATION: clone

<400> SEQUENCE: 316

Gln Val Gln Leu Val Gln Ser Gly Ala Glu Val Lys Lys Pro Gly Ala
1               5                   10                  15

Ser Val Lys Val Ser Cys Ala Ala Ser Gly Tyr Thr Leu Thr Asp Tyr
            20                  25                  30

Tyr Leu His Trp Val Arg Gln Ala Pro Gly Gln Gly Leu Glu Trp Met
        35                  40                  45

Gly Trp Ile Asn Pro Asn Thr Gly Thr Thr Lys Tyr Ala Arg Glu Phe
    50                  55                  60

Glu Gly Arg Val Thr Met Thr Arg Asp Thr Ser Ile Ser Thr Ala Tyr
65                  70                  75                  80

Met Glu Leu Ser Gly Leu Arg Ser Asp Asp Thr Ala Val Tyr Tyr Cys
                85                  90                  95

Ala Ser Leu Asp Arg Asp Trp Arg Ser Pro Asn Asp Tyr Phe Gly Trp
            100                 105                 110
```

```
Phe Asp Ser Trp Gly Gln Gly Thr Leu Val Thr Val Ser Ser
        115                 120                 125
```

<210> SEQ ID NO 317
<211> LENGTH: 5
<212> TYPE: PRT
<213> ORGANISM: Artificial Sequence
<220> FEATURE:
<223> OTHER INFORMATION: clone

<400> SEQUENCE: 317

```
Ala Tyr His Ile Asn
1               5
```

<210> SEQ ID NO 318
<211> LENGTH: 17
<212> TYPE: PRT
<213> ORGANISM: Artificial Sequence
<220> FEATURE:
<223> OTHER INFORMATION: clone

<400> SEQUENCE: 318

```
Ser Ile Lys Pro Asn Ser Gly Ala Thr Lys Tyr Ala Gln Lys Phe Gln
1               5                   10                  15

Gly
```

<210> SEQ ID NO 319
<211> LENGTH: 17
<212> TYPE: PRT
<213> ORGANISM: Artificial Sequence
<220> FEATURE:
<223> OTHER INFORMATION: clone

<400> SEQUENCE: 319

```
Met Asp Arg Asp Tyr Tyr Asp Thr Ser Gly Tyr Phe Gly Trp Phe Asp
1               5                   10                  15

Ser
```

<210> SEQ ID NO 320
<211> LENGTH: 126
<212> TYPE: PRT
<213> ORGANISM: Artificial Sequence
<220> FEATURE:
<223> OTHER INFORMATION: clone

<400> SEQUENCE: 320

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asp Ala Tyr
            20                  25                  30

His Ile Asn Trp Val Arg Gln Ala Pro Gly Gln Gly Leu Glu Trp Met
        35                  40                  45

Gly Ser Ile Lys Pro Asn Ser Gly Ala Thr Lys Tyr Ala Gln Lys Phe
    50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Met Asp Arg Asp Tyr Tyr Asp Thr Ser Gly Tyr Phe Gly Trp
            100                 105                 110

Phe Asp Ser Trp Gly Gln Gly Thr Leu Val Thr Val Ser Ser
        115                 120                 125
```

```
<210> SEQ ID NO 321
<211> LENGTH: 5
<212> TYPE: PRT
<213> ORGANISM: Artificial Sequence
<220> FEATURE:
<223> OTHER INFORMATION: clone

<400> SEQUENCE: 321

Ala Tyr His Ile Asn
1               5

<210> SEQ ID NO 322
<211> LENGTH: 17
<212> TYPE: PRT
<213> ORGANISM: Artificial Sequence
<220> FEATURE:
<223> OTHER INFORMATION: clone

<400> SEQUENCE: 322

Ser Ile Lys Pro Asn Ser Gly Ala Thr Lys Tyr Ala Gln Lys Phe Gln
1               5                   10                  15

Gly

<210> SEQ ID NO 323
<211> LENGTH: 17
<212> TYPE: PRT
<213> ORGANISM: Artificial Sequence
<220> FEATURE:
<223> OTHER INFORMATION: clone

<400> SEQUENCE: 323

Met Asp Arg Asp Gln Phe Tyr Phe Gly Asp Tyr Phe Gly Trp Phe Asp
1               5                   10                  15

Ser

<210> SEQ ID NO 324
<211> LENGTH: 126
<212> TYPE: PRT
<213> ORGANISM: Artificial Sequence
<220> FEATURE:
<223> OTHER INFORMATION: clone

<400> SEQUENCE: 324

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asp Ala Tyr
                20                  25                  30

His Ile Asn Trp Val Arg Gln Ala Pro Gly Gln Gly Leu Glu Trp Met
            35                  40                  45

Gly Ser Ile Lys Pro Asn Ser Gly Ala Thr Lys Tyr Ala Gln Lys Phe
        50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Met Asp Arg Asp Gln Phe Tyr Phe Gly Asp Tyr Phe Gly Trp
                100                 105                 110

Phe Asp Ser Trp Gly Gln Gly Thr Leu Val Thr Val Ser Ser
            115                 120                 125
```

```
<210> SEQ ID NO 325
<211> LENGTH: 5
<212> TYPE: PRT
<213> ORGANISM: Artificial Sequence
<220> FEATURE:
<223> OTHER INFORMATION: clone

<400> SEQUENCE: 325

Ala Tyr His Ile Asn
1               5

<210> SEQ ID NO 326
<211> LENGTH: 17
<212> TYPE: PRT
<213> ORGANISM: Artificial Sequence
<220> FEATURE:
<223> OTHER INFORMATION: clone

<400> SEQUENCE: 326

Ser Ile Lys Pro Asn Ser Gly Ala Thr Lys Tyr Ala Gln Lys Phe Gln
1               5                   10                  15

Gly

<210> SEQ ID NO 327
<211> LENGTH: 17
<212> TYPE: PRT
<213> ORGANISM: Artificial Sequence
<220> FEATURE:
<223> OTHER INFORMATION: clone

<400> SEQUENCE: 327

Leu Asp Arg Asp Thr Trp Tyr Pro His Ser Tyr Phe Gly Trp Phe Asp
1               5                   10                  15

Ser

<210> SEQ ID NO 328
<211> LENGTH: 126
<212> TYPE: PRT
<213> ORGANISM: Artificial Sequence
<220> FEATURE:
<223> OTHER INFORMATION: clone

<400> SEQUENCE: 328

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asp Ala Tyr
                20                  25                  30

His Ile Asn Trp Val Arg Gln Ala Pro Gly Gln Gly Leu Glu Trp Met
            35                  40                  45

Gly Ser Ile Lys Pro Asn Ser Gly Ala Thr Lys Tyr Ala Gln Lys Phe
    50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Leu Asp Arg Asp Thr Trp Tyr Pro His Ser Tyr Phe Gly Trp
            100                 105                 110

Phe Asp Ser Trp Gly Gln Gly Thr Leu Val Thr Val Ser Ser
        115                 120                 125

<210> SEQ ID NO 329
<211> LENGTH: 5
```

<212> TYPE: PRT
<213> ORGANISM: Artificial Sequence
<220> FEATURE:
<223> OTHER INFORMATION: clone

<400> SEQUENCE: 329

Ala Tyr His Ile Asn
1               5

<210> SEQ ID NO 330
<211> LENGTH: 17
<212> TYPE: PRT
<213> ORGANISM: Artificial Sequence
<220> FEATURE:
<223> OTHER INFORMATION: clone

<400> SEQUENCE: 330

Ser Ile Lys Pro Asn Ser Gly Ala Thr Lys Tyr Ala Gln Lys Phe Gln
1               5                   10                  15

Gly

<210> SEQ ID NO 331
<211> LENGTH: 17
<212> TYPE: PRT
<213> ORGANISM: Artificial Sequence
<220> FEATURE:
<223> OTHER INFORMATION: clone

<400> SEQUENCE: 331

Met Asp Arg Asp Thr Trp Tyr Pro His Ser Tyr Phe Gly Trp Phe Asp
1               5                   10                  15

Ser

<210> SEQ ID NO 332
<211> LENGTH: 126
<212> TYPE: PRT
<213> ORGANISM: Artificial Sequence
<220> FEATURE:
<223> OTHER INFORMATION: clone

<400> SEQUENCE: 332

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asp Ala Tyr
                20                  25                  30

His Ile Asn Trp Val Arg Gln Ala Pro Gly Gln Gly Leu Glu Trp Met
            35                  40                  45

Gly Ser Ile Lys Pro Asn Ser Gly Ala Thr Lys Tyr Ala Gln Lys Phe
        50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Met Asp Arg Asp Thr Trp Tyr Pro His Ser Tyr Phe Gly Trp
                100                 105                 110

Phe Asp Ser Trp Gly Gln Gly Thr Leu Val Thr Val Ser Ser
            115                 120                 125

<210> SEQ ID NO 333
<211> LENGTH: 5
<212> TYPE: PRT
<213> ORGANISM: Artificial Sequence

```
<220> FEATURE:
<223> OTHER INFORMATION: clone

<400> SEQUENCE: 333

Ala Tyr His Ile Asn
1               5

<210> SEQ ID NO 334
<211> LENGTH: 17
<212> TYPE: PRT
<213> ORGANISM: Artificial Sequence
<220> FEATURE:
<223> OTHER INFORMATION: clone

<400> SEQUENCE: 334

Ser Ile Lys Pro Asn Ser Gly Ala Thr Lys Tyr Ala Gln Lys Phe Gln
1               5                   10                  15

Gly

<210> SEQ ID NO 335
<211> LENGTH: 17
<212> TYPE: PRT
<213> ORGANISM: Artificial Sequence
<220> FEATURE:
<223> OTHER INFORMATION: clone

<400> SEQUENCE: 335

Leu Asp Arg Asp Thr Trp Tyr Pro His Ser Tyr Ala Gly Trp Phe Asp
1               5                   10                  15

Ser

<210> SEQ ID NO 336
<211> LENGTH: 126
<212> TYPE: PRT
<213> ORGANISM: Artificial Sequence
<220> FEATURE:
<223> OTHER INFORMATION: clone

<400> SEQUENCE: 336

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asp Ala Tyr
                20                  25                  30

His Ile Asn Trp Val Arg Gln Ala Pro Gly Gln Gly Leu Glu Trp Met
            35                  40                  45

Gly Ser Ile Lys Pro Asn Ser Gly Ala Thr Lys Tyr Ala Gln Lys Phe
        50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Ser Leu Asp Arg Asp Thr Trp Tyr Pro His Ser Tyr Ala Gly Trp
            100                 105                 110

Phe Asp Ser Trp Gly Gln Gly Thr Leu Val Thr Val Ser Ser
        115                 120                 125

<210> SEQ ID NO 337
<211> LENGTH: 5
<212> TYPE: PRT
<213> ORGANISM: Artificial Sequence
<220> FEATURE:
<223> OTHER INFORMATION: clone
```

-continued

<400> SEQUENCE: 337

Ala Tyr Tyr Ile Asn
1               5

<210> SEQ ID NO 338
<211> LENGTH: 17
<212> TYPE: PRT
<213> ORGANISM: Artificial Sequence
<220> FEATURE:
<223> OTHER INFORMATION: clone

<400> SEQUENCE: 338

Ser Ile Lys Pro Asn Ser Gly Ala Thr Lys Tyr Ala Gln Lys Phe Gln
1               5                   10                  15

Gly

<210> SEQ ID NO 339
<211> LENGTH: 17
<212> TYPE: PRT
<213> ORGANISM: Artificial Sequence
<220> FEATURE:
<223> OTHER INFORMATION: clone

<400> SEQUENCE: 339

Leu Asp Arg Asp Thr Trp Tyr Pro His Ser Tyr Phe Gly Trp Phe Asp
1               5                   10                  15

Ser

<210> SEQ ID NO 340
<211> LENGTH: 126
<212> TYPE: PRT
<213> ORGANISM: Artificial Sequence
<220> FEATURE:
<223> OTHER INFORMATION: clone

<400> SEQUENCE: 340

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Ser Asp Ala Tyr
            20                  25                  30

Tyr Ile Asn Trp Val Arg Gln Ala Pro Gly Gln Gly Leu Glu Trp Met
        35                  40                  45

Gly Ser Ile Lys Pro Asn Ser Gly Ala Thr Lys Tyr Ala Gln Lys Phe
    50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Leu Asp Arg Asp Thr Trp Tyr Pro His Ser Tyr Phe Gly Trp
            100                 105                 110

Phe Asp Ser Trp Gly Gln Gly Thr Leu Val Thr Val Ser Ser
        115                 120                 125

<210> SEQ ID NO 341
<211> LENGTH: 5
<212> TYPE: PRT
<213> ORGANISM: Artificial Sequence
<220> FEATURE:
<223> OTHER INFORMATION: clone

<400> SEQUENCE: 341

```
Ser Tyr Trp Met Asn
1               5

<210> SEQ ID NO 342
<211> LENGTH: 17
<212> TYPE: PRT
<213> ORGANISM: Artificial Sequence
<220> FEATURE:
<223> OTHER INFORMATION: clone

<400> SEQUENCE: 342

Thr Ile Lys Gln Asp Gly Ser Glu Lys Tyr Tyr Val Asp Ser Val Lys
1               5                   10                  15

Gly

<210> SEQ ID NO 343
<211> LENGTH: 11
<212> TYPE: PRT
<213> ORGANISM: Artificial Sequence
<220> FEATURE:
<223> OTHER INFORMATION: clone

<400> SEQUENCE: 343

Gly Asp Thr Ile Phe Asp Gly Ala Phe Asp Ile
1               5                   10

<210> SEQ ID NO 344
<211> LENGTH: 120
<212> TYPE: PRT
<213> ORGANISM: Artificial Sequence
<220> FEATURE:
<223> OTHER INFORMATION: clone

<400> SEQUENCE: 344

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Thr Ile Lys Gln Asp Gly Ser Glu Lys Tyr Tyr Val Asp Ser Val
    50                  55                  60

Lys Gly Arg Phe Thr Ile Ser Arg Asp Asn Ala Thr Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Asp Thr Ile Phe Asp Gly Ala Phe Asp Ile Trp Gly Gln
            100                 105                 110

Gly Thr Met Val Thr Val Ser Ser
        115                 120

<210> SEQ ID NO 345
<211> LENGTH: 5
<212> TYPE: PRT
<213> ORGANISM: Artificial Sequence
<220> FEATURE:
<223> OTHER INFORMATION: clone

<400> SEQUENCE: 345

Ser Tyr Trp Met Ser
1               5
```

<210> SEQ ID NO 346
<211> LENGTH: 17
<212> TYPE: PRT
<213> ORGANISM: Artificial Sequence
<220> FEATURE:
<223> OTHER INFORMATION: clone

<400> SEQUENCE: 346

Asn Ile Lys Gln Asp Gly Ser Glu Lys Tyr Tyr Val Asp Ser Val Lys
1               5                   10                  15

Gly

<210> SEQ ID NO 347
<211> LENGTH: 8
<212> TYPE: PRT
<213> ORGANISM: Artificial Sequence
<220> FEATURE:
<223> OTHER INFORMATION: clone

<400> SEQUENCE: 347

Gly Gln Trp Pro Phe Phe Asp Tyr
1               5

<210> SEQ ID NO 348
<211> LENGTH: 117
<212> TYPE: PRT
<213> ORGANISM: Artificial Sequence
<220> FEATURE:
<223> OTHER INFORMATION: clone

<400> SEQUENCE: 348

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala His Gly Gln Trp Pro Phe Phe Asp Tyr Trp Gly Gln Gly Thr Met
            100                 105                 110

Val Thr Val Ser Ser
        115

<210> SEQ ID NO 349
<211> LENGTH: 357
<212> TYPE: DNA
<213> ORGANISM: Artificial Sequence
<220> FEATURE:
<223> OTHER INFORMATION: VH 1.1

<400> SEQUENCE: 349
gaggtgcagc tggtggagtc tgggggaggc ttggtccagc ctggggggtc cctgagactc     60
tcctgtgcag cctctggatt cacctttagt agttattcga tgtactgggt ccgccaggct    120
ccagggaagg ggctggagtg ggtggccaac ataaagcaag atggaagtga aaatactat     180 gtggactctg tgaagggccg attcaccatc tccagagaca cgccaagaa ctcactgttt     240 ctgcaaatga atagcctgag agccgaggac acggctgtgt attactgtgc gaaaggggaa    300
atactacccc tccactttga ctactggggc cagggaaccc tggtcactgt ctcctca      357

<210> SEQ ID NO 350
<211> LENGTH: 357
<212> TYPE: DNA
<213> ORGANISM: Artificial Sequence
<220> FEATURE:
<223> OTHER INFORMATION: VH 1.2

<400> SEQUENCE: 350
gaggttcagt tggtggaaag cggcggtggc ctggtccagc cgggtggtag cctgcgcctg    60
tcctgcgcgg ctagcggttt cacgtttagc agctacagca tgtactgggt gcgtcaagcg   120
ccaggcaaag gtctggaatg ggttgccgag attaagcaag acggttctgt tcagtattat   180
gtcagcgacg tgaagggtcg tttaccatc agccgtgaca acgcgaaaaa cagcctgtat   240
ttgcagatga attccctgcg cgctgaagat accgcggtgt attactgtgc gaaaggtgag   300
attctgccgc tgtacttcga ttactggggc caaggcaccc tggttactgt ctcgagc      357

<210> SEQ ID NO 351
<211> LENGTH: 357
<212> TYPE: DNA
<213> ORGANISM: Artificial Sequence
<220> FEATURE:
<223> OTHER INFORMATION: VH 1.3

<400> SEQUENCE: 351
gaggtgcagc tggtggagtc tggggggaggc ttggtccagc ctggggggtc cctgagactc    60
tcctgtgcag cctctggatt cacctttagt agttatagca tgtactgggt ccgccaggct   120
ccagggaagg ggctggagtg ggtggccgag ataaagcaag atggaagtgt gcaatactat   180
gtggactctg tgaagggccg attcaccatc tccagagaca acgccaagaa ctcactgtat   240
ctgcaaatga atagcctgag agccgaggac acggctgtgt attactgtgc gaaaggggaa   300
atactacccc tctactttga ctactggggc cagggaaccc tggtcactgt ctcttca      357

<210> SEQ ID NO 352
<211> LENGTH: 357
<212> TYPE: DNA
<213> ORGANISM: Artificial Sequence
<220> FEATURE:
<223> OTHER INFORMATION: VH 1.4

<400> SEQUENCE: 352
gaggttcagt tggtggaaag cggcggtggc ctggtccagc cgggtggtag cctgcgcctg    60
tcctgcgcgg ctagcggttt cacgtttagc agctacagca tgtactgggt gcgtcaagcg   120
ccaggcaaag gtctggaatg ggttgccgag attaagcaaa ccggttctgt tcagtattat   180
gtcgacagcg tgaagggtcg ttttaccatc agccgtgaca acgcgaaaaa cagcctgtat   240
ttgcagatga attccctgcg cgctgaagat accgcggtgt attactgtgc gaaaggtgag   300
attctgccgc tgtacttcga ttactggggc caaggcaccc tggttactgt ctcgagc      357

<210> SEQ ID NO 353
<211> LENGTH: 357
<212> TYPE: DNA
<213> ORGANISM: Artificial Sequence
<220> FEATURE:
<223> OTHER INFORMATION: VH 1.5

<400> SEQUENCE: 353

```
gaggttcagt tggtggaaag cggcggtggc ctggtccagc cgggtggtag cctgcgcctg    60
tcctgcgcgg ctagcggttt cacgtttagc agctacagca tgtactgggt gcgtcaagcg   120
ccaggcaaag gtctggaatg ggttgccgag attaagccga ccggttctgt tcagtattat   180
gtcgacagcg tgaagggtcg ttttaccatc agccgtgaca acgcgaaaaa cagcctgtat   240
ttgcagatga attccctgcg cgctgaagat accgcggtgt attactgtgc gaaaggtgag   300
attctgccgc tgtacttcga ttactggggc caaggcaccc tggttactgt ctcgagc      357
```

<210> SEQ ID NO 354
<211> LENGTH: 357
<212> TYPE: DNA
<213> ORGANISM: Artificial Sequence
<220> FEATURE:
<223> OTHER INFORMATION: VH 1.6

<400> SEQUENCE: 354

```
gaggtgcagc tggtggagtc tgggggaggc ttggtccagc ctggggggtc cctgagactc    60
tcctgtgcag cctctggatt cacctttagt agttatagca tgtactgggt ccgccaggct   120
ccagggaagg ggctggagtg ggtggccgag ataaagcaag atggaagtga gcaatactat   180
gtggactctg tgaagggccg attcaccatc tccagagaca acgccaagaa ctcactgtat   240
ctgcaaatga atagcctgag agccgaggac acggctgtgt attactgtgc gaaaggggaa   300
atactacccc tctactttga ctactggggc cagggaaccc tggtcaccgt ctcctca      357
```

<210> SEQ ID NO 355
<211> LENGTH: 357
<212> TYPE: DNA
<213> ORGANISM: Artificial Sequence
<220> FEATURE:
<223> OTHER INFORMATION: VH 1.7

<400> SEQUENCE: 355

```
caggtgcagc tggtggagtc tgggggaggc ttggtccagc ctggggggtc cctgagactc    60
tcctgtgcag cctctggatt cacctttagt agttatggga tgtactgggt ccgccaggct   120
ccagggaagg ggctggagtg ggtggccaag atagagcaag atggaagtga ggaatactat   180
gtggactctg tgaagggccg attcaccatc tccagagaca acgccaagaa gtcactgtat   240
ctgcaaatga atagcctgag agccgaggac acggctgtgt attactgtgc gaaaggggaa   300
atactacccc tctactttga ctactggggc cagggaaccc tggtcaccgt ctcctca      357
```

<210> SEQ ID NO 356
<211> LENGTH: 357
<212> TYPE: DNA
<213> ORGANISM: Artificial Sequence
<220> FEATURE:
<223> OTHER INFORMATION: VH 1.8

<400> SEQUENCE: 356

```
caggtgcagc tggtggagtc tgggggaggc ttggtccagc ctggggggtc cctgagactc    60
tcctgtgcag cctctggatt cacctttagt agttatggta tgtactgggt ccgccaggct   120
ccagggaagg ggctggagtg ggtggccaag atagagcaag atggaagtga gaaatactat   180
gtggactctg tgaagggccg attcaccatc tccagagaca acgccaagaa ctcactgttt   240
ctgcaaatga atagcctgag agccgaggac acggctgtgt attactgtgc gaaaggggaa   300
atactacccc tctactttga ctactggggc cagggaaccc tggtcaccgt ctcctca      357
```

<210> SEQ ID NO 357
<211> LENGTH: 357
<212> TYPE: DNA
<213> ORGANISM: Artificial Sequence
<220> FEATURE:
<223> OTHER INFORMATION: VH 1.9

<400> SEQUENCE: 357

```
caggtgcagc tggtggagtc tgggggaggc ttggtccagc ctgggggtc  cctgagactc    60
tcctgtgcag cctctggatt cacctttagt agttatggaa tgtactgggt ccgccaggct   120
ccagggaagg ggctggagtg ggtggccgag ataaaacaag atggaagtga aaatactat    180
gtggactctg tgaagggccg attcaccatc tccagagaca acgccaagaa ctcactgtat   240
ctgcaaatga atagcctgag agccgaggac acggctgtgt attactgtgc gaaggggaa    300
atactacccc tctactttga ctactgggc  cagggaaccc tggtcactgt ctcttca      357
```

<210> SEQ ID NO 358
<211> LENGTH: 357
<212> TYPE: DNA
<213> ORGANISM: Artificial Sequence
<220> FEATURE:
<223> OTHER INFORMATION: VH 1.10

<400> SEQUENCE: 358

```
gaggtgcagc tggtggagtc tgggggaggc ttggtccagc ctgggggtc  cctgagactc    60
tcctgtgcag cctctggatt cacctttagt agttatcgca tgtactgggt ccgccaggct   120
ccagggaagg ggctggagtg ggtggccagc atagaacaag atggaagtga ggaatactat   180
gtggactctg tgaagggccg attcaccatc tccagagaca acgccaagaa gtcactgttt   240
ctgcaaatga atagcctgag agccgaggac acggctgtgt attactgtgc gaaggggaa    300
atactacccc tctactttga ctactgggc  cagggaaccc tggtcactgt ctcttca      357
```

<210> SEQ ID NO 359
<211> LENGTH: 357
<212> TYPE: DNA
<213> ORGANISM: Artificial Sequence
<220> FEATURE:
<223> OTHER INFORMATION: VH 1.11

<400> SEQUENCE: 359

```
gaggtgcagc tggtggagtc tgggggaggc ttggtccagc ctgggggtc  cctgagactc    60
tcctgtgcag cctctggatt caccttagt agttatcaga tgtactgggt ccgccaggct    120
ccagggaagg ggctggagtg ggtggccagc ataaaacaag atggaagtga ggaatactat   180
gtggactctg tgaagggccg attcaccatc tccagagaca acgccaagaa ctcactgttt   240
ctgcaaatga atagcctgag agccgaggac acggctgtgt attactgtgc gaaggggaa    300
atactacccc tctactttga ctactgggc  cagggaaccc tggtcactgt ctcttca      357
```

<210> SEQ ID NO 360
<211> LENGTH: 357
<212> TYPE: DNA
<213> ORGANISM: Artificial Sequence
<220> FEATURE:
<223> OTHER INFORMATION: VH 1.12

<400> SEQUENCE: 360

```
caggtgcagc tggtggagtc tgggggaggc ttggtccagc ctgggggtc  cctgagactc    60
```

```
tcctgtgcag cctctggatt cacctttagt agttatggga tgtactgggt ccgccaggct    120
ccagggaagg ggctggagtg ggtggccaag atagagcaag atggaagtga ggaatactat    180
gtggactctg tgaagggccg attcaccatc tccagagaca acgccaagaa ctcactgtat    240
ctgcaaatga atagcctgag agccgaggac acggctgtgt attactgtgc gaaagggaa     300 atactacccc tctactttga ctactggggc cagggaaccc tggtcactgt ctcctca      357
```

<210> SEQ ID NO 361
<211> LENGTH: 357
<212> TYPE: DNA
<213> ORGANISM: Artificial Sequence
<220> FEATURE:
<223> OTHER INFORMATION: VH 1.13

<400> SEQUENCE: 361

```
gaggtgcagc tggtggagtc tgggggaggc ttggtccagc ctggggggtc cctgagactc     60
tcctgtgcag cctctggatt cacctttagt agttatggga tgtactgggt ccgccaggct    120
ccagggaagg ggctggagtg ggtggccagc atagaacaag atggaagtga gaaatactat    180
gtggactctg tgaagggccg attcaccatc tccagagaca acgccaagaa ctcactgtat    240
ctgcaaatga atagcctgag agccgaggac acggctgtgt attactgtgc gaaaggggaa    300
atactacccc tctactttga ctactggggc cagggaaccc tggtcaccgt ctcctca       357
```

<210> SEQ ID NO 362
<211> LENGTH: 357
<212> TYPE: DNA
<213> ORGANISM: Artificial Sequence
<220> FEATURE:
<223> OTHER INFORMATION: VH 1.14

<400> SEQUENCE: 362

```
gaggtgcagc tggtggagtc tgggggaggc ttggtccagc gtggggggtc cctgagactc     60
tcctgtgcag cctctggatt cacctttagt agttatcgga tgtactgggt ccgccaggct    120
ccagggaagg ggctggagtg ggtggccagc atagaacaag atggaagtga ggaatactat    180
gtggactctg tgaagggccg attcaccatc tccagagaca acgccaagaa gtcactgttt    240
ctgcaaatga atagcctgag agccgaggac acggctgtgt attactgtgc gaaaggggaa    300
atactacccc tctactttga ctactggggc cagggaaccc tggtcactgt ctcttca       357
```

<210> SEQ ID NO 363
<211> LENGTH: 357
<212> TYPE: DNA
<213> ORGANISM: Artificial Sequence
<220> FEATURE:
<223> OTHER INFORMATION: VH 1.15

<400> SEQUENCE: 363

```
gaggtgcagc tggtggagtc tgggggaggc ttggtccagc ctggggggtc cctgagactc     60
tcctgtgcag cctctggatt cacctttagt agttatagca tgtactgggt ccgccaggct    120
ccagggaagg ggctggagtg ggtggccgag ataaggcaag atggaagtga gcaatactat    180
gtggactctg tgaagggccg attcaccatc tccagagaca acgccaagaa ctcactgtat    240
ctgcaaatga atagcctgag agccgaggac acggctgtgt attactgtgc gaaaggggaa    300
atactacccc tctactttga ctactggggc cagggaaccc tggtcactgt ctcttca       357
```

<210> SEQ ID NO 364
<211> LENGTH: 357

<212> TYPE: DNA
<213> ORGANISM: Artificial Sequence
<220> FEATURE:
<223> OTHER INFORMATION: VH 1.16

<400> SEQUENCE: 364

| | | | | |
|---|---|---|---|---|
| gaggtgcagc tggtggagtc tgggggaggc ttggtccagc ctgggggtc cctgagactc | | | | 60 |
| tcctgtgcag cctctggatt cacctttagt agttatagca tgtactgggt ccgccaggct | | | | 120 |
| ccagggaagg ggctggagtg ggtggccgag ataaagcaag atggaagtga gcaatactat | | | | 180 |
| gtggactctg tgaagggccg attcaccatc tccagagaca acgccaagaa ctcactgtat | | | | 240 |
| ctgcaaatga atggcctgag agccgaggac acggctgtgt attactgtgc gaaaggggaa | | | | 300 |
| atactgcccc tctacttcga ctactggggc cagggaaccc tggtcactgt ctcttca | | | | 357 |

<210> SEQ ID NO 365
<211> LENGTH: 357
<212> TYPE: DNA
<213> ORGANISM: Artificial Sequence
<220> FEATURE:
<223> OTHER INFORMATION: VH 1.17

<400> SEQUENCE: 365

| | | | | |
|---|---|---|---|---|
| gaggtgcagc tggtggagtc tgggggaggc ttggtccagc ctgggggtc cctgagactc | | | | 60 |
| tcctgtgcag cctctggatt cacctttagt agttatagca tgtactgggt ccgccaggct | | | | 120 |
| ccagggaagg ggctggagtg ggtggccgag ataaagccaa ccgggagtgt gcaatactat | | | | 180 |
| gtgtccgacg tgaagggccg attcaccatc tccagagaca acgccaagaa ctcactgtat | | | | 240 |
| ctgcaaatga atagcctgag agccgaggac acggctgtgt attactgtgc gaaaggggaa | | | | 300 |
| atactacccc tctactttga ctactggggc cagggaaccc tggtcactgt ctcttca | | | | 357 |

<210> SEQ ID NO 366
<211> LENGTH: 357
<212> TYPE: DNA
<213> ORGANISM: Artificial Sequence
<220> FEATURE:
<223> OTHER INFORMATION: VH 1.18

<400> SEQUENCE: 366

| | | | | |
|---|---|---|---|---|
| gaggtgcagc tggtggagtc tgggggaggc ttggtccagc ctgggggtc cctgagactc | | | | 60 |
| tcctgtgcag cctctggatt cacctttagt agttatagca tgtactgggt ccgccaggct | | | | 120 |
| ccagggaagg ggctggagtg ggtggccgag ataaagcaag acggcagtgt gcaatactat | | | | 180 |
| gtgggggggcg tgaagggccg attcaccatc tccagagaca acgccaagaa ctcactgtat | | | | 240 |
| ctgcaaatga atagcctgag agccgaggac acggctgtgt attactgtgc gaaaggggaa | | | | 300 |
| atactacccc tctactttga ctactggggc cagggaaccc tggtcactgt ctcttca | | | | 357 |

<210> SEQ ID NO 367
<211> LENGTH: 357
<212> TYPE: DNA
<213> ORGANISM: Artificial Sequence
<220> FEATURE:
<223> OTHER INFORMATION: VH 1.19

<400> SEQUENCE: 367

| | | | | |
|---|---|---|---|---|
| gaggtgcagc tggtggagtc tgggggaggc ttggtccagc ctgggggtc cctgagactc | | | | 60 |
| tcctgtgcaa cctctggatt cacctttagt agttatggaa tgtactgggt ccgccaggct | | | | 120 |
| ccagggaagg ggctggagtg ggtggccgag ataaaacaag atggaagtga gaaatactat | | | | 180 |

| | |
|---|---|
| gtggactccg tgaagggccg attcaccatc tccagagaca acgccaagaa ctcactgtat | 240 |
| ctgcaaatga atagcctgag agccgaggac acggctgtgt attactgtgc gaaaggggaa | 300 |
| atactacccc tctactttga ctactggggc cagggaaccc tggtcactgt ctcttca | 357 |

<210> SEQ ID NO 368
<211> LENGTH: 357
<212> TYPE: DNA
<213> ORGANISM: Artificial Sequence
<220> FEATURE:
<223> OTHER INFORMATION: VH 1.20

<400> SEQUENCE: 368

| | |
|---|---|
| gaggtgcagc tggtggagtc tgggggaggc ctggtccagc ctgggggtc cctgagactc | 60 |
| tcctgtgcag cctctggatt cacctttagt agttatggga tgtactgggt ccgccaggct | 120 |
| ccagggaagg ggctggagtg ggtggccaag atagagcaag atggaagtga ggaatactat | 180 |
| gcggactctg tgaagggccg attcaccatc tccagagaca acgccaagaa gtcactgtat | 240 |
| ctgcaaatga atagcctgag agccgaggac acggctgtgt attactgtgc gaaaggggaa | 300 |
| atactacccc tctactttga ctactggggc cagggaaccc tggtcactgt ctcttca | 357 |

<210> SEQ ID NO 369
<211> LENGTH: 357
<212> TYPE: DNA
<213> ORGANISM: Artificial Sequence
<220> FEATURE:
<223> OTHER INFORMATION: VH 1.21

<400> SEQUENCE: 369

| | |
|---|---|
| gaggtgcagc tggtggagtc tgggggaggc ttggtcctgc ctgggggtc cctgagactc | 60 |
| tcctgtgcgg cctctggatt cacctttagt agttatagca tgtactgggt ccgccaggct | 120 |
| ccagggaagg ggctggagtg ggtggccgag ataaagcaag atggaagtga gcaatactat | 180 |
| gtggactctg tgaagggccg attcaccatc tccagagaca acgccaagaa ctcactgtat | 240 |
| ctgcaaatga atagcctgag agccgaggac acggctgtgt attactgtgc gaaaggggaa | 300 |
| atactacccc tctactttga ctactggggc cagggaaccc tggtcactgt ctcttca | 357 |

<210> SEQ ID NO 370
<211> LENGTH: 357
<212> TYPE: DNA
<213> ORGANISM: Artificial Sequence
<220> FEATURE:
<223> OTHER INFORMATION: VH 1.22

<400> SEQUENCE: 370

| | |
|---|---|
| gaggtgcagc tggtggagtc tgggggaggc ttggtccggc ctgggggtc cctgagactc | 60 |
| tcctgtgcag cctctggatt cacctttagt agttatggga tgtactgggt ccgccaggct | 120 |
| ccagggaagg ggctggagtg ggtggccaag atagagcaag atggaagtga ggaatactat | 180 |
| gtggactctg tgaagggccg attcaccatc tccagagaca acgccaagaa gtcactgtat | 240 |
| ctgcaaatga atagcctgag agccgaggac acggccgtgt attactgtgc gaaaggggaa | 300 |
| atactacccc tctactttga ctactggggc cagggaaccc tggtcactgt ctcttca | 357 |

<210> SEQ ID NO 371
<211> LENGTH: 354
<212> TYPE: DNA
<213> ORGANISM: Artificial Sequence
<220> FEATURE:
<223> OTHER INFORMATION: VH 2.1

<400> SEQUENCE: 371

| caggtgcagc | tggtggagtc | tgggggaggc | ttggtccagc | ctggggggtc | cctgagactc | 60 |
| tcctgtgcag | cctctggatt | cacctttagt | agctatggga | tgggctgggt | ccgccaggct | 120 |
| ccagggaagg | ggctggagtg | ggtggccaaa | ataaaacaag | atggaagtga | aaaagactat | 180 |
| gtggactctg | tgaagggccg | attcaccatc | tccagagaca | acgccaagaa | gtcactgttt | 240 |
| ctgcaaatga | acagcctgag | agccgaggac | acggctgtgt | attattgtgc | gagagagagt | 300 |
| atatttggaa | tccccgagga | ctggggccag | ggaaccctgg | tcaccgtctc | ctca | 354 |

<210> SEQ ID NO 372
<211> LENGTH: 378
<212> TYPE: DNA
<213> ORGANISM: Artificial Sequence
<220> FEATURE:
<223> OTHER INFORMATION: nucleic acid encoding VH 3.1

<400> SEQUENCE: 372

| caggtgcagc | tggtgcagtc | tggggctgag | gtgaagaagc | ctggggcctc | agtgaaggtc | 60 |
| tcctgcaagg | cttctggata | caccttcacc | ggctactata | tgcactgggt | gcgacaggcc | 120 |
| cctggacaag | ggcttgagtg | gatgggatgg | atcaacccta | acagtggtgg | cacaaactat | 180 |
| gcacagaagt | tcagggcag | ggtcaccatg | accaggaca | cgtccatcag | cacagcctac | 240 |
| atggagctga | gcaggctgag | atctgacgac | acggccgtgt | attactgtgc | gagtatggat | 300 |
| cgggattatt | atgatactag | tggttacttt | ggctggttcg | actcctgggg | ccagggaacc | 360 |
| ctggtcaccg | tctcttca |  |  |  |  | 378 |

<210> SEQ ID NO 373
<211> LENGTH: 378
<212> TYPE: DNA
<213> ORGANISM: Artificial Sequence
<220> FEATURE:
<223> OTHER INFORMATION: nucleic acid encoding VH 3.2

<400> SEQUENCE: 373

| caggttcagc | tggtgcagtc | tggagctgag | gtaaagaagc | ctggggcctc | ggtgaaggtc | 60 |
| tcctgtaagg | cttccggata | taacgcggac | gcctattata | taaattgggt | gcgacaggcc | 120 |
| cctggacaag | gtcttgagtg | gatgggaagt | atcaagccta | ataccggtgc | cacaaaatat | 180 |
| gcacagaagt | tcagggcag | agtcaccata | accaggaca | cgtccatcag | cacagcctac | 240 |
| atggagctga | gcaggctgag | atctgacgac | acggccgtgt | attactgtgc | gagtctggat | 300 |
| cgggatacgt | ggtacccgca | ctcctacgcg | gggtggttcg | acgcgtgggg | ccagggaacc | 360 |
| ctggtcaccg | tctcttca |  |  |  |  | 378 |

<210> SEQ ID NO 374
<211> LENGTH: 378
<212> TYPE: DNA
<213> ORGANISM: Artificial Sequence
<220> FEATURE:
<223> OTHER INFORMATION: nucleic acid encoding VH 3.3

<400> SEQUENCE: 374

| caggtgcagc | tggtgcagtc | tggggctgag | gtgaagaagc | ctggggcctc | agtgaaggtc | 60 |
| tcctgcgcag | cttccggata | caccttcacc | gactactatc | tgcactgggt | gcgacaggcc | 120 |
| cctggacaag | ggcttgagtg | gatggggtgg | atcaacccta | acactggcac | cacaaagtat | 180 |

| | |
|---|---|
| gcacgggagt ttgagggcag agtcaccatg accagggaca cgtccatcag cacagcctac | 240 |
| atggagctga gcaggctgag atctgacgac acggccgtgt attactgtgc gagtatggat | 300 |
| cgggattatt atgatactag tggttacttt ggctggttcg actcctgggg ccagggaacc | 360 |
| ctggtcaccg tctcttca | 378 |

<210> SEQ ID NO 375
<211> LENGTH: 378
<212> TYPE: DNA
<213> ORGANISM: Artificial Sequence
<220> FEATURE:
<223> OTHER INFORMATION: nucleic acid encoding VH 3.5

<400> SEQUENCE: 375

| | |
|---|---|
| caggtccagc tggtgcagtc tggggctgag gtgaagaagc ctggggcctc agtgaaggtc | 60 |
| tcctgcgcag cttccggata caccttcacc gactactatc tgcactgggt gcgacaggcc | 120 |
| cctggacaag gcttgagtg gatggggtgg atcaaccta acactggcac cacaaagtat | 180 |
| gcacgggagt ttgagggcag agtcaccatg accagggaca cgtccatcag cacagcctac | 240 |
| atggagctga gcaggctgag atctgacgac acggccgtgt attactgtgc gagtctggat | 300 |
| cgggattggc gctcgcccaa cgactacttt ggctggttcg actcgtgggg ccagggaacc | 360 |
| ctggtcaccg tctcttca | 378 |

<210> SEQ ID NO 376
<211> LENGTH: 378
<212> TYPE: DNA
<213> ORGANISM: Artificial Sequence
<220> FEATURE:
<223> OTHER INFORMATION: nucleic acid encoding VH 3.6

<400> SEQUENCE: 376

| | |
|---|---|
| caggtccagc tggtgcagtc tggggctgag gtgaagaagc ctggggcctc agtgaaggtc | 60 |
| tcctgcgcag cttccggata caccttcacc gactactatc tgcactgggt gcgacaggcc | 120 |
| cctggacaag gcttgagtg gatggggtgg atcaaccta acactggcac cacaaagtat | 180 |
| gcacgggagt ttgagggcag agtcaccatg accagggaca cgtccatcag cacagcctac | 240 |
| atggagctga gcaggctgag atctgacgac acggccgtgt attactgtgc gagtctggat | 300 |
| cgggattggc gctcgcccaa cgactactac gggtggttcg actcgtgggg ccagggaacc | 360 |
| ctggtcaccg tctcttca | 378 |

<210> SEQ ID NO 377
<211> LENGTH: 378
<212> TYPE: DNA
<213> ORGANISM: Artificial Sequence
<220> FEATURE:
<223> OTHER INFORMATION: nucleic acid encoding VH 3.9

<400> SEQUENCE: 377

| | |
|---|---|
| caggtgcagc tggtgcagtc tggggctgag gtgaagaagc ctggggcctc agtgaaggtc | 60 |
| tcctgtaagg cttccggata taacttcgac gcctatcata taaattgggt gcgacaggcc | 120 |
| cctggacaag gcttgagtg gatgggaagt atcaagccta atagtggtgc cacaaaatat | 180 |
| gcacagaagt ttcagggcag agtcaccata accagggaca cgtccatcag cacagcctac | 240 |
| atggagctga gcaggctgag atctgacgac acggccgtgt attactgtgc gagtatggat | 300 |
| cgggattact atgatactag tggttacttt ggctggttcg actcctgggg ccagggaacc | 360 |
| ctggtcaccg tctcctca | 378 |

<210> SEQ ID NO 378
<211> LENGTH: 378
<212> TYPE: DNA
<213> ORGANISM: Artificial Sequence
<220> FEATURE:
<223> OTHER INFORMATION: nucleic acid encoding VH 3.11

<400> SEQUENCE: 378

```
caggtgcagc tggtgcagtc tggggctgag gtgaagaagc ctggggcctc agtgaaggtc    60
tcctgtaagg cttccggata aacttcgac gcctatcata taaattgggt gcgacaggcc   120
cctggacaag gtcttgagtg gatgggaagt atcaagccta atagtggtgc cacaaaatat   180
gcacagaagt tcagggcag agtcaccata accagggaca cgtccatcag cacagcctac   240
atggagctga gcaggctgag atctgacgac acggccgtgt attactgtgc gagtctggat   300
cgggatacgt ggtacccgca ctcctacttt ggctggttcg actcgtgggg ccagggaacc   360
ctggtcaccg tctcttca                                                378
```

<210> SEQ ID NO 379
<211> LENGTH: 378
<212> TYPE: DNA
<213> ORGANISM: Artificial Sequence
<220> FEATURE:
<223> OTHER INFORMATION: nucleic acid encoding VH 3.13

<400> SEQUENCE: 379

```
caggtccagc tggtgcagtc tggggctgag gtgaagaagc ctggggcctc agtgaaggtc    60
tcctgtaagg cttccggata aacttcgac gcctatcata taaattgggt gcgacaggcc   120
cctggacaag gtcttgagtg gatgggaagt atcaagccta atagtggtgc cacaaaatat   180
gcacagaagt tcagggcag agtcaccata accagggaca cgtccatcag cacagcctac   240
atggagctga gcaggctgag atctgacgac acggccgtgt attactgtgc gagtctggat   300
cgggatacgt ggtacccgca ctcctacgcg gggtggttcg actcgtgggg ccagggaacc   360
ctggtcaccg tctcttca                                                378
```

<210> SEQ ID NO 380
<211> LENGTH: 360
<212> TYPE: DNA
<213> ORGANISM: Artificial Sequence
<220> FEATURE:
<223> OTHER INFORMATION: nucleic acid encoding VH 4.1

<400> SEQUENCE: 380

```
caggtgcagc tggtggagtc tgggggaggc ttggtccagc ctgggggtc cctgagactc    60
tcctgtgcag cctctggatt cacctttagt agctattgga tgaactgggt ccgccaggct   120
ccagggaagg gctggaatg ggtggccacc ataaaacaag atggaagtga gaaatactat   180
gtggactctg tgaagggccg attcaccatc tccagagaca cgccacgaa ctcactgttt   240
ctgcaaatga acagcctgag agccgaggac acggctgtgt attactgtgc gaggggagat   300
acgatttttcg acggtgcttt tgatatctgg ggccaaggga caatggtcac tgtctcctca   360
```

<210> SEQ ID NO 381
<211> LENGTH: 348
<212> TYPE: DNA
<213> ORGANISM: Artificial Sequence
<220> FEATURE:
<223> OTHER INFORMATION: nucleic acid encoding VH 5.1

<400> SEQUENCE: 381

```
gaggtgcagc tggtggagtc tgggggaggc ttggtccagc ctgggggtc cctgagactc        60
tcctgtgcag cctctggatt cacctttagt agctattgga tgagctgggt ccgccaggct       120
ccagggaagg ggctggagtg ggtggccaac ataaagcaag atggaagtga gaaatactat       180
gtggactctg tgaagggccg attcaccatc tccagagaca cgccaagaa ctcactgtat        240
ctgcaaatga acagcctgag agccgaggac acggctgtgt attactgtgc gcatcagtgg       300
cccttctttg actactgggg ccaagggaca atggtcactg tctcctca                    348
```

<210> SEQ ID NO 382
<211> LENGTH: 73
<212> TYPE: DNA
<213> ORGANISM: Artificial Sequence
<220> FEATURE:
<223> OTHER INFORMATION: Primer

<400> SEQUENCE: 382

```
gccgctggat tgttattact cgcggcccag ccggccatgg cccaggtbca gctggtgcag        60
tctggggctg agg                                                          73
```

<210> SEQ ID NO 383
<211> LENGTH: 65
<212> TYPE: DNA
<213> ORGANISM: Artificial Sequence
<220> FEATURE:
<223> OTHER INFORMATION: Primer

<400> SEQUENCE: 383

```
gccgctggat tgttattact cgcggcccag ccggccatgg cccagatcac cttgaaggag        60
tctgg                                                                   65
```

<210> SEQ ID NO 384
<211> LENGTH: 71
<212> TYPE: DNA
<213> ORGANISM: Artificial Sequence
<220> FEATURE:
<223> OTHER INFORMATION: Primer

<400> SEQUENCE: 384

```
gccgctggat tgttattact cgcggcccag ccggccatgg ccsaggtgca gctggtggag        60
tctgggggag g                                                            71
```

<210> SEQ ID NO 385
<211> LENGTH: 65
<212> TYPE: DNA
<213> ORGANISM: Artificial Sequence
<220> FEATURE:
<223> OTHER INFORMATION: Primer

<400> SEQUENCE: 385

```
gccgctggat tgttattact cgcggcccag ccggccatgg cccaggtgca gctgcaggag        60
tcggg                                                                   65
```

<210> SEQ ID NO 386
<211> LENGTH: 65
<212> TYPE: DNA
<213> ORGANISM: Artificial Sequence
<220> FEATURE:
<223> OTHER INFORMATION: Primer

<400> SEQUENCE: 386
gccgctggat tgttattact cgcggcccag ccggccatgg cccaggtaca gctgcagcag    60
tcagg                                                                65

<210> SEQ ID NO 387
<211> LENGTH: 54
<212> TYPE: DNA
<213> ORGANISM: Artificial Sequence
<220> FEATURE:
<223> OTHER INFORMATION: Primer

<400> SEQUENCE: 387
ccgtggtgat ggtggtgatg gctaccgcca ccctcgagtg argagacrgt gacc          54

<210> SEQ ID NO 388
<211> LENGTH: 31
<212> TYPE: DNA
<213> ORGANISM: Artificial Sequence
<220> FEATURE:
<223> OTHER INFORMATION: primer

<400> SEQUENCE: 388
ctcgagggtg gcggtagcca tcaccaccat c                                   31

<210> SEQ ID NO 389
<211> LENGTH: 29
<212> TYPE: DNA
<213> ORGANISM: Artificial Sequence
<220> FEATURE:
<223> OTHER INFORMATION: primer

<400> SEQUENCE: 389
tccatggcca tcgccggctg ggccgcgag                                      29

<210> SEQ ID NO 390
<211> LENGTH: 34
<212> TYPE: DNA
<213> ORGANISM: Artificial Sequence
<220> FEATURE:
<223> OTHER INFORMATION: Primer

<400> SEQUENCE: 390
gctaccgcca ccctcgagtg argagacrgt gacc                                34

<210> SEQ ID NO 391
<211> LENGTH: 50
<212> TYPE: DNA
<213> ORGANISM: Artificial Sequence
<220> FEATURE:
<223> OTHER INFORMATION: Primer

<400> SEQUENCE: 391
ggaacagacc accatggccc aggtbcagct ggtgcagtct ggggctgagg               50

<210> SEQ ID NO 392
<211> LENGTH: 23
<212> TYPE: DNA
<213> ORGANISM: Artificial Sequence
<220> FEATURE:
<223> OTHER INFORMATION: Primer

<400> SEQUENCE: 392
gacacggccg tgtattactg tgc                                            23

<210> SEQ ID NO 393

```
<211> LENGTH: 23
<212> TYPE: DNA
<213> ORGANISM: Artificial Sequence
<220> FEATURE:
<223> OTHER INFORMATION: Primer

<400> SEQUENCE: 393
gcacagtaat acacggccgt gtc                                             23

<210> SEQ ID NO 394
<211> LENGTH: 98
<212> TYPE: PRT
<213> ORGANISM: Artificial Sequence
<220> FEATURE:
<223> OTHER INFORMATION: scaffold sequence

<400> SEQUENCE: 394
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

```
<210> SEQ ID NO 395
<211> LENGTH: 294
<212> TYPE: DNA
<213> ORGANISM: Artificial Sequence
<220> FEATURE:
<223> OTHER INFORMATION: scaffold sequence

<400> SEQUENCE: 395
caggtgcagc tggtgcagtc tggggctgag gtgaagaagc ctggggcctc agtgaaggtc     60
tcctgcaagg cttctggata caccttcacc ggctactata tgcactgggt gcgacaggcc    120
cctggacaag ggcttgagtg gatgggatgg atcaaccccta acagtggtgg cacaaactat    180
gcacagaagt tcagggcag ggtcaccatg accagggaca cgtccatcag cacagcctac    240
atggagctga gcaggctgag atctgacgac acggccgtgt attactgtgc gaga          294

<210> SEQ ID NO 396
<211> LENGTH: 12
<212> TYPE: PRT
<213> ORGANISM: Artificial Sequence
<220> FEATURE:
<223> OTHER INFORMATION: C terminal extension

<400> SEQUENCE: 396
```

Leu Glu Gly Gly Gly Ser His His His His His His
1               5                   10

```
<210> SEQ ID NO 397
<211> LENGTH: 71
<212> TYPE: DNA
<213> ORGANISM: Artificial Sequence
<220> FEATURE:
```

<223> OTHER INFORMATION: primer

<400> SEQUENCE: 397
gccgctggat tgttattact cgcggcccag ccggccatgg ccsaggtgca gctggtggag     60
tctgggggag g     71

<210> SEQ ID NO 398
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (18)..(18)
<223> OTHER INFORMATION: a, c, t, g, unknown or other

<400> SEQUENCE: 398
tggcggaccc agtacatnyb ataactacta aagtg     36

<210> SEQ ID NO 399
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (28)..(28)
<223> OTHER INFORMATION: a, c, t, g, unknown or other

<400> SEQUENCE: 399
cacatagtat tbctcacttc catcttgnty tatsyyggcc acccactcca g     51

<210> SEQ ID NO 400
<211> LENGTH: 37
<212> TYPE: DNA
<213> ORGANISM: Artificial Sequence
<220> FEATURE:
<223> OTHER INFORMATION: primer

<400> SEQUENCE: 400
caagatggaa gtgagvaata ctatgtggac tctgtga     37

<210> SEQ ID NO 401
<211> LENGTH: 45
<212> TYPE: DNA
<213> ORGANISM: Artificial Sequence
<220> FEATURE:
<223> OTHER INFORMATION: primer

<400> SEQUENCE: 401
aggctattca tttgcagawa cagtgasttc ttggcgttgt ctctg     45

<210> SEQ ID NO 402
<211> LENGTH: 45
<212> TYPE: DNA
<213> ORGANISM: Artificial Sequence
<220> FEATURE:
<223> OTHER INFORMATION: primer

<400> SEQUENCE: 402
cagagacaac gccaagaast cactgtwtct gcaaatgaat agcct     45

<210> SEQ ID NO 403
<211> LENGTH: 36

```
<212> TYPE: DNA
<213> ORGANISM: Artificial Sequence
<220> FEATURE:
<223> OTHER INFORMATION: primer

<400> SEQUENCE: 403
agtatttccc ctttcgcaca gtaatacaca gccgtg                              36

<210> SEQ ID NO 404
<211> LENGTH: 67
<212> TYPE: DNA
<213> ORGANISM: Artificial Sequence
<220> FEATURE:
<223> OTHER INFORMATION: primer

<400> SEQUENCE: 404
cacggctgtg tattactgtg cgaaagggga aatactaccc ctcyastttg acyactgggg   60
ccaggga                                                              67

<210> SEQ ID NO 405
<211> LENGTH: 54
<212> TYPE: DNA
<213> ORGANISM: Artificial Sequence
<220> FEATURE:
<223> OTHER INFORMATION: primer

<400> SEQUENCE: 405
ccgtggtgat ggtggtgatg gctaccgcca ccctcgagtg argagacrgt gacc         54

<210> SEQ ID NO 406
<211> LENGTH: 72
<212> TYPE: DNA
<213> ORGANISM: Artificial Sequence
<220> FEATURE:
<223> OTHER INFORMATION: Primer

<400> SEQUENCE: 406
gcactctccc ctgttgaagc tctttgtgac gggcgagctc aggccctgat gggtgacttc   60
gcaggcgtag ac                                                        72

<210> SEQ ID NO 407
<211> LENGTH: 41
<212> TYPE: DNA
<213> ORGANISM: Artificial Sequence
<220> FEATURE:
<223> OTHER INFORMATION: Primer

<400> SEQUENCE: 407
gcagctaata cgactcacta tagggagaca gaccaccatg g                        41

<210> SEQ ID NO 408
<211> LENGTH: 21
<212> TYPE: DNA
<213> ORGANISM: Artificial Sequence
<220> FEATURE:
<223> OTHER INFORMATION: Primer

<400> SEQUENCE: 408
gcactctccc ctgttgaagc t                                              21

<210> SEQ ID NO 409
<211> LENGTH: 128
<212> TYPE: PRT
<213> ORGANISM: Artificial Sequence
<220> FEATURE:
```

<223> OTHER INFORMATION: clone

<400> SEQUENCE: 409

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Glu Gln Asp Gly Ser Glu Glu Tyr Tyr Val Asp Ser Val
    50                  55                  60

Lys Gly Arg Phe Thr Ile Ser Arg Asp Asn Ala Lys Lys Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser Ala Ala Ala His His His His His His
        115                 120                 125

<210> SEQ ID NO 410
<211> LENGTH: 128
<212> TYPE: PRT
<213> ORGANISM: Artificial Sequence
<220> FEATURE:
<223> OTHER INFORMATION: clone

<400> SEQUENCE: 410

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Val Gln Tyr Tyr Val Ser Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser Ala Ala Ala His His His His His His
        115                 120                 125

<210> SEQ ID NO 411
<211> LENGTH: 120
<212> TYPE: PRT
<213> ORGANISM: Artificial Sequence
<220> FEATURE:
<223> OTHER INFORMATION: clone

<400> SEQUENCE: 411

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val

```
            35                  40                  45
Ala Glu Ile Lys Gln Asp Gly Ser Val Gln Tyr Tyr Val Ser Asp Val
        50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                85                  90                  95
Ala Lys Gly Glu Ile Leu Pro Leu Tyr Phe Asp Tyr Trp Gly Gln Gly
            100                 105                 110
Thr Leu Val Thr Val Ser Ser Ala
            115                 120

<210> SEQ ID NO 412
<211> LENGTH: 128
<212> TYPE: PRT
<213> ORGANISM: Artificial Sequence
<220> FEATURE:
<223> OTHER INFORMATION: clone

<400> SEQUENCE: 412

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ser Met Tyr Trp Val Arg Gln Ala Pro Gly Lys Gly Leu Glu Trp Val
        35                  40                  45
Ala Glu Ile Lys Gln Asp Gly Ser Val Gln Tyr Tyr Val Asp Ser Val
        50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                85                  90                  95
Ala Lys Gly Glu Ile Leu Pro Leu Tyr Phe Asp Tyr Trp Gly Gln Gly
            100                 105                 110
Thr Leu Val Thr Val Ser Ser Ala Ala Ala His His His His His His
            115                 120                 125

<210> SEQ ID NO 413
<211> LENGTH: 120
<212> TYPE: PRT
<213> ORGANISM: Artificial Sequence
<220> FEATURE:
<223> OTHER INFORMATION: clone

<400> SEQUENCE: 413

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ser Met Tyr Trp Val Arg Gln Ala Pro Gly Lys Gly Leu Glu Trp Val
        35                  40                  45
Ala Glu Ile Lys Gln Asp Gly Ser Val Gln Tyr Tyr Val Asp Ser Val
        50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                85                  90                  95
```

Ala Lys Gly Glu Ile Leu Pro Leu Tyr Phe Asp Tyr Trp Gly Gln Gly
            100                 105                 110

Thr Leu Val Thr Val Ser Ser Ala
        115                 120

<210> SEQ ID NO 414
<211> LENGTH: 131
<212> TYPE: PRT
<213> ORGANISM: Artificial Sequence
<220> FEATURE:
<223> OTHER INFORMATION: clone

<400> SEQUENCE: 414

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser Leu Glu Gly Gly Gly Ser His His His
        115                 120                 125

His His His
        130

<210> SEQ ID NO 415
<211> LENGTH: 131
<212> TYPE: PRT
<213> ORGANISM: Artificial Sequence
<220> FEATURE:
<223> OTHER INFORMATION: clone

<400> SEQUENCE: 415

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Lys Ile Glu Gln Asp Gly Ser Glu Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser Leu Glu Gly Gly Gly Ser His His His
        115                 120                 125

His His His
        130

```
<210> SEQ ID NO 416
<211> LENGTH: 131
<212> TYPE: PRT
<213> ORGANISM: Artificial Sequence
<220> FEATURE:
<223> OTHER INFORMATION: clone

<400> SEQUENCE: 416

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Glu Gln Asp Gly Ser Glu Glu Tyr Tyr Val Asp Ser Val
    50                  55                  60

Lys Gly Arg Phe Thr Ile Ser Arg Asp Asn Ala Lys Lys Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser Leu Glu Gly Gly Gly Ser His His His
        115                 120                 125

His His His
        130

<210> SEQ ID NO 417
<211> LENGTH: 131
<212> TYPE: PRT
<213> ORGANISM: Artificial Sequence
<220> FEATURE:
<223> OTHER INFORMATION: clone

<400> SEQUENCE: 417

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Val Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser Leu Glu Gly Gly Gly Ser His His His
        115                 120                 125

His His His
        130

<210> SEQ ID NO 418
<211> LENGTH: 138
<212> TYPE: PRT
```

<213> ORGANISM: Artificial Sequence
<220> FEATURE:
<223> OTHER INFORMATION: clone

<400> SEQUENCE: 418

```
Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Asn Ala Asp Ala Tyr
            20                  25                  30
Tyr Ile Asn Trp Val Arg Gln Ala Pro Gly Gln Gly Leu Glu Trp Met
        35                  40                  45
Gly Ser Ile Lys Pro Asn Thr Gly Ala Thr Lys Tyr Ala Gln Lys Phe
    50                  55                  60
Gln Gly Arg Val Thr Ile Thr Arg Asp Thr Ser Ile Ser Thr Ala Tyr
65                  70                  75                  80
Met Glu Leu Ser Arg Leu Arg Ser Asp Thr Ala Val Tyr Tyr Cys
                85                  90                  95
Ala Ser Leu Asp Arg Asp Thr Trp Tyr Pro His Ser Tyr Ala Gly Trp
            100                 105                 110
Phe Asp Ala Trp Gly Gln Gly Thr Leu Val Thr Val Ser Ser Leu Glu
        115                 120                 125
Gly Gly Gly Ser His His His His His
    130                 135
```

<210> SEQ ID NO 419
<211> LENGTH: 131
<212> TYPE: PRT
<213> ORGANISM: Artificial Sequence
<220> FEATURE:
<223> OTHER INFORMATION: clone

<400> SEQUENCE: 419

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ser Met Tyr Trp Val Arg Gln Ala Pro Gly Lys Gly Leu Glu Trp Val
        35                  40                  45
Ala Asn Ile Lys Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Phe
65                  70                  75                  80
Leu Gln Met Asn Ser Leu Arg Ala Glu Asp Thr Ala Val Tyr Tyr Cys
                85                  90                  95
Ala Lys Gly Glu Ile Leu Pro Leu His Phe Asp Tyr Trp Gly Gln Gly
            100                 105                 110
Thr Leu Val Thr Val Ser Ser Leu Glu Gly Gly Gly Ser His His His
        115                 120                 125
His His His
    130
```

<210> SEQ ID NO 420
<211> LENGTH: 131
<212> TYPE: PRT
<213> ORGANISM: Artificial Sequence
<220> FEATURE:
<223> OTHER INFORMATION: clone

<400> SEQUENCE: 420

```
Glu Val Gln Leu Val Glu Ser Gly Gly Gly Leu Val Gln Pro Gly Gly
 1               5                  10                 15

Ser Leu Arg Leu Ser Cys Ala Ala Ser Gly Phe Thr Phe Ser Ser Tyr
             20                  25                  30

Ser Met Tyr Trp Val Arg Gln Ala Pro Gly Lys Gly Leu Glu Trp Val
         35                  40                  45

Ala Glu Ile Lys Gln Asp Gly Ser Glu Gln Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Gly Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
             100                 105                 110

Thr Leu Val Thr Val Ser Ser Leu Glu Gly Gly Gly Ser His His His
         115                 120                 125

His His His
    130

<210> SEQ ID NO 421
<211> LENGTH: 131
<212> TYPE: PRT
<213> ORGANISM: Artificial Sequence
<220> FEATURE:
<223> OTHER INFORMATION: clone

<400> SEQUENCE: 421

Glu Val Gln Leu Val Glu Ser Gly Gly Gly Leu Val Gln Pro Gly Gly
 1               5                  10                 15

Ser Leu Arg Leu Ser Cys Ala Ala Ser Gly Phe Thr Phe Ser Ser Tyr
             20                  25                  30

Gly Met Tyr Trp Val Arg Gln Ala Pro Gly Lys Gly Leu Glu Trp Val
         35                  40                  45

Ala Lys Ile Glu Gln Asp Gly Ser Glu Tyr Tyr Ala Asp Ser Val
     50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
             100                 105                 110

Thr Leu Val Thr Val Ser Ser Leu Glu Gly Gly Gly Ser His His His
         115                 120                 125

His His His
    130

<210> SEQ ID NO 422
<211> LENGTH: 131
<212> TYPE: PRT
<213> ORGANISM: Artificial Sequence
<220> FEATURE:
<223> OTHER INFORMATION: clone

<400> SEQUENCE: 422

Glu Val Gln Leu Val Glu Ser Gly Gly Gly Leu Val Gln Pro Gly Gly
 1               5                  10                 15

Ser Leu Arg Leu Ser Cys Ala Thr Ser Gly Phe Thr Phe Ser Ser Tyr
```

```
                    20                  25                  30
Gly Met Tyr Trp Val Arg Gln Ala Pro Gly Lys Gly Leu Glu Trp Val
                35                  40                  45

Ala Glu Ile Lys Gln Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser Leu Glu Gly Gly Gly Ser His His His
            115                 120                 125

His His His
    130

<210> SEQ ID NO 423
<211> LENGTH: 131
<212> TYPE: PRT
<213> ORGANISM: Artificial Sequence
<220> FEATURE:
<223> OTHER INFORMATION: clone

<400> SEQUENCE: 423

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
                35                  40                  45

Ala Glu Ile Lys Pro Thr Gly Ser Val Gln Tyr Tyr Val Ser Asp Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser Leu Glu Gly Gly Gly Ser His His His
            115                 120                 125

His His His
    130

<210> SEQ ID NO 424
<211> LENGTH: 131
<212> TYPE: PRT
<213> ORGANISM: Artificial Sequence
<220> FEATURE:
<223> OTHER INFORMATION: clone

<400> SEQUENCE: 424

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
                35                  40                  45
```

Ala Glu Ile Lys Gln Asp Gly Ser Val Gln Tyr Tyr Val Gly Val
   50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
            100                 105                 110

Thr Leu Val Thr Val Ser Ser Leu Glu Gly Gly Gly Ser His His
            115                 120                 125

His His His
   130

<210> SEQ ID NO 425
<211> LENGTH: 131
<212> TYPE: PRT
<213> ORGANISM: Artificial Sequence
<220> FEATURE:
<223> OTHER INFORMATION: clone

<400> SEQUENCE: 425

Glu Val Gln Leu Val Glu Ser Gly Gly Gly Leu Val Leu Pro Gly Gly
 1               5                  10                  15

Ser Leu Arg Leu Ser Cys Ala Ala Ser Gly Phe Thr Phe Ser Ser Tyr
                20                  25                  30

Ser Met Tyr Trp Val Arg Gln Ala Pro Gly Lys Gly Leu Glu Trp Val
             35                  40                  45

Ala Glu Ile Lys Gln Asp Gly Ser Glu Gln Tyr Tyr Val Asp Ser Val
   50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
            100                 105                 110

Thr Leu Val Thr Val Ser Ser Leu Glu Gly Gly Gly Ser His His His
            115                 120                 125

His His His
   130

<210> SEQ ID NO 426
<211> LENGTH: 15
<212> TYPE: DNA
<213> ORGANISM: Artificial Sequence
<220> FEATURE:
<223> OTHER INFORMATION: linker sequence

<400> SEQUENCE: 426
ggggsggggs ggggs                                                15

<210> SEQ ID NO 427
<211> LENGTH: 12
<212> TYPE: DNA
<213> ORGANISM: Artificial Sequence
<220> FEATURE:
<223> OTHER INFORMATION: linker sequence

<400> SEQUENCE: 427
aaggggsggg gs                                                   12

<210> SEQ ID NO 428
<211> LENGTH: 22
<212> TYPE: DNA
<213> ORGANISM: Artificial Sequence
<220> FEATURE:
<223> OTHER INFORMATION: linker sequence

<400> SEQUENCE: 428
aaggggsggg gsggggsggg gs        22

<210> SEQ ID NO 429
<211> LENGTH: 33
<212> TYPE: DNA
<213> ORGANISM: Artificial Sequence
<220> FEATURE:
<223> OTHER INFORMATION: linker sequence

<400> SEQUENCE: 429
aaggggsggg gsggggsggg ggsggggsgg ggs        33

<210> SEQ ID NO 430
<211> LENGTH: 253
<212> TYPE: PRT
<213> ORGANISM: Artificial Sequence
<220> FEATURE:
<223> OTHER INFORMATION: 1.10-3(G4S)-1.1(E1/6Q)

<400> SEQUENCE: 430

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Glu Gln Asp Gly Ser Glu Glu Tyr Tyr Val Asp Ser Val
    50                  55                  60

Lys Gly Arg Phe Thr Ile Ser Arg Asp Asn Ala Lys Lys Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Val Gln Leu Val Gln Ser Gly Gly Gly
    130                 135                 140

Leu Val Gln Pro Gly Gly Ser Leu Arg Leu Ser Cys Ala Ala Ser Gly
145                 150                 155                 160

Phe Thr Phe Ser Ser Tyr Ser Met Tyr Trp Val Arg Gln Ala Pro Gly
                165                 170                 175

Lys Gly Leu Glu Trp Val Ala Asn Ile Lys Gln Asp Gly Ser Glu Lys
            180                 185                 190

Tyr Tyr Val Asp Ser Val Lys Gly Arg Phe Thr Ile Ser Arg Asp Asn
        195                 200                 205

Ala Lys Asn Ser Leu Phe Leu Gln Met Asn Ser Leu Arg Ala Glu Asp
    210                 215                 220

Thr Ala Val Tyr Tyr Cys Ala Lys Gly Glu Ile Leu Pro Leu His Phe
225                 230                 235                 240
```

Asp Tyr Trp Gly Gln Gly Thr Leu Val Thr Val Ser Ser
              245                 250

<210> SEQ ID NO 431
<211> LENGTH: 759
<212> TYPE: DNA
<213> ORGANISM: Artificial Sequence
<220> FEATURE:
<223> OTHER INFORMATION: clone

<400> SEQUENCE: 431

```
gaggtgcagc tggtggagtc tgggggaggc ttggtccagc ctggggggtc cctgagactc      60
tcctgtgcag cctctggatt cacctttagt agttatcgca tgtactgggt ccgccaggct     120
ccagggaagg gctggagtg gtggccagc atagaacaag atggaagtga ggaatactat      180
gtggactctg tgaagggccg attcaccatc tccagagaca acgccaagaa gtcactgttt     240
ctgcaaatga atagcctgag agccgaggac acggctgtgt attactgtgc gaaggggaa     300
atactacccc tctactttga ctactgggc cagggaaccc tggtcaccgt ctcctcaggt     360
ggaggaggta gtggtggagg aggtagtggt ggaggaggta gtcaggtgca gctggtgcag     420
tctgggggag gcttggtcca gcctgggggg tccctgagac tctcctgtgc agcctctgga     480
ttcacccttta gtagttattc gatgtactgg gtccgccagg ctccagggaa ggggctggag     540
tgggtggcca acataaagca agatggaagt gagaaatact atgtggactc tgtgaagggc     600
cgattcacca tctccagaga caacgccaag aactcactgt ttctgcaaat gaatagcctg     660
agagccgagg acacggctgt gtattactgt gcgaaagggg aaaatactacc cctccacttt     720
gactactggg gccagggaac cctggtcacc gtctcttca                             759
```

<210> SEQ ID NO 432
<211> LENGTH: 267
<212> TYPE: PRT
<213> ORGANISM: Artificial Sequence
<220> FEATURE:
<223> OTHER INFORMATION: 3.2-4(G4S)-1.2

<400> SEQUENCE: 432

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Ala Asp Ala Tyr
            20                  25                  30

Tyr Ile Asn Trp Val Arg Gln Ala Pro Gly Gln Gly Leu Glu Trp Met
        35                  40                  45

Gly Ser Ile Lys Pro Asn Thr Gly Ala Thr Lys Tyr Ala Gln Lys Phe
    50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Ser Leu Asp Arg Asp Thr Trp Tyr Pro His Ser Tyr Ala Gly Trp
            100                 105                 110

Phe Asp Ala Trp Gly Gln Gly Thr Leu Val Thr Val Ser Ser Ala Ala
        115                 120                 125

Gly Gly Gly Gly Ser Gly Gly Gly Gly Ser Gly Gly Gly Gly Ser Gly
    130                 135                 140

Gly Gly Gly Ser Glu Val Gln Leu Val Glu Ser Gly Gly Gly Leu Val
145                 150                 155                 160

| Gln | Pro | Gly | Gly | Ser | Leu | Arg | Leu | Ser | Cys | Ala | Ala | Ser | Gly | Phe | Thr |
|---|---|---|---|---|---|---|---|---|---|---|---|---|---|---|---|
| | | | | 165 | | | | | 170 | | | | | 175 | |

| Phe | Ser | Ser | Tyr | Ser | Met | Tyr | Trp | Val | Arg | Gln | Ala | Pro | Gly | Lys | Gly |
|---|---|---|---|---|---|---|---|---|---|---|---|---|---|---|---|
| | | | 180 | | | | | 185 | | | | | 190 | | |

| Leu | Glu | Trp | Val | Ala | Glu | Ile | Lys | Gln | Asp | Gly | Ser | Val | Gln | Tyr | Tyr |
|---|---|---|---|---|---|---|---|---|---|---|---|---|---|---|---|
| | | | 195 | | | | | 200 | | | | | 205 | | |

| Val | Ser | Asp | Val | Lys | Gly | Arg | Phe | Thr | Ile | Ser | Arg | Asp | Asn | Ala | Lys |
|---|---|---|---|---|---|---|---|---|---|---|---|---|---|---|---|
| 210 | | | | | 215 | | | | | 220 | | | | | |

| Asn | Ser | Leu | Tyr | Leu | Gln | Met | Asn | Ser | Leu | Arg | Ala | Glu | Asp | Thr | Ala |
|---|---|---|---|---|---|---|---|---|---|---|---|---|---|---|---|
| 225 | | | | | 230 | | | | | 235 | | | | | 240 |

| Val | Tyr | Tyr | Cys | Ala | Lys | Gly | Glu | Ile | Leu | Pro | Leu | Tyr | Phe | Asp | Tyr |
|---|---|---|---|---|---|---|---|---|---|---|---|---|---|---|---|
| | | | 245 | | | | | 250 | | | | | 255 | | |

| Trp | Gly | Gln | Gly | Thr | Leu | Val | Thr | Val | Ser | Ser |
|---|---|---|---|---|---|---|---|---|---|---|
| | | | 260 | | | | | 265 | | |

<210> SEQ ID NO 433
<211> LENGTH: 771
<212> TYPE: DNA
<213> ORGANISM: Artificial Sequence
<220> FEATURE:
<223> OTHER INFORMATION: clone

<400> SEQUENCE: 433

| caggttcagc | tggtgcagtc | tggagctgag | gtaaagaagc | ctggggcctc | ggtgaaggtc | 60 |
|---|---|---|---|---|---|---|
| tcctgtaagg | cttccggata | taacgcggac | gcctattata | taaattgggt | gcgacaggcc | 120 |
| cctggacaag | gtcttgagtg | gatgggaagt | atcaagccta | ataccggtgc | acaaaatat | 180 |
| gcacagaagt | ttcagggcag | agtcaccata | accgggaca | cgtccatcag | cacagcctac | 240 |
| atggagctga | gcaggctgag | atctgacgac | acggccgtgt | attactgtgc | gagtctggat | 300 |
| cgggatacgt | ggtacccgca | ctcctacgcg | gggtggttcg | acgcgtgggg | ccagggaacc | 360 |
| ctggtcaccg | tctcttcagc | ggccggtggt | ggcggttcag | gtggaggtgg | tagtgaggtt | 420 |
| cagttggtgg | aaagcggcgg | tggcctggtc | agccgggtg | gtagcctgcg | cctgtcctgc | 480 |
| gcggctagcg | gtttcacgtt | tagcagctac | agcatgtact | gggtgcgtca | agcgccaggc | 540 |
| aaaggtctgg | aatgggttgc | cgagattaag | caagacggtt | ctgttcagta | ttatgtcagc | 600 |
| gacgtgaagg | gtcgttttac | catcagccgt | gacaacgcga | aaaacagcct | gtatttgcag | 660 |
| atgaattccc | tgcgcgctga | agataccgcg | gtgtattact | gtgcgaaagg | tgagattctg | 720 |
| ccgctgtact | tcgattactg | gggccaaggc | accctggtta | ctgtctcgag | c | 771 |

<210> SEQ ID NO 434
<211> LENGTH: 267
<212> TYPE: PRT
<213> ORGANISM: Artificial Sequence
<220> FEATURE:
<223> OTHER INFORMATION: clone

<400> SEQUENCE: 434

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Asn | Ala | Asp | Ala | Tyr |
|---|---|---|---|---|---|---|---|---|---|---|---|---|---|---|---|
| | | | 20 | | | | | 25 | | | | | 30 | | |

| Tyr | Ile | Asn | Trp | Val | Arg | Gln | Ala | Pro | Gly | Gln | Gly | Leu | Glu | Trp | Met |
|---|---|---|---|---|---|---|---|---|---|---|---|---|---|---|---|
| | | | 35 | | | | | 40 | | | | | 45 | | |

| Gly | Ser | Ile | Lys | Pro | Asn | Thr | Gly | Ala | Thr | Lys | Tyr | Ala | Gln | Lys | Phe |
|---|---|---|---|---|---|---|---|---|---|---|---|---|---|---|---|
| 50 | | | | | 55 | | | | | 60 | | | | | |

Gln Gly Arg Val Thr Ile Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Ser Leu Asp Arg Asp Thr Trp Tyr Pro His Ser Tyr Ala Gly Trp
            100                 105                 110

Phe Asp Ala Trp Gly Gln Gly Thr Leu Val Thr Val Ser Ser Ala Ala
            115                 120                 125

Gly Gly Gly Gly Ser Gly Gly Gly Ser Gly Gly Gly Ser
            130                 135                 140

Gly Gly Gly Ser Glu Val Gln Leu Val Glu Ser Gly Gly Gly Leu Val
145                 150                 155                 160

Gln Pro Gly Gly Ser Leu Arg Leu Ser Cys Ala Ala Ser Gly Phe Thr
                165                 170                 175

Phe Ser Ser Tyr Ser Met Tyr Trp Val Arg Gln Ala Pro Gly Lys Gly
            180                 185                 190

Leu Glu Trp Val Ala Glu Ile Lys Gln Asp Gly Ser Val Gln Tyr Tyr
            195                 200                 205

Val Ser Asp Val Lys Gly Arg Phe Thr Ile Ser Arg Asp Asn Ala Lys
210                 215                 220

Asn Ser Leu Tyr Leu Gln Met Asn Ser Leu Arg Ala Glu Asp Thr Ala
225                 230                 235                 240

Val Tyr Tyr Cys Ala Lys Gly Glu Ile Leu Pro Leu Tyr Phe Asp Tyr
                245                 250                 255

Trp Gly Gln Gly Thr Leu Val Thr Val Ser Ser
            260                 265

<210> SEQ ID NO 435
<211> LENGTH: 801
<212> TYPE: DNA
<213> ORGANISM: Artificial Sequence
<220> FEATURE:
<223> OTHER INFORMATION: clone

<400> SEQUENCE: 435
caggttcagc tggtgcagtc tggagctgag gtaaagaagc tggggcctc ggtgaaggtc      60 tcctgtaagg cttccggata taacgcggac gcctattata taaattgggt gcgacaggcc     120
cctggacaag gtcttgagtg gatgggaagt atcaagccta ataccggtgc acaaaatat     180 gcacagaagt ttcagggcag agtcaccata accagggaca cgtccatcag cacagcctac     240
atggagctga gcaggctgag atctgacgac acggccgtgt attactgtgc gagtctggat     300
cgggatacgt ggtacccgca ctcctacgcg gggtggttcg acgcgtgggg ccagggaacc     360
ctggtcaccg tctcttcagc ggccggtggt ggcggttcag gaggtggagg ttcaggaggt     420
ggtggttctg gtggaggtgg tagtgaggtt cagttggtgg aaagcggcgg tggcctggtc     480
cagccgggtg gtagcctgcg cctgtcctgc gcggctagcg gtttcacgtt tagcagctac     540
agcatgtact gggtgcgtca agcgccaggc aaaggtctgg aatgggttgc cgagattaag     600
caagacggtt ctgttcagta ttatgtcagc gacgtgaagg gtcgttttac catcagccgt     660
gacaacgcga aaaacagcct gtatttgcag atgaattccc tgcgcgctga agataccgcg     720
gtgtattact gtgcgaaagg tgagattctg ccgctgtact cgattactg gggccaaggc     780 accctggtta ctgtctcgag c                                                801

<210> SEQ ID NO 436

<211> LENGTH: 277
<212> TYPE: PRT
<213> ORGANISM: Artificial Sequence
<220> FEATURE:
<223> OTHER INFORMATION: clone

<400> SEQUENCE: 436

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Ala Asp Ala Tyr
            20                  25                  30

Tyr Ile Asn Trp Val Arg Gln Ala Pro Gly Gln Gly Leu Glu Trp Met
        35                  40                  45

Gly Ser Ile Lys Pro Asn Thr Gly Ala Thr Lys Tyr Ala Gln Lys Phe
    50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Leu Asp Arg Asp Thr Trp Tyr Pro His Ser Tyr Ala Gly Trp
            100                 105                 110

Phe Asp Ala Trp Gly Gln Gly Thr Leu Val Thr Val Ser Ser Ala Ala
        115                 120                 125

Gly Gly Gly Gly Ser Gly Gly Gly Ser Gly Gly Gly Ser Gly
    130                 135                 140

Gly Gly Gly Ser Gly Gly Gly Ser Gly Gly Gly Ser Glu Val
145                 150                 155                 160

Gln Leu Val Glu Ser Gly Gly Leu Val Gln Pro Gly Gly Ser Leu
                165                 170                 175

Arg Leu Ser Cys Ala Ala Ser Gly Phe Thr Phe Ser Ser Tyr Ser Met
            180                 185                 190

Tyr Trp Val Arg Gln Ala Pro Gly Lys Gly Leu Glu Trp Val Ala Glu
        195                 200                 205

Ile Lys Gln Asp Gly Ser Val Gln Tyr Tyr Val Ser Asp Val Lys Gly
    210                 215                 220

Arg Phe Thr Ile Ser Arg Asp Asn Ala Lys Asn Ser Leu Tyr Leu Gln
225                 230                 235                 240

Met Asn Ser Leu Arg Ala Glu Asp Thr Ala Val Tyr Tyr Cys Ala Lys
                245                 250                 255

Gly Glu Ile Leu Pro Leu Tyr Phe Asp Tyr Trp Gly Gln Gly Thr Leu
            260                 265                 270

Val Thr Val Ser Ser
        275

<210> SEQ ID NO 437
<211> LENGTH: 831
<212> TYPE: DNA
<213> ORGANISM: Artificial Sequence
<220> FEATURE:
<223> OTHER INFORMATION: clone

<400> SEQUENCE: 437
caggttcagc tggtgcagtc tggagctgag gtaaagaagc ctggggcctc ggtgaaggtc      60
tcctgtaagg cttccggata taacgcggac gcctattata taaattgggt gcgacaggcc     120
cctggacaag gtcttgagtg gatgggaagt atcaagccta ataccggtgc cacaaaatat     180
gcacagaagt ttcagggcag agtcaccata accagggaca cgtccatcag cacagcctac     240

```
atggagctga gcaggctgag atctgacgac acggccgtgt attactgtgc gagtctggat    300
cgggatacgt ggtacccgca ctcctacgcg gggtggttcg acgcgtgggg ccagggaacc    360
ctggtcaccg tctcttcagc ggccggtggt ggcggttcag cggaggtggg ctctggaggt    420
ggaggttcag gaggtggtgg ttctggcggc ggtggatcgg gtggaggtgg tagtgaggtt    480
cagttggtgg aaagcggcgg tggcctggtc cagccgggtg gtagcctgcg cctgtcctgc    540
gcggctagcg gtttcacgtt tagcagctac agcatgtact gggtgcgtca agcgccaggc    600
aaaggtctgg aatgggttgc cgagattaag caagacggtt ctgttcagta ttatgtcagc    660
gacgtgaagg gtcgttttac catcagccgt gacaacgcga aaacagcct gtatttgcag    720 atgaattccc tgcgcgctga agataccgcg gtgtattact gtgcgaaagg tgagattctg    780
ccgctgtact cgattactg gggccaaggc accctggtta ctgtctcgag c             831
```

<210> SEQ ID NO 438
<211> LENGTH: 5
<212> TYPE: PRT
<213> ORGANISM: Artificial Sequence
<220> FEATURE:
<223> OTHER INFORMATION: clone

<400> SEQUENCE: 438

Ser Tyr Gly Met Tyr
1               5

<210> SEQ ID NO 439
<211> LENGTH: 17
<212> TYPE: PRT
<213> ORGANISM: Artificial Sequence
<220> FEATURE:
<223> OTHER INFORMATION: clone

<400> SEQUENCE: 439

Lys Ile Glu Gln Asp Gly Ser Glu Glu Tyr Tyr Val Asp Ser Val Lys
1               5                   10                  15

Gly

<210> SEQ ID NO 440
<211> LENGTH: 10
<212> TYPE: PRT
<213> ORGANISM: Artificial Sequence
<220> FEATURE:
<223> OTHER INFORMATION: clone

<400> SEQUENCE: 440

Gly Glu Ile Leu Pro Leu Tyr Phe Asp Tyr
1               5                   10

<210> SEQ ID NO 441
<211> LENGTH: 119
<212> TYPE: PRT
<213> ORGANISM: Artificial Sequence
<220> FEATURE:
<223> OTHER INFORMATION: clone

<400> SEQUENCE: 441

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val

```
                35                  40                  45
Ala Lys Ile Glu Gln Asp Gly Ser Glu Tyr Tyr Val Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Lys Gly Glu Ile Leu Pro Leu Tyr Phe Asp Tyr Trp Gly Gln Gly
            100                 105                 110
Thr Leu Val Thr Val Ser Ser
            115

<210> SEQ ID NO 442
<211> LENGTH: 5
<212> TYPE: PRT
<213> ORGANISM: Artificial Sequence
<220> FEATURE:
<223> OTHER INFORMATION: clone

<400> SEQUENCE: 442

Ser Tyr Gly Met Tyr
1               5

<210> SEQ ID NO 443
<211> LENGTH: 17
<212> TYPE: PRT
<213> ORGANISM: Artificial Sequence
<220> FEATURE:
<223> OTHER INFORMATION: clone

<400> SEQUENCE: 443

Lys Ile Glu Gln Asp Gly Ser Val Glu Tyr Tyr Val Asp Ser Val Lys
1               5                  10                  15
Gly

<210> SEQ ID NO 444
<211> LENGTH: 10
<212> TYPE: PRT
<213> ORGANISM: Artificial Sequence
<220> FEATURE:
<223> OTHER INFORMATION: clone

<400> SEQUENCE: 444

Gly Glu Ile Leu Pro Leu Tyr Phe Asp Tyr
1               5                  10

<210> SEQ ID NO 445
<211> LENGTH: 119
<212> TYPE: PRT
<213> ORGANISM: Artificial Sequence
<220> FEATURE:
<223> OTHER INFORMATION: clone

<400> SEQUENCE: 445

Glu Val Gln Leu Val Glu Ser Gly Gly Gly Leu Val Gln Pro Gly Gly
1               5                  10                  15
Ser Leu Arg Leu Ser Cys Ala Ala Ser Gly Phe Thr Phe Ser Ser Tyr
             20                  25                  30
Gly Met Tyr Trp Val Arg Gln Ala Pro Gly Lys Gly Leu Glu Trp Val
         35                  40                  45
Ala Lys Ile Glu Gln Asp Gly Ser Val Glu Tyr Tyr Val Asp Ser Val
 50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 446
<211> LENGTH: 5
<212> TYPE: PRT
<213> ORGANISM: Artificial Sequence
<220> FEATURE:
<223> OTHER INFORMATION: clone

<400> SEQUENCE: 446

Ser Tyr Gln Met Tyr
1               5

<210> SEQ ID NO 447
<211> LENGTH: 17
<212> TYPE: PRT
<213> ORGANISM: Artificial Sequence
<220> FEATURE:
<223> OTHER INFORMATION: clone

<400> SEQUENCE: 447

Gly Ile Lys Gln Asp Gly Ser Glu Gln Tyr Tyr Val Asp Ser Val Lys
1               5                   10                  15

Gly

<210> SEQ ID NO 448
<211> LENGTH: 10
<212> TYPE: PRT
<213> ORGANISM: Artificial Sequence
<220> FEATURE:
<223> OTHER INFORMATION: clone

<400> SEQUENCE: 448

Gly Glu Ile Leu Pro Leu Tyr Phe Asp His
1               5                   10

<210> SEQ ID NO 449
<211> LENGTH: 119
<212> TYPE: PRT
<213> ORGANISM: Artificial Sequence
<220> FEATURE:
<223> OTHER INFORMATION: clone

<400> SEQUENCE: 449

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Tyr Trp Val Arg Gln Ala Pro Gly Lys Gly Leu Glu Trp Val
        35                  40                  45

Ala Gly Ile Lys Gln Asp Gly Ser Glu Gln Tyr Tyr Val Asp Ser Val
    50                  55                  60

Lys Gly Arg Phe Thr Ile Ser Arg Asp Asn Ala Lys Lys Ser Leu Tyr
 65                  70                  75                  80
```

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp His Trp Gly Gln Gly
        100                 105                 110

Thr Leu Val Thr Val Ser Ser
        115

<210> SEQ ID NO 450
<211> LENGTH: 5
<212> TYPE: PRT
<213> ORGANISM: Artificial Sequence
<220> FEATURE:
<223> OTHER INFORMATION: clone

<400> SEQUENCE: 450

Ser Tyr Gly Met Tyr
1               5

<210> SEQ ID NO 451
<211> LENGTH: 17
<212> TYPE: PRT
<213> ORGANISM: Artificial Sequence
<220> FEATURE:
<223> OTHER INFORMATION: clone

<400> SEQUENCE: 451

Glu Ile Lys Gln Asp Gly Ser Glu Glu Tyr Tyr Val Asp Ser Val Lys
1               5                   10                  15

Gly

<210> SEQ ID NO 452
<211> LENGTH: 10
<212> TYPE: PRT
<213> ORGANISM: Artificial Sequence
<220> FEATURE:
<223> OTHER INFORMATION: clone

<400> SEQUENCE: 452

Gly Glu Ile Leu Pro Leu Tyr Phe Asp Tyr
1               5                   10

<210> SEQ ID NO 453
<211> LENGTH: 119
<212> TYPE: PRT
<213> ORGANISM: Artificial Sequence
<220> FEATURE:
<223> OTHER INFORMATION: clone

<400> SEQUENCE: 453

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Lys Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp Tyr Trp Gly Gln Gly

```
                    100                 105                 110
Thr Leu Val Thr Val Ser Ser
            115

<210> SEQ ID NO 454
<211> LENGTH: 5
<212> TYPE: PRT
<213> ORGANISM: Artificial Sequence
<220> FEATURE:
<223> OTHER INFORMATION: clone

<400> SEQUENCE: 454

Ser Tyr Ser Met Tyr
1               5

<210> SEQ ID NO 455
<211> LENGTH: 17
<212> TYPE: PRT
<213> ORGANISM: Artificial Sequence
<220> FEATURE:
<223> OTHER INFORMATION: clone

<400> SEQUENCE: 455

Gly Ile Glu Gln Asp Gly Ser Glu Glu Tyr Tyr Val Asp Ser Val Lys
1               5                   10                  15

Gly

<210> SEQ ID NO 456
<211> LENGTH: 10
<212> TYPE: PRT
<213> ORGANISM: Artificial Sequence
<220> FEATURE:
<223> OTHER INFORMATION: clone

<400> SEQUENCE: 456

Gly Glu Ile Leu Pro Leu Tyr Phe Asp Tyr
1               5                   10

<210> SEQ ID NO 457
<211> LENGTH: 119
<212> TYPE: PRT
<213> ORGANISM: Artificial Sequence
<220> FEATURE:
<223> OTHER INFORMATION: clone

<400> SEQUENCE: 457

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Gly Ile Glu Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115
```

```
<210> SEQ ID NO 458
<211> LENGTH: 5
<212> TYPE: PRT
<213> ORGANISM: Artificial Sequence
<220> FEATURE:
<223> OTHER INFORMATION: clone

<400> SEQUENCE: 458

Ser Tyr Arg Met Tyr
1               5

<210> SEQ ID NO 459
<211> LENGTH: 17
<212> TYPE: PRT
<213> ORGANISM: Artificial Sequence
<220> FEATURE:
<223> OTHER INFORMATION: clone

<400> SEQUENCE: 459

Glu Ile Glu Gln Asp Gly Ser Glu Gln Tyr Tyr Val Asp Ser Val Lys
1               5                  10                  15

Gly

<210> SEQ ID NO 460
<211> LENGTH: 10
<212> TYPE: PRT
<213> ORGANISM: Artificial Sequence
<220> FEATURE:
<223> OTHER INFORMATION: clone

<400> SEQUENCE: 460

Gly Glu Ile Leu Pro Leu Tyr Phe Asp Tyr
1               5                  10

<210> SEQ ID NO 461
<211> LENGTH: 119
<212> TYPE: PRT
<213> ORGANISM: Artificial Sequence
<220> FEATURE:
<223> OTHER INFORMATION: clone

<400> SEQUENCE: 461

Glu Val Gln Leu Val Glu Ser Gly Gly Met Val Gln Pro Gly Gly
1               5                  10                  15

Ser Leu Arg Leu Ser Cys Ala Ala Ser Gly Phe Thr Phe Ser Ser Tyr
                20                  25                  30

Arg Met Tyr Trp Val Arg Gln Ala Pro Gly Lys Gly Leu Glu Trp Val
            35                  40                  45

Ala Glu Ile Glu Gln Asp Gly Ser Glu Gln Tyr Tyr Val Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 462
<211> LENGTH: 5
```

-continued

```
<212> TYPE: PRT
<213> ORGANISM: Artificial Sequence
<220> FEATURE:
<223> OTHER INFORMATION: clone

<400> SEQUENCE: 462

Ser Tyr Gly Met Tyr
1               5

<210> SEQ ID NO 463
<211> LENGTH: 17
<212> TYPE: PRT
<213> ORGANISM: Artificial Sequence
<220> FEATURE:
<223> OTHER INFORMATION: clone

<400> SEQUENCE: 463

Glu Ile Asn Gln Asp Gly Ser Glu Gln Tyr Tyr Val Asp Ser Val Lys
1               5                   10                  15

Gly

<210> SEQ ID NO 464
<211> LENGTH: 10
<212> TYPE: PRT
<213> ORGANISM: Artificial Sequence
<220> FEATURE:
<223> OTHER INFORMATION: clone

<400> SEQUENCE: 464

Gly Glu Ile Leu Pro Leu Tyr Phe Asp Tyr
1               5                   10

<210> SEQ ID NO 465
<211> LENGTH: 155
<212> TYPE: PRT
<213> ORGANISM: Homo sapiens

<400> SEQUENCE: 465

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
                100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
        130                 135                 140

Thr Cys Val Thr Pro Ile Val His His Val Ala
145                 150                 155

<210> SEQ ID NO 466
<211> LENGTH: 119
```

```
<212> TYPE: PRT
<213> ORGANISM: Artificial Sequence
<220> FEATURE:
<223> OTHER INFORMATION: clone

<400> SEQUENCE: 466

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Asn Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115
```

UNITED STATES PATENT AND TRADEMARK OFFICE
CERTIFICATE OF CORRECTION

| | | |
|---|---|---|
| PATENT NO. | : 11,667,705 B2 | Page 1 of 1 |
| APPLICATION NO. | : 16/843474 | |
| DATED | : June 6, 2023 | |
| INVENTOR(S) | : Bryan Edwards et al. | |

It is certified that error appears in the above-identified patent and that said Letters Patent is hereby corrected as shown below:

In the Claims

Column 327, Line 42 Claim 2 should be displayed as follows:
2. The binding molecule according to claim 1, wherein said human heavy chain variable immunoglobulin domain ($V_H$) comprises the amino acid sequence of SEQ ID NO. 8.

Signed and Sealed this
Twentieth Day of February, 2024

*Katherine Kelly Vidal*

Katherine Kelly Vidal
*Director of the United States Patent and Trademark Office*